US006812333B1

(12) United States Patent
Hudson et al.

(10) Patent No.: US 6,812,333 B1
(45) Date of Patent: Nov. 2, 2004

(54) IDENTIFICATION OF ARSACS MUTATIONS AND METHODS OF USE THEREFOR

(75) Inventors: Thomas J. Hudson, Westmount (CA); James Engert, Montreal (CA); Andrea Richter, Montreal (CA)

(73) Assignees: Hopital Sainte-Justine, Montreal (CA); McGill University, Montreal (CA)

( * ) Notice: Subject to any disclaimer, the term of this patent is extended or adjusted under 35 U.S.C. 154(b) by 0 days.

(21) Appl. No.: 09/693,205

(22) Filed: Oct. 20, 2000

Related U.S. Application Data

(60) Provisional application No. 60/160,588, filed on Oct. 20, 1999.

(51) Int. Cl.$^7$ ........................ C07H 21/04; C07K 14/00; C12N 5/00; C12N 15/00

(52) U.S. Cl. ........................ 536/23.1; 435/6; 435/320.1; 435/325; 435/252.1; 530/350

(58) Field of Search ........................ 536/23.1; 530/350; 435/6, 320.1, 325, 252.1

(56) References Cited

U.S. PATENT DOCUMENTS 6,150,091 A 11/2000 Pandolfo et al. ............... 435/6

FOREIGN PATENT DOCUMENTS

WO WO 97/32996 9/1997

OTHER PUBLICATIONS

NCI–CGAP, National Cancer Institute, Cancer Genome Anatomy Project (CGAP), Tumor Gene Index, AA897198 (Jan. 4, 1999).*

Bouillaud, Gene Bank Accession No. R17106 (last updated Jun. 12, 1996).*

Bouchard, J. et al., "Autosomal recessive spastic ataxia of Charlevoix–Saguenay," *Neuromuscular Disorders* 8(7):474–479 (1998).

Engert, J.C. et al., "ARSACS, a spastic ataxia common in northeastern Québec, is caused by mutations in a new gene encoding an 11.5–kb ORF," *Nature Genetics* 24:120–125 (2000).

Nagase, T. et al., "Prediction of the Coding Sequences of Unidentified Human Genes. XI. The Complete Sequences of 100 New cDNA Clones from Brain Which Code for Large Proteins in vitro," *DNA Research* 5:277–286 (1998).

Richter, A. et al., "Location Score and Haplotype Analyses of the Locus for Autosomal Recessive Spastic Ataxia of Charlevoix–Saguenay, in Chromosome Region 13q11," *Am. J. Hum. Genet.* 64:768–775 (1999).

Dickie, M.M., "Tumbler, tb," *Mouse News Letts.* 32:45 (1965).

Mouse Genome Informatics, The Jackson Labs, (http://www.informatics.jax.org/searches/marker.cqi?13755), entry for tumbler gene, (1965).

Catalog page from ATCC on–line catalog regarding I.M.A.G.E. Consortium Clone (Human): ATCC No. 536371, (http://phage.atcc.org/cgi–bin/searchengine/longview.cgi?view=mb–hum, 88981076&text=2). (2001).

GenBank Accession No. 3401959, Locus 3401959, "Structure Of The N–Terminal Domain Of The Yeast Hsp90 Chaperone In Complex With Geldanamycin" (1998).

GenBank Accession No. AB006708, BA000015, Locus AB006708, "*Arabidopsis thaliana* genomic DNA, chromosome 5, P1 clone:MYJ24" (2000).

GenBank Accession No. R17106, EST name: EST20108, "EST20108 Clontech adult human fat cell library HL1108A *Homo sapiens* cDNA clone 20108, mRNA sequence" (1995).

GenBank Accession No. AA776169, EST name: ae80c02.sl, "ae80c02.sl *Stratagene schizo* brain S11 *Homo sapiens* cDNA clone IMAGE:970466 3'!, mRNA sequence" (1998).

GenBank Accession No. AA776670, EST name: ae80g02.sl, "ae80g02.sl *Stratagene schizo* brain S11 *Homo sapiens* cDNA clone IMAGE: 970514 3', mRNA sequence" (1998).

GenBank Accession No. AA897178, EST name: am09e08.sl, "am09e08.sl Soares_NFL_T_GBC_S1 *Homo sapiens* cDNA clone IMAGE: 1466342 3', mRNA sequence" (1998).

GenBank Accession No. AB018273, Locus AB018273, "*Homo sapiens* mRNA for KIAA0730 protein, partial cds" (1999).

GenBank Accession No. AA987300, EST name: or81g03.sl, "or81g03.sl NCI_CGAP_Lu5 *Homo sapiens* cDNA clone IMAGE: 1602292 3', mRNA sequence" (1998).

GenBank Accession No. AA476635, EST name: zw85e07.rl, zw85e07.rl Soares_total_fetus Nb2HF8_9w *Homo sapiens* cDNA clone IMAGE: 783780 5', mRNA sequence (1997).

GenBank Accession No. AI351876, EST name: qq21g03.xl, "qq21g03.xl Soares_NhHMPu_S1 *Homo sapiens* cDNA clone IMAGE: 1933204 3', mRNA sequence" (1998).

GenBank Accession No. W25994, EST name: 17f7, "17f7 Human retina cDNA randomly primed sublibrary *Homo sapiens* cDNA, mRNA sequence" (1996).

GenBank Accession No. AI377467, EST name: tc23h08.x1, "tc23h08.x1 Soares_total_fetus_Nb2HF8_9w *Homo sapiens* cDNA clone IMAGE: 2065503 3', mRNA sequence" (1999).

GenBank Accession No. AA601007, EST name: nk67a04.s1, "nk67a04.s1 NCI CGAP_Sch1 *Homo sapiens* cDNA clone IMAGE: 1018542 3', mRNA sequence" (1997).

GenBank Accession No.AA324964, EST name: EST27877, "EST27877 Cerebellum II *Homo sapiens* cDNA 5' end, mRNA sequence" (1997).

(List continued on next page.)

*Primary Examiner*—Christopher S. F. Low
*Assistant Examiner*—Chih-Min Kam
(74) *Attorney, Agent, or Firm*—Ropes & Gray LLP

(57) ABSTRACT

Isolated spastin genes and fragments thereof, as well as Spastin proteins and fragments thereof are disclosed. Also disclosed are altered forms of spastin, as well as methods for the diagnosis and treatment of neurodegenerative disease.

6 Claims, 24 Drawing Sheets

OTHER PUBLICATIONS

Desseyn, J–L., et al., "Human Mucin Gene MUC5B, the 10.7–kb Large Central Exon Encodes Various Alternate Subdomains Resulting in a Super–repeat," *The Journal of Biological Chemistry*, 272(6):3168–3178 (1997).

Engert, J.C., et al., "Autosomal Recessive Spastic Ataxia of Charlevoix–Saguenay (ARSACS): High–Resolution Physical and Transcript Map of the Candidate Region in Chromosome Region 13q11," *Genomics*, 62:156–164 (1999).

Hazan, J., et al., "Spastin, a New AAA Protein, is Altered in the Most Frequent Form of Autosomal Dominant Spastic Paraplegia," *Nature Genetics*, 23(11):296–303 (1999).

* cited by examiner

6594T

6594Δ

A A A G C G A C A C
(SEQ ID NO: 19)

5254C

A A A G N G A C A C
(SEQ ID NO: 20)

5254C/T

```
HUMAN-REP 1     705    GQREPLTVRIKNILEEYPSVSDIFKEILQNADOAN-ATECSFLIDMRRNMDIRENLLDPG
MOUSE-REP 1     705    GQREPLTVRIKNILEEYPSVSDIFKEILQNADOAN-ATECSFmIDMRRNMDIRENLLDPG
HUMAN-REP 2     1773   GqkE.LT.RIK.IL..YPS..em.KEILQNADOA..ATE..Fv.D.R......d.i.D..
ARABIDOPSIS     987    GQhE.LT.RIK.ILE.Y.....I..EIvQNAeOA..AsE.tFLlD..h.....d.LL.P.
HSP90 (YEAST)   18     .Q.E...l....I...Y.......rELi.NA.OA........L.D.k......d..i...

HUMAN-REP 1     764    MAACHGPALWSFNNSQ-FSDSDFVN----ITRLG-----ESLKRGE-VDKVGKFGLGFNS
HUMAN-REP 1     764    MAACHGPALWSFNNSe-FSDSDFIN....ITRLG.....ESLKRGE-VDKVGKFGLGFNS
HUMAN-REP 2     1830   .A...GPAL..yNN...Fte.D.......I..LG........K.G....K.G.yGiGFNS
ARABIDOPSIS     1044   MA...GPALy.FNNS..Ft..D.......IsRiG.....qa.K.......iGrPGLGFN.
HSP90 (YEAST)   78     ........L...d.....t.ae.iN....I.k.G.....EaL..G..V..iG.FGvGF.S

HUMAN-REP 1     813    VYHITDIPIIMSR--------------EFMIMFDP
MOUSE-REP 1     813    VYHITDIPIIMSR...............EFMIMFDP
MOUSE-REP 2     1879   VYHITD.P..iS................d.l.iFD.
ARABIDOPSIS     1093   VYH.TDIP..vS................E.ivMFDP
HSP90 (YEAST)   137    If.v.D...viSk................F.v..D.
```

Underline = conserved
Bold = identical

Figure 4B

MNTFWPGRELIVQWYPFDENRNHPSVSWLKMVWKNLYIHFSEDLTLFDEMPLIPRTILEE 60
..........V......S.DKR...L..............................L.N.

GQTCVELIRLRIPSLVILDDESEAQLPEFLADIVQKLGGFVLKKLDASIQHPLIKKYIHS 120
D............V......T.................I...R..T......V.......

PLPSAVLQIMEKMPLQKLCNQITSLLPTHKDALRKFLASLTDSSEKEKRIIQELAIFKRI 180
.....I......I.........A..................T...........T......

NHSSDQGISSYTKLKGCKVLHHTAKLPADLRLSISVIDSSDEATIRLANMLKIEQLKTTS 240
...................D......T....V......................K.....

CLKLVLKDIENAFYSHEEVTQLMLWVLENLSSLKNENPNVLEWLTPLKFIQISQEQMVSA 300
...F.....G....TQ.........I...........S...D..M.....HM..GHV.A.

GELFDPDIEVLKDLFCNEEGTYFPPSVFTSPDILHSLRQIGLKNEASLKEKDVVQVAKKI 360
.D.........R.:.Y...EAC...TI..................S...........R..

EALQVGACPDQDVLLKKAKTLLLVLNKNHTLLQSSEGKMTLKKIKWVPACKERPPNYPGS 420
.....SS.QN...M.............Q..........A.....................

LVWKGDLCNLCAPPDMCDVGHAILIGSSLPLVESIHVNLEKALGIFTKPSLSAVLKHFKI 480
..................AA..V.V..........V....Q..S.....TIN.......T

VVDWYSSKTFSDEDYYQFQHILLEIYGFMHDHLNEGKDSFRALKFPWVWTGKKFCPLAQA 540
.....T............................S......K..........N.......

VIKPIHDLDLQPYLHNVPKTMAKFHQLFKVCGSIEELTSDHISMVIQKIYLKSDQDLSEQ 600
....T........Y..............A...................V......E...E

ESKQNLHLMLNIIRWLYSNQIPASPNTPVPIHHSKNPSKLIMKPIHECCYCDIKVDDLND 660
............M.......................Y..R....V...............

LLEDSVEPIILVHEDIPMKTAEWLKVPCLSTRLINPENMGFEQSGQREPLTVRIKNILEE 720
............................................................

YPSVSDIFKELLQNADDANATECSFLIDMRRNMDIRENLLDPGMAACHGPALWSFNNSQF 780
..........................M...............................E.

SDSDFVNITRLGESLKRGEVDKVGKFGLGFNSVYHITDIPIIMSREFMIMFDPNINHISK 840
.....L......................................................

HIKDKSNPGIKINWSKQQKRLRKFPNQFKPFIDVFGCQLPLTVEAPYSYNGTLFRLSFRT 900
....R.....................................A.................

QQEAKVSEVSSTCYNTADIYSLVDEFSLCGHRLIIFTQSVKSMYLKYLKIEETNPSLAQD 960
..........................................N.................

TVIIKKKSCSSKALNTPVLSVLKEAAKLMKTCSSSNKKLPSDEPKSSCILQITVEEFHHV 1020
.I.....V.P.....A..........................T.V...............

FRRIADLQSPLFRGPDDDPAALFEMAKSGQSKKPSDELSQKTVECTTWLLCTCMDTGEAL 1080
.....................T..................P...D....I..........

KFSLSESGRRLGLVPCGAVGVQLSEIQDQKWTVKPHIGEVFCYLPLRIKTGLPVHINGCF 1140
....N................L.H.T.E.........................I......

AVTSNRKEIWKTDTKGRWNTTFMRHVIVKAYLQVLSVLRDLATSGELMDYTYYAVWPDPD 1200
.................................A........IG...T............

LVHDDFSVICQGFYEDIAHGKGKELTKVFSDGSTWVSMKNVRFLDDSILKRRDVGSAAFK 1260
..........K...............R.....M................Q.K........

IFLKYLKKTGSKNLCAVELPSSVKLGFEEAGCKQILLENTFSEKQFFSEVFFPNIQEIEA 1320
........................A...................................

ELRDPLMIFVLNEKVDEFSGVLRVTPCIPCSLEGHPLVLPSRLIHPEGRVAKLFDIKDGR 1380
.......N......L.....I.....V............................T....

FPYGSTQDYLNPIILIKLVQLGKAKDDILWDDMLERAVSVAEINKSDHVAACLRSSILLS 1440
.........................M.............E.........A..........

Figure 5A

LIDEKLKIRDPRAKDFAAKYQTIRFLPFLTKPAGFSLDWKGNSFKPETMFAATDLYTAEH 1500
........K...............P............E................I....Y

QDIVCLLQPILNENSHSFRGCGSVSLAVKEFLGLLKKPTVDLVINQLKEVAKSVDDGITL 1560
................................................Q...........

YQENITNACYKYLHEALMQNEITKMSIIDKLKPFSFILVENAYVDSEKVSFHLNFEAAPY 1620
................VL...MA.AT..E.....C......V..E...............

LYQLPNKYKNNFRELFETVGVRQSCTVEDFALVLESIDQERGTKQITEENFQLCRRIISE 1680
.................S......F.................K.................

GIWSLIREKKQEFCEKNYGKILLPDTNLMLLPAKSLCYNDCPWIKVKDTTVKYCHADIPR 1740
.........R..................L...................S...........

EVAVKLGAVPKRHKALERYASNVCFTTLGTEFGQKEKLTSRIKSILNAYPSEKEMLKELL 1800
........I.............I...A.................................

QNADDAKATEICFVFDPRQHPVDRIFDDKWAPLQGPALCVYNNQPFTEDDVRGIQNLGKG 1860
............................................................

TKEGNPYKTGQYGIGFNSVYHITDCPSFISGNDILCIFDPHARYAPGATSISPGRMFRDL 1920
......C...H........................G..............V.........

DADFRTQFSDVLDLYLGTHFKLDNCTMFRFPLRNAEMAKVSEISSVPASDRMVQNLLDKL 1980
.................N....................Q........S............

RSDGAELLMFLNHMEKISICEIDKSTGALNVLYSVKGKITDGDRLKRKQFHASVIDSVTK 2040
........................A..G................................

KRQLKDIPVQQITYTMDTEDSEGNLTTWLICNRSGFSSMEKVSKSVISAHKNQDITLFPR 2100
............................................................

GGVAACITHNYKKPHRAFCFLPLSLETGLPFHVNGHFALDSARRNLWRDDNGVGVRSDWN 2160
............................................................

NSLMTALIAPAYVELLIQLKKRYFPGSDPTLSVLQNTPIHVVKDTLKKFLSFFPVNRLDL 2220
............................................................

QPDLYCLVKALYNCIHEDMKRLLPVVRAPNIDGSDLHSAVIITWINMSTSNKTRPFFDNL 2280
............S...............................................

LQDELQHLKNADYNITTRKTVAENVYRLKHLLLEIGFNLVYNCDETANLYHCLIDADIPV 2340
.....................................................V......

SYVTPADIRSFLMTFSSPDTNCHIGKLPCRLQQTNLKLFHSLKLLVDYCFKDAEENEIEV 2400
.......V...............................................S.F..

EGLPLLITLDSVLQTFDAKRPKFLTTYHELIPSRKDLFMNTLYLKYSNILLNCKVAKVFD 2460
..............I..G.............................SV...........

ISSFADLLSSVLPREYKTKSCTKWKDNFASESWLKNAWHFISESVSVKEDQEETKPTFDI 2520
...................N.A.........................TD....P..A..V

VVDTLKDWALLPGTKFTVSANQLVVPEGDVLLPLSLMHIAVFPNAQSDKVFHALMKAGCI 2580
I..I...............TS..........I............................

QLALNKICSKDSAFVPLLSCHTANIESPTSILKALHYMVQTSTFRAEKLVENDFEALLMY 2640
.............L...........D..A.....V..........T...M..........

FNCNLNHLMSQDDIKILKSLPCYKSISGRYVSIGKFGTCYVLTKSIPSAEVEKWTQSSSS 2700
.....S........................M..A..........................

AFLEEKIHLKELYEVIGCVPVDDLEVYLKHLLPKIENLSYDAKLEHLIYLKNRLSSAEEL 2760
......V........L......................................A.I..P

SEIKEQLFEKLESLLIIHDANSRLKQAKHFYDRTVRVFEVMLPEKLFIPNDFFKKLEQLI 2820
.....................N...........................KE.......V.

KPKNHVTFMTSWVEFLRNIGLKYILSQQQLLQFAKEISVRANTENWSKETLQNTVDILLH 2880
....QAA................A............................S.......

Figure 5B

HIFQERMDLLSGNFLKELSLIPFLCPERAPAEFIRFHPQYQEVNGTLPLIKFNGAQVNPK 2940

................................Y...........................

FKQCDVLQLLWTSCPILPEKATPLSIKEQEGSDLGPQEQLEQVLNMLNVNLDPPLDKVIN 3000

..................................A.........................

NCRNICNITTLDEEMVKTRAKVLRSIYEFLSAEKREFRFQLRGVAFVMVEDGWKLLKPEE 3060

............................................................

VVINLEYESDFKPYLYKLPLELGTFHQLFKHLGTEDIISTKQYVEVLSRIFKNSEGKQLD 3120

........A...........................................S.......

PNEMRTVKRVVSGLFRSLQNDSVKVRSDLENVRDLALYLPSQDGRLVKSSILVFDDAPHY 3180

...............K...............A............K...............

KSRIQGNIGVQMLVDLSQCYLGKDHGFHTKLIMLFPQKLRPRLLSSILEEQLDEETPKVC 3240

............................................................

QFGALCSLQGRLQLLLSSEQFITGLIRIMKHENDNAFLANEEKAIRLCKALREGLKVSCF 3300

............................................................

EKLQTTLRVKGFNPIPHSRSETFAFLKRFGNAVILLYIQHSDSKDINFLLALAMTLKSAT 3360

............................................................

DNLISDTSYLIAMLGCNDIYRIGEKLDSLGVKYDSSEPSKLELPMPGTPIPAEIHYTLLM 3420

......................S.....................................

DPMNVFYPGEYVGYLVDAEGGDIYGSYQPTYTYAIIVQEVEREDADNSSFLGKIYQIDIG 3480

...............................................T............

YSEYKIVSSLDLYKFSRPEESSQSRDSAPSTPTSPTEFLTPGLRSIPPLFSGRESHKT-S 3540

..................D....N.....T......................K....SP.

SKHQSPKKLKVNSLPEILKEVTSVVEQAWKL*PESERKKIIRRLYLKWHPDKNPFNHDIAN* 3600

T..H..R.....A...............................................

*EVFKHLQNEINRLEKQAFLDQNADRASRRTF*STSASRFQSDKYSFQRFYTSWNQEATSHK 3660

............................................................

SERQQQNKEKCPPSAGQTYSQRFFVPPTFKSVGNPVEARRWLRQARANFSAARNDLHKNA 3720

......S.....................................................

NEWVCFKCYLSTKLALIAADYAVRGKSDKDVKPTALAQKIEEYSQQLEGLTNDVHTLEAY 3780

............................................................

GVDSLKTRYPDLLPFPQIPNDRFTSEVAMRVMECTACIIIKLENFMQQKV 3830

Table 1 ESTs identified by sample-sequencing of the ARSACS critical interval

| BAC clone | GenBank # | UniGene | Identity* | Tissue Source |
|---|---|---|---|---|
| 235_I,_20 | AA987300 | IIs. 129092 | 221/230 | neuroendocrine lung carcinoids |
| 235_I,_20 | AA476635* | | 249/296 | total fetus |
| 235_I,_20 | AI351876* | | 272/335 | melanocyte, fetal heart, pregnant uterus (pool) |
| 235_I,_20 | W25994 | IIs. 163732 | 447/464 | retina |
| 235_I,_20 | AI377467 | IIs. 163732 | 257/263 | total fetus |
| 235_I,_20 | AA601007 | | 488/491 | schwannoma tumor |
| 235_I,_20 | AA324964 | | 214/234 | cerebellum |
| 235_I,_20, 206_I,_I | AA897178[b] | | 238/238 | fetal lung, testis, and B-cell |
| 235_I,_20, 206_I,_I | RI7106[b] | IIs. 188560 | 747/784 | brain, adipose tissue |
| 235_I,_20, 206_I,_I | AB018273[b] | IIs. 159492 | 4318/4318 | multiple tissue types including brain, CNS, and whole embryo |

a: Number of homologous nucleotides between the BAC subclone sequence and the GenBank sequence.
b: AA897178, RI7106, and AB018273 are all contained within *spastin*.
*: AA176335 and AI351876 were homologous to non-overlapping portions of the same M13 subclone sequence.

Figure 6

**Table 2 Primers for PCR amplification of the human *spastin* ORF**

| Primer set | | Forward primer | Reverse primer | | Product size (bp) |
|---|---|---|---|---|---|
| 1 | (SEQ ID NO: 21) | CCTTCCAGTACTGTGTTATTTGTGAG | CAAGAACTTCCTCAGGGCATC | (SEQ ID NO: 22) | 603 |
| 2 | (SEQ ID NO: 23) | GATGCATCTATACAACATCCGCT | GGTGGGAAATAGGTTCCTTC | (SEQ ID NO: 24) | 581 |
| 3 | (SEQ ID NO: 25) | AAAAATGAGAATCCAAATGTGCT | GCACTAAGGCTAGGTTTTGTGAAG | (SEQ ID NO: 26) | 592 |
| 4 | (SEQ ID NO: 27) | GCTCCTCACTTCCTCTTGTTG | CGTGAATTGGCTTCATGATAA | (SEQ ID NO: 28) | 602 |
| 5 | (SEQ ID NO: 29) | AGCAATCAGATTCCAGCAAGC | GATGGGAATGTCAGTGATATGG | (SEQ ID NO: 30) | 611 |
| 6 | (SEQ ID NO: 31) | GGGAGAAGTTGACAAAGTTGGA | CTTTGGTTCATCACTGGGAAG | (SEQ ID NO: 32) | 624 |
| 7 | (SEQ ID NO: 33) | TCCAAAGCATTGAACACACCT | CAGGTCCCGTAAGACACTCAG | (SEQ ID NO: 34) | 631 |
| 8 | (SEQ ID NO: 35) | CAATGGGTGCTTTGCTGTTAC | CGAAGAACTCCCGAGAACTCA | (SEQ ID NO: 36) | 620 |
| 9 | (SEQ ID NO: 37) | GCTGGCTGCAAACAGATACTAC | GCAAACATGGTTTCAGGCTTA | (SEQ ID NO: 38) | 604 |
| 10 | (SEQ ID NO: 39) | CAAACAATCCGCTTCCTTCCAT | ATTATTCGTCGGCAAAGCTGA | (SEQ ID NO: 40) | 651 |
| 11 | (SEQ ID NO: 41) | TTCCGCGAACTTTTTGAAACC | ACACAAAGTGCTGGCCCTTGC | (SEQ ID NO: 42) | 625 |
| 12 | (SEQ ID NO: 43) | GATGCAAAGGCGACAGAAATC | ATACAGCACATTTAGAGCTCCAGT | (SEQ ID NO: 44) | 626 |
| 13 | (SEQ ID NO: 45) | GCATCAGACAGAATGGTCCAG | GCAATTCAACATATGCAGGAG | (SEQ ID NO: 46) | 624 |
| 14 | (SEQ ID NO: 47) | GTGAATGGCCACTTTGCACT | TGATATCAGCAGGGGTCACAT | (SEQ ID NO: 48) | 648 |
| 15 | (SEQ ID NO: 49) | ACCACACGCAAAACAGTAGCA | GCCATGCATTCTTAAGCCAAG | (SEQ ID NO: 50) | 609 |
| 16 | (SEQ ID NO: 51) | TGACATTTCCAGCTTTGCTGA | AGCGGCCACTGATGGATTTAT | (SEQ ID NO: 52) | 631 |
| 17 | (SEQ ID NO: 53) | AAATGATTTTGAGGCACTTTTG | TTCCACCCAGGATGTCATAAA | (SEQ ID NO: 54) | 609 |
| 18 | (SEQ ID NO: 55) | ACAGTAGACTAAAGCAAGCAAAGC | ATCAAGAGGAGGATCCAGGTT | (SEQ ID NO: 56) | 645 |
| 19 | (SEQ ID NO: 57) | CATCCTGCCCTATTCTTCCAG | TAAAGCGCAAGGTCTCGTACA | (SEQ ID NO: 58) | 618 |
| 20 | (SEQ ID NO: 59) | TGAGGGCAAACAATTAGATCC | TCTGCTGTGGGGAATAGGATT | (SEQ ID NO: 60) | 612 |
| 21 | (SEQ ID NO: 61) | GCAAAGCCCTAAGAGAAGGATT | TGCTTTGAGAGCTTTCCTCAG | (SEQ ID NO: 62) | 647 |
| 22 | (SEQ ID NO: 63) | TGAAAGAGAAGATGCTGACAATTC | GTAAGTCTGTCCGGCTGAAGG | (SEQ ID NO: 64) | 654 |
| 23 | (SEQ ID NO: 66) | CATCCCGATTTCAGTCAGACA | TTCGTGCTACAACACATTCAAGA | (SEQ ID NO: 66) | 638 |

Figure 7

```
LOCUS       AF193557     11493 bp    DNA             ROD
DEFINITION  Mus musculus sacsin gene, complete cds.
ACCESSION   AF193557
VERSION     AF193557.1  GI:6907043
KEYWORDS    .
SOURCE      house mouse.
  ORGANISM  Mus musculus
            Eukaryota; Metazoa; Chordata; Craniata; Vertebrata; Euteleostomi;
            Mammalia; Eutheria; Rodentia; Sciurognathi; Muridae; Murinae; Mus.
REFERENCE   1  (bases 1 to 11493)
  AUTHORS   Engert,J.C., Berube,P., Mercier,J., Dore,C., Lepage,P., Ge,B.,
            Bouchard,J.P., Mathieu,J., Melancon,S.B., Schalling,M.,
            Lander,E.S., Morgan,K., Hudson,T.J. and Richter,A.
  TITLE     ARSACS, a spastic ataxia common in northeastern Quebec, is caused
            by mutations in a new gene encoding an 11.5-kb ORF
  JOURNAL   Nat. Genet. 24 (2), 120-125 (2000)
  MEDLINE   20120709
REFERENCE   2  (bases 1 to 11493)
  AUTHORS   Engert,J.C., Berube,P., Dore,C., Lepage,P., Ge,B., Hudson,T.J. and
            Richter,A.
  TITLE     Direct Submission
  JOURNAL   Submitted (08-OCT-1999) Genome Centre, Montreal General Hospital,
            1650 Cedar Ave., Montreal, QC H3G 1A4, Canada
FEATURES             Location/Qualifiers
     source          1..11493
                     /organism="Mus musculus"
                     /db_xref="taxon:10090"
     mRNA            <1..>11493
                     /product="sacsin"
     CDS             1..11493
                     /note="molecular chaperone"
                     /codon_start=1
                     /product="sacsin"
                     /protein_id="AAF31263.1"
                     /db_xref="GI:6907044"

/translation="MNTFWPGRELVVQWYPFSEDKRHPSLSWLKMVWKNLYIHFSEDL
TLFDEMPLIPRTLLNEDQTCVELIRLRIPSVVILDDETEAQLPEFLADIVQKLGGIVL
KRLDTSIQHPLVKKYIHSPLPSAILQIMEKIPLQKLCNQIASLLPTHKDALRKFLASL
TDTSEKEKRIIQELTIFKRINHSSDQGISSYTKLKGCKVLDHTAKLPTDLRLSVSVID
SSDEATIRLANMLKIEKLKTTSCLKFVLKDIGNAFYTQEEVTQLMLWILENLSSLKNE
NSNVLDWLMPLKFIHMSQGHVVAAGDLFDPDIEVLRDLFYNEEEACFPPTIFTSPDIL
HSLRQIGLKNESSLKEKDVVQVARKIEALQVSSCQNQDVLMKKAKTLLLVLNKNQTLL
QSSEGKMALKKIKWVPACKERPPNYPGSLVWKGDLCNLCAPPDMCDAAHAVLVGSSLP
LVESVHVNLEQALSIFTKPTINAVLKHFKTVVDWYTSKTFSDEDYYQFQHILLEIYGF
MHDHLSEGKDSFKALKFPWVWTGKNFCPLAQAVIKPTHDLDLQPYLYNVPKTMAKFHQ
LFKACGSIEELTSDHISMVIQKVYLKSDQELSEEESKQNLHLMLNIMRWLYSNQIPAS
```

Figure 8A

PNTPVPIYHSRNPSKLVMKPIHECCYCDIKVDDLNDLLEDSVEPIILVHEDIPMKTAE
WLKVPCLSTRLINPENMGFEQSGQREPLTVRIKNILEEYPSVSDIFKELLQNADDANA
TECSFMIDMRRNMDIRENLLDPGMAACHGPALWSFNNSEFSDSDFLNITRLGESLKRG
EVDKVGKFGLGFNSVYHITDIPIIMSREFMIMFDPNINHISKHIKDRSNPGIKINWSK
QQKRLRKFPNQFKPFIDVFGCQLPLAVEAPYSYNGTLFRLSFRTQQEAKVSEVSSTCY
NTADIYSLVDEFSLCGHRLIIFTQSVNSMYLKYLKIEETNPSLAQDTIIIKKKVCPSK
ALNAPVLSVLKEAAKLMKTCSSSNKKLPTDVPKSSCILQITVEEFHHVFRRIADLQSP
LFRGPDDDPATLFEMAKSGQSKKPSDELPQKTVDCTTWLICTCMDTGEALKFSLNESG
RRLGLVPCGAVGVLLHETQEQKWTVKPHIGEVFCYLPLRIKTGLPIHINGCFAVTSNR
KEIWKTDTKGRWNTTFMRHVIVKAYLQALSVLRDLAIGGELTDYTYYAVWPDPDLVHD
DFSVICKGFYEDIAHGKGKELTRVFSDGSMWVSMKNVRFLDDSILQRKDVGSAAFKIF
LKYLKKTGSKNLCAVELPSSVKAGFEEAGCKQILLENTFSEKQFFSEVFFPNIQEIEA
ELRDPLMNFVLNEKLDEFSGILRVTPCVPCSLEGHPLVLPSRLIHPEGRVAKLFDTKD
GRFPYGSTQDYLNPIILIKLVQLGMAKDDILWDDMLERAESVAEINKSDHAAACLRSS
ILLSLIDEKLKIKDPRAKDFAAKYQTIPFLPFLTKPAGFSLEWKGNSFKPETMFAATD
IYTAEYQDIVCLLQPILNENSHSFRGCGSVSLAVKEFLGLLKKPTVDLVINQLKQVAK
SVDDGITLYQENITNACYKYLHEAVLQNEMAKATIIEKLKPFCFILVENVYVESEKVS
FHLNFEAAPYLYQLPNKYKNNFRELFESVGVRQSFTVEDFALVLESIDQERGKKQITE
ENFQLCRRIISEGIWSLIREKRQEFCEKNYGKILLPDTNLLLLPAKSLCYNDCPWIKV
KDSTVKYCHADIPREVAVKLGAIPKRHKALERYASNICFTALGTEFGQKEKLTSRIKS
ILNAYPSEKEMLKELLQNADDAKATEICFVFDPRQHPVDRIFDDKWAPLQGPALCVYN
NQPFTEDDVRGIQNLGKGTKEGNPCKTGHYGIGFNSVYHITDCPSFISGNDILGIFDP
HARYAPGATSVSPGRMFRDLDADFRTQFSDVLDLYLGNHFKLDNCTMFRFPLRNAEMA
QVSEISSVPSSDRMVQNLLDKLRSDGAELLMFLNHMEKISICEIDKATGGLNVLYSVK
GKITDGDRLKRKQFHASVIDSVTKKRQLKDIPVQQITYTMDTEDSEGNLTTWLICNRS
GFSSMEKVSKSVISAHKNQDITLFPRGGVAACITHNYKKPHRAFCFLPLSLETGLPFH
VNGHFALDSARRNLWRDDNGVGVRSDWNNSLMTALIAPAYVELLIQLKKRYFPGSDPT
LSVLQNTPIHVVKDTLKKFLSFFPVNRLDLQPDLYCLVKALYSCIHEDMKRLLPVVRA

Figure 8B

PNIDGSDLHSAVIITWINMSTSNKTRPFFDNLLQDELQHLKNADYNITTRKTVAENVY
RLKHLLLEIGFNLVYNCDETANLYHCLVDADIPVSYVTPADVRSFLMTFSSPDTNCHI
GKLPCRLQQTNLKLFHSLKLLVDYCFKDAEESEFEVEGLPLLITLDSVLQIFDGKRPK
FLTTYHELIPSRKDLFMNTLYLKYSSVLLNCKVAKVFDISSFADLLSSVLPREYKTKN
CAKWKDNFASESWLKNAWHFISESVSVTDDQEEPKPAFDVIVDILKDWALLPGTKFTV
STSQLVVPEGDVLIPLSLMHIAVFPNAQSDKVFHALMKAGCIQLALNKICSKDSALVP
LLSCHTANIDSPASILKAVHYMVQTSTFRTEKLMENDFEALLMYFNCNLSHLMSQDDI
KILKSLPCYKSISGRYMSIAKFGTCYVLTKSIPSAEVEKWTQSSSSAFLEEKVHLKEL
YEVLGCVPVDDLEVYLKHLLPKIENLSYDAKLEHLIYLKNRLASIEEPSEIKEQLFEK
LESLLIIHDANNRLKQAKHFYDRTVRVFEVMLPEKLFIPKEFFKKLEQVIKPKNQAAF
MTSWVEFLRNIGLKYALSQQQLLQFAKEISVRANTENWSKETLQSTVDILLHHIFQER
MDLLSGNFLKELSLIPFLCPERAPAEYIRFHPQYQEVNGTLPLIKFNGAQVNPKFKQC
DVLQLLWTSCPILPEKATPLSIKEQEGSDLAPQEQLEQVLNMLNVNLDPPLDKVINNC
RNICNITTLDEEMVKTRAKVLRSIYEFLSAEKREFRFQLRGVAFVMVEDGWKLLKPEE
VVINLEYEADFKPYLYKLPLELGTFHQLFKHLGTEDIISTKQYVEVLSRIFKSSEGKQ
LDPNEMRTVKRVVSGLFKSLQNDSVKVRSDLENARDLALYLPSQDGKLVKSSILVFDD
APHYKSRIQGNIGVQMLVDLSQCYLGKDHGFHTKLIMLFPQKLRPRLLSSILEEQLDE
ETPKVCQFGALCSLQGRLQLLLSSEQFITGLIRIMKHENDNAFLANEEKAIRLCKALR
EGLKVSCFEKLQTTLRVKGFNPIPHSRSETFAFLKRFGNAVILLYIQHSDSKDINFLL
ALAMTLKSATDNLISDTSYLIAMLGCNDIYRISEKLDSLGVKYDSSEPSKLELPMPGT
PIPAEIHYTLLMDPMNVFYPGEYVGYLVDAEGGDIYGSYQPTYTYAIIVQEVEREDAD
NTSFLGKIYQIDIGYSEYKIVSSLDLYKFSRPDESSQNRDSAPTTPTSPTEFLTPGLR
SIPPLFSGKESHKSPSTKHHSPRKLKVNALPEILKEVTSVVEQAWKLPESERKKIIRR
LYLKWHPDKNPENHDIANEVFKHLQNEINRLEKQAFLDQNADRASRRTFSTSASRFQS
DKYSFQRFYTSWNQEATSHKSERQQQSKEKCPPSAGQTYSQRFFVPPTFKSVGNPVEA
RRWLRQARANFSAARNDLHKNANEWVCFKCYLSTKLALIAADYAVRGKSDKDVKPTAL
AQKIEEYSQQLEGLTNDVHTLEAYGVDSLKTRYPDLLPFPQIPNDRFTSEVAMRVMEC
TACIIIKLENFIQQKV"

Figure 8C

BASE COUNT 3599 a 2281 c 2387 g 3226 t
ORIGIN

```
   1 atgaatacat tctggcctgg tcgagagttg gtggttcagt ggtatccatt tagtgaagac
  61 aaacgtcacc catccctttc atggcttaag atggtttgga agaatctcta tatacatttc
 121 tcggaagatt tgactttatt tgatgagatg ccacttatcc ctagaactct actgaatgag
 181 gaccagacgt gtgtggaact catcagactc aggatcccat cagtagtcat tttagatgat
 241 gaaactgaag ctcagcttcc agaattctta gcagatattg tacaaaaact tggagggatt
 301 gtcctgaaaa gactagatac ctctattcag catccacttg ttaaaaaata cattcattcc
 361 ccactcccga gtgctatttt gcagataatg gagaagatac ctctacagaa gttgtgtaat
 421 caaatagcat cattacttcc aacccacaaa gatgctctaa ggaagttttt ggccagctta
 481 actgatacca gtgaaaaaga gaaaagaata attcaagaat tgacaatatt caaaagaatt
 541 aatcactcat cagatcaagg gatttcctct tacacaaaat taaaaggatg taaagttttg
 601 gatcataccg ccaagcttcc aacagatcta cggctatcag tttcagtaat agatagtagt
 661 gatgaagcca ccattcgttt ggcaaacatg ttgaaaattg aaaaattgaa gactacaagc
 721 tgtttaaagt ttgttttaaa agatattgga aatgcatttt atacacagga agaggtaaca
 781 caacttatgc tttggatcct tgagaatcta tcctctctta aaaatgagaa ttcaaatgtg
 841 cttgattggt taatgccact aaaattcatt catatgtccc agggacatgt ggtagcagct
 901 ggtgatctct ttgatcctga tatagaagta ctaagggatc tcttttataa tgaagaagaa
 961 gcttgtttcc cacctacaat tttacctca ccagatatcc ttcactcttt gagacagatt
1021 ggcttaaaaa atgaatccag tctaaaagaa aaagatgttg tacaagtggc aagaaaaatt
1081 gaagctttac aggtcagttc ctgtcagaat caggatgttc tcatgaagaa agccaaaaca
1141 ctcttactgg tcttgaataa aaaccagaca ctcttgcagt cttctgaagg gaagatggca
1201 ttgaagaaaa tcaaatgggt tccagcctgc aaggaaagac ctccaaatta tcccggttcc
1261 ttagtctgga aaggggatct ctgtaatctt tgtgcacctc cagatatgtg tgatgcggca
1321 catgcagttc tagtaggctc ctcacttcct cttgttgaaa gtgtccatgt gaacctggag
1381 caggcgctca gcatcttcac aaagcctact atcaatgctg tcttaaaaca ctttaaaact
1441 gttgttgact ggtatacttc aaaaaccttt agtgatgaag attactatca gttccaacat
1501 attttgcttg aaatttatgg gttcatgcat gatcatctga gtgaagggaa ggattctttt
1561 aaagccttga agtttccatg ggtttggact ggcaaaaact tttgtccctct tgcccaggct
1621 gtgataaagc caacccatga tctggatctt cagccttatt tatataatgt gcctaaaacc
1681 atggcaaaat tccaccagct gttcaaggct tgtggctcaa tagaagagtt gacatcagat
1741 catatttcca tggtcattca gaaagtttat ctcaaaagtg accaggagtt gagtgaagaa
1801 gaaagtaaac aaaatcttca tctcatgttg aatattatga gatggctcta tagcaatcag
1861 attccagcaa gccctaatac accagttcct atttatcaca gcagaaatcc ttccaaactt
1921 gtcatgaagc caattcatga atgctgttat tgtgacatca aagttgatga cctcaatgac
1981 ttgcttgaag attcagtgga accaattatc ttggtacatg aagatatacc catgaaaact
2041 gcagaatggc taaaagttcc gtgccttagt acaagactga tcaatcctga aaacatgggg
2101 tttgagcagt cagggcaaag agagcctctt actgtaagga ttaaaaatat tttggaagaa
2161 tacccttccg tgtcagatat ttttaaagag ctacttcaaa atgctgatga tgcaaatgcc
2221 acagaatgca gcttcatgat tgatatgaga aggaatatgg acatacggga aaatctcctg
2281 gacccaggga tggcagcttg tcatggacct gctctgtggt cattcaacaa ttctgaattc
2341 tcagattcag atttcttaaa cataacgagg ttaggagagt ctttaaaaag gggagaagtt
2401 gacaaggttg ggaaatttgg tcttggtttt aattctgtgt accacatcac tgacattccc
2461 atcattatga gcagagaatt tatgataatg tttgatccaa acataaatca tatcagcaaa
2521 cacattaaag atagatcgaa tcctggaatc aaaattaatt ggagtaagca gcagaaaaga
2581 cttaggaagt tccccaacca gttcaaacca tttatagatg tatttggctg tcagttacct
2641 ttggctgttg aagctcctta cagctacaat ggaactcttt tccgactgtc ctttagaaca
2701 cagcaggaag caaaagtgag tgaagttagc agtacttgct acaatactgc ggatatttac
2761 tccctagtgg atgaatttag tctttgtggg cacagactta tcatttttac tcagagtgta
2821 aactcgatgt atttgaaata cttgaaaatt gaagaaacca atcctagctt agcacaagat
2881 acaatcataa ttaagaaaaa agtttgcccc tccaaagcat tgaatgcacc agttttaagt
2941 gttttaaaag aagctgctaa actcatgaag acttgtagca gcagcaacaa gaagcttccc
3001 acggatgtgc caaagtcatc ttgcattctt cagatcacag tcgaagaatt ccaccatgtg
3061 tttaggagga ttgctgactt acagtcacca ctatttcgag gtccagatga tgacccagct
3121 actctctttg aaatggctaa atctggccaa tcaaaaaagc catcagatga gttgccacaa
3181 aagacagtag attgtaccac atggcttata tgcacatgca tggatacagg agaagctctc
3241 aagttttcct tgaatgaaag tggaagaaga ttagggctgg ttccttgtgg ggcagtaggg
```

Figure 8D 3301 gttctcttgc atgaaaccca ggaacagaag tggaccgtga aaccacacat aggagaagtg
3361 ttttgctatt tacctctacg aatcaaaaca gggttgccaa ttcacatcaa tgggtgcttt
3421 gctgttactt caaataggaa agaaatctgg aagacagata caaaaggtcg atggaatacc
3481 acattcatga ggcatgtcat tgtgaaagct tacttacaag ccctcagtgt cttacgggac
3541 ctagccattg gtggtgagct gactgattat acttactatg cagtgtggcc tgatcctgat
3601 ctagttcatg atgacttctc tgtgatctgt aaaggatttt atgaagacat tgctcatggg
3661 aaggggaagg agttgaccag agtcttctct gatgggtcta tgtgggtttc catgaagaat
3721 gtgaggtttc tggatgactc tatacttcaa aggaaagatg ttggttcagc agccttcaag
3781 atatttctga agtacctcaa gaaaacagga tccaaaaacc tctgtgctgt tgagcttcct
3841 tcttcagtaa aagcaggatt tgaagaggct ggctgtaaac agatactgct ggaaaataca
3901 ttttcagaga aacagttctt ttcagaagtc ttctttccta atatccagga aattgaagca
3961 gaacttagag atcctctgat gaattttgtc ctaaatgaaa aacttgatga gttctcagga
4021 attcttcgtg ttaccccttg tgttccttgc tccttggagg gccatccttt ggttttgcct
4081 tcaagattga tccatcctga aggacgagtt gcaaagttat ttgatactaa agatggaaga
4141 ttcccttatg gttccacaca ggattacctc aatcctatta tcttgattaa gctcgttcag
4201 ttaggcatgg caaaagatga tattttgtgg gatgacatgc tagagcgtgc agagtctgta
4261 gctgagatta ataaaagtga ccatgctgct gcctgcttaa ggagtagtat tctgctaagc
4321 cttattgatg agaagctaaa aataaaggat cctagagcaa aggattttgc tgcaaaatat
4381 caaacaattc ccttcctccc atttctaaca aagccagcag gtttttcttt agaatggaaa
4441 gggaacagct ttaagcctga aaccatgttt gcagcaactg acatttacac agctgaatat
4501 caagatatag tctgtctttt gcaaccaatt cttaatgaaa attcccattc ctttagaggc
4561 tgtggttcag tgtctttggc tgttaaggag tttttgggtt tactaaagaa gccaacagtt
4621 gatctggtaa taaaccagtt gaagcaagtt gcaaaatcag ttgatgatgg cattacattg
4681 taccaggaaa atatcaccaa cgcttgctac aaatacctcc atgaagcagt attgcagaat
4741 gaaatggcca aggcaacaat tattgagaag ctaaagccat tttgtttcat tctagttgag
4801 aatgtatatg ttgagtcaga aaaggtttct tttcacttga actttgaagc agcaccatac
4861 ctttatcagt tacctaacaa gtataaaaat aatttccgtg agctttttga aagtgtgggt
4921 gtgcgacagt catttactgt tgaagacttt gcccctagttt tggagtctat tgatcaagag
4981 agaggaaaaa aacaaataac agaagagaat tttcagcttt gccgacgaat aatcagtgaa
5041 ggcatctgga gtctcattag agaaaagaga caagaatttt gtgagaaaaa ttatggcaaa
5101 atattactgc cagacactaa cctgctgctg ctccctgcta agtcattatg ctacaatgac
5161 tgtccctgga taaaagtaaa ggactccact gtcaagtatt gccatgccga cataccccgg
5221 gaagtagctg taaaacttgg tgcaatacca aagagacata aagcattaga aagatatgca
5281 tccaacatct gtttcacagc tctaggtaca gaatttgggc agaaagaaaa actgaccagc
5341 agaattaaga gcattctcaa tgcctatcct tcagaaaagg aaatgctgaa agagcttctt
5401 caaaatgctg atgatgcaaa ggccacagag atctgctttg tgtttgatcc tagacagcat
5461 cctgttgacc gaatatttga tgataagtgg gccccactgc aagggccagc actgtgtgtt
5521 tacaacaacc agccatttac agaagatgat gttagaggaa ttcagaatct tgggaaaggc
5581 accaaagaag ggaatccttg caaaacagga cattatggaa tcggattcaa ttccgtttat
5641 catattacag actgcccttc ttttatttct ggcaatgaca tcctgggtat ttttgatccc
5701 catgccagat atgcaccagg agccacatca gttagccctg gacgcatgtt tagagatttg
5761 gatgcagact ttagaaccca gttctcagat gttctagatc tgtacttggg aaaccacttt
5821 aaactggaca attgtacaat gtttagattt cctctgcgta atgcagagat ggcacaagtt
5881 tcagaaattt cttccgttcc atcatcagac agaatggtcc agaatctttt ggacaagtta
5941 cggtctgatg gggcagaact tctaatgttt ctcaaccaca tggagaaaat atctatttgt
6001 gaaatagata aggccacagg aggtctgaat gtgctctatt cagtaaaagg caagatcact
6061 gatggagacc gattgaaaag gaagcaattc cacgcctctg taattgacag tgttactaaa
6121 aagagacagc tcaaggacat accagttcaa caaataacct acactatgga tactgaggat
6181 tctgaaggaa atctgaccac atggctcatc tgtaatagat caggattttc aagtatggaa
6241 aaagtatcca agagtgtaat atcagctcac aagaaccaag atatcaccct tttcccacgt
6301 ggtggagtag cagcctgcat tactcacaat tataaaaagc cccacagagc cttctgcttt
6361 ctgcctctct ctttggagac agggctgcca tttcatgtga atggccactt tgctctagat
6421 tcagccagaa gaaacttgtg gcgtgatgat aatggggttg gtgttcgaag tgactggaat
6481 aatagtttaa tgacagcatt aatagcacct gcatatgttg agttactaat ccagttaaaa
6541 aaacggtatt tccctggttc tgacccaaca ttatcagttt tacagaacac acccattcat
6601 gtcgtaaagg acacattaaa gaagtttctg tccttctttc cagttaacag gctggatctg
6661 cagccggact tatattgctt agtaaaagca ctttacagtt gcattcatga agacatgaag

Figure 8E

```
6721 cgtcttttgc ctgttgttcg ggctccaaat attgatggct cagatttgca ctctgcagtc
6781 ataattactt ggatcaatat gtctacttca aataaaacta gaccattttt tgataactta
6841 ctacaggatg aattacagca ccttaaaaat gcagattata acatcacaac tcgaaaaaca
6901 gtcgcagaga atgtctacag actgaagcac ctgctcttag aaattggttt caacttggtt
6961 tataactgtg atgaaactgc taacctttac cattgccttg tagatgcaga tatccctgtc
7021 agctatgtga ctcctgctga tgttaggtcc ttcttaatga ctttctcttc tcctgacact
7081 aattgccata ttgggaagct gccttgtcgt cttcagcaga ctaacctaaa actttttcac
7141 agtttaaaac ttttagttga ttactgtttt aaagatgctg aagaaagtga gtttgaagtt
7201 gagggactgc ccctactcat tacactggac agtgtcttgc agatttttga tggtaaacga
7261 cccaagtttc taacaacata ccatgaatta attccatcgc gtaaagactt gtttatgaac
7321 accttatact tgaaatacag tagtgttttg ttgaactgca aagttgcaaa agtgtttgac
7381 atttccagct ttgctgactt actctcttct gtgttgcctc gtgagtacaa gaccaaaaac
7441 tgtgcaaagt ggaaagacaa ttttgccagt gaatcttggc ttaagaacgc atggcatttt
7501 atcagtgaat cagtaagtgt aacggatgat caggaagaac caaagccagc atttgatgtc
7561 attgttgaca tccttaaaga ctgggcattg cttccaggaa caaagttcac tgtgtcaacc
7621 agtcagcttg tggttcctga gggagacgtg ttgattcccc tgagcctcat gcacattgct
7681 gtgttcccaa atgctcagag tgataaggtt tttcacgctc tgatgaaagc tggctgtatt
7741 cagctggctt tgaacaaaat ctgctctaaa gacagcgcat tagttcctct gttgtcatgc
7801 cacacagcaa acatagatag ccctgcaagc atcttgaagg ctgtgcatta tatggttcag
7861 acgtcaacat ttagaactga aaaactaatg gaaaatgact ttgaagcact tttgatgtat
7921 ttcaactgta atttgagtca cttgatgtcc caagatgaca taaaaatttt aaagtccctc
7981 ccatgctaca aatccatcag tggccgctat atgagcattg caaaatttgg aacgtgctat
8041 gtgcttacca aaagtattcc ttcagctgaa gtggaaaaat ggacacagtc atcctcttcc
8101 gcgtttcttg aagaaaaggt gcatttaaaa gaactctatg aggtgcttgg ctgtgtgcca
8161 gtagatgatc tggaggtgta tttgaaacat cttctgccaa aaattgaaaa tctctcttat
8221 gatgcaaagt tggagcacct gatttatctg aagaatagac tggcaagcat cgaggaaccg
8281 tcagagatta aggagcaact tttgaaaaa ctggaaagct tattgattat ccacgatgcc
8341 aacaatcgac taaagcaagc aaaacatttc tatgacagaa ctgtgagagt tttgaagtt
8401 atgcttcctg aaaaattgtt tattcctaag gagttcttta aaaaattgga acaagtaatc
8461 aaacctaaaa atcaagctgc atttatgacg tcctgggtgg aattcttgag aaatattgga
8521 ctgaagtacg cgctctccca gcagcagttg ttacagtttg ccaaggaaat cagtgtgagg
8581 gcaaatacag aaaactggtc taaagaaacc ctgcaaagta cagttgacat ccttctccat
8641 cacatattcc aagaacgaat ggatttgtta tctggaaatt ttctgaaaga actgtcctta
8701 ataccattct tgtgtcctga acgggccccc gctgagtaca ttcggtttca ccctcagtac
8761 caggaggtaa acggaacact tcctcttata aagttcaatg gagcacaagt gaatccaaag
8821 ttcaagcaat gtgatgtact ccagctgctg tggacatctt gccctattct tccagagaaa
8881 gccacaccgt tgagcattaa agaacaagaa ggcagtgacc tcgctccaca ggaacagctt
8941 gaacaagttt taaatatgct taatgttaac ctggaccccc ctcttgataa ggtcattaat
9001 aattgcagaa acatatgcaa cataacaact ttggatgagg aaatggtaaa aactagagca
9061 aaggtcctaa ggagcatata tgaatttctg agtgcagaaa aacgagagtt ccgttttcag
9121 cttcggggtg tggcctttgt aatggtagaa gacggatgga aacttctgaa gcctgaggaa
9181 gtagtgataa acctggagta tgaggctgat tttaaacctt atctgtacaa gctgccttta
9241 gagcttggca cttttcatca gctgttcaaa catttaggta ctgaagatat catttccact
9301 aagcaatatg ttgaagtgtt aagccgaata ttcaaaagct ctgaaggaaa gcagctagac
9361 cctaatgaaa tgcgtacagt taagagagtg gtttctggcc tattcaagag tctacaaaat
9421 gattcagtca aggtgaggag tgacctggag aatgcccggg acctcgcact ctaccttcca
9481 agccaggatg ggaagttggt gaagtcaagc atcttggtgt tcgatgatgc gccacattat
9541 aaaagtagga tccaggggaa tattggcgtg cagatgctag ttgatcttag ccagtgctac
9601 ttagggaaag accatggatt tcacactaag ctgataatgc tctttcctca aaagcttcga
9661 cctcgtctgc tgagcagtat acttgaagag cagcttgatg aggagacccc taaagtgtgc
9721 cagtttggcg cattgtgctc tcttcaggga agactgcagc ttctcttgtc ttcagagcag
9781 ttcatcacag gactcattcg aatcatgaag catgaaaatg ataatgcttt cctggccaat
9841 gaagaaaaag ccataagact ttgcaaagct ctaagagaag ggctgaaagt ttcctgtttt
9901 gagaagcttc agacaacatt aagggttaaa ggttttaatc ctattcccca tagcaggagt
9961 gaaactttcg cttttctaaa gcgatttggc aatgcagtca tcttgctcta catccaacat
10021 tcagacagca aagacattaa ctttctgcta gccttagcga tgacacttaa atcagcaact
10081 gacaatttga tttctgacac gtcatactta attgctatgc tgggatgcaa tgacatttac
```

Figure 8F

```
10141 aggatcagtg agaagcttga cagtttaggg gtgaaatacg actcctctga gccatcaaaa
10201 ctggaactcc ccatgcctgg cacaccaata cccgctgaga tccattacac actacttatg
10261 gatccaatga atgtttttta tcctggggaa tatgttggtt accttgtgga tgctgaaggt
10321 ggtgatatct atgggtcata ccagccaaca tacacatacg caattattgt gcaagaagtt
10381 gaaagagaag atgctgacaa tactagtttc ttaggaaaga tctatcagat cgatattggc
10441 tacagtgaat ataagatagt cagctctctt gatctgtaca agttctcaag gcctgatgaa
10501 agctcccaaa acagagacag tgctcccacc acaccaacaa gccccaccga attcctgact
10561 cctggtctga gaagcatccc tcctcttttc tctggcaagg agagccacaa gtctccctcc
10621 accaaacacc attcccccag aaagctcaag gtgaatgctt taccagaaat cttaaaagaa
10681 gtgacatcag tggtggagca agcttggaag cttccagaat cagagcggaa aaagatcatt
10741 agacgcttgt atttgaagtg gcaccctgac aaaaatccag aaaatcatga tattgctaat
10801 gaagtgttca agcacctgca gaatgaaatc aacagattag aaaaacaggc ttttctggat
10861 caaaatgcag acagagcttc aagaagaaca ttttcaacct ctgcatctcg atttcagtca
10921 gacaagtact catttcaaag attttacact tcgtggaatc aagaagccac aagtcataaa
10981 tctgaaaggc aacagcaaag caaagagaaa tgccctcctt ctgctggaca gacatactct
11041 caaaggttct ttgttcctcc caccttcaag tcagtgggca atccagtgga agcccggaga
11101 tggttaagac aagccagagc aaacttctca gctgccagga atgaccttca caaaaatgcc
11161 aatgaatggg tgtgcttcaa gtgttacctt tccaccaagc tggctttgat tgcagccgac
11221 tatgctgtca gggggaaatc tgataaagat gtaaagccaa ctgcacttgc acaaaagata
11281 gaggagtaca gtcagcagct ggaaggactg acaaacgatg tgcacacatt ggaagcttat
11341 ggtgtagaca gcttgaaaac aaggtacccc gatttgcttc cttttccgca gattcccaat
11401 gacaggttca catctgaggt tgccatgagg gtgatggaat gcactgcctg tatcatcata
11461 aaacttgaaa attttataca acagaaggtg tga
//
```

Figure 8G

LOCUS AF193556 12793 bp DNA PRI 07-FEB-2000
DEFINITION Homo sapiens sacsin (SACS) gene, complete cds.
ACCESSION AF193556 VERSION AF193556.1 GI:6907041KEYWORDS .
SOURCE human.
ORGANISM Homo sapiens Eukaryota; Metazoa; Chordata; Craniata; Vertebrata; Euteleostomi; Mammalia; Eutheria; Primates; Catarrhini; Hominidae; Homo.

REFERENCE 1 (bases 1 to 12793) AUTHORS Engert,J.C., Berube,P., Mercier,J., Dore,C., Lepage,P., Ge,B., Bouchard,J.P., Mathieu,J., Melancon,S.B., Schalling,M., Lander,E.S., Morgan,K., Hudson,T.J. and Richter,A. TITLE ARSACS, a spastic ataxia common in northeastern Quebec, is caused by mutations in a new gene encoding an 11.5-kb ORF JOURNAL Nat. Genet. 24 (2), 120-125 (2000) MEDLINE 20120709

REFERENCE 2 (bases 1 to 12793) AUTHORS Engert,J.C., Berube,P., Dore,C., Lepage,P., Ge,B., Hudson,T.J. and Richter,A. TITLE Direct Submission JOURNAL Submitted (08-OCT-1999) Genome Centre, Montreal General Hospital, 1650 Cedar Ave., Montreal, QC H3G 1A4, CanadaFEATURES Location/Qualifiers source 1..12793 /organism="Homo sapiens" /db_xref="taxon:9606" /chromosome="13" /map="between D13S232 and D13S292" mRNA 1..12793 /gene="SACS" /product="sacsin" gene 1..12793 /gene="SACS" CDS 77..11566 /gene="SACS" /note="molecular chaperone" /codon_start=1 /product="sacsin" /protein_id="AAF31262.1" /db_xref="GI:6907042" /translation="

MNTFWPGRELIVQWYPFDENRNHPSVSWLKMVWKNLYIHFSEDL
TLFDEMPLIPRTILEEGQTCVELIRLRIPSLVILDDESEAQLPEFLADIVQKLGGFVL
KKLDASIQHPLIKKYIHSPLPSAVLQIMEKMPLQKLCNQITSLLPTHKDALRKFLASL
TDSSEKEKRIIQELAIFKRINHSSDQGISSYTKLKGCKVLHHTAKLPADLRLSISVID
SSDEATIRLANMLKIEQLKTTSCLKLVLKDIENAFYSHEEVTQLMLWVLENLSSLKNE
NPNVLEWLTPLKFIQISQEQMVSAGELFDPDIEVLKDLFCNEEGTYFPPSVFTSPDIL
HSLRQIGLKNEASLKEKDVVQVAKKIEALQVGACPDQDVLLKKAKTLLLVLNKNHTLL
QSSEGKMTLKKIKWVPACKERPPNYPGSLVWKGDLCNLCAPPDMCDVGHAILIGSSLP
LVESIHVNLEKALGIFTKPSLSAVLKHFKIVVDWYSSKTFSDEDYYQFQHILLEIYGF
MHDHLNEGKDSFRALKFPWVWTGKKFCPLAQAVIKPIHDLDLQPYLHNVPKTMAKFHQ
LFKVCGSIEELTSDHISMVIQKIYLKSDQDLSEQESKQNLHLMLNIIRWLYSNQIPAS
PNTPVPIHHSKNPSKLIMKPIHECCYCDIKVDDLNDLLEDSVEPIILVHEDIPMKTAE
WLKVPCLSTRLINPENMGFEQSGQREPLTVRIKNILEEYPSVSDIFKELLQNADDANA
TECSFLIDMRRNMDIRENLLDPGMAACHGPALWSFNNSQFSDSDFVNITRLGESLKRG
EVDKVGKFGLGFNSVYHITDIPIIMSREFMIMFDPNINHISKHIKDKSNPGIKINWSK
QQKRLRKFPNQFKPFIDVFGCQLPLTVEAPYSYNGTLFRLSFRTQQEAKVSEVSSTCY
NTADIYSLVDEFSLCGHRLIIFTQSVKSMYLKYLKIEETNPSLAQDTVIIKKKSCSSK
ALNTPVLSVLKEAAKLMKTCSSSNKKLPSDEPKSSCILQITVEEFHHVFRRIADLQSP
LFRGPDDDPAALFEMAKSGQSKKPSDELSQKTVECTTWLLCTCMDTGEALKFSLSESG
RRLGLVPCGAVGVQLSEIQDQKWTVKPHIGEVFCYLPLRIKTGLPVHINGCFAVTSNR
KEIWKTDTKGRWNTTFMRHVIVKAYLQVLSVLRDLATSGELMDYTYYAVWPDPDLVHD
DFSVICQGFYEDIAHGKGKELTKVFSDGSTWVSMKNVRFLDDSILKRRDVGSAAFKIF
LKYLKKTGSKNLCAVELPSSVKLGFEEAGCKQILLENTFSEKQFFSEVFFPNIQEIEA
ELRDPLMIFVLNEKVDEFSGVLRVTPCIPCSLEGHPLVLPSRLIHPEGRVAKLFDIKD
GRFPYGSTQDYLNPIILIKLVQLGMAKDDILWDDMLERAVSVAEINKSDHVAACLRSS
ILLSLIDEKLKIRDPRAKDFAAKYQTIRFLPFLTKPAGFSLDWKGNSFKPETMFAATD
LYTAEHQDIVCLLQPILNENSHSFRGCGSVSLAVKEFLGLLKKPTVDLVINQLKEVAK
SVDDGITLYQENITNACYKYLHEALMQNEITKMSIIDKLKPFSFILVENAYVDSEKVS
FHLNFEAAPYLYQLPNKYKNNFRELFETVGVRQSCTVEDFALVLESIDQERGTKQITE
ENFQLCRRIISEGIWSLIREKKQEFCEKNYGKILLPDTNLMLLPAKSLCYNDCPWIKV

Figure 9A

KDTTVKYCHADIPREVAVKLGAVPKRHKALERYASNVCFTTLGTEFGQKEKLTSRIKS
ILNAYPSEKEMLKELLQNADDAKATEICFVFDPRQHPVDRIFDDKWAPLQGPALCVYN
NQPFTEDDVRGIQNLGKGTKEGNPYKTGQYGIGFNSVYHITDCPSFISGNDILCIFDP
HARYAPGATSISPGRMFRDLDADFRTQFSDVLDLYLGTHFKLDNCTMFRFPLRNAEMA
KVSEISSVPASDRMVQNLLDKLRSDGAELLMFLNHMEKISICEIDKSTGALNVLYSVK
GKITDGDRLKRKQFHASVIDSVTKKRQLKDIPVQQITYTMDTEDSEGNLTTWLICNRS
GFSSMEKVSKSVISAHKNQDITLFPRGGVAACITHNYKKPHRAFCFLPLSLETGLPFH
VNGHFALDSARRNLWRDDNGVGVRSDWNNSLMTALIAPAYVELLIQLKKRYFPGSDPT
LSVLQNTPIHVVKDTLKKFLSFFPVNRLDLQPDLYCLVKALYNCIHEDMKRLLPVVRA
PNIDGSDLHSAVIITWINMSTSNKTRPFFDNLLQDELQHLKNADYNITTRKTVAENVY
RLKHLLLEIGFNLVYNCDETANLYHCLIDADIPVSYVTPADIRSFLMTFSSPDTNCHI
GKLPCRLQQTNLKLFHSLKLLVDYCFKDAEENEIEVEGLPLLITLDSVLQTFDAKRPK
FLTTYHELIPSRKDLFMNTLYLKYSNILLNCKVAKVFDISSFADLLSSVLPREYKTKS
CTKWKDNFASESWLKNAWHFISESVSVKEDQEETKPTFDIVVDTLKDWALLPGTKFTV
SANQLVVPEGDVLLPLSLMHIAVFPNAQSDKVFHALMKAGCIQLALNKICSKDSAFVP
LLSCHTANIESPTSILKALHYMVQTSTFRAEKLVENDFEALLMYFNCNLNHLMSQDDI
KILKSLPCYKSISGRYVSIGKFGTCYVLTKSIPSAEVEKWTQSSSSAFLEEKIHLKEL
YEVIGCVPVDDLEVYLKHLLPKIENLSYDAKLEHLIYLKNRLSSAEELSEIKEQLFEK
LESLLIIHDANSRLKQAKHFYDRTVRVFEVMLPEKLFIPNDFFKKLEQLIKPKNHVTF
MTSWVEFLRNIGLKYILSQQQLLQFAKEISVRANTENWSKETLQNTVDILLHHIFQER
MDLLSGNFLKELSLIPFLCPERAPAEFIRFHPQYQEVNGTLPLIKFNGAQVNPKFKQC
DVLQLLWTSCPILPEKATPLSIKEQEGSDLGPQEQLEQVLNMLNVNLDPPLDKVINNC
RNICNITTLDEEMVKTRAKVLRSIYEFLSAEKREFRFQLRGVAFVMVEDGWKLLKPEE
VVINLEYESDFKPYLYKLPLELGTFHQLFKHLGTEDIISTKQYVEVLSRIFKNSEGKQ
LDPNEMRTVKRVVSGLFRSLQNDSVKVRSDLENVRDLALYLPSQDGRLVKSSILVFDD
APHYKSRIQGNIGVQMLVDLSQCYLGKDHGFHTKLIMLFPQKLRPRLLSSILEEQLDE
ETPKVCQFGALCSLQGRLQLLLSSEQFITGLIRIMKHENDNAFLANEEKAIRLCKALR
EGLKVSCFEKLQTTLRVKGFNPIPHSRSETFAFLKRFGNAVILLYIQHSDSKDINFLL
ALAMTLKSATDNLISDTSYLIAMLGCNDIYRIGEKLDSLGVKYDSSEPSKLELPMPGT
PIPAEIHYTLLMDPMNVFYPGEYVGYLVDAEGGDIYGSYQPTYTYAIIVQEVEREDAD
NSSFLGKIYQIDIGYSEYKIVSSLDLYKFSRPEESSQSRDSAPSTPTSPTEFLTPGLR
SIPPLFSGRESHKTSSKHQSPKKLKVNSLPEILKEVTSVVEQAWKLPESERKKIIRRL
YLKWHPDKNPENHDIANEVFKHLQNEINRLEKQAFLDQNADRASRRTFSTSASRFQSD
KYSFQRFYTSWNQEATSHKSERQQQNKEKCPPSAGQTYSQRFFVPPTFKSVGNPVEAR
RWLRQARANFSAARNDLHKNANEWVCFKCYLSTKLALIAADYAVRGKSDKDVKPTALA
QKIEEYSQQLEGLTNDVHTLEAYGVDSLKTRYPDLLPFPQIPNDRFTSEVAMRVMECT
ACIIIKLENFMQQKV"

BASE COUNT 4163 a 2256 c 2487 g 3887 tORIGIN
atgatttaca ggaagaccat gtactcagct gcagcttcta aatccagaac gatttgcacg
tcttatcaag gaagtaatga atacattctg gcctggcaga gaattgattg ttcaatggta
tccatttgat gaaaacagaa atcacccatc tgtttcatgg cttaagatgg tttggaaaaa
tctttatata catttttcag aggatttgac tttatttgat gagatgccac ttatccccag
aactatacta gaggaaggtc agacatgtgt ggaactcatt agactcagga ttccatcgtt
agtcatttta gacgatgaat ctgaagcaca gcttccagaa tttttagcag acattgtaca
aaaacttgga gggtttgtcc ttaaaaaatt agatgcatct atacaacatc cgcttattaa
aaaatatatt cattcaccat taccaagtgc tgttttgcag ataatggaga agatgccatt
gcagaaattg tgtaatcaaa taacttcgct acttccaaca cacaaagatg ccctgaggaa
gttcttggct agtttaaccg atagcagtga gaaagagaaa agaattattc aagaattggc
aatattcaag cgcattaacc attcttctga tcagggaatt tcctcttata caaaattgaa
aggttgtaaa gtcttacacc atactgccaa actcccagca gatctgcgac tttctatttc
agtaatagac agtagtgatg aagctactat tcgtctggca aacatgttga aaatagaaca
gttaaagacc actagctgct taaagcttgt tttaaaagat attgaaaatg cattttattc
acatgaagag gtaacacagc ttatgttatg ggtccttgag aatctatctt ctcttaaaaa

Figure 9B tgagaatcca aatgtgcttg agtggttaac accattaaaa ttcatccaga tatcacagga
acagatggta tcagctggtg aactctttga ccctgatata gaagtactaa aggatctctt
ttgtaatgaa gaaggaacct atttcccacc ctcagttttt acctcaccag atattcttca
ctccttaaga cagattggtt taaaaaacga agccagtctc aaagaaaagg atgttgtgca
agtggcaaaa aaaattgaag ccttacaggt cggtgcttgt cctgatcaag atgttcttct
gaagaaagcc aaaaccctct tactggtttt aaataagaat cacacactgt tgcaatcatc
tgaaggaaag atgacattga agaaaataaa atgggttcca gcctgcaagg aaaggcctcc
aaattatcca ggctctttgg tctggaaagg agatctctgt aatctctgtg caccaccaga
tatgtgtgat gtaggccatg caattctcat tggctcctca cttcctcttg ttgaaagtat
ccatgtaaac ctggaaaaag cattagggat cttcacaaaa cctagcctta gtgctgtctt
aaaacacttt aaaattgttg ttgattggta ttcttcaaaa acctttagtg atgaagacta
ctatcaattc cagcatattt tgcttgagat ttacggattc atgcatgatc atctaaatga
agggaaagat tcttttagag ccttaaaatt tccatgggtt tggactggca aaaagttttg
tccacttgcc caggctgtga ttaaaccaat ccatgatctt gaccttcagc cttatttgca
taatgtacct aaaaccatgg caaaattcca ccaactattt aaggtctgtg gttcaataga
ggagttgaca tcagatcata tttccatggt tattcagaag atatatctca aaagtgacca
agatctcagt gaacaagaaa gcaaacaaaa tcttcatctt atgttgaata ttatcagatg
gctgtatagc aatcagattc cagcaagccc caacacacca gttcctatac atcatagcaa
aaatccttct aaacttatca tgaagccaat tcacgaatgc tgttattgtg acattaaagt
tgatgacctt aatgacttac ttgaagattc tgtggaacca atcattttgg tgcatgagga
catacccatg aaaactgcag aatggctaaa agttccatgc cttagtacaa gactgataaa
tcctgaaaac atgggatttg agcagtcagg acaaagagag ccacttactg taagaattaa
aaatattctg gaagaatacc cttcagtgtc agatattttt aaagaactac ttcaaaacgc
tgatgatgca aatgcaacag aatgcagttt cttgattgat atgagaagaa atatggacat
aagagagaat ctcctagacc cagggatggc agcttgtcat ggacctgctt tgtggtcatt
caacaattct caattctcag attcagattt tgtgaacata actaggttag gagaatcttt
aaaaagggga gaagttgaca aagttggaaa atttggtctt ggatttaatt ctgtgtacca
tatcactgac attcccatca ttatgagtcg ggaattcatg ataatgttcg atccaaacat
aaatcatatc agtaaacaca ttaaagacaa atccaatcct gggatcaaaa ttaattggag
taaacaacag aaaagactta gaaaatttcc taatcagttc aaaccattta tagatgtatt
tggctgtcag ttacctttga ctgtagaagc accttacagc tataatggaa cccttttccg
actgtccttt agaactcaac aggaagcaaa agtgagtgaa gttagtagta cgtgctacaa
tacagcagat atttattctc ttgtggatga atttagtctc tgtggacaca ggcttatcat
tttcactcag agtgtaaagt caatgtattt gaagtacttg aaaattgagg aaaccaaccc
cagtttagca caagatacag taataattaa aaaaaaatcc tgctcttcca aagcattgaa
cacacctgtc ttaagtgttt taaaagaggc tgctaagctc atgaagactt gcagcagcag
taataaaaag cttcccagtg atgaaccaaa gtcatcttgc attcttcaga tcacagtgga
agaatttcac catgtgttca gaaggattgc tgatttacag tcgccacttt ttagaggtcc
agatgatgac ccagctgctc tctttgaaat ggctaagtct ggccaatcaa aaaagccatc
agatgagttg tcacagaaaa cagtagagtg taccacgtgg cttctgtgta cttgcatgga
cacaggagag gctctgaagt tttccctgag tgagagtgga agaagactag gactggttcc
atgtggggca gtaggagttc agctgtcaga aatccaggac cagaagtgga cagtgaaacc
acacattgga gaggtgtttt gctatttacc tttacgaata aaaacaggct tgccagttca
tatcaatggg tgctttgctg ttacatcaaa taggaaagaa atctggaaaa cagatacaaa
aggacgatgg aataccacgt tcatgagaca tgttattgtg aaagcttact tacaggtact
gagtgtctta cgggacctgg ccactagtgg ggagctaatg gattatactt actatgcagt
atggcccgat cctgatttag ttcatgatga tttttctgta atttgccaag gattttatga
agatatagct catggaaaag ggaaagaact gaccaaagtc ttctctgatg gatctacttg
ggtttccatg aagaacgtaa gatttctaga tgactctata cttaaaagaa gagatgttgg
ttcagcagcc ttcaagatat ttttgaaata cctcaagaag actgggtcca aaaacctttg
tgctgttgaa cttccttctt cggtaaaatt aggatttgaa gaagctggct gcaaacagat
actacttgaa aacacatttt cagagaaaca gttttttttct gaagtgtttt ttccaaatat
tcaagaaatt gaagcagaac ttagagatcc tttaatgatc tttgttctaa atgaaaaagt
tgatgagttc tcgggagttc ttcgtgttac tccatgtatt ccttgttcct tggaggggca

Figure 9C tcctttggtt ttgccatcaa gattgatcca ccccgaagga cgagttgcaa agttatttga
tattaaagat gggagattcc cttatggttc tactcaggat tatctcaatc ctattatttt
gattaaacta gttcagttag gtatggcaaa agatgatatt ttatgggatg atatgctaga
acgtgcagtg tcagtagctg aaattaataa aagtgatcat gttgctgcat gcctaagaag
tagtatctta ttgagtctta tcgatgagaa actaaaaata agggatccta gagcaaagga
ttttgctgca aaatatcaaa caatccgctt ccttccattt ctgacaaaac cagcaggttt
ttctttggac tggaaaggca acagttttaa gcctgaaacc atgtttgcag caactgacct
ttatacagct gaacatcaag atatagtttg tcttttgcaa ccaattctaa atgaaaattc
ccattctttt agaggttgtg gttcagtgtc attggctgtt aaagagtttt tgggattact
caagaagcca acagttgatc tggttataaa ccaattgaaa gaagtagcaa aatcagttga
tgatggaatt acactgtacc aggagaatat caccaatgct tgctacaaat accttcatga
agccttgatg caaaatgaaa tcactaagat gtcaattatt gataagttaa aacccttag
cttcattcta gttgagaatg catatgttga ctcagaaaag gtttcttttc atttaaattt
tgaggcggca ccataccttt atcagttgcc taataagtat aaaaataatt tccgcgaact
ttttgaaacc gtgggtgtga ggcagtcatg cactgttgaa gattttgctc ttgttttgga
atctattgat caagaaagag gaacaaagca aataacagaa gagaattttc agctttgccg
acgaataatc agtgaaggaa tatggagtct cattagagaa aagaaacaag aattttgtga
gaaaaattat ggcaagatat tattgccaga tactaatctt atgcttctcc ctgctaaatc
gttatgctac aatgattgcc cttggataaa agtaaaggat accactgtaa aatattgtca
tgctgacata cccagggaag tagcagtaaa actaggagca gtcccaaagc gacacaaagc
cttagaaaga tatgcatcca atgtctgttt tacaacactt ggcacagaat ttgggcagaa
agaaaaattg accagcagaa ttaagagcat ccttaatgca tatccttctg aaaaggaaat
gttgaaagag cttcttcaaa atgctgatga tgcaaaggcg acagaaatct gttttgtgtt
tgatcctaga cagcatccag ttgatagaat atttgatgat aagtgggccc cattgcaagg
gccagcactt tgtgtgtaca acaaccagcc atttacagaa gatgatgtta gaggaattca
gaatcttgga aaaggcacga aagagggaaa tccttataaa actggacagt atggaatagg
attcaattct gtgtatcata tcacagactg cccatctttt atttctggca atgacatcct
gtgtattttt gatcctcatg ccagatatgc accaggggcc acatccatta gtcccggacg
catgtttaga gatttggatg cagattttag gacacagttc tcagatgttc tggatcttta
tctgggaacc cattttaaac tggataattg cacaatgttc agatttcctc ttcgtaatgc
agaaatggca aaagtttcgg aaatttcgtc tgttccagca tcagacagaa tggtccagaa
tcttttggac aaactgcgct cagatggggc agaacttcta atgtttctta atcacatgga
aaaaatttct atttgtgaaa tagataagag tactggagct ctaaatgtgc tgtattcagt
aaagggcaaa atcacagatg gagacagatt gaaaaggaaa caatttcatg catctgtaat
tgatagtgtt actaaaaaga ggcagctcaa agacatacca gttcaacaaa taacctatac
tatggatact gaggactctg aaggaaatct tactacgtgg ctaatttgta atagatcagg
cttttcaagt atggagaaag tatctaaaag tgtcatatca gctcacaaga accaagatat
tactcttttc ccacgtggtg gagtagctgc ctgcattact cacaactata aaaaacccca
tagggccttc tgtttttgc ctctttcttt ggagactggg ctgccatttc atgtgaatgg
ccactttgca ctggattcag ccagaaggaa cctgtggcgt gatgataatg gagttggtgt
tcgaagtgac tggaataaca gtttaatgac agcattaata gctcctgcat atgttgaatt
gctaatacag ttaaaaaaac ggtatttccc tggttctgat ccaacattat cagtgttaca
gaacacccct attcatgttg taaaggacac tttaaagaag tttttatcgt ttttcccagt
taaccgtctt gatctacagc cagatttata ttgtctagtg aaagcacttt acaattgcat
tcacgaagac atgaaacgtc ttttacctgt tgtgcgggct ccaaatattg atggctctga
cttgcactct gcagttataa ttacttggat caatatgtct acttctaata aaactagacc
attttttgac aatttactac aggatgaatt acaacacctt aaaaatgcag attataatat
caccacacgc aaaacagtag cagagaatgt ctataggctg aaacatctcc ttttagaaat
tggtttcaac ttggtttata actgtgatga aactgctaat ctttaccact gtcttataga
tgcagatatt cctgttagtt atgtgacccc tgctgatatc agatcttttt taatgacatt
ttcctctcct gacactaatt gccatattgg gaagctgcct tgtcgtctgc agcagactaa
tctaaaactt tttcatagtt taaaactttt agttgattat tgttttaaag atgcagaaga
aaatgagatt gaagttgagg gattgcccct tctcatcaca ctggacagtg ttttgcaaac
ttttgatgca aaacgaccca agtttctaac aacatatcat gaattgattc catcccgcaa

Figure 9D agacttgttt atgaatacat tatatttgaa atatagtaat attttattga actgtaaagt
tgcaaaagtg tttgacattt ccagctttgc tgatttgtta tcctctgtgt tgcctcgaga
atataagacc aaaagttgca caaagtggaa agacaatttt gcaagtgagt cttggcttaa
gaatgcatgg cattttatta gtgaatctgt aagtgtgaaa gaagatcagg aagaaacaaa
accaacattt gacattgttg ttgatactct aaaagactgg gcattgcttc caggaacaaa
gtttactgtt tcagccaacc agcttgtggt tcctgaagga gatgttctgc ttcctctcag
ccttatgcac attgcagttt ttccaaatgc ccagagtgat aaagtttttc atgctctaat
gaaagccggc tgtattcagc ttgctttgaa caaaatctgt tccaaagaca gtgcatttgt
tcctttgttg tcatgtcaca cagcaaatat agagagcccc acaagcatct tgaaggctct
acattatatg gtccaaactt caacatttag agcagaaaaa ttagtagaaa atgattttga
ggcacttttg atgtatttca actgcaattt gaatcatttg atgtcccaag atgatataaa
aattctaaag tcacttccgt gctataaatc catcagtggc cgctatgtaa gcattggaaa
atttggaaca tgctacgtac ttacaaaaag tatcccttca gctgaagtgg agaaatggac
acaatcatca tcatctgcat ttcttgaaga aaaaatacac ttaaaagaac tatatgaggt
gattggttgt gtacctgtag atgatcttga ggtatatttg aaacacctct taccaaaaat
tgaaaatctc tcttatgatg caaaattaga gcacttgatc taccttaaga atagattatc
aagtgctgag gaattatcag agattaagga acaacttttt gaaaaactgg aaagtttatt
gataatccat gatgctaaca gtagactaaa gcaagcaaag catttctatg atagaactgt
gagagttttt gaagttatgc ttcctgaaaa attgtttatt cctaatgatt tctttaagaa
attggaacaa cttataaaac ccaaaaatca tgttacattt atgacatcct gggtggaatt
cttaagaaat attggactaa aatacatact ttctcagcag cagttgttac agtttgctaa
ggaaatcagt gtgagggcta atacagaaaa ctggtccaaa gaaacattgc aaaatacagt
tgatatcctt ctgcatcata tattccaaga acgaatggat ttgttatctg gaaatttttct
gaaagaacta tctttaatac cattcttatg tcctgagcgg gcccccgcgg aattcattag
atttcatcct caatatcaag aggtaaatgg aacacttcct cttataaagt tcaatggagc
acaggtaaat ccaaaattca agcaatgtga tgtactccag ctgttatgga catcctgccc
tattcttcca gagaaagcta cacccttaag cattaaagaa caagaaggta gtgaccttgg
tccacaagaa cagcttgaac aagttttaaa tatgcttaat gttaacctgg atcctcctct
tgataaggta atcaataact gcagaaacat atgcaacata acgacgttgg atgaagaaat
ggtaaaaact agagcaaaag tcttaaggag catatatgaa ttcctcagtg cagaaaaaag
ggaatttcgt tttcagttgc gaggggttgc ttttgtgatg gtagaagatg gttggaaact
tctgaagcct gaggaggtag tcataaacct agaatatgaa tctgatttta aaccttattt
gtacaagcta cctttagaac ttggcacatt tcaccagttg ttcaaacact taggtactga
agatattatt tcaactaagc aatatgttga agtgttgagc cgcatattta aaaattctga
gggcaaacaa ttagatccta atgaaatgcg tacagttaag agagtagttt ctggtctgtt
caggagtcta cagaatgatt cagtcaaggt gaggagtgat ctcgagaatg tacgagacct
tgcgctttac ctcccaagcc aggatggtag attggtaaag tcaagcatct tagtgtttga
cgatgcgcca cattataaaa gtagaatcca ggggaatatt ggtgtgcaaa tgttagttga
tctcagccag tgctacttag ggaaagacca tggatttcac actaagttga taatgctctt
tcctcaaaaa cttagacctc gattattgag cagtatactt gaagaacaat tagatgaaga
gactcccaaa gtttgtcagt ttggagcgtt gtgttctctt caaggaagat tgcagttact
cttgtcttct gaacagttca ttacaggact gattagaatt atgaagcatg aaaatgataa
tgctttctg gccaatgaag aaaaagccat aagactttgc aaagccctaa gagaaggatt
gaaagtatcc tgctttgaaa agcttcaaac aacattaaga gttaaaggtt ttaatcctat
tccccacagc agaagtgaaa cttttgcttt tttgaagcga tttggtaatg cagtcatctt
gctctacatt caacattcag acagtaaaga cattaatttc ctgttagcac tggcaatgac
tcttaaatca gcaactgaca atttgatttc tgacacttca tatttaattg ctatgctagg
atgcaatgat atttacagga ttggtgagaa acttgacagt ttaggagtga aatatgactc
ttcggagcca tcaaaactgg aacttccaat gcctggcaca ccaattcctg ctgaaattca
ttacactctg cttatggacc caatgaatgt tttttacccg ggagaatatg ttgggtacct
tgttgatgct gaaggtggtg atatctatgg atcataccag ccaacataca catatgcaat
tattgtacaa gaagttgaaa gagaagatgc tgacaattct agttttctag gaaagatata
tcagatagat attggttata gtgaatataa aatagttagc tctcttgatc tgtataagtt
ttcaagacct gaggaaagct ctcaaagcag ggacagtgct ccttctacac caaccagccc

Figure 9E

```
cactgagttc ctcacccctg gcctgagaag cattcctcct cttttctctg gtagagagag
ccacaagact tcttccaaac atcagtcccc caaaaagctt aaggttaatt ctttaccaga
aatcttaaaa gaagtgacat ctgtggtgga gcaagcatgg aagcttccag aatcggaacg
aaaaaagatt attaggcggt tgtatttgaa atggcatcct gacaaaaatc cagagaacca
tgacattgcc aatgaagttt ttaaacattt gcagaatgaa atcaacagat tagaaaaaca
ggcttttcta gatcaaaatg cagacagggc ctccagacga acattttcaa cctcagcatc
ccgatttcag tcagacaaat actcatttca gagattctat acttcatgga atcaagaagc
aacgagccat aaatctgaaa gacagcaaca gaacaaagaa aaatgccccc cttcagccgg
acagacttac tctcaaaggt tctttgttcc tcccactttc aagtcggttg gcaatccagt
ggaagcacgc agatggctaa gacaagccag agcaaacttc tcagctgcca ggaatgacct
tcataaaaat gccaatgagt gggtgtgctt taaatgttac ctttctacca agttagcttt
gattgcagct gactatgctg tgaggggaaa gtctgataaa gatgtaaaac caactgcact
tgctcagaaa atagaggaat atagtcagca acttgaagga ctgacaaatg atgttcacac
attggaagct tatggtgtag acagtttaaa aacaagatac cctgatttgc ttccctttcc
tcagatccca aatgacaggt tcacttctga ggttgctatg agggtgatgg aatgtactgc
ctgtatcata ataaaacttg aaaattttat gcaacaaaaa gtgtgaagat atttaacgaa
aaaaaaggta gatcttgaat gtgttgtagc acgaataaat tgctgtactt cattaagctt
cattgccaat tagctaggaa ttgttaagca cattgcagat tgttcttgga gaattctgga
gttgttatga acatgaatac caacggaaaa ccttaactga atctaaaaga aaactatttt
gaagatggtg gtgagctgca aaatagctgg atggatttga atgattggga tgatacatca
ttgaactgca ctttatataa ccaaagctta gcagtttgtt agataagagt ctatgtatgt
ctctggttag gatgaagtta attttatgtt tttaacatgg tatttttgaa ggagctaatg
aaacactgga catataattg gtttaaacat aaggggaatt aagtctttgt agtctgtcat
tttttaagt ggatcctctt ggatgcgtta ttttctcatc agctggctct gatcatgaat
ttgttgtaat tttatgttgt actcagtgca tttaagaaat ggtagagtat tttaatccta
ttacttgact aagagtgtga aggtagtact ttttagagtg cactgagtgc actttacatc
tttatttaaa ttttttttta acatcttatg tttacaggct tcctgtttga tgaagatagc
aacggaaaac tcaaaatggt ggcagttctt attaccagtt gttagtattg tttctggaaa
ctgcttgcca agacaacatt tattaactgt tagaacactt gctttatgtt tgtgtgtaca
tattttccac aaatgttata atttatatag tgtggttgaa caggatgcaa tcttttgttg
tctaaaggtg ctgcagttaa aaaaaaaaca acctttttctt tcaatatggc atgtagtgga
gttttttaa ctttaaaaac atcaaaaatt gttaaaatca ttgtgttatc tagtagttta
taattatcgg cttatatttc cccatgaatg atcagaactg acatttaatt catgtttgtc
tcgccatgct tctttacttt aacatatttc ttttgcagaa tgtaaaaggt aatgataatt
agtttatata agtgtactgg ctgtaaatga tgctaaatat actttatgca attaagggct
tacagaacat gttgaaactt tttttacttt tattgggaat aaggaatgtt tgcacctcca
cattttattg ctt
```

Figure 9F

IDENTIFICATION OF ARSACS MUTATIONS AND METHODS OF USE THEREFOR

RELATED APPLICATIONS

This application claims the benefit of U.S. Provisional application Ser. No. 60/160,588, filed Oct. 20, 1999, the entire teachings of which are incorporated herein by reference.

BACKGROUND OF THE INVENTION

Autosomal recessive spastic ataxia of Charlevoix-Saguenay (ARSACS) is an early-onset neurodegenerative disease with high prevalence in the Charlevoix-Saguenay-Lac-Saint-Jean (CSLSJ) region of Quebec. Disease progression is rapid through young adulthood, with most patients requiring wheelchairs by their early forties. The disease is characterized by abolished sensory nerve conduction, reduced motor nerve velocity, and a unique clinical feature of hypermyelination of retinal nerve fibers. Additional pathological features include atrophy of the upper cerebellar vermis, absence of Purkinje cells, and possibly abnormal neuronal lipid storage (Bouchard, J -P., In: Handbook of Clinical Neurology 16: Hereditary neuropathies and spinocerebellar degenerations, J.M.B.V. de Jong, Ed., pp. 451–459, Elsevier Science Publishers, Amsterdam (1991)). A developmental defect in the myelination of both retinal and peripheral nerve fibers has been proposed as the physiological basis of the disease (Bouchard, J -P., et al., *Neuromuscular Disorders* 8:474–479 (1998)). More than 300 patients have been identified, and the estimated carrier frequency is 1 in 22 in the Charlevoix-Saguenay-Lac-Saint-Jean (CSLSJ) population of northeastern Quebec (3).

SUMMARY OF THE INVENTION

As described herein, the ARSACS gene, referred to herein as "spastin" (also known as sacsin), has been mapped to chromosome 13q11 by linkage analysis and cloned from human, mouse and hamster. The gene was identified by using fine-structure linkage disequilibrium (LD) mapping to narrow the disease interval and then performing sample-sequencing to identify candidate genes. The spastin gene has a remarkable feature in that it contains a large exon spanning at least 12,793 base pairs of genomic DNA and comprises an open-reading frame of 11,487 base pairs. As described herein the gene is highly conserved in mouse. This exon of spastin is the largest found in any vertebrate organism. The deduced protein contains three large domains with sequence similarity to each other, as well as to the protein predicted to be encoded by an open reading frame identified in Arabidopsis genomic DNA. These domains contain a subdomain with sequence similarity to heat-shock proteins, suggesting a role in chaperone-mediated protein folding. Spastin appears to be expressed in a wide variety of tissues including brain and central nervous system. Alterations in the spastin gene have been identified as described herein which correlate strongly with ARSACS, including at least two alterations which have severe effects on the encoded protein, providing strong evidence that mutations in the open reading frame of the spastin gene are responsible for ARSACS.

The present invention relates to an isolated nucleic acid molecule comprising a spastin gene or portion of said gene as described herein. In one embodiment, the invention relates to an isolated nucleic acid molecule comprising a nucleotide sequence selected from the group consisting of SEQ ID NOS: 1, 3, 7, 9, 11, 12, 13, 14 and 15 and the complement of SEQ ID NOS: 1, 3, 7, 9, 11, 12, 13, 14 and 15. In another embodiment the invention relates to an isolated nucleic acid molecule comprising an exon from a vertebrate gene wherein said exon is at least 1150 base pairs in length. The invention also relates to an isolated nucleic acid molecule consisting of a nucleotide sequence selected from the group consisting of SEQ ID NOS: 1, 3, 7, 9, 11, 12, 13, 14 and 15 and the complement of SEQ ID NOS: 1, 3, 7, 9, 11, 12, 13, 14 and 15. In a preferred embodiment the genes of the invention are human genes. The invention also relates to an isolated nucleic acid molecule consisting of a nucleotide sequence selected from the group consisting of SEQ ID NOS: 21–66 and the complement of SEQ ID NOS: 21–66.

The present invention also includes fragments of the spastin genes described herein. For example, the invention relates to an isolated portion of a nucleic acid sequence selected from the group consisting of SEQ ID NOS: 1, 3, 7, 9, 11, 12, 13, 14 and 15 and the complement of SEQ ID NOS: 1, 3, 7, 9, 11, 12, 13, 14 and 15, wherein the portion is at least about 10 nucleotides in length.

The invention also relates to nucleic acid molecules having substantial sequence identity to the specific sequences disclosed herein. In one embodiment, the invention relates to a nucleic acid molecule comprising a nucleotide sequence which is at least about 60% identical to a nucleotide sequence selected from the group consisting of SEQ ID NOS: 1, 3, 7, 9, 11, 12, 13, 14 and 15 and the complement of SEQ ID NOS: 1, 3, 7, 9, 11, 12, 13, 14 and 15. In another embodiment, the invention relates to a nucleic acid molecule which hybridizes under high stringency conditions to a nucleotide sequence selected from the group consisting of SEQ ID NOS: 1, 3, 7, 9, 11, 12, 13, 14 and 15 and the complement of SEQ ID NOS: 1, 3, 7, 9, 11, 12, 13, 14 and 15.

The nucleic acid molecules of the present invention, or portions thereof, can be used as probes to isolate and/or clone substantially similar or functionally equivalent homologues of the spastin family of genes. The polynucleotides of the present invention can also be used as probes to detect and or measure expression of the genes encoded by the present invention. The probes of the present invention can be DNA, RNA or PNA. Expression assays, such as Southern blot analysis and whole mount in situ hybridization, are well known in the art. The polynucleotides of the present invention, or portions thereof, can also be used as primers to clone homologues or family members by PCR using techniques well known in the art.

The invention further relates to nucleic acid constructs comprising the isolated nucleic acid molecules of the invention, as well as to a recombinant host cell comprising the isolated nucleic acid molecules of the invention. The invention further relates to a method for preparing a polypeptide encoded by an isolated nucleic acid molecule of the invention, comprising culturing the recombinant host cells of the invention.

Also encompassed by the present invention are isolated polypeptides encoded by nucleic acid molecules described herein. For example, the invention relates to an isolated polypeptide comprising an amino acid sequence selected from the group consisting of SEQ ID NOS: 2, 4, 8, 10, 16 and 67–69. The invention also relates to an isolated polypeptide comprising an amino acid sequence having greater than 75% identity to an amino acid sequence selected from the group consisting of SEQ ID NOS: 2, 4, 8, 10, 16 and 67–69. The invention also provides antibodies, and antigen binding fragments thereof, to the polypeptides of the invention, particularly antibodies and antigen binding fragments thereof which specifically bind the polypeptides described herein.

The invention also provides a method for assaying the presence of a nucleic acid molecule in a sample, comprising contacting said sample with a nucleotide sequence selected from the group consisting of SEQ ID NOS: 1, 3, 7, 9, 11, 12, 13, 14, 15, 17–66, 72 and 73; the complement of SEQ ID NOS: 1, 3, 7, 9, 11, 12, 13, 14, 15, 17–66, 72 and 73; a portion of any one of SEQ ID NOS: 1, 3, 7, 9, 11, 12, 13, 14, 15, 17–66, 72 and 73 which is at least 10 nucleotides in length; and a portion of the complement of any one of SEQ ID NOS: 1, 3, 7, 9, 11, 12, 13, 14, 15, 17–66, 72 and 73 which is at least 10 nucleotides in length, under conditions appropriate for selective hybridization of the sequence to the nucleic acid molecule in the sample. Presence or absence of a hybridization signal indicates presence or absence, respectively, of the target nucleic acid molecule. The invention also relates to a method for assaying the presence of a polypeptide encoded by an isolated nucleic acid molecule of the invention in a sample, comprising contacting said sample with an antibody which specifically binds to the encoded polypeptide.

The invention further relates to a method of diagnosing or aiding in the diagnosis of neurodegenerative disease in an individual comprising obtaining a nucleic acid sample from the individual and determining the nucleotide present at nucleotide position 5254 of SEQ ID NO: 1, wherein the nucleotide position is numbered from the putative initiation codon, wherein presence of a thymine at said position is indicative of increased likelihood of neurodegenerative disease in the individual as compared with an appropriate control, e.g., an individual having a cytosine at said position. The invention also relates to a method of diagnosing or aiding in the diagnosis of neurodegenerative disease in an individual comprising obtaining a nucleic acid sample from the individual and determining whether there is a deletion of a thymine at nucleotide position 6594 of SEQ ID NO: 1, wherein the nucleotide position is numbered from the putative initiation codon, wherein deletion of a thymine at said position is indicative of increased likelihood of neurodegenerative disease in the individual as compared with an appropriate control, e.g., an individual who does not have a deletion at said position.

The invention also relates to a method of treating a neurodegenerative disorder associated with the presence of a thymine at nucleotide position 5254 of SEQ ID NO: 1 in an individual, wherein the nucleotide position is numbered from the putative initiation codon, comprising administering to the individual an agent selected from the group consisting of a polypeptide encoded by SEQ ID NO: 2 or an active portion thereof, a nucleic acid molecule which encodes SEQ ID NO: 2 or an active portion of SEQ ID NO: 2, and an agonist of SEQ ID NO: 2. The invention further relates to a method of treating a neurodegenerative disorder associated with a deletion at nucleotide position 6594 of SEQ ID NO: 1 in an individual, wherein the nucleotide position is numbered from the putative initiation codon, comprising administering to the individual an agent selected from the group consisting of a polypeptide encoded by SEQ ID NO: 2 or an active portion thereof, a nucleic acid molecule which encodes SEQ ID NO: 2 or an active portion of SEQ ID NO: 2, and an agonist of SEQ ID NO: 2.

The invention also encompasses a method of diagnosing or aiding in the diagnosis of neurodegenerative disease associated with the presence of a thymine at nucleotide position 5254 of SEQ ID NO: 1 in an individual, wherein the nucleotide position is numbered from the putative initiation codon, comprising obtaining a sample comprising a Spastin polypeptide from the individual and determining the size of the Spastin polypeptide, wherein if the Spastin polypeptide is significantly shorter than SEQ ID NO: 2 it is indicative of neurodegenerative disease. The invention also provides a method of diagnosing or aiding in the diagnosis of neurodegenerative disease associated with the presence of a deletion at nucleotide position 6594 of SEQ ID NO: 1 in an individual, wherein the nucleotide position is numbered from the putative initiation codon, comprising obtaining a sample comprising a Spastin polypeptide from the individual and determining the size of the Spastin polypeptide, wherein if the Spastin polypeptide is significantly shorter than SEQ ID NO: 2 it is indicative of neurodegenerative disease. In one embodiment, the Spastin polypeptide is significantly shorter than SEQ ID NO: 2 if the Spastin polypeptide comprises less than about 75% of the amino acids of SEQ ID NO: 2.

In one embodiment, the neurodegenerative disease comprises one or more symptoms selected from the group consisting of: reduced sensory nerve conduction, reduced motor nerve velocity, hypermyelination of retinal nerve fibers, atrophy of upper cerebellar vermis, absence of Purkinje cells and abnormal neuronal lipid storage. In a particular embodiment, the nucleic acid sample is obtained from a tissue selected from the group consisting of: brain tissue, CNS, lung, fetal lung, testis, lymphocytes, adipose, fibroblasts, skeletal muscle, pancreas, uterus, kidney, tonsil, embryo and isolated cells thereof. For example, brain tissue can be selected from the group consisting of cerebral cortex, granular cell layer of the cerebellum and hippocampus. In a particular embodiment, the neurodegenerative disease is an early onset neurodegenerative disease.

BRIEF DESCRIPTION OF TEE DRAWINGS

FIG. 1 is a schematic diagram of the structure and organization of the spastin gene. Markers used for the genetic map of the spastin gene are shown above. SGCG is the sarcoglycan, gamma gene. hCIT 26_$L_{13}$ 1 and hCIT 235_L_20, the overlapping clones that contain the spastin ORF, are 110 kilobases (kb) and 60 kb, respectively. Exploded view shows the location of the spastin gene. The thick bar is the predicted coding region. The thin bars represent the 5' and 3' UTRs. M is the first methionine. S is the location fo the introduced stop codon found on the minor haplotype. Δ indicates the location of the deleted base pair found on the major haplotype. AB018273 is the mRNA sequence KIAA0730 (42) which is part of a UniGene cluster (Hs.159492) containing 32 ESTs. R17106, AA776169, AA776670, and AA897178 are additional ESTs with homology to the spastin gene.

FIGS. 2A–2B show the results of sequence analysis and identification of spastin mutations found on ARSACS chromosomes. The sequences displayed are from direct sequencing of PCR products and flank the two mutations (indicated by arrows) found on ARSACS chromosomes. Nucleotide numbering is from the putative initiation codon. FIG. 2A shows nucleotide 6594 (codon 2198) for an unaffected individual (top panel) and a homozygous affected individual (bottom panel). FIG. 2B shows nucleotide 5254 (codon 1752) for an unaffected individual (top panel) and an affected compound heterozygous individual (bottom panel).

FIG. 3 shows a Northern blot analysis of spastin mRNA. A $^{32}$P-labelled 1.8 kb cDNA fragment from the 3' end of the spastin gene (Image clone #279258) was hybridized to a blot of fibroblast RNA and to a multiple tissue blot (MTN, Clontech). Lanes 1–5 contain patient fibroblast RNAs and lane 6 contains control fibroblast RNA. The lanes of the MTN blot correspond to the following tissues: 7, heart; 8, brain; 9, placenta; 10, lung; 11, liver; 12, skeletal muscle; 13, kidney; and 14, pancreas. The marker (M) is the 0.24–9.5 kb RNA ladder (Life Technologies).

FIGS. 4A–4B are schematic representations of the Spastin protein and relevant homologies. FIG. 4A shows a schematic representation of the Spastin protein and location of motifs. rep. 1, 2, and 3 represent the domains with homology (28, 30 and 21% identity, respectively) to the Arabidopsis open reading frame. FIG. 4B shows homology between the two Hsp90 domains of Spastin, the first mouse domain, the Arabidopsis open reading frame (GenBank accession #AB006708), and the yeast Hsp90 (GenBank accession #3401959). Alignment was performed with ClustalW (1.7) (43) through the BCM Search Launcher interface (34) with the BLOSUM weight matrix. The numbering for all sequences is from the first methionine (nucleotide 50,773 is the first methionine of the Arabidopsis open reading frame).

FIGS. 5A–5C show the alignment of the human Spastin with the mouse Spastin. Identical amino acids and gaps are represented by dots and hyphens, respectively. The self-homologous region containing the Hsp90 homology occurs at positions 705–833 and 1773–1895, and italics indicate the DnaJ region. The bolded sequences represent leucine zipper motifs, underlined sequences represent coiled coil domains, and the boxed and underlined sequence delineates the putative hydrophilic region. The first coiled coil domain is interrupted by a proline in the mouse sequence.

FIG. 6 is a table showing ESTs identified by sample-sequencing of the ARSACS critical interval.

FIG. 7 is a table showing primers for PCR amplification of the human spastin gene.

FIGS. 8A–8G show the complete exon (SEQ ID NO: 3) of the murine spastin gene as shown in FIGS. 8A–8G.

FIGS. 9A–9F show the complete exon (SEQ ID NO: 1) of the human spastin gene.

DETAILED DESCRIPTION OF THE INVENTION

The gene responsible for ARSACS was mapped to chromosome region 13q11 by genotyping 322 microsatellite markers in a genome-wide scan and noting a high degree of homozygosity at locus D13S787 (Bouchard, J -P., et al., *Neuromuscular Disorders* 8:474–479 (1998)). Extensive genetic analysis of the region defined a maximum multipoint LOD score of 42.3 and revealed a major conserved haplotype among ARSACS chromosomes in a 11.1 cM region flanked by D13S1236 and D13S1285 (5). Two groups of ARSACS haplotypes were found between D13SJ275 and D13S292. The overwhelming majority (96%) of ARSACS chromosomes carried a single haplotype, defined by D13S232 and two single nucleotide polymorphisms (SNPs) within the sarcoglycan, gamma gene (SGCG). Location score analysis demonstrated that the most likely position of the ARSACS was between D13S232 and D13S292 (the critical interval)(5).

A high-resolution physical and transcript map of the ARSACS critical interval was constructed in yeast artificial chromosomes (YACs), bacterial artificial chromosomes (BACs) and plasmid artificial chromosomes (PACs). The identification of the ARSACS gene (i.e., a gene in which alteration is associated with ARSACS) was carried out as described herein by performing sample-sequencing of six BAC and PAC clones spanning about 450 kilobases (kb) included in the critical interval. Analysis of the sample sequences revealed human ESTs (FIG. 6) and the presence of two known genes: sodium/potassium-ATPase (ATP1AL1), that was excluded on the basis of recombination in ARSACS families, and SGCG, a gene in which no sequence variants unique to ARSACS chromosomes were found.

Figure 1:
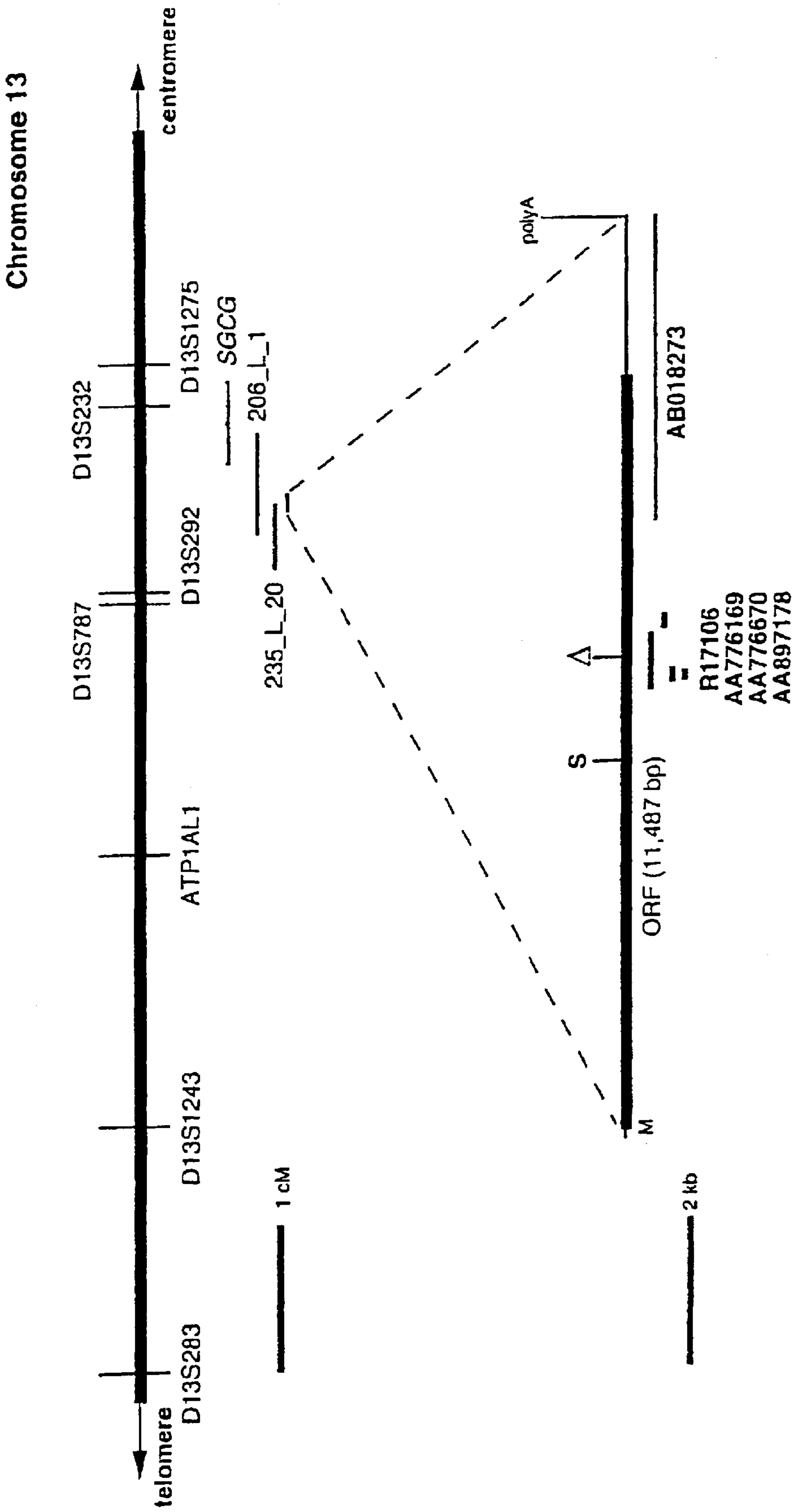

A 20 kb sequence contig revealed a huge genomic open reading frame (ORF) of 11,487-base pairs that encodes 3829 amino acids (SEQ ID NO: 2). The open reading frame (ORF) begins with an AUG codon preceded by an in-frame stop codon 75 bp upstream and continues for a total of 3,829 codons before encountering a stop codon. One large cDNA (KIAA0730) derived from a brain library and over 30 ESTs overlap the ORF and allowed the determination of the 3' untranslated region (UTR), which extends 1,307 bp to a polyadenylation site (FIG. 1). The existence of this gigantic exon was confirmed by analyzing RT-PCR products spanning the entire mRNA; this analysis showed perfect correspondence between the mRNA and genomic DNA sequence. Thus, the total length of the exon must be at least 12,793 bp. A probe derived from within this sequence detects a transcript of approximately 12.8 kb on a Northern blot, suggesting that the identified exonic sequence may constitute an intronless gene, although the possibility of a small 5' exon cannot be excluded.

Figure 2A:
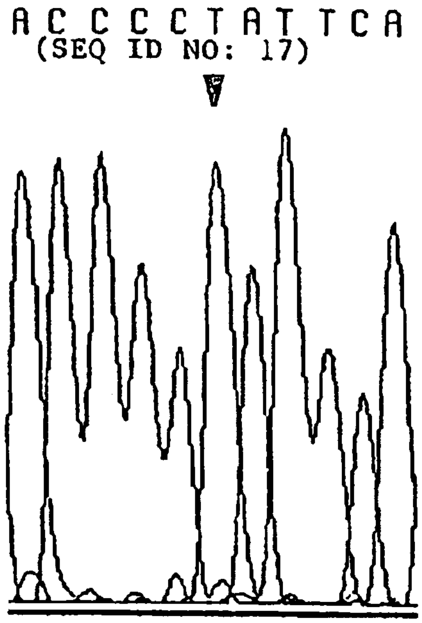
Figure 2A:
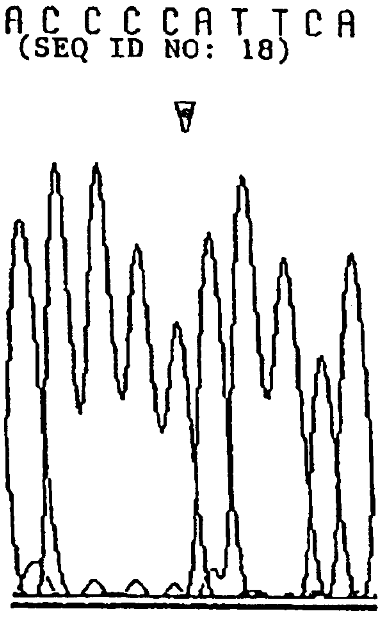
Figure 2B:
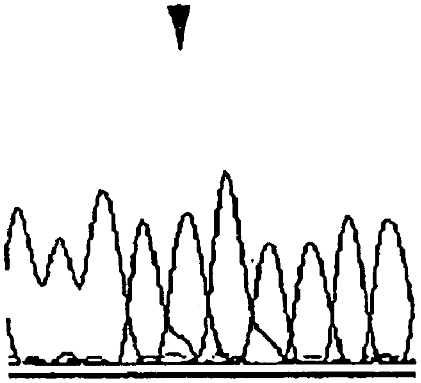
Figure 2B:
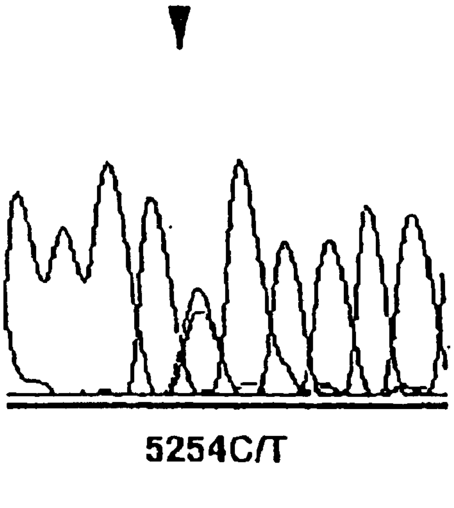

To characterize the full sequence of the ORF and to identify potential disease-causing mutations, PCR products from ARSACS patient and control DNA were sequenced. The primers for these reactions are shown in FIG. 7. A single-base deletion of a thymine at position 6594 (6594ΔT) (FIG. 2A), wherein the nucleotide position is numbered from the putative initiation codon, was found on all copies of the major ancestral haplotype examined (a total of 32 chromosomes), but was absent in all chromosomes of carrier parents that were not transmitted to ARSACS offspring. This mutation causes a frame shift and results in a subsequent stop codon that truncates the final 43% of the predicted protein. A second mutation, a nonsense mutation of substitution of a thymine for a cytosine at nucleotide position 5254 (c5254T) (FIG. 2B), wherein the nucleotide position is numbered from the putative initiation codon results in the substitution of a stop codon for an arginine and was found on the minor ARSACS haplotype carried in a heterozygous state (in trans to the major ARSACS mutation) in six patients from two families (5). Both mutations are thus completely associated with their respective core haplotypes and are predicted to have severe effects on the encoded protein. The presence of these two mutations provides strong evidence that mutations in this ORF are responsible for ARSACS. The gene is referred to herein as spastin (gene symbol: SPAS).

In the course of the complete resequencing of the spastin gene in ARSACS patients, additional sequence variants were found which proved to be polymorphisms found on non-ARSACS-bearing chromosomes as well. These included four silent substitutions: substitution of a thymine for a cytosine at nucleotide position 3945, substitution of a cytosine for a thymine at nucleotide position 6603, substitution of a thymine for a cytosine at nucleotide position 7731, and substitution of a thymine for a cytosine at nucleotide position 10054 (C3945T, T6603C, C7731T and C10054T, respectively), and an amino acid-altering substitution of a cytosine for a thymine at nucleotide position 7856 (T7856C), wherein the nucleotide position is numbered from the putative initiation codon, that results in the substitution of an alanine for a valine in the predicted protein.

Figure 3:
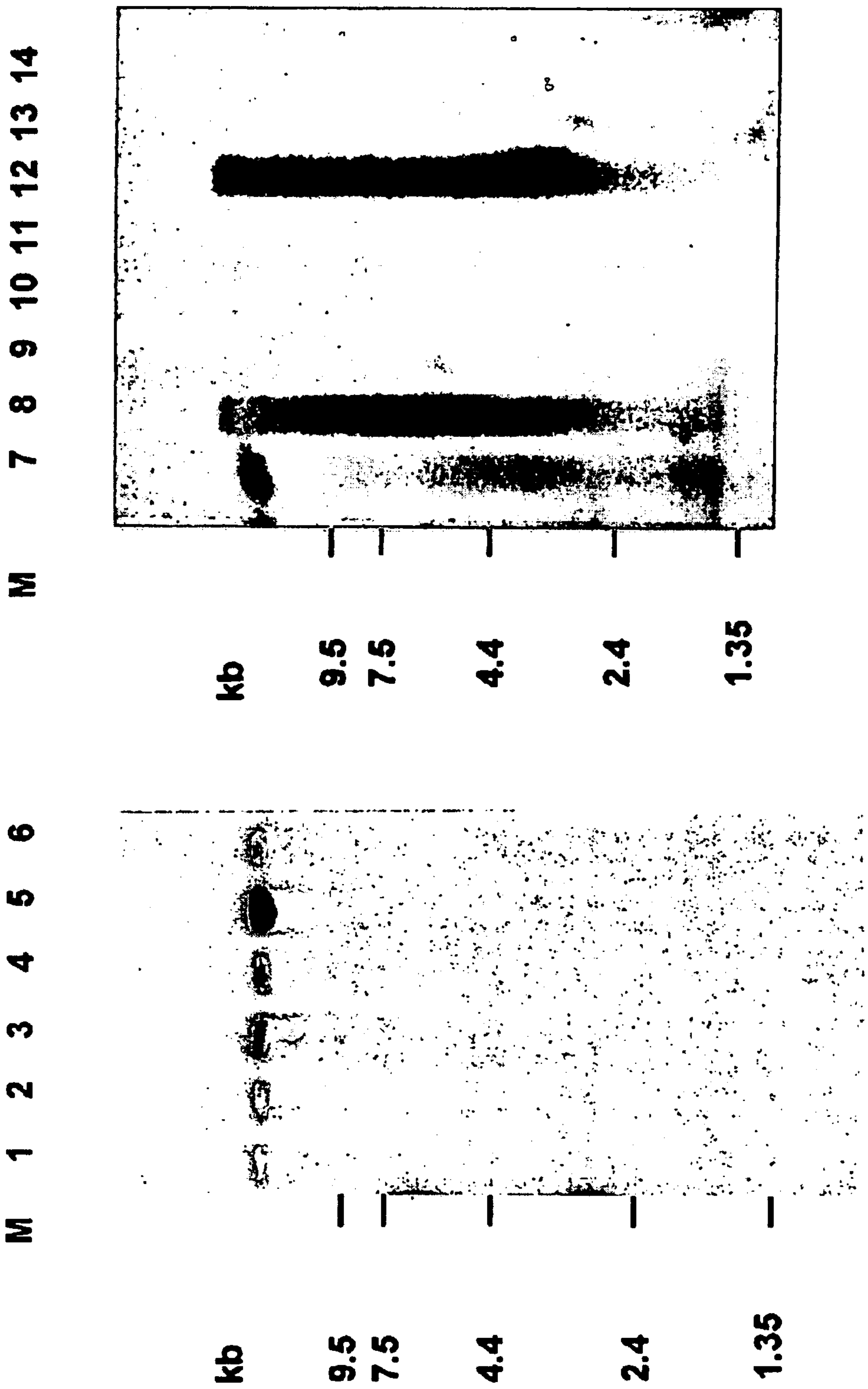
Figure 4A:
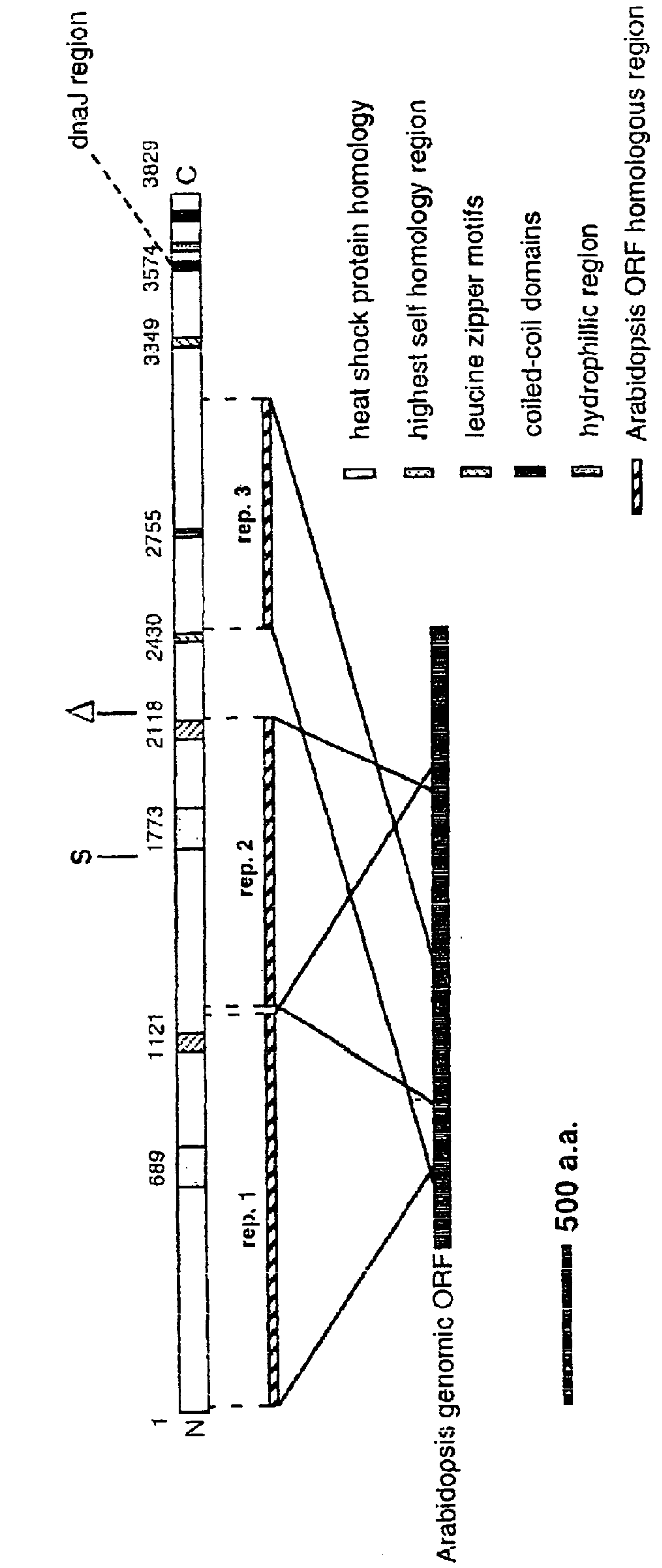

Spastin mRNA was detected by northern blot analysis in fibroblasts, brain and skeletal muscle (FIG. 3, lanes 1–6, 8 and 12) and at very low levels in pancreas (FIG. 3, lane 14). A single transcript of roughly 12.8 kb was seen in all cases. Spastin mRNA was expressed in the fibroblasts of ARSACS patients (FIG. 3, lanes 1–5) at the same size as controls, which is not unexpected because both mutations alter only a single nucleotide.

To examine the tissue expression pattern of spastin more closely, in situ hybridizations were performed. Human, monkey, and rat brain all demonstrated high levels of staining, which included all layers of the cerebral cortex and the granular cell layer of the cerebellum. In a sagittal section of the adult rat brain, strong labeling was seen in most if not all areas of the central nervous system (CNS). Particularly intense labeling was observed on the hippocampus. No labeling is seen with the sense probe. In addition, specific staining of spastin mRNA was seen throughout the CNS of the 18–19 day fetal rat. Background staining with the sense probe does not include the CNS. Spastin ESTs were identified from the cDNA libraries of many tissues including brain, uterus, kidney, tonsils, liver, and T cells. Transcripts from brain and multiple sclerosis libraries comprise 13 of the 35 human ESTs with homology to spastin. Taken together, these lines of evidence indicate that spastin is expressed in a variety of tissues, including many that are neural-derived.

On the basis of its amino acid sequence, the Spastin protein product is predicted to have a molecular weight of 437 kD and a pI of 6.85. Structure prediction programs suggest the presence of two leucine zippers, three coiled coils and a hydrophilic domain, all within the C-terminal half of the protein (FIGS. 4A and 5A–5C). The predicted protein product does not show extensive similarity to any known protein, based on analyses using a variety of different sequence comparison tools. However, two related motifs were identified. The C-terminal portion of the predicted protein contains a 'DnaJ' protein motif (FIGS. 4A and 5A–5C, residues 3574–3590). Both human and mouse proteins also contain three large segments with sequence similarity to each other, of which two have homology to the N-terminal domain of the Hsp90 class of heat-shock proteins from a variety of organisms. These Hsp90 subdomains are found in spastin residues 705–833 and 1773–1895 (FIGS. 4A and 5A–5C). As discussed below, the DnaJ and Hsp90 protein classes are both involved in molecular chaperone complexes. Interestingly, the three large segments also show strong similarity to a BAC clone recently sequenced as part of the Arabidopsis genome project (GenBank #AB006708). Specifically, they are homologous to a portion of a 5,871 bp ORF of unknown function in Arabidopsis (FIG. 5A). An alignment of the Hsp90 domain is shown for the first and second large segments from human, the first segment for mouse, the Arabidopsis ORF and the yeast Hsp90 (FIG. 5B). The highly conserved residues correspond to regions already identified as highly conserved "signature sequences" in an extensive phylogenetic analysis of the Hsp90 family (9). Molecular chaperones are known to function in multiple sub-cellular compartments. A knowledge-based program for predicted subcellular localization, PSORT II (10) favored a nuclear localization for the Spastin protein, but the prediction score was relatively weak (47%).

As provided herein, the spastin gene is also conserved in mouse. Homologous mouse ESTs were identified, including one having a polyadenylation signal. Using these ESTs to screen a mouse BAC library (CitbCJ7), the mouse spastin gene was isolated, identified and sequenced. Sequence analysis of the mouse spastin genomic clone revealed the presence of a huge ORF, which is three nucleotides longer than the human homologue and thus, the mouse Spastin protein is predicted to be one amino acid longer. The entire ORF is well conserved between mouse and human, both at the DNA level (88% homology) and at the protein level (94% identity, 97% similarity). The areas of high sequence conservation between mouse and human included the two leucine zippers, two coiled coils, the Hsp90 and DnaJ domains, and the repeated Arabidopsis ORF homology (FIGS. 5A–5C). The 3' UTRs show greater divergence between the mouse and human, but still retain 72% homology. The mouse spastin gene was mapped to chromosome 1, near D1Mit373, on the basis of radiation hybrid mapping (LOD score of 25.5) using the Whitehead Institute mouse T31 RH framework (11, 12).

Work described herein strongly supports that a frameshift and a nonsense mutation identified within the spastin gene cause ARSACS. Though the gene appears to be widely expressed, the truncation of the Spastin protein caused either by homozygous (6594ΔT/6594ΔT) or compound heterozygous (C5254T/6594ΔT) genotypes, wherein the nucleotide position is numbered from the putative initiation codon, apparently lead to symptoms predominantly affecting the nervous system. The high level of expression of spastin mRNA in the granular cell layer of the adult rat cerebellum is especially interesting in light of an earlier observation of the reduced thickness of the granular layer found during the postmortem examination of tissue from an ARSACS patient (Bouchard, J -P., In: Handbook of Clinical Neurology 16: hereditary neuropathies and spinocerebellar degenerations, pp.451–459, Elsevier Science Publishers, Amsterdam (1991)). Thus, the high mRNA expression levels seen in the CNS indicate a possibly unique role for Spastin in the genesis or maintenance of neural cell function.

As described herein, sample-sequencing of the ARSACS critical region, in combination with directed sequencing of specific subclones and computer-aided analysis led to the characterization of a very large exon directly from genomic DNA. This likely represents the entire coding sequence of the spastin gene as the first methionine is preceded by an in-frame stop codon 75 bp upstream. RT-PCR demonstrated that the sequence, from this 75 bp until the polyadenylation site, is transcribed. Spastin appears to be an intronless gene, although a non-coding upstream exon cannot be ruled out. The spastin exon of at least 12,793 bp encoding an ORF of 11,487 bp represents the largest exon and the largest ORF within an exon found in any vertebrate so far. The next largest exons reported are the X (inactive)-specific transcript (XIST) (11,363 bp) which does not code for a protein (13), and the large central exon of the mucin gene (MUC5B) which is 10,713 bp long (14).

Intronless ORFs are uncommon and thought to represent at most 5% of human genes. A few gene families are frequently intronless, including histones and G-protein-coupled receptors (GPCRs) (15). Members of the Hsp70 family, but not the Hsp90, are also intronless. The strong conservation between both the human and the mouse spastic and the unusually large 5,871 bp Arabidopsis ORF suggest both that spastin is ancient and that the large size of the exon is functionally important.

The presence of similarities to DnaJ and Hsp90 proteins sheds light on spastin's potential function. Examples of interacting protein pairs having homologues of the two proteins fused into a single protein are well known in the art (17). Spastin possesses both the N-terminal domain of the Hsp90 protein class and a DnaJ domain. These two domains are from proteins that interact in chaperone-mediated protein folding. The DnaJ motif has long been known to form heterocomplexes with the Hsp70 class of proteins in a variety of cellular processes, including ATP-dependent folding of target proteins. The N-terminal domain of the Hsp90 protein class contains an ATP-binding site that is very similar to the one found in DNA gyrase B (18). More recently, it has been shown that the yeast DNAJ homologue, YDJ1, physically associates with Hsp90 and this interaction has specific effects on Hsp90 substrates (19). In addition, other studies have shown that a rabbit DnaJ homologue (p40) interacts with Hsp70 and Hsp90 (both molecular chaperones) to form heterocomplexes known as "foldosomes" (20). Together, these data suggest that spastin functions in chaperone-mediated protein folding.

As described herein the mouse spastin gene was mapped to chromosome 1 near D1Mit373. A recessive mouse mutation known as tumbler (tb: MGI Accession ID:98489) was previously mapped to this region by linkage (21). Tumbler mice had an ataxia that caused them to "walk in a crab-like fashion." They somersaulted, fell over, or jumped when trying to go forward. Most of the homozygotes survived and bred (21). These observations are similar to those seen in ARSACS patients whose life expectancy, although reduced (mean age at death is 51 years) still permits some to survive until the eighth decade. The fertility of affected females seems unchanged, but because overall nuptiality is low, male fertility has been difficult to assess (Bouchard, J -P., et al., *Nueromuscular Disorders* 8:474–479 (1998)). Unfortunately, the tb mouse line has died out (Mouse Genome Database: URL:http://www.informatics.jax.org/). However, gene knock-out of the mouse spastin gene could serve to confirm that the tb mutation was a mutation in the mouse spastin gene.

SEQ ID NOS: referred to herein are as follows. SEQ ID NO: 1 refers to the complete exon of the human spastin gene as shown in FIGS. 9A–9F. SEQ ID NO: 2 refers to the protein encoded by the ORF of SEQ ID NO: 1, particularly as shown in FIGS. 9A–9F and 5A–5C. SEQ ID NO: 3 refers to the complete exon of the murine spastin gene as shown in FIGS. 8A–8G. SEQ ID NO: 4 refers to the protein encoded by the ORF of SEQ ID NO: 3, particularly as shown in FIGS. 9A–9F and 5A–5C. SEQ ID NOS: 5 and 6 are intentionally omitted. SEQ ID NO: 7 refers to a nucleotide sequence which is identical to SEQ ID NO: 1 except for a deletion of a thymine at position 6594, wherein the nucleotide position is numbered from the putative initiation codon. SEQ ID NO: 8 refers to the protein encoded by the ORF of SEQ ID NO: 7. SEQ ID NO: 9 refers to a nucleotide sequence which is identical to SEQ ID NO: 1 except for a substitution of a thymine for a cytosine at position 5254, wherein the nucleotide position is numbered from the putative initiation codon. SEQ ID NO: 10 refers to the protein encoded by the ORF of SEQ ID NO: 9. SEQ ID NO: 11, 12, 13 and 14 refer to nucleotide sequences which are identical to SEQ ID NO: 1 except for a substitution of a thymine for a cytosine at position 3945, substitution of a cytosine for a thymine at position 6603, substitution of a thymine for a cytosine at position 7731, and substitution of a thymine for a cytosine at position 10054, wherein the nucleotide position is numbered from the putative initiation codon, respectively. SEQ ID NO: 15 refers to a nucleotide sequence which is identical to SEQ ID NO: 1 except for substitution of a cytosine for a thymine at position 7856, wherein the nucleotide position is numbered from the putative initiation codon. SEQ ID NO: 16 refers to the protein encoded by the ORF of SEQ ID NO: 15. The sequences corresponding to all other SEQ ID NOS: used herein are shown throughout the application.

As appropriate, the isolated nucleic acid molecules of the present invention can be RNA, for example, mRNA, or DNA, such as cDNA and genomic DNA. DNA molecules can be double-stranded or single-stranded; single stranded RNA or DNA can be either the coding, or sense, strand or the non-coding, or antisense, strand. The nucleic acid molecule can include all or a portion of the coding sequence of a gene and can further comprise additional non-coding sequences such as introns and non-coding 3' and 5' sequences (including regulatory sequences, for example). Additionally, the nucleic acid molecule can be fused to a marker sequence, for example, a sequence that encodes a polypeptide to assist in isolation or purification of the polypeptide. Such sequences include, but are not limited to, those which encode a glutathione-S-transferase (GST) fusion protein and those which encode a hemaglutin A (HA) polypeptide marker from influenza.

As used herein, "isolated" is intended to mean that the isolated item is not in the form or environment in which it exists in nature. For example, an "isolated" nucleic acid molecule, as used herein, is one that is separated from nucleic acid which normally flanks the nucleic acid molecule in nature. With regard to genomic DNA, the term "isolated" refers to nucleic acid molecules which are separated from the chromosome with which the genomic DNA is naturally associated. For example, the isolated nucleic acid molecule can contain less than about 5 kb, 4 kb, 3 kb, 2 kb, 1 kb, 0.5 kb or 0.1 kb of nucleotides which flank the nucleic acid molecule in the genomic DNA of the cell from which the nucleic acid is derived.

Moreover, an isolated nucleic acid of the invention, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated. In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

Further, recombinant DNA contained in a vector is included in the definition of "isolated" as used herein. Also, isolated nucleic acid molecules include recombinant DNA molecules in heterologous host cells, as well as partially or substantially purified DNA molecules in solution. "Isolated" nucleic acid molecules also encompass in vivo and in vitro RNA transcripts of the DNA molecules of the present invention.

The invention further provides variants of the isolated nucleic acid molecules of the invention. Such variants can be naturally occurring, such as allelic variants (same locus), homologs (different locus), and orthologs (different organism), or may be constructed by recombinant DNA methods or by chemical synthesis. Such non-naturally occurring variants can be made using well-known mutagenesis techniques, including those applied to polynucleotides, cells, or organisms. Accordingly, variants can contain nucleotide substitutions, deletions, inversions and/or insertions in either or both the coding and non-coding region of the nucleic acid molecule. Further, the variations can produce both conservative and non-conservative amino acid substitutions.

Typically, variants have a substantial identity with a nucleic acid molecule disclosed herein and the complements thereof. Particularly preferred are nucleic acid molecules and fragments which have at least about 60%, preferably at least about 70, 80 or 85%, more preferably at least about 90%, even more preferably at least about 95%, and most preferably at least about 98% identity with nucleic acid molecules described herein.

Such nucleic acid molecules can be readily identified as being able to hybridize under stringent conditions to a nucleotide sequence selected from the group consisting of SEQ ID NOS: 1, 3, 7, 9, 11, 12, 13, 14, 15, 17–66, 72 and 73 and the complements thereof. In one embodiment, the variants hybridize under high stringency hybridization conditions (e.g., for selective hybridization) to a nucleotide sequence selected from SEQ ID NOS:1, 3, 7, 9, 11, 12, 13, 14, 15, 17–66, 72 and 73.

A general description of stringent hybridization conditions are discussed in Ausubel, F. M., et al., *Current Protocols in Molecular Biology*, Greene Publishing Assoc. and Wiley-Interscience 1989, the teachings of which are incorporated herein by reference. Factors such as probe length, base composition, percent mismatch between the hybridizing sequences, temperature and ionic strength influence the stability of nucleic acid hybrids. Thus, stringency conditions sufficient to identify the polynucleotides of the present invention, (e.g., high or moderate stringency conditions) can be determined empirically, depending in part upon the characteristics of the known DNA to which other unknown nucleic acids are being compared for sequence similarity. Equivalent conditions can be determined by varying one or more of these parameters while maintaining a similar degree of identity or similarity between the two nucleic acid molecules. Typically, conditions are used such that sequences at least about 60%, at least about 70%, at least about 80%, at least about 90% or at least about 95% or more identical to each other remain hybridized to one another.

Alternatively, conditions for stringency are as described in WO 98/40404, the teachings of which are incorporated herein by reference. In particular, examples of highly stringent, stringent, reduced and least stringent conditions are provided in WO 98/40404 in the Table on page 36. In one embodiment, highly stringent conditions are those that are at least as stringent as, for example, 1× SSC at 65° C., or 1× SSC and 50% formamide at 42° C. Moderate stringency conditions are those that are at least as stringent as 4× SSC at 65° C., or 4× SSC and 50% formamide at 42° C. Reduced stringency conditions are those that are at least as stringent as 4× SSC at 50° C., or 6× SSC and 50% formamide at 40° C.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity # of identical positions/total # of positions×100). In certain embodiments, the length of a sequence aligned for comparison purposes is at least 30%, preferably at least 40%, more preferably at least 60%, and even more preferably at least 70%, 80% or 90% of the length of the reference sequence. The actual comparison of the two sequences can be accomplished by well-known methods, for example, using a mathematical algorithm. A preferred, non-limiting example of such a mathematical algorithm is described in Karlin et al., *Proc. Natl. Acad. Sci. USA*, 90:5873–5877 (1993). Such an algorithm is incorporated into the NBLAST and XBLAST programs (version 2.0) as described in Altschul et al., *Nucleic Acids Res.*, 25:389–3402 (1997). When utilizing BLAST and Gapped BLAST programs, the default parameters of the respective programs (e.g., NBLAST) can be used. See http://www.ncbi.nlm.nih.gov. In one embodiment, parameters for sequence comparison can be set at score=100, wordlength=12, or can be varied (e.g., W=5 or W=20).

The present invention also provides isolated nucleic acids that contain a fragment or portion that hybridizes under highly stringent conditions to a nucleotide sequence selected from the group consisting of SEQ ID NOS: 1, 3, 7, 9, 11, 12, 13, 14, 15, 17–66, 72 and 73 described herein and the complements of these SEQ ID NOS. The nucleic acid fragments of the invention are at least about 15, preferably at least about 18, 20, 23 or 25 nucleotides, and can be 30, 40, 50, 100, 200 or more nucleotides in length. Longer fragments, for example, 30 or more nucleotides in length, which encode antigenic proteins or polypeptides described herein are useful.

In a related aspect, the nucleic acid fragments of the invention are used as probes or primers in assays such as those described herein. "Probes" are oligonucleotides that hybridize in a base-specific manner to a complementary strand of nucleic acid. Such probes include polypeptide nucleic acids, as described in Nielsen et al., *Science,* 254, 1497–1500 (1991). Typically, a probe comprises a region of nucleotide sequence that hybridizes under highly stringent conditions to at least about 15, typically about 20–25, and more typically about 40, 50 or 75 consecutive nucleotides of a nucleic acid molecule of the invention. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The nucleic acid molecules of the invention such as those described above can be identified and isolated using standard molecular biology techniques and the sequence information provided herein. For example, nucleic acid molecules can be amplified and isolated by the polymerase chain reaction using synthetic oligonucleotide primers designed based on one or more of the sequences provided herein and the complements thereof. See generally *PCR Technology: Principles and Applications for DNA Amplification* (ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.,* 19:4967 (1991); Eckert et al., *PCR Methods and Applications,* 1:17 (1991); PCR (eds. McPherson et al., IRL Press, Oxford); and U.S. Pat. No. 4,683,202. The nucleic acid molecules can be amplified using cDNA, mRNA or genomic DNA as a template, cloned into an appropriate vector and characterized by DNA sequence analysis.

Other suitable amplification methods include the ligase chain reaction (LCR) (see Wu and Wallace, *Genomics,* 4:560

(1989), Landegren et al., *Science,* 241:1077 (1988), transcription amplification (Kwoh et al., *Proc. Natl. Acad. Sci. USA,* 86:1173 (1989)), and self-sustained sequence replication (Guatelli et al., *Proc. Nat. Acad. Sci. USA,* 87:1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

For example, the amplified DNA can be radiolabelled and used as a probe for screening a cDNA library derived from fibroblast or brain, e.g., human fibroblast or brain, mRNA in zap express, ZIPLOX or other suitable vector. Corresponding clones can be isolated, DNA can obtained following in vivo excision, and the cloned insert can be sequenced in either or both orientations by art recognized methods to identify the correct reading frame encoding a protein of the appropriate molecular weight. For example, the direct analysis of the nucleotide sequence of nucleic acid molecules of the present invention can be accomplished using well-known methods that are commercially available. See, for example, Sambrook et al., *Molecular Cloning, A Laboratory Manual* (2nd Ed., CSHP, New York 1989); Zyskind et al., *Recombinant DNA Laboratory Manual*, (Acad. Press, 1988)). Using these or similar methods, the protein(s) and the DNA encoding the protein can be isolated, sequenced and further characterized.

Antisense nucleic acids of the invention can be designed using the nucleotide sequences described herein, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

In general, the isolated nucleic acid sequences can be used as molecular weight markers on Southern gels, and as chromosome markers which are labeled to map related gene positions. The nucleic acid sequences can also be used to compare with endogenous DNA sequences in patients to identify genetic disorders, and as probes, such as to hybridize and discover related DNA sequences or to subtract out known sequences from a sample. The nucleic acid sequences can further be used to derive primers for genetic fingerprinting, to raise anti-protein antibodies using DNA immunization techniques, and as an antigen to raise anti-DNA antibodies or elicit immune responses. Additionally, the nucleotide sequences of the invention can be used identify and express recombinant proteins for analysis, characterization or therapeutic use, or as markers for tissues in which the corresponding protein is expressed, either constitutively, during tissue differentiation, or in diseased states.

The invention also relates to constructs which comprise a vector into which a sequence of the invention has been inserted in a sense or antisense orientation. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses) that serve equivalent functions.

Preferred recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc.

The expression vectors of the invention can be introduced into host cells to thereby produce proteins or peptides, including fusion proteins or peptides, encoded by nucleic acids as described herein. The recombinant expression vectors of the invention can be designed for expression of a polypeptide of the invention in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a nucleic acid of the invention can be expressed in bacterial cells (e.g. *E. coli*), insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals. A host cell of the invention, such as a prokaryotic or eukaryotic host cell in culture, can be used to produce (i.e., express) a polypeptide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a nucleic acid of the invention have been introduced. Such host cells can then be used to create non-human transgenic animals in which exogenous nucleotide sequences have been introduced into their genome or homologous recombinant animals in which endogenous nucleotide sequences have been altered. Such animals are useful for studying the function and/or activity of the nucleotide sequence and polypeptide encoded by the sequence and for identifying and/or evaluating modulators of their activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid of the invention into the male pronuclei of a fertilized oocyte, e.g., by microinjection, retroviral infection, and allowing the oocyte to develop in a pseudopregnant female foster animal. The sequence can be introduced as a transgene into the genome of a non-human animal. Intronic sequences and polyadenylation signals can also be included in the transgene to increase the efficiency of expression of the transgene. A tissue-specific regulatory sequence(s) can be operably linked to the transgene to direct expression of a polypeptide in particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA in tissues or cells of the animals. A transgenic founder animal can then be used to breed additional animals carrying the transgene. Moreover, transgenic animals carrying a transgene encoding the transgene can further be bred to other transgenic animals carrying other transgenes.

The present invention also provides isolated polypeptides and variants and fragments thereof that are encoded by the nucleic acid molecules of the invention. For example, as described above, the nucleotide sequences can be used to design primers to clone and express cDNAs encoding the polypeptides of the invention.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be "isolated" or "purified."

The polypeptides of the invention can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity. In one embodiment, the language "substantially free of cellular material" includes preparations of the polypeptide having less than about 30% (by dry weight) other proteins (i.e., contaminating protein), less than about 20% other proteins, less than about 10% other proteins, or less than about 5% other proteins.

When a polypeptide is recombinantly produced, it can also be substantially free of culture medium, i.e., culture medium represents less than about 20%, less than about 10%, or less than about 5% of the volume of the protein preparation. The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, a polypeptide comprises an amino acid sequence selected from the group consisting of SEQ ID NOS: 2, 4, 8, 10 and 16 and the complements thereof. However, the invention also encompasses sequence variants. Variants include a substantially homologous protein encoded by the same genetic locus in an organism, i.e., an allelic variant. Variants also encompass proteins derived from other genetic loci in an organism, but having substantial homology to a polypeptide of the invention. Variants also include proteins substantially homologous to these polypeptides but derived from another organism, i.e., an ortholog. Variants also include proteins that are substantially homologous to these polypeptides that are produced by chemical synthesis. Variants also include proteins that are substantially homologous or identical to these polypeptides that are produced by recombinant methods.

As used herein, two proteins (or a region of the proteins) are substantially homologous or identical when the amino acid sequences are at least about 45–55%, typically at least about 70–75%, more typically at least about 80–85%, and most typically at least about 90–95% or more homologous or identical. A substantially homologous amino acid sequence, according to the present invention, will be encoded by a nucleic acid hybridizing to a nucleic acid sequence described herein, or portion thereof, under stringent conditions as more described above.

To determine the percent homology or identity of two amino acid sequences, or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position. As used herein, amino acid or nucleic acid "homology" is equivalent to amino acid or nucleic acid "identity". The percent homology between the two sequences is a function of the number of identical positions shared by the sequences (i.e., percent homology equals the number of identical positions/total number of positions times 100).

The invention also encompasses polypeptides having a lower degree of identity but having sufficient similarity so as to perform one or more of the same functions performed by a polypeptide encoded by a nucleic acid of the invention. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ine; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., Science 247:1306–1310 (1990).

Preferred computer program methods to determine identify and similarity between two sequences include, but are not limited to, GCG program package (Devereux, J., et al., *Nucleic Acids Res.,* 12(1):387 (1984)), BLASTP, BLASTN, FASTA (Atschul, S. F. et al., *J. Molec. Biol.,* 215:403 (1990)).

A variant polypeptide can differ in amino acid sequence by one or more substitutions, deletions, insertions, inversions, fusions, and truncations or a combination of any of these. Further, variant polypeptides can be fully functional or can lack function in one or more activities. Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region. As indicated, variants can be naturally-occurring or can be made by recombinant means or chemical synthesis to provide useful and novel characteristics for the polypeptide. This includes preventing immunogenicity from pharmaceutical formulations by preventing protein aggregation.

Amino acids that are essential for function can be identified by methods known in the art, such as site-directed mutagenesis or alanine-scanning mutagenesis (Cunningham et al., *Science,* 244:1081–1085 (1989)). The latter procedure introduces single alanine mutations at every residue in the molecule. The resulting mutant molecules are then tested for biological activity in vitro, or in vitro proliferative activity. Sites that are critical for polypeptide activity can also be determined by structural analysis such as crystallization, nuclear magnetic resonance or photoaffinity labeling (Smith et al., J. Mol. Biol., 224:899–904 (1992); de Vos et al. *Science,* 255:306–312 (1992)).

The invention also includes polypeptide fragments or portions of the polypeptides of the invention, as well as fragments of the variants of the polypeptides described herein. As used herein, a fragment comprises at least 6 contiguous amino acids. Useful fragments include those that retain one or more of the biological activities of the polypeptide as well as fragments that can be used as an immunogen to generate polypeptide specific antibodies.

Biologically active fragments (peptides which are, for example, 6, 9, 12, 15, 20, 30, 35, 36, 37, 38, 39, 40, 50, 100 or more amino acids in length) can comprise a domain, segment, or motif that has been identified by analysis of the polypeptide sequence using well-known methods, e.g., signal peptides, extracellular domains, one or more transmembrane segments or loops, ligand binding regions, zinc finger domains, DNA binding domains, acylation sites, glycosylation sites, or phosphorylation sites.

The invention also provides fragments with immunogenic properties. These contain an epitope-bearing portion of the polypeptides and variants of the invention. These epitope-bearing peptides are useful to raise antibodies that bind specifically to a polypeptide or region or fragment. These peptides can contain at least 6, 7, 8, 9, 12, at least 14, or between at least about 15 to about 30 amino acids. The epitope-bearing peptide and polypeptides may be produced by any conventional means (Houghten, R. A., *Proc. Natl. Acad. Sci. USA,* 82:5131–5135 (1985)). Simultaneous multiple peptide synthesis is described in U.S. Pat. No. 4,631, 211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The invention thus provides chimeric or fusion proteins. These comprise a polypeptide of the invention operatively linked to a heterologous protein having an amino acid sequence not substantially homologous to the polypeptide. "Operatively linked" indicates that the polypeptide protein and the heterologous protein are fused in-frame. The heterologous protein can be fused to the N-terminus or C-terminus of the polypeptide. In one embodiment the fusion protein does not affect function of the polypeptide per se. For example, the fusion protein can be a GST-fusion protein in which the polypeptide sequences are fused to the C-terminus of the GST sequences. The isolated polypeptide can be purified from cells that naturally express it, such as from mammary epithelium, purified from cells that have been altered to express it (recombinant), or synthesized using known protein synthesis methods.

In one embodiment, the protein is produced by recombinant DNA techniques. For example, a nucleic acid molecule encoding the polypeptide is cloned into an expression vector, the expression vector introduced into a host cell and the protein expressed in the host cell. The protein can then be isolated from the cells by an appropriate purification scheme using standard protein purification techniques.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

In general, polypeptides or proteins of the present invention can be used as a molecular weight marker on SDS-PAGE gels or on molecular sieve gel filtration columns using art-recognized methods. The polypeptides of the present invention can be used to raise antibodies or to elicit an immune response. The polypeptides can also be used as a reagent, e.g., a labeled reagent, in assays to quantitatively determine levels of the protein or a molecule to which it binds (e.g., a receptor or a ligand) in biological fluids. The polypeptides can also be used as markers for tissues in which the corresponding protein is preferentially expressed, either constitutively, during tissue differentiation, or in a diseased state. The polypeptides can be used to isolate a corresponding binding partner, e.g., receptor or ligand, such as, for example, in an interaction trap assay, and to screen for peptide or small molecule antagonists or agonists of the binding interaction.

In another aspect, the invention provides antibodies to the polypeptides and polypeptide fragments of the invention. The term "antibody" as used herein refers to immunoglobulin molecules and immunologically active portions of immunoglobulin molecules, i.e., molecules that contain an antigen binding site that specifically binds an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind to a polypeptide of the invention; such antibodies can be made using methods known in the art. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science,* 240:1041–1043; Liu et al. (1987) *Proc. Natl. Acad. Sci. USA,* 84:3439–3443; Liu et al. (1987) *J. Immunol.,* 139:3521–3526; Sun et al. (1987) *Proc. Natl. Acad. Sci. USA,* 84:214–218; Nishimura et al. (1987) *Canc. Res.,* 47:999–1005; Wood et al. (1985) *Nature,* 314:446–449; and Shaw et al. (1988) *J. Natl. Cancer Inst.,* 80:1553–1559); Morrison (1985) *Science,* 229:1202–1207; Oi et al. (1986) *Bio/Techniques,* 4:214; U.S. Pat. No. 5,225,539; Jones et al. (1986) *Nature,* 321:552–525; Verhoeyan et al. (1988) *Science,* 239:1534; and Beidler et al. (1988) *J. Immunol.,* 141:4053–4060.

In general, antibodies of the invention (e.g. a monoclonal antibody) can be used to isolate a polypeptide of the invention by standard techniques, such as affinity chromatography or immunoprecipitation. A polypeptide specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, (β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

The present invention also pertains to diagnostic assays and prognostic assays used for prognostic (predictive) purposes to thereby treat an individual prophylactically. Accordingly, one aspect of the present invention relates to diagnostic assays for determining protein and/or nucleic acid expression as well as activity of proteins of the invention, in the context of a biological sample (e.g., blood, serum, cells, tissue) to thereby determine whether an individual is afflicted with a disease or disorder, or is at risk of developing a disorder, e.g., a neurodegenerative disorders such as ARSACS, associated with aberrant expression or activity. The invention also provides for prognostic (or predictive) assays for determining whether an individual is at risk of developing a disorder associated with activity or expression of proteins or nucleic acids of the invention.

Disorders which may be treated or diagnosed by methods described herein include, but are not limited to, neurodegenerative disease comprising one or more symptoms or effects selected from the group consisting of: reduced sensory nerve conduction, reduced motor nerve velocity, hypermyelination of retinal nerve fibers, atrophy of upper cerebellar vermis, absence of Purkinje cells and abnormal neuronal lipid storage. The invention is particularly suited to treat and diagnose ARSACS.

Another aspect of the invention pertains to monitoring the influence of agents (e.g., drugs, compounds) on the expression or activity of proteins of the invention in clinical trials.

An exemplary method for detecting the presence or absence of proteins or nucleic acids of the invention in a biological sample involves obtaining a biological sample from a test subject and contacting the biological sample with a compound or an agent capable of detecting the protein, or nucleic acid (e.g., mRNA, genomic DNA) that encodes the protein, such that the presence of the protein or nucleic acid is detected in the biological sample. A preferred agent for detecting mRNA or genomic DNA is a labeled nucleic acid probe capable of hybridizing to mRNA or genomic DNA sequences described herein. The nucleic acid probe can be, for example, a full-length nucleic acid, or a portion thereof, such as an oligonucleotide of at least 15, 30, 50, 100, 250 or 500 nucleotides in length and sufficient to specifically hybridize under stringent conditions to appropriate mRNA or genomic DNA. Other suitable probes for use in the diagnostic assays of the invention are described herein.

In one embodiment, the agent for detecting proteins of the invention is an antibody capable of binding to the protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. In a preferred embodiment, the antibody is able to distinguish between complete or nearly complete proteins and truncated versions of the same protein.

The term "biological sample" is intended to include tissues, calls and biological fluids isolated from a subject, as well as tissues, cells and fluids present within a subject. For example, the sample can be obtained from a tissue selected from the group consisting of: brain tissue, CNS, lung, fetal lung, testis, lymphocytes, adipose, fibroblasts, skeletal muscle, pancreas, uterus, kidney, tonsil, embryo and isolated cells thereof. That is, the detection method of the invention can be used to detect mRNA, protein, or genomic DNA of the invention in a biological sample in vitro as well as in vivo. For example, in vitro techniques for detection of mRNA include Northern hybridizations and in situ hybridizations. In vitro techniques for detection of protein include enzyme linked immunosorbent assays (ELISAs), Western blots, immunoprecipitations and immunofluorescence. In vitro techniques for detection of genomic DNA include Southern hybridizations. Furthermore, in vivo techniques for detection of protein include introducing into a subject a labeled anti-protein antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample or mammary epithelium isolated by conventional means from a subject. A nucleic acid sample is a sample, e.g., a biological sample, which contains nucleic acid molecules.

The invention also encompasses kits for detecting the presence of proteins or nucleic acid molecules of the invention in a biological sample. For example, the kit can comprise a labeled compound or agent capable of detecting protein or mRNA in a biological sample; means for determining the amount of in the sample; and means for comparing the amount of in the sample with a standard. The compound or agent can be packaged in a suitable container. The kit can further comprise instructions for using the kit to detect protein or nucleic acid.

The diagnostic methods described herein can also be utilized to identify subjects having or at risk of developing a disease or disorder associated with aberrant expression or activity of proteins and nucleic acid molecules of the invention. For example, the assays described herein can be utilized to identify a subject having or at risk of developing a disorder associated with Spastin protein or spastin nucleic acid expression or activity such as a neurodegenerative disorder. Thus, the present invention provides a method for identifying a disease or disorder associated with aberrant expression or activity of proteins or nucleic acid molecules of the invention, in which a test sample is obtained from a subject and protein or nucleic acid molecule (e.g., mRNA, genomic DNA) is detected, wherein the presence of an altered protein or nucleic acid molecule is diagnostic for a subject having or at risk of developing a disease or disorder associated with aberrant expression or activity of the protein or nucleic acid sequence of the invention. In certain embodiments as described herein, it is valuable to determine the genotype of an individual, particularly where a specific allelic form is associated with disease. For example, it will be valuable for purposes of diagnosis to determine an individual's genotype for the C52454T mutation with respect to ARSACS diagnosis, i.e., to identify alteration in the spastin gene or Spastin protein.

Detection of the alteration can involve the use of a probe/primer in a polymerase chain reaction (PCR) (see, e.g., U.S. Pat. Nos. 4,683,195 and 4,683,202), such an anchor PCR or RACE PCR, or, alternatively, in a ligation chain reaction (LCR) (see, e.g., Landegran et al. (1988) *Science,* 241:1077–1080; and Nakazawa et al. (1994) *PNAS,* 91:360–364), the latter of which can be particularly useful for detecting point mutations (see Abravaya et al. (1995) *Nucleic Acids Res.,* 23:675–682). This method can include the steps of collecting a sample of cells from a patient, isolating nucleic acid molecules (e.g., genomic, mRNA or both) from the cells of the sample, contacting the nucleic acid sample with one or more primers which specifically hybridize to the gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. In one embodiment allele-specific primers are utilized.

Alternative amplification methods include: self sustained sequence replication (Guatelli, J. C. et al. (1990) *Proc. Natl. Acad. Sci. USA,* 87:1874–1878), transcriptional amplification system (Kwoh, D. Y. et al., (1989) *Proc. Natl. Acad. Sci. USA,* 86:1173–1177), Q-Beta Replicase (Lizardi, P. M. et al., (1988) *Bio/Technology,* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a given gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicate mutations in the sample DNA. Moreover, the use of sequence specific ribozymes (see, for sample, U.S. Pat. No. 5,498,531) can be used to score for the presence of specific mutations, e.g., the C5254T mutation, by development or loss of a ribozyme cleavage site.

In other embodiments, genetic mutations can be identified by hybridizing a sample and control nucleic acids, e.g., DNA or RNA, to high density arrays containing many oligonucleotide probes (Cronin, M. T. et al. (1996) *Human Mutation,* 7:244–255; Kozal, M. J. et al. (1996) *Nature Medicine,* 2:753–759). For example, genetic mutations can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the gene and detect specific mutations by comparing the sequence of the gene from the sample with the corresponding wild-type (control) gene sequence. Examples of sequencing reactions include those based on techniques developed by Maxim and Gilbert ((1997) *PNAS,* 74:560) or Sanger ((1977) *PNAS,* 74:5463). It is also contemplated that any of a variety of automated sequencing procedures can be utilized when performing the diagnostic assays ((1995) *Biotechniques,* 19:448), including sequencing by mass spectrometry (see, e.g., PCT International Publication No. WO 94/16101; Cohen et al. (1996) *Adv. Chromatogr.,* 36:127–162; and Griffin et al. (1993) *Appl. Biochem. Biotechnol.,* 38:147–159).

Other methods for detecting mutations include methods in which protection from cleavage agents is used to detect mismatched bases in RNA/RNA or RNA/DNA heteroduplexes (Myers et al. (1985) *Science,* 230:1242). In general, the art technique of "mismatch cleavage" starts by providing heteroduplexes formed by hybridizing (labeled) RNA or DNA containing the wild-type sequence with potentially mutant RNA or DNA obtained from a tissue sample. The double-standard duplexes are treated with an agent that cleaves single-stranded regions of the duplex such as which will exist due to base pair mismatches between the control and sample strands. For instance, RNA/DNA duplexes can be treated with Rnase and DNA/DNA hybrids treated with S1 nuclease to enzymatically digest the mismatched regions. After digestion of the mismatched regions, the resulting material is then separated by size on denaturing polyacrylamide gels to determine the site of mutation. See, for example Cotton et al. (1988) *Proc. Natl. Acad. Sci. USA,* 85:4397; Saleeba et al. (1992) *Methods Enzymol.,* 217:286–295. In certain embodiments, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis,* 15:1657–1662). According to an exemplary embodiment, a probe based on an nucleotide sequence of the invention is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in nucleic acid molecules described herein. For example, single strand conformation polymorphism (SSCP) may be used to detect differences in electrophoretic mobility between mutant and wild type nucleic acids (Orita et al. (1989) *Proc. Natl. Acad. Sci. USA,* 86:2766, see also Cotton (1993) *Mutat Res,* 285:125–144; and Hayashi (1992) *Genet Anal. Tech. Appl.,* 9:73–79). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.,* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature,* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.,* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature,* 324:163); Saiki et al. (1989) *Proc. Natl. Acad. Sci. USA,* 86:6320). Such allele-specific oligonucleotides are hybridized to PCR amplified target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.,* 17:2437–2448) or at the extreme 3' end of one primer where, under appropriate conditions, mismatch can prevent, or reduce polymerase extension (Prossner (1993) *Tibtech,* 11:238). In addition it may be desirable to introduce a novel restriction site in the region of the mutation to create cleavage-based detection (Gasparini et al. (1992) *Mol. Cell Probes,* 6:1). It is anticipated that in certain embodiments amplification may also be performed using Taq ligase for amplification (Barany (1991) *Proc. Natl. Acad. Sci. USA,* 88:189). In such cases, ligation will occur only if there is a perfect match at the 3' end of the 5' sequence making it possible to detect the presence of a known mutation at a specific site by looking for the presence or absence of amplification. Single base extension (SBE) and SBE fluorescence resonance energy transfer (SBE-FRET) can also be used to identify the specific nucleotide which occupies a given position in a nucleic acid molecule.

The methods described herein may be performed, for example, by utilizing pre-packaged diagnostic kits comprising at least one probe nucleic acid molecule or antibody reagent described herein, which may be conveniently used, e.g., in clinical settings to diagnose patients exhibiting symptoms or family history of a disease or illness involving a gene of the present invention. Any cell type or tissue in which the gene is expressed may be utilized in the prognostic assays described herein.

The invention will now be described by the following non-limiting examples. The teachings of all references cited herein are incorporated herein by reference in their entirety.

EXEMPLIFICATION

Methods

All subjects participating in this study gave informed consent according to institutional and national standards (29). Sequence analysis was performed on 24 ARSACS patients from 17 families.

BAC/PAC DNA Preparation

Small quantities of DNA were prepared from BAC and PAC cell cultures (12.5 μl Chloramphenicol for BACS, 30 μg/ml Kanamycin for PACs) using a modified alkaline lysis procedure according to a published protocol (30). Larger quantities of DNA for the construction of libraries and direct sequencing were prepared using Qiagen (Qiagen, Valencia, Calif.) or Nucleobond columns (The Nest Group, Southboro, Mass.) according to the manufacturers' protocols.

M13 Library Construction and Preparation of M13 Single-Stranded DNA

BAC and PAC DNA was sheared in a sonicator to an average size of 2 kb and the ends were made blunt with Mung Bean Nuclease (New England Biolabs, Beverly, Mass.). The fragments were gel-purified, and subcloned into an M13 mp18 Sma I-cut dephosphorylated cloning vector (Amersham, Uppsala, Sweden). Ligation reactions were transformed into XL2-Blue competent cells (Stratagene, LaJolla, Calif.). Phage plaques of M13 subclones from the BACs and PACs were grown overnight in 0.5 ml of 2× YT media with 10 μl of log phase TG-1 cells. Single-stranded M13 DNA for sequencing was purified from 100 μl of the culture supernatant with magnetic beads (PerSeptive Diagnostics, Cambridge, Mass.) according to the manufacturers instructions.

Sequencing

Fluorescent sequencing of PCR products and M13 single-stranded DNA was accomplished using the Dye Primer Cycle Sequencing Ready Reaction kit (Perkin Elmer, Foster City, Calif.). Sequencing reactions contained approximately 400 ng of template in 1.5 μl and 3 μl of assay mixture for each primer. The thermal cycling parameters for the sequencing reactions were: 96° C. for 10 seconds, 55° C. for 5 seconds, and 70° C. for 1 minute (15 cycles) followed by 96° C. for 10 seconds, and 70° C. for 1 minute (15 cycles). Reaction products for each primer were combined and purified with an ethanol precipitation. Sequence samples were prepared, loaded, and run on ABI 377 sequencers according to the manufacturer's instructions (Perkin Elmer). The sequences were assembled into contigs and analyzed with the STADEN software package (version 1997.1) (31, 32) and Auto Assembler (version 2.0) (Perkin Elmer). Direct sequencing of BACs was accomplished with Dye Terminator chemistry according to a previously published protocol (33). The sequence of the entire mouse and human ORFs was verified by either sequencing unambiguously on both strands or by sequencing a single strand with both the Dye Primer and the Dye Terminator reaction systems. All sequences were compared with GenBank databases and dbEST using the Search Launcher Batch Client software for Macintosh from Baylor College of Medicine (34) with Repeat/Masker prescreening.

Computational Analyses

World Wide Web-based hyper-text (http) sequence analysis included (using default parameters): BLAST; FASTA; PSORT; EXPASY Proteomics tools; BCM Search Launcher; COILS (35) web server, and the ftp site, mac-search-launcher.

Mutation Analysis 50 ng of genomic DNA, extracted from peripheral blood leukocytes, was amplified using the primers in FIG. 7. Primer pairs were designed using the web-based version of the Primer 3.0 program and PCR reactions were individually optimized. The resulting products were purified using magnetic beads (PerSeptive Diagnostics) according to the manufacturer's instructions and sequenced as above.

RNA Preparation and Northern Blot Analysis

Total RNA was extracted using the guanidinium/CsCl method from skin fibroblast cell lines from ARSACS patients and a control individual; the cell lines were grown in Eagle modified MEM (CellGro, Herndon, Va.) with 10% FBS (Canadian Life Technology, Burlington, Ontario). 10 μg of RNA was electrophoresed in a 1% agarose gel and then transferred to a nylon membrane (Magna Charge, MSI, Westboro, Mass.) by capillary transfer with 20× SSC buffer. Pre-transfer alkaline hydrolysis of the gel was performed with 0.05M NaOH. The $^{32}P$-labeled spastin probe was generated by random priming with the Rediprime II system (Amersham) using the 1.8 kb insert from an IMAGE cDNA clone (279258) purified after separation on low melting point agarose (Life Technologies, Rockville, Md.). Hybridization for both the fibroblast blot and the multiple tissue northern blot (MTN, Human I #7760-1, Clontech) was done in ExpressHyb buffer (Clontech, Palo Alto, Calif.) followed by washing according to manufacturer's instructions. The size standard for both northern blots was a 0.249.5 kb RNA ladder (Life Technologies).

RT-PCR 500 ng of total RNA from skin fibroblasts of ARSACS patients and controls, as well as a commercial preparation of total RNA from cerebellum (Clontech), were amplified using sense and antisense primers (FIG. 7) and the Superscript one step kit (Life Technologies). In all cases a parallel control reaction was set up in the absence of RT. The resulting products were purified and sequenced as above.

In Situ Hybridizations

Oligonucleotides complementary to nucleotides 11,009–11,055 of the human spastin gene (probe NIB226-1) and a sense 45-mer for the same region were synthesized and purified (MedProbe, Oslo, Norway). To exclude the possibility of any cross-hybridization to other human mRNAs, homology searches were carried out. A database search revealed no significant homologies, except for the intended targets. The oligonucleotides were subsequently labeled with a $^{35}S$-labeled dATP (NEG 034H, NEN DuPont, Boston, Mass.) at the 3' end using terminal dideoxy nucleotides transferase to a specific activity of $2\times10^9$ cpm/$\mu$g and purified on a Nensorb 20 column.

The tissue was cut to 14 $\mu$m thickness in a cryostat, thawed onto Fisher probe on (+) slides (Fisher Biotech, Springfield, N.J.), and processed for in situ hybridization according to Schalling et al (36). In brief, sections were incubated at 42° C. for 15–18 hours with 106 cpm of labeled probe per 100 $\mu$l of a solution containing 50% formamide, 4× SSC, 1× Denhardt's solution, 1% sarcosyl, 0.02 M sodium phosphate ($NaPO_4$, pH 7.0) and 10% dextran sulfate mixed with 500 $\mu$g/ml sonicated salmon sperm DNA and 200 mM dithiothreitol. Sections were rinsed in 1× SSC at 55° C. for one hour, dried and exposed to x-ray film (Amersham Hyperfilm β-max) for 14–21 days.

Mouse BAC Clone and Radiation Hybrid (RH) Panel Analysis

The clone containing the mouse genomic sequence (418__B__11) is from a 129 SV mouse BAC library, CitbCJ7B cloned in the vector pBeloBAC11 (Research Genetics, Huntsville, Ala.). The RH mapping of mouse spastin was performed using the T31 mouse-hamster hybrid mapping panel (11). The initial attempts with several mouse spastin primers failed due to the amplification of a hamster PCR product of similar size to the mouse product. A hamster PCR product was sequenced, which revealed minor sequence differences with mouse spastin. The successful mouse spastin primers were MARS-3F ((TCATTCATATGTCCCAGGGACATGT; SEQ ID NO: 72) and MARS-3R (CTACTAGAACTGCATGTGCCGC; SEQ ID NO: 73). The RH vector obtained from testing the T31 panel was compared to the reference map generated at MIT (12) using the "placement" function of RHMAPPER Computation of the $P_{excess}$ Statistic Seven-marker haplotypes for 55 ARSACS and 58 normal chromosomes were obtained from 68 obligate carrier parents by not counting copies that were considered to be identical by descent within a pedigree (5). Marker haplotypes were constructed using the SIMWALK2 program (37). The simple linkage disequilibrium mapping measure $P_{excess}$=($p_{affected}$−$p_{normal}$)(1−$p_{normal}$) was calculated from the frequencies of haplotypes.

While this invention has been particularly shown and described with references to preferred embodiments thereof, it will be understood by those skilled in the art that various changes in form and details may be made therein without departing from the scope of the invention encompassed by the appended claims.

REFERENCES

1. Bouchard J -P. Recessive spastic ataxia of Charlevoix-Saguenay. In: "Handbook of Clinical Neurology 16: hereditary neuropathies and spinocerebellar degenerations", (J.M.B.V. de Jong, Ed) pp. 451–459, Elsevier Science Publishers, Amsterdam. (1991).
2. Bouchard, J. P., et al. Autosomal recessive spastic ataxia of Charlevoix-Saguenay, *Neuromuscular Disorders* 8, 474–479 (1998).
3. De Braekeleer, M., et al. Genetic epidemiology of autosomal recessive spastic ataxia of Charlevoix-Saguenay in northeastern Quebec. *Genetic Epidemiology* 10, 17–25 (1993).
4. Charbonneau H. & Robert N. The French origins of the Canadian population 1608–1759. In: Harris R C (ed) Historical atlas of Canada Volume I: from the beginning to 1800, University of Toronto Press, Toronto, plate 45 (1987).
5. Richter, A., et al. Location score and haplotype analyses of the locus for autosomal recessive spastic ataxia of Charlevoix-Saguenay in chromosome region 13q11. *Am. J. Hum. Genet* 64, 768–775 (1999).
6. Engert, J. C., et al. High Resolution Physical and Transcript Map of the Autosomal Recessive Spastic Ataxia of Charlevoix-Saguenay (ARSACS) Candidate Region in Chromosome 13q11. *Submitted* (1999).
7. Fink, A L. Chaperone-mediated protein folding. *Physiological Reviews.* 79, 425–49 (1999).
8. Buchner J. Hsv90 & Co.—a holding for folding. *Trends in Biochemical Sciences.* 24, 136–41, (1999).
9. Gupta, R. S. Phylogenetic analysis of the 90 kD heat shock family of protein sequences and an examination of the relationship among animals, plants, and fungi species. *Molecular Biology & Evolution;* 12, 1063–1073 (1995).
10. Nakai, K. & Kanehisa, M. A knowledge base for predicting protein localization sites in eukaryotic cells, *Genomics* 14, 897–911 (1992).
11. McCarthy, L. C., et al. A First-Generation Whole-Genome Radiation Hybrid Map Spanning the Mouse Genome. *Genome Research* 7, 1153–1161 (1997).
12, W. J, Van Etten, et at, Radiation hybrid map of the mouse genome. *Nature Gene.* ?2, 384–387 (1999).
13. Brown C J. et al. The human XIST gene: analysis of a 17 kb inactive X-specific RNA that contains conserved repeats and is highly localized within the nucleus. *Cell. T*1, 527–42, (1992).
14. Porchet, N, Aubert, J P, & Laine, A MUC5B, the 10.7-kb large central exon encodes various alternate subdomains resulting in a super-repeat. *Journal of Biological Chemistry* 272, 3168–78 (1997).
15. Gentles A J. & Karlin S. Why are human G-protein-coupled receptors predominantly intronless? *Trends in Genetics.* 15, 47–49 (1999).
16. Palmer J D. & Logsdon J M Jr The recent origins of introns. *Current Opinion in Genetics & Development.* 1, 470–7, (1991).
17. Edward M. Marcotte et al. Detecting Protein Function and Protein-Protein Interactions from Genome Sequences. *Science* 285, 751–753 (1999).

18. Prodromou C. et al. Identification and structural characterization of the ATP/ADP-binding site in the Hsp90 molecular chaperone. *Cell* 90, 65–75 (1997).

19. Kimura Y. Yahara I. & Lindquist S. Role of the protein chaperone YDJ1 in establishing Hsp90-mediated signal transduction pathways. *Science* 268, 1362–1365, (1995).

20. Dittmar K D. Banach M. Galigniana M D. & Pratt W B. The role of DnaJ-like proteins in glucocorticoid receptor.hsp90 heterocomplex assembly by the reconstituted hsp90.p60.hsp70 foldosome complex. *Journal of Biological Chemistry* 273, 7358–66, (1998).

21. Dickie, M. M. Tumbler, tb, *Mouse News Lett;* 32, 45 (1965),

22. L. Kruglyak. Prospects for whole-genome linkage disequilibrium mapping of common disease genes. *Nature Genet.* 22, 139–144 (1999).

23. Hästbacka J., et al Linkage disequilibrium mapping in isolated founder populations: diastrophic dysplasia in Finland. *Nature Genet.* 2, 204–211 (1992).

24. Thompson E A. & Neel J V. Allelic disequilibrium and allele frequency distribution as a function of social and demographic history. *American Journal of Human Generics.* 60, 197–204, (1997).

25. Graham J. & Thompson E A. Disequilibrium likelihoods for fine-scale mapping of a rare allele. *American Journal of Human Genetics.* 63, 1517–30, (1998).

26. Baehnke M. Limits of resolution of genetic linkage studies: implications for the positional cloning of human disease genes. *American Journal of Human Genetics.* 55, 379–390 (1994).

27. Graham J. (thesis) Disequilibrium fine-mapping a rare allele via coalesent models of gene ancestry Ph.D., Univ. of Washington, Seattle (1998).

28. De Braekeleer, M. Geographic distribution of 18 autosomal recessive disorders in the French Canadian population of Saguenay-Lac-St-Jean, Quebec. *Annals of Human Biology* 22, 111–122 (1995).

29. Knoppers B M, & Laberge C DNA sampling and informed consent. *Can Med Assoc J* 144, 128–129 (1991).

30. Birren., B. W., Mancino, V., & Shizuya, H. Bacterial Artificial Chromosomes. In "Genome Analysis: A Laboratory Manual" Volume 3 (Birren, B., Green, E. D., Klaphoz, S., Myers, R. M., Riethman, H., and Roskams, J. Eds.), pp. 241–295, Cold Spring Harbor Laboratory. Press, Plainview N.Y. (1999).

31. Bonfield J K. Smith K L. & Staden, R. A new DNA sequence assembly program. *Nucleic Acids Research.* 23, 4992–4999 (1995).

32. Bonfield J K. & Staden, R. Experiment files and their application during large-scale sequencing projects. *DNA Sequence* 6, 109–117, (1996).

33. Boysen C., Simon M I, & Hood L. Fluorescence-based sequencing directly from bacterial and P1-derived artificial chromosomes *Biotechniques* 23, 978–82 (1997).

34. Smith R F, Wiese B A, Wojzynski M K, Davison D B, & Worley K C. BCM Search Launcher—An Integrated Interface to Molecular Biology Data Base Search and Analysis Services Available on the World Wide Web. *Genome Res* 6, 454–62 (1996).

35. Lupas, A., M. Van Dyke, & J. Stock Predicting Coiled Coils from Protein Sequences. *Science* 52, 1162–1164 (1991).

36. Schalling M. et al Neuropeptide Y and catecholamine synthesizing enzymes and their mRNAs in rat sympathetic neurons and adrenal glands: Studies on expression, synthesis and axonal transport after pharmacological and experimental manipulations using hybridization techniques and radioimmunoassay. *Neuroscience* 41, 753–766 (1991), 37. Weeks D E, Sobel E, O{Connell J R, & Lange K. Compute programs for multilocus haplotyping of general pedigrees. *Am J Hum Genet* 56, 1506–1507 (1995).

38. Devlin B. & Risch N. A comparison of linkage disequilibrium measures for fine-scale mapping. *Genomics* 29, 311–322 (1995).

39. de la Chapelle, A. & Wright, F. A.D. Linkage disequilibrium mapping in isolated populations: the example of Finland revisited. *Proc. Natl. Acad. Sci., USA* 95, 12416–23 (1998).

40. Austerlitz F. & Heyer E. Impact of demographic distribution and population growth rate on haplotypic diversity linked to a disease gene and their consequences for the estimation of recombination rate: example of a French Canadian population. *Genetic Epidemiology.* 16, 2–14, (1999).

41. McNally, E. M., et al., Mild and severe muscular dystrophy caused by a single gamma-sarcoglyean mutation. *Am. J. Hum. Genet.* 59, 1040–1047 (1996).

42. Nagase, T., et al., Prediction of the coding sequences of unidentified human genes, X1. The complete sequences of 100 new cDNA clones from brain which code for large proteins in vitro. *DNA Res.* 5, 277–286 (1998).

43. Thompson, J. D., Higgins, D. G. & Gibson, T. J. CLUSTAL W: improving the sensitivity of progressive multiple sequence alignment through sequence weighting, positions-specific gap penalties and weight matrix choice. *Nucleic Acids Research,* 22, 4673–4680 (1994).

---

What is claimed is:

1. An isolated nucleic acid molecule comprising a nucleotide sequence of SEQ ID NO: 7 or the complement of SEQ ID NO: 7.

2. A nucleic acid construct comprising the isolated nucleic acid molecule of claim 1.

3. The nucleic acid construct of claim 2 wherein the isolated nucleic acid molecule is operatively linked to a regulatory sequence.

4. A recombinant host cell comprising the isolated nucleic acid molecule of claim 1.

5. The recombinant host cell of claim 4 wherein the isolated nucleic acid is operatively linked to a regulatory sequence.

6. An isolated nucleic acid molecule consisting of a nucleotide sequence of SEQ ID NO: 47 or the complement of SEQ ID NO: 47.

* * * * *

SEQUENCE LISTING

```
<160> NUMBER OF SEQ ID NOS: 73

<210> SEQ ID NO 1
<211> LENGTH: 12793
<212> TYPE: DNA
<213> ORGANISM: Homo sapiens

<400> SEQUENCE: 1

atgatttaca ggaagaccat gtactcagct gcagcttcta aatccagaac gatttgcacg      60

tcttatcaag gaagtaatga atacattctg gcctggcaga gaattgattg ttcaatggta     120

tccatttgat gaaaacagaa atcacccatc tgtttcatgg cttaagatgg tttggaaaaa     180
```

-continued

```
tctttatata catttttcag aggatttgac tttatttgat gagatgccac ttatccccag    240
aactatacta gaggaaggtc agacatgtgt ggaactcatt agactcagga ttccatcgtt    300
agtcatttta gacgatgaat ctgaagcaca gcttccagaa tttttagcag acattgtaca    360
aaaacttgga gggtttgtcc ttaaaaaatt agatgcatct atacaacatc cgcttattaa    420
aaaatatatt cattcaccat taccaagtgc tgttttgcag ataatggaga agatgccatt    480
gcagaaattg tgtaatcaaa taacttcgct acttccaaca cacaaagatg ccctgaggaa    540
gttcttggct agtttaaccg atagcagtga gaaagagaaa agaattattc aagaattggc    600
aatattcaag cgcattaacc attcttctga tcagggaatt tcctcttata caaaattgaa    660
aggttgtaaa gtcttacacc atactgccaa actcccagca gatctgcgac tttctatttc    720
agtaatagac agtagtgatg aagctactat tcgtctggca aacatgttga aaatagaaca    780
gttaaagacc actagctgct taaagcttgt tttaaaagat attgaaaatg cattttattc    840
acatgaagag gtaacacagc ttatgttatg ggtccttgag aatctatctt ctcttaaaaa    900
tgagaatcca aatgtgcttg agtggttaac accattaaaa ttcatccaga tatcacagga    960
acagatggta tcagctggtg aactctttga ccctgatata gaagtactaa aggatctctt   1020
ttgtaatgaa gaaggaacct atttcccacc ctcagttttt acctcaccag atattcttca   1080
ctccttaaga cagattggtt taaaaaacga agccagtctc aaagaaaagg atgttgtgca   1140
agtggcaaaa aaaattgaag ccttacaggt cggtgcttgt cctgatcaag atgttcttct   1200
gaagaaagcc aaaaccctct tactggtttt aaataagaat cacacactgt tgcaatcatc   1260
tgaaggaaag atgacattga agaaaataaa atgggttcca gcctgcaagg aaaggcctcc   1320
aaattatcca ggctctttgg tctggaaagg agatctctgt aatctctgtg caccaccaga   1380
tatgtgtgat gtaggccatg caattctcat tggctcctca cttcctcttg ttgaaagtat   1440
ccatgtaaac ctggaaaaag cattagggat cttcacaaaa cctagcctta gtgctgtctt   1500
aaaacacttt aaaattgttg ttgattggta ttcttcaaaa acctttagtg atgaagacta   1560
ctatcaattc cagcatattt tgcttgagat ttacggattc atgcatgatc atctaaatga   1620
agggaaagat tcttttagag ccttaaaatt tccatgggtt tggactggca aaaagttttg   1680
tccacttgcc caggctgtga ttaaaccaat ccatgatctt gaccttcagc cttatttgca   1740
taatgtacct aaaaccatgg caaaattcca ccaactattt aaggtctgtg gttcaataga   1800
ggagttgaca tcagatcata tttccatggt tattcagaag atatatctca aaagtgacca   1860
agatctcagt gaacaagaaa gcaaacaaaa tcttcatctt atgttgaata ttatcagatg   1920
gctgtatagc aatcagattc cagcaagccc caacacacca gttcctatac atcatagcaa   1980
aaatccttct aaacttatca tgaagccaat tcacgaatgc tgttattgtg acattaaagt   2040
tgatgacctt aatgacttac ttgaagattc tgtggaacca atcattttgg tgcatgagga   2100
catacccatg aaaactgcag aatggctaaa agttccatgc cttagtacaa gactgataaa   2160
tcctgaaaac atgggatttg agcagtcagg acaaagagag ccacttactg taagaattaa   2220
aaatattctg gaagaatacc cttcagtgtc agatattttt aaagaactac ttcaaaacgc   2280
tgatgatgca aatgcaacag aatgcagttt cttgattgat atgagaagaa atatggacat   2340
aagagagaat ctcctagacc cagggatggc agcttgtcat ggacctgctt tgtggtcatt   2400
caacaattct caattctcag attcagattt tgtgaacata actaggttag gagaatcttt   2460
aaaaagggga gaagttgaca aagttggaaa atttggtctt ggatttaatt ctgtgtacca   2520
tatcactgac attcccatca ttatgagtcg ggaattcatg ataatgttcg atccaaacat   2580
```

-continued

```
aaatcatatc agtaaacaca ttaaagacaa atccaatcct gggatcaaaa ttaattggag   2640
taaacaacag aaaagactta gaaaatttcc taatcagttc aaaccattta tagatgtatt   2700
tggctgtcag ttacctttga ctgtagaagc accttacagc tataatggaa ccctttttccg   2760
actgtccttt agaactcaac aggaagcaaa agtgagtgaa gttagtagta cgtgctacaa   2820
tacagcagat atttattctc ttgtggatga atttagtctc tgtggacaca ggcttatcat   2880
tttcactcag agtgtaaagt caatgtattt gaagtacttg aaaattgagg aaaccaaccc   2940
cagtttagca caagatacag taataattaa aaaaaaatcc tgctcttcca aagcattgaa   3000
cacacctgtc ttaagtgttt taaaagaggc tgctaagctc atgaagactt gcagcagcag   3060
taataaaaag cttcccagtg atgaaccaaa gtcatcttgc attcttcaga tcacagtgga   3120
agaatttcac catgtgttca gaaggattgc tgatttacag tcgccacttt ttagaggtcc   3180
agatgatgac ccagctgctc tctttgaaat ggctaagtct ggccaatcaa aaaagccatc   3240
agatgagttg tcacagaaaa cagtagagtg taccacgtgg cttctgtgta cttgcatgga   3300
cacaggagag gctctgaagt tttccctgag tgagagtgga agaagactag gactggttcc   3360
atgtggggca gtaggagttc agctgtcaga aatccaggac cagaagtgga cagtgaaacc   3420
acacattgga gaggtgtttt gctatttacc tttacgaata aaaacaggct tgccagttca   3480
tatcaatggg tgctttgctg ttacatcaaa taggaaagaa atctggaaaa cagatacaaa   3540
aggacgatgg aataccacgt tcatgagaca tgttattgtg aaagcttact tacaggtact   3600
gagtgtctta cgggacctgg ccactagtgg ggagctaatg gattatactt actatgcagt   3660
atggcccgat cctgatttag ttcatgatga tttttctgta atttgccaag gattttatga   3720
agatatagct catggaaaag ggaaagaact gaccaaagtc ttctctgatg gatctacttg   3780
ggtttccatg aagaacgtaa gatttctaga tgactctata cttaaaagaa gagatgttgg   3840
ttcagcagcc ttcaagatat tttgaaata cctcaagaag actgggtcca aaaacctttg   3900
tgctgttgaa cttccttctt cggtaaaatt aggatttgaa gaagctggct gcaaacagat   3960
actacttgaa aacacatttt cagagaaaca gtttttttct gaagtgtttt ttccaaatat   4020
tcaagaaatt gaagcagaac ttagagatcc tttaatgatc tttgttctaa atgaaaaagt   4080
tgatgagttc tcgggagttc ttcgtgttac tccatgtatt ccttgttcct tggaggggca   4140
tcctttggtt ttgccatcaa gattgatcca ccccgaagga cgagttgcaa agttatttga   4200
tattaaagat gggagattcc cttatggttc tactcaggat tatctcaatc ctattatttt   4260
gattaaacta gttcagttag gtatggcaaa agatgatatt ttatgggatg atatgctaga   4320
acgtgcagtg tcagtagctg aaattaataa aagtgatcat gttgctgcat gcctaagaag   4380
tagtatctta ttgagtctta tcgatgagaa actaaaaata agggatccta gagcaaagga   4440
ttttgctgca aaatatcaaa caatccgctt ccttccattt ctgacaaaac cagcaggttt   4500
ttctttggac tggaaaggca acagttttaa gcctgaaacc atgtttgcag caactgacct   4560
ttatacagct gaacatcaag atatagtttg tctttttgcaa ccaattctaa atgaaaattc   4620
ccattctttt agaggttgtg gttcagtgtc attggctgtt aaagagtttt tgggattact   4680
caagaagcca acagttgatc tggttataaa ccaattgaaa gaagtagcaa aatcagttga   4740
tgatggaatt acactgtacc aggagaatat caccaatgct tgctacaaat accttcatga   4800
agccttgatg caaaatgaaa tcactaagat gtcaattatt gataagttaa aaccctttag   4860
cttcattcta gttgagaatg catatgttga ctcagaaaag gtttcttttc atttaaattt   4920
```

-continued

```
tgaggcggca ccatacctt atcagttgcc taataagtat aaaaataatt tccgcgaact   4980
ttttgaaacc gtgggtgtga ggcagtcatg cactgttgaa gattttgctc ttgttttgga   5040
atctattgat caagaaagag gaacaaagca aataacagaa gagaattttc agctttgccg   5100
acgaataatc agtgaaggaa tatggagtct cattagagaa aagaaacaag aattttgtga   5160
gaaaaattat ggcaagatat tattgccaga tactaatctt atgcttctcc ctgctaaatc   5220
gttatgctac aatgattgcc cttggataaa agtaaaggat accactgtaa aatattgtca   5280
tgctgacata cccagggaag tagcagtaaa actaggagca gtcccaaagc gacacaaagc   5340
cttagaaaga tatgcatcca atgtctgttt tacaacactt ggcacagaat ttgggcagaa   5400
agaaaaattg accagcagaa ttaagagcat ccttaatgca tatccttctg aaaaggaaat   5460
gttgaaagag cttcttcaaa atgctgatga tgcaaaggcg acagaaatct gttttgtgtt   5520
tgatcctaga cagcatccag ttgatagaat atttgatgat aagtgggccc cattgcaagg   5580
gccagcactt tgtgtgtaca acaaccagcc atttacagaa gatgatgtta gaggaattca   5640
gaatcttgga aaaggcacga aagagggaaa tccttataaa actggacagt atggaatagg   5700
attcaattct gtgtatcata tcacagactg cccatctttt atttctggca atgacatcct   5760
gtgtattttt gatcctcatg ccagatatgc accaggggcc acatccatta gtcccggacg   5820
catgtttaga gatttggatg cagattttag gacacagttc tcagatgttc tggatcttta   5880
tctgggaacc cattttaaac tggataattg cacaatgttc agatttcctc ttcgtaatgc   5940
agaaatggca aaagtttcgg aaatttcgtc tgttccagca tcagacagaa tggtccagaa   6000
tcttttggac aaactgcgct cagatggggc agaacttcta atgtttctta atcacatgga   6060
aaaaatttct atttgtgaaa tagataagag tactggagct ctaaatgtgc tgtattcagt   6120
aaagggcaaa atcacagatg gagacagatt gaaaaggaaa caatttcatg catctgtaat   6180
tgatagtgtt actaaaaaga ggcagctcaa agacatacca gttcaacaaa taacctatac   6240
tatggatact gaggactctg aaggaaatct tactacgtgg ctaatttgta atagatcagg   6300
cttttcaagt atggagaaag tatctaaaag tgtcatatca gctcacaaga accaagatat   6360
tactcttttc ccacgtggtg gagtagctgc ctgcattact cacaactata aaaaacccca   6420
tagggccttc tgtttttttgc ctctttcttt ggagactggg ctgccatttc atgtgaatgg   6480
ccactttgca ctggattcag ccagaaggaa cctgtggcgt gatgataatg gagttggtgt   6540
tcgaagtgac tggaataaca gtttaatgac agcattaata gctcctgcat atgttgaatt   6600
gctaatacag ttaaaaaaac ggtatttccc tggttctgat ccaacattat cagtgttaca   6660
gaacacccct attcatgttg taaaggacac tttaaagaag tttttatcgt tttcccagt   6720
taaccgtctt gatctacagc cagatttata ttgtctagtg aaagcacttt acaattgcat   6780
tcacgaagac atgaaacgtc ttttacctgt tgtgcgggct ccaaatattg atggctctga   6840
cttgcactct gcagttataa ttacttggat caatatgtct acttctaata aaactagacc   6900
attttttgac aatttactac aggatgaatt acaacacctt aaaaatgcag attataatat   6960
caccacacgc aaaacagtag cagagaatgt ctataggctg aaacatctcc ttttagaaat   7020
tggtttcaac ttggtttata actgtgatga aactgctaat ctttaccact gtcttataga   7080
tgcagatatt cctgttagtt atgtgacccc tgctgatatc agatcttttt taatgacatt   7140
ttcctctcct gacactaatt gccatattgg gaagctgcct tgtcgtctgc agcagactaa   7200
tctaaaactt tttcatagtt taaaactttt agttgattat tgttttaaag atgcagaaga   7260
aaatgagatt gaagttgagg gattgcccct tctcatcaca ctggacagtg ttttgcaaac   7320
```

-continued

```
ttttgatgca aaacgaccca agtttctaac aacatatcat gaattgattc catcccgcaa   7380
agacttgttt atgaatacat tatatttgaa atatagtaat attttattga actgtaaagt   7440
tgcaaaagtg tttgacattt ccagctttgc tgatttgtta tcctctgtgt tgcctcgaga   7500
atataagacc aaaagttgca caaagtggaa agacaatttt gcaagtgagt cttggcttaa   7560
gaatgcatgg cattttatta gtgaatctgt aagtgtgaaa gaagatcagg aagaaacaaa   7620
accaacattt gacattgttg ttgatactct aaaagactgg gcattgcttc caggaacaaa   7680
gtttactgtt tcagccaacc agcttgtggt tcctgaagga gatgttctgc ttcctctcag   7740
ccttatgcac attgcagttt ttccaaatgc ccagagtgat aaagtttttc atgctctaat   7800
gaaagccggc tgtattcagc ttgctttgaa caaaatctgt tccaaagaca gtgcatttgt   7860
tcctttgttg tcatgtcaca cagcaaatat agagagcccc acaagcatct tgaaggctct   7920
acattatatg gtccaaactt caacatttag agcagaaaaa ttagtagaaa atgattttga   7980
ggcacttttg atgtatttca actgcaattt gaatcatttg atgtcccaag atgatataaa   8040
aattctaaag tcacttccgt gctataaatc catcagtggc cgctatgtaa gcattggaaa   8100
atttggaaca tgctacgtac ttacaaaaag tatcccttca gctgaagtgg agaaatggac   8160
acaatcatca tcatctgcat ttcttgaaga aaaaatacac ttaaaagaac tatatgaggt   8220
gattggttgt gtacctgtag atgatcttga ggtatatttg aaacacctct taccaaaaat   8280
tgaaaatctc tcttatgatg caaaattaga gcacttgatc taccttaaga atagattatc   8340
aagtgctgag gaattatcag agattaagga acaacttttt gaaaaactgg aaagtttatt   8400
gataatccat gatgctaaca gtagactaaa gcaagcaaag catttctatg atagaactgt   8460
gagagttttt gaagttatgc ttcctgaaaa attgtttatt cctaatgatt tctttaagaa   8520
attggaacaa cttataaaac ccaaaaatca tgttacattt atgacatcct gggtggaatt   8580
cttaagaaat attggactaa aatacatact ttctcagcag cagttgttac agtttgctaa   8640
ggaaatcagt gtgagggcta atacagaaaa ctggtccaaa gaaacattgc aaaatacagt   8700
tgatatcctt ctgcatcata tattccaaga acgaatggat ttgttatctg gaaattttct   8760
gaaagaacta tctttaatac cattcttatg tcctgagcgg gcccccgcgg aattcattag   8820
atttcatcct caatatcaag aggtaaatgg aacacttcct cttataaagt tcaatggagc   8880
acaggtaaat ccaaaattca agcaatgtga tgtactccag ctgttatgga catcctgccc   8940
tattcttcca gagaaagcta caccccttaag cattaaagaa caagaaggta gtgaccttgg   9000
tccacaagaa cagcttgaac aagttttaaa tatgcttaat gttaacctgg atcctcctct   9060
tgataaggta atcaataact gcagaaacat atgcaacata acgacgttgg atgaagaaat   9120
ggtaaaaact agagcaaaag tcttaaggag catatatgaa ttcctcagtg cagaaaaaag   9180
ggaatttcgt tttcagttgc gaggggttgc ttttgtgatg gtagaagatg gttggaaact   9240
tctgaagcct gaggaggtag tcataaacct agaatatgaa tctgatttta aaccttattt   9300
gtacaagcta cctttagaac ttggcacatt tcaccagttg ttcaaacact taggtactga   9360
agatattatt tcaactaagc aatatgttga agtgttgagc cgcatattta aaaattctga   9420
gggcaaacaa ttagatccta atgaaatgcg tacagttaag agagtagttt ctggtctgtt   9480
caggagtcta cagaatgatt cagtcaaggt gaggagtgat ctcgagaatg tacgagacct   9540
tgcgctttac ctcccaagcc aggatggtag attggtaaag tcaagcatct tagtgtttga   9600
cgatgcgcca cattataaaa gtagaatcca ggggaatatt ggtgtgcaaa tgttagttga   9660
```

-continued

```
tctcagccag tgctacttag ggaaagacca tggatttcac actaagttga taatgctctt   9720
tcctcaaaaa cttagacctc gattattgag cagtatactt gaagaacaat tagatgaaga   9780
gactcccaaa gtttgtcagt ttggagcgtt gtgttctctt caaggaagat tgcagttact   9840
cttgtcttct gaacagttca ttacaggact gattagaatt atgaagcatg aaaatgataa   9900
tgcttttctg gccaatgaag aaaaagccat aagactttgc aaagccctaa gagaaggatt   9960
gaaagtatcc tgctttgaaa agcttcaaac aacattaaga gttaaaggtt ttaatcctat  10020
tccccacagc agaagtgaaa cttttgcttt tttgaagcga tttggtaatg cagtcatctt  10080
gctctacatt caacattcag acagtaaaga cattaatttc ctgttagcac tggcaatgac  10140
tcttaaatca gcaactgaca atttgatttc tgacacttca tatttaattg ctatgctagg  10200
atgcaatgat atttacagga ttggtgagaa acttgacagt ttaggagtga aatatgactc  10260
ttcggagcca tcaaaactgg aacttccaat gcctggcaca ccaattcctg ctgaaattca  10320
ttacactctg cttatggacc caatgaatgt tttttacccg ggagaatatg ttgggtacct  10380
tgttgatgct gaaggtggtg atatctatgg atcataccag ccaacataca catatgcaat  10440
tattgtacaa gaagttgaaa gagaagatgc tgacaattct agttttctag gaaagatata  10500
tcagatagat attggttata gtgaatataa aatagttagc tctcttgatc tgtataagtt  10560
ttcaagacct gaggaaagct ctcaaagcag ggacagtgct ccttctacac caaccagccc  10620
cactgagttc ctcacccctg gcctgagaag cattcctcct cttttctctg gtagagagag  10680
ccacaagact tcttccaaac atcagtcccc caaaaagctt aaggttaatt ctttaccaga  10740
aatcttaaaa gaagtgacat ctgtggtgga gcaagcatgg aagcttccag aatcggaacg  10800
aaaaaagatt attaggcggt tgtatttgaa atggcatcct gacaaaaatc cagagaacca  10860
tgacattgcc aatgaagttt ttaaacattt gcagaatgaa atcaacagat tagaaaaaca  10920
ggcttttcta gatcaaaatg cagacagggc ctccagacga acattttcaa cctcagcatc  10980
ccgatttcag tcagacaaat actcatttca gagattctat acttcatgga atcaagaagc  11040
aacgagccat aaatctgaaa gacagcaaca gaacaaagaa aaatgccccc cttcagccgg  11100
acagacttac tctcaaaggt tctttgttcc tcccactttc aagtcggttg gcaatccagt  11160
ggaagcacgc agatggctaa gacaagccag agcaaacttc tcagctgcca ggaatgacct  11220
tcataaaaat gccaatgagt gggtgtgctt taaatgttac ctttctacca agttagcttt  11280
gattgcagct gactatgctg tgaggggaaa gtctgataaa gatgtaaaac caactgcact  11340
tgctcagaaa atagaggaat atagtcagca acttgaagga ctgacaaatg atgttcacac  11400
attggaagct tatggtgtag acagtttaaa aacaagatac cctgatttgc ttccctttcc  11460
tcagatccca aatgacaggt tcacttctga ggttgctatg agggtgatgg aatgtactgc  11520
ctgtatcata ataaaacttg aaaattttat gcaacaaaaa gtgtgaagat atttaacgaa  11580
aaaaaaggta gatcttgaat gtgttgtagc acgaataaat tgctgtactt cattaagctt  11640
cattgccaat tagctaggaa ttgttaagca cattgcagat tgttcttgga gaattctgga  11700
gttgttatga acatgaatac caacggaaaa ccttaactga atctaaaaga aaactatttt  11760
gaagatggtg gtgagctgca aaatagctgg atggatttga atgattggga tgatacatca  11820
ttgaactgca ctttatataa ccaaagctta gcagtttgtt agataagagt ctatgtatgt  11880
ctctggttag gatgaagtta attttatgtt tttaacatgg tatttttgaa ggagctaatg  11940
aaacactgga catataattg gtttaaacat aaggggaatt aagtctttgt agtctgtcat  12000
ttttttaagt ggatcctctt ggatgcgtta ttttctcatc agctggctct gatcatgaat  12060
```

-continued

```
ttgttgtaat tttatgttgt actcagtgca tttaagaaat ggtagagtat tttaatccta  12120

ttacttgact aagagtgtga aggtagtact ttttagagtg cactgagtgc actttacatc  12180

tttatttaaa ttttttttta acatcttatg tttacaggct tcctgtttga tgaagatagc  12240

aacggaaaac tcaaaatggt ggcagttctt attaccagtt gttagtattg tttctggaaa  12300

ctgcttgcca agacaacatt tattaactgt tagaacactt gctttatgtt tgtgtgtaca  12360

tattttccac aaatgttata atttatatag tgtggttgaa caggatgcaa tcttttgttg  12420

tctaaaggtg ctgcagttaa aaaaaaaaca accttttctt tcaatatggc atgtagtgga  12480

gtttttttaa ctttaaaaac atcaaaaatt gttaaaatca ttgtgttatc tagtagttta  12540

taattatcgg cttatatttc cccatgaatg atcagaactg acatttaatt catgtttgtc  12600

tcgccatgct tctttacttt aacatatttc ttttgcagaa tgtaaaaggt aatgataatt  12660

agtttatata agtgtactgg ctgtaaatga tgctaaatat actttatgca attaagggct  12720

tacagaacat gttgaaactt tttttacttt tattgggaat aaggaatgtt tgcacctcca  12780

cattttattg ctt                                                     12793
```

<210> SEQ ID NO 2
<211> LENGTH: 3829
<212> TYPE: PRT
<213> ORGANISM: Homo sapiens

<400> SEQUENCE: 2

```
Met Asn Thr Phe Trp Pro Gly Arg Glu Leu Ile Val Gln Trp Tyr Pro
 1               5                  10                  15

Phe Asp Glu Asn Arg Asn His Pro Ser Val Ser Trp Leu Lys Met Val
            20                  25                  30

Trp Lys Asn Leu Tyr Ile His Phe Ser Glu Asp Leu Thr Leu Phe Asp
        35                  40                  45

Glu Met Pro Leu Ile Pro Arg Thr Ile Leu Glu Glu Gly Gln Thr Cys
    50                  55                  60

Val Glu Leu Ile Arg Leu Arg Ile Pro Ser Leu Val Ile Leu Asp Asp
65                  70                  75                  80

Glu Ser Glu Ala Gln Leu Pro Glu Phe Leu Ala Asp Ile Val Gln Lys
                85                  90                  95

Leu Gly Gly Phe Val Leu Lys Lys Leu Asp Ala Ser Ile Gln His Pro
            100                 105                 110

Leu Ile Lys Lys Tyr Ile His Ser Pro Leu Pro Ser Ala Val Leu Gln
        115                 120                 125

Ile Met Glu Lys Met Pro Leu Gln Lys Leu Cys Asn Gln Ile Thr Ser
    130                 135                 140

Leu Leu Pro Thr His Lys Asp Ala Leu Arg Lys Phe Leu Ala Ser Leu
145                 150                 155                 160

Thr Asp Ser Ser Glu Lys Glu Lys Arg Ile Ile Gln Glu Leu Ala Ile
                165                 170                 175

Phe Lys Arg Ile Asn His Ser Ser Asp Gln Gly Ile Ser Ser Tyr Thr
            180                 185                 190

Lys Leu Lys Gly Cys Lys Val Leu His His Thr Ala Lys Leu Pro Ala
        195                 200                 205

Asp Leu Arg Leu Ser Ile Ser Val Ile Asp Ser Ser Asp Glu Ala Thr
    210                 215                 220

Ile Arg Leu Ala Asn Met Leu Lys Ile Glu Gln Leu Lys Thr Thr Ser
225                 230                 235                 240
```

-continued

```
Cys Leu Lys Leu Val Leu Lys Asp Ile Glu Asn Ala Phe Tyr Ser His
                245                 250                 255

Glu Glu Val Thr Gln Leu Met Leu Trp Val Leu Glu Asn Leu Ser Ser
            260                 265                 270

Leu Lys Asn Glu Asn Pro Asn Val Leu Glu Trp Leu Thr Pro Leu Lys
        275                 280                 285

Phe Ile Gln Ile Ser Gln Glu Gln Met Val Ser Ala Gly Glu Leu Phe
    290                 295                 300

Asp Pro Asp Ile Glu Val Leu Lys Asp Leu Phe Cys Asn Glu Glu Gly
305                 310                 315                 320

Thr Tyr Phe Pro Pro Ser Val Phe Thr Ser Pro Asp Ile Leu His Ser
                325                 330                 335

Leu Arg Gln Ile Gly Leu Lys Asn Glu Ala Ser Leu Lys Glu Lys Asp
            340                 345                 350

Val Val Gln Val Ala Lys Lys Ile Glu Ala Leu Gln Val Gly Ala Cys
        355                 360                 365

Pro Asp Gln Asp Val Leu Leu Lys Lys Ala Lys Thr Leu Leu Leu Val
    370                 375                 380

Leu Asn Lys Asn His Thr Leu Leu Gln Ser Ser Glu Gly Lys Met Thr
385                 390                 395                 400

Leu Lys Lys Ile Lys Trp Val Pro Ala Cys Lys Glu Arg Pro Pro Asn
                405                 410                 415

Tyr Pro Gly Ser Leu Val Trp Lys Gly Asp Leu Cys Asn Leu Cys Ala
            420                 425                 430

Pro Pro Asp Met Cys Asp Val Gly His Ala Ile Leu Ile Gly Ser Ser
        435                 440                 445

Leu Pro Leu Val Glu Ser Ile His Val Asn Leu Glu Lys Ala Leu Gly
    450                 455                 460

Ile Phe Thr Lys Pro Ser Leu Ser Ala Val Leu Lys His Phe Lys Ile
465                 470                 475                 480

Val Val Asp Trp Tyr Ser Ser Lys Thr Phe Ser Asp Glu Asp Tyr Tyr
                485                 490                 495

Gln Phe Gln His Ile Leu Leu Glu Ile Tyr Gly Phe Met His Asp His
            500                 505                 510

Leu Asn Glu Gly Lys Asp Ser Phe Arg Ala Leu Lys Phe Pro Trp Val
        515                 520                 525

Trp Thr Gly Lys Lys Phe Cys Pro Leu Ala Gln Ala Val Ile Lys Pro
    530                 535                 540

Ile His Asp Leu Asp Leu Gln Pro Tyr Leu His Asn Val Pro Lys Thr
545                 550                 555                 560

Met Ala Lys Phe His Gln Leu Phe Lys Val Cys Gly Ser Ile Glu Glu
                565                 570                 575

Leu Thr Ser Asp His Ile Ser Met Val Ile Gln Lys Ile Tyr Leu Lys
            580                 585                 590

Ser Asp Gln Asp Leu Ser Glu Gln Glu Ser Lys Gln Asn Leu His Leu
        595                 600                 605

Met Leu Asn Ile Ile Arg Trp Leu Tyr Ser Asn Gln Ile Pro Ala Ser
    610                 615                 620

Pro Asn Thr Pro Val Pro Ile His His Ser Lys Asn Pro Ser Lys Leu
625                 630                 635                 640

Ile Met Lys Pro Ile His Glu Cys Cys Tyr Cys Asp Ile Lys Val Asp
                645                 650                 655
```

-continued

```
Asp Leu Asn Asp Leu Leu Glu Asp Ser Val Glu Pro Ile Ile Leu Val
            660                 665                 670

His Glu Asp Ile Pro Met Lys Thr Ala Glu Trp Leu Lys Val Pro Cys
        675                 680                 685

Leu Ser Thr Arg Leu Ile Asn Pro Glu Asn Met Gly Phe Glu Gln Ser
    690                 695                 700

Gly Gln Arg Glu Pro Leu Thr Val Arg Ile Lys Asn Ile Leu Glu Glu
705                 710                 715                 720

Tyr Pro Ser Val Ser Asp Ile Phe Lys Glu Leu Leu Gln Asn Ala Asp
                725                 730                 735

Asp Ala Asn Ala Thr Glu Cys Ser Phe Leu Ile Asp Met Arg Arg Asn
            740                 745                 750

Met Asp Ile Arg Glu Asn Leu Leu Asp Pro Gly Met Ala Ala Cys His
        755                 760                 765

Gly Pro Ala Leu Trp Ser Phe Asn Asn Ser Gln Phe Ser Asp Ser Asp
    770                 775                 780

Phe Val Asn Ile Thr Arg Leu Gly Glu Ser Leu Lys Arg Gly Glu Val
785                 790                 795                 800

Asp Lys Val Gly Lys Phe Gly Leu Gly Phe Asn Ser Val Tyr His Ile
                805                 810                 815

Thr Asp Ile Pro Ile Ile Met Ser Arg Glu Phe Met Ile Met Phe Asp
            820                 825                 830

Pro Asn Ile Asn His Ile Ser Lys His Ile Lys Asp Lys Ser Asn Pro
        835                 840                 845

Gly Ile Lys Ile Asn Trp Ser Lys Gln Gln Lys Arg Leu Arg Lys Phe
    850                 855                 860

Pro Asn Gln Phe Lys Pro Phe Ile Asp Val Phe Gly Cys Gln Leu Pro
865                 870                 875                 880

Leu Thr Val Glu Ala Pro Tyr Ser Tyr Asn Gly Thr Leu Phe Arg Leu
                885                 890                 895

Ser Phe Arg Thr Gln Gln Glu Ala Lys Val Ser Glu Val Ser Ser Thr
            900                 905                 910

Cys Tyr Asn Thr Ala Asp Ile Tyr Ser Leu Val Asp Glu Phe Ser Leu
        915                 920                 925

Cys Gly His Arg Leu Ile Ile Phe Thr Gln Ser Val Lys Ser Met Tyr
    930                 935                 940

Leu Lys Tyr Leu Lys Ile Glu Glu Thr Asn Pro Ser Leu Ala Gln Asp
945                 950                 955                 960

Thr Val Ile Ile Lys Lys Lys Ser Cys Ser Ser Lys Ala Leu Asn Thr
                965                 970                 975

Pro Val Leu Ser Val Leu Lys Glu Ala Ala Lys Leu Met Lys Thr Cys
            980                 985                 990

Ser Ser Ser Asn Lys Lys Leu Pro Ser Asp Glu Pro Lys Ser Ser Cys
        995                 1000                1005

Ile Leu Gln Ile Thr Val Glu Glu Phe His His Val Phe Arg Arg Ile
    1010                1015                1020

Ala Asp Leu Gln Ser Pro Leu Phe Arg Gly Pro Asp Asp Asp Pro Ala
1025                1030                1035                1040

Ala Leu Phe Glu Met Ala Lys Ser Gly Gln Ser Lys Lys Pro Ser Asp
                1045                1050                1055

Glu Leu Ser Gln Lys Thr Val Glu Cys Thr Thr Trp Leu Leu Cys Thr
            1060                1065                1070

Cys Met Asp Thr Gly Glu Ala Leu Lys Phe Ser Leu Ser Glu Ser Gly
```

-continued

```
        1075                1080                1085

Arg Arg Leu Gly Leu Val Pro Cys Gly Ala Val Gly Val Gln Leu Ser
    1090                1095                1100

Glu Ile Gln Asp Gln Lys Trp Thr Val Lys Pro His Ile Gly Glu Val
1105                1110                1115                1120

Phe Cys Tyr Leu Pro Leu Arg Ile Lys Thr Gly Leu Pro Val His Ile
                1125                1130                1135

Asn Gly Cys Phe Ala Val Thr Ser Asn Arg Lys Glu Ile Trp Lys Thr
            1140                1145                1150

Asp Thr Lys Gly Arg Trp Asn Thr Thr Phe Met Arg His Val Ile Val
        1155                1160                1165

Lys Ala Tyr Leu Gln Val Leu Ser Val Leu Arg Asp Leu Ala Thr Ser
    1170                1175                1180

Gly Glu Leu Met Asp Tyr Thr Tyr Tyr Ala Val Trp Pro Asp Pro Asp
1185                1190                1195                1200

Leu Val His Asp Asp Phe Ser Val Ile Cys Gln Gly Phe Tyr Glu Asp
                1205                1210                1215

Ile Ala His Gly Lys Gly Lys Glu Leu Thr Lys Val Phe Ser Asp Gly
            1220                1225                1230

Ser Thr Trp Val Ser Met Lys Asn Val Arg Phe Leu Asp Asp Ser Ile
        1235                1240                1245

Leu Lys Arg Arg Asp Val Gly Ser Ala Ala Phe Lys Ile Phe Leu Lys
    1250                1255                1260

Tyr Leu Lys Lys Thr Gly Ser Lys Asn Leu Cys Ala Val Glu Leu Pro
1265                1270                1275                1280

Ser Ser Val Lys Leu Gly Phe Glu Glu Ala Gly Cys Lys Gln Ile Leu
                1285                1290                1295

Leu Glu Asn Thr Phe Ser Glu Lys Gln Phe Phe Ser Glu Val Phe Phe
            1300                1305                1310

Pro Asn Ile Gln Glu Ile Glu Ala Glu Leu Arg Asp Pro Leu Met Ile
        1315                1320                1325

Phe Val Leu Asn Glu Lys Val Asp Glu Phe Ser Gly Val Leu Arg Val
    1330                1335                1340

Thr Pro Cys Ile Pro Cys Ser Leu Glu Gly His Pro Leu Val Leu Pro
1345                1350                1355                1360

Ser Arg Leu Ile His Pro Glu Gly Arg Val Ala Lys Leu Phe Asp Ile
                1365                1370                1375

Lys Asp Gly Arg Phe Pro Tyr Gly Ser Thr Gln Asp Tyr Leu Asn Pro
            1380                1385                1390

Ile Ile Leu Ile Lys Leu Val Gln Leu Gly Lys Ala Lys Asp Asp Ile
        1395                1400                1405

Leu Trp Asp Asp Met Leu Glu Arg Ala Val Ser Val Ala Glu Ile Asn
    1410                1415                1420

Lys Ser Asp His Val Ala Ala Cys Leu Arg Ser Ser Ile Leu Leu Ser
1425                1430                1435                1440

Leu Ile Asp Glu Lys Leu Lys Ile Arg Asp Pro Arg Ala Lys Asp Phe
                1445                1450                1455

Ala Ala Lys Tyr Gln Thr Ile Arg Phe Leu Pro Phe Leu Thr Lys Pro
            1460                1465                1470

Ala Gly Phe Ser Leu Asp Trp Lys Gly Asn Ser Phe Lys Pro Glu Thr
        1475                1480                1485

Met Phe Ala Ala Thr Asp Leu Tyr Thr Ala Glu His Gln Asp Ile Val
    1490                1495                1500
```

-continued

Cys Leu Leu Gln Pro Ile Leu Asn Glu Asn Ser His Ser Phe Arg Gly
1505 1510 1515 1520

Cys Gly Ser Val Ser Leu Ala Val Lys Glu Phe Leu Gly Leu Leu Lys
1525 1530 1535

Lys Pro Thr Val Asp Leu Val Ile Asn Gln Leu Lys Glu Val Ala Lys
1540 1545 1550

Ser Val Asp Asp Gly Ile Thr Leu Tyr Gln Glu Asn Ile Thr Asn Ala
1555 1560 1565

Cys Tyr Lys Tyr Leu His Glu Ala Leu Met Gln Asn Glu Ile Thr Lys
1570 1575 1580

Met Ser Ile Ile Asp Lys Leu Lys Pro Phe Ser Phe Ile Leu Val Glu
1585 1590 1595 1600

Asn Ala Tyr Val Asp Ser Glu Lys Val Ser Phe His Leu Asn Phe Glu
1605 1610 1615

Ala Ala Pro Tyr Leu Tyr Gln Leu Pro Asn Lys Tyr Lys Asn Asn Phe
1620 1625 1630

Arg Glu Leu Phe Glu Thr Val Gly Val Arg Gln Ser Cys Thr Val Glu
1635 1640 1645

Asp Phe Ala Leu Val Leu Glu Ser Ile Asp Gln Glu Arg Gly Thr Lys
1650 1655 1660

Gln Ile Thr Glu Glu Asn Phe Gln Leu Cys Arg Arg Ile Ile Ser Glu
1665 1670 1675 1680

Gly Ile Trp Ser Leu Ile Arg Glu Lys Lys Gln Glu Phe Cys Glu Lys
1685 1690 1695

Asn Tyr Gly Lys Ile Leu Leu Pro Asp Thr Asn Leu Met Leu Leu Pro
1700 1705 1710

Ala Lys Ser Leu Cys Tyr Asn Asp Cys Pro Trp Ile Lys Val Lys Asp
1715 1720 1725

Thr Thr Val Lys Tyr Cys His Ala Asp Ile Pro Arg Glu Val Ala Val
1730 1735 1740

Lys Leu Gly Ala Val Pro Lys Arg His Lys Ala Leu Glu Arg Tyr Ala
1745 1750 1755 1760

Ser Asn Val Cys Phe Thr Thr Leu Gly Thr Glu Phe Gly Gln Lys Glu
1765 1770 1775

Lys Leu Thr Ser Arg Ile Lys Ser Ile Leu Asn Ala Tyr Pro Ser Glu
1780 1785 1790

Lys Glu Met Leu Lys Glu Leu Leu Gln Asn Ala Asp Asp Ala Lys Ala
1795 1800 1805

Thr Glu Ile Cys Phe Val Phe Asp Pro Arg Gln His Pro Val Asp Arg
1810 1815 1820

Ile Phe Asp Asp Lys Trp Ala Pro Leu Gln Gly Pro Ala Leu Cys Val
1825 1830 1835 1840

Tyr Asn Asn Gln Pro Phe Thr Glu Asp Asp Val Arg Gly Ile Gln Asn
1845 1850 1855

Leu Gly Lys Gly Thr Lys Glu Gly Asn Pro Tyr Lys Thr Gly Gln Tyr
1860 1865 1870

Gly Ile Gly Phe Asn Ser Val Tyr His Ile Thr Asp Cys Pro Ser Phe
1875 1880 1885

Ile Ser Gly Asn Asp Ile Leu Cys Ile Phe Asp Pro His Ala Arg Tyr
1890 1895 1900

Ala Pro Gly Ala Thr Ser Ile Ser Pro Gly Arg Met Phe Arg Asp Leu
1905 1910 1915 1920

-continued

```
Asp Ala Asp Phe Arg Thr Gln Phe Ser Asp Val Leu Asp Leu Tyr Leu
                1925                1930                1935

Gly Thr His Phe Lys Leu Asp Asn Cys Thr Met Phe Arg Phe Pro Leu
            1940                1945                1950

Arg Asn Ala Glu Met Ala Lys Val Ser Glu Ile Ser Ser Val Pro Ala
        1955                1960                1965

Ser Asp Arg Met Val Gln Asn Leu Leu Asp Lys Leu Arg Ser Asp Gly
    1970                1975                1980

Ala Glu Leu Leu Met Phe Leu Asn His Met Glu Lys Ile Ser Ile Cys
1985                1990                1995                2000

Glu Ile Asp Lys Ser Thr Gly Ala Leu Asn Val Leu Tyr Ser Val Lys
                2005                2010                2015

Gly Lys Ile Thr Asp Gly Asp Arg Leu Lys Arg Lys Gln Phe His Ala
            2020                2025                2030

Ser Val Ile Asp Ser Val Thr Lys Lys Arg Gln Leu Lys Asp Ile Pro
        2035                2040                2045

Val Gln Gln Ile Thr Tyr Thr Met Asp Thr Glu Asp Ser Glu Gly Asn
    2050                2055                2060

Leu Thr Thr Trp Leu Ile Cys Asn Arg Ser Gly Phe Ser Ser Met Glu
2065                2070                2075                2080

Lys Val Ser Lys Ser Val Ile Ser Ala His Lys Asn Gln Asp Ile Thr
                2085                2090                2095

Leu Phe Pro Arg Gly Gly Val Ala Ala Cys Ile Thr His Asn Tyr Lys
            2100                2105                2110

Lys Pro His Arg Ala Phe Cys Phe Leu Pro Leu Ser Leu Glu Thr Gly
        2115                2120                2125

Leu Pro Phe His Val Asn Gly His Phe Ala Leu Asp Ser Ala Arg Arg
    2130                2135                2140

Asn Leu Trp Arg Asp Asp Asn Gly Val Gly Val Arg Ser Asp Trp Asn
2145                2150                2155                2160

Asn Ser Leu Met Thr Ala Leu Ile Ala Pro Ala Tyr Val Glu Leu Leu
                2165                2170                2175

Ile Gln Leu Lys Lys Arg Tyr Phe Pro Gly Ser Asp Pro Thr Leu Ser
            2180                2185                2190

Val Leu Gln Asn Thr Pro Ile His Val Val Lys Asp Thr Leu Lys Lys
        2195                2200                2205

Phe Leu Ser Phe Phe Pro Val Asn Arg Leu Asp Leu Gln Pro Asp Leu
    2210                2215                2220

Tyr Cys Leu Val Lys Ala Leu Tyr Asn Cys Ile His Glu Asp Met Lys
2225                2230                2235                2240

Arg Leu Leu Pro Val Val Arg Ala Pro Asn Ile Asp Gly Ser Asp Leu
                2245                2250                2255

His Ser Ala Val Ile Ile Thr Trp Ile Asn Met Ser Thr Ser Asn Lys
            2260                2265                2270

Thr Arg Pro Phe Phe Asp Asn Leu Leu Gln Asp Glu Leu Gln His Leu
        2275                2280                2285

Lys Asn Ala Asp Tyr Asn Ile Thr Thr Arg Lys Thr Val Ala Glu Asn
    2290                2295                2300

Val Tyr Arg Leu Lys His Leu Leu Leu Glu Ile Gly Phe Asn Leu Val
2305                2310                2315                2320

Tyr Asn Cys Asp Glu Thr Ala Asn Leu Tyr His Cys Leu Ile Asp Ala
                2325                2330                2335

Asp Ile Pro Val Ser Tyr Val Thr Pro Ala Asp Ile Arg Ser Phe Leu
```

-continued

```
        2340                2345                2350

Met Thr Phe Ser Ser Pro Asp Thr Asn Cys His Ile Gly Lys Leu Pro
        2355                2360                2365

Cys Arg Leu Gln Gln Thr Asn Leu Lys Leu Phe His Ser Leu Lys Leu
    2370                2375                2380

Leu Val Asp Tyr Cys Phe Lys Asp Ala Glu Glu Asn Glu Ile Glu Val
2385                2390                2395                2400

Glu Gly Leu Pro Leu Leu Ile Thr Leu Asp Ser Val Leu Gln Thr Phe
                2405                2410                2415

Asp Ala Lys Arg Pro Lys Phe Leu Thr Thr Tyr His Glu Leu Ile Pro
            2420                2425                2430

Ser Arg Lys Asp Leu Phe Met Asn Thr Leu Tyr Leu Lys Tyr Ser Asn
        2435                2440                2445

Ile Leu Leu Asn Cys Lys Val Ala Lys Val Phe Asp Ile Ser Ser Phe
    2450                2455                2460

Ala Asp Leu Leu Ser Ser Val Leu Pro Arg Glu Tyr Lys Thr Lys Ser
2465                2470                2475                2480

Cys Thr Lys Trp Lys Asp Asn Phe Ala Ser Glu Ser Trp Leu Lys Asn
                2485                2490                2495

Ala Trp His Phe Ile Ser Glu Ser Val Ser Val Lys Glu Asp Gln Glu
            2500                2505                2510

Glu Thr Lys Pro Thr Phe Asp Ile Val Val Asp Thr Leu Lys Asp Trp
        2515                2520                2525

Ala Leu Leu Pro Gly Thr Lys Phe Thr Val Ser Ala Asn Gln Leu Val
    2530                2535                2540

Val Pro Glu Gly Asp Val Leu Leu Pro Leu Ser Leu Met His Ile Ala
2545                2550                2555                2560

Val Phe Pro Asn Ala Gln Ser Asp Lys Val Phe His Ala Leu Met Lys
                2565                2570                2575

Ala Gly Cys Ile Gln Leu Ala Leu Asn Lys Ile Cys Ser Lys Asp Ser
            2580                2585                2590

Ala Phe Val Pro Leu Leu Ser Cys His Thr Ala Asn Ile Glu Ser Pro
        2595                2600                2605

Thr Ser Ile Leu Lys Ala Leu His Tyr Met Val Gln Thr Ser Thr Phe
    2610                2615                2620

Arg Ala Glu Lys Leu Val Glu Asn Asp Phe Glu Ala Leu Leu Met Tyr
2625                2630                2635                2640

Phe Asn Cys Asn Leu Asn His Leu Met Ser Gln Asp Asp Ile Lys Ile
                2645                2650                2655

Leu Lys Ser Leu Pro Cys Tyr Lys Ser Ile Ser Gly Arg Tyr Val Ser
            2660                2665                2670

Ile Gly Lys Phe Gly Thr Cys Tyr Val Leu Thr Lys Ser Ile Pro Ser
        2675                2680                2685

Ala Glu Val Glu Lys Trp Thr Gln Ser Ser Ser Ser Ala Phe Leu Glu
    2690                2695                2700

Glu Lys Ile His Leu Lys Glu Leu Tyr Glu Val Ile Gly Cys Val Pro
2705                2710                2715                2720

Val Asp Asp Leu Glu Val Tyr Leu Lys His Leu Leu Pro Lys Ile Glu
                2725                2730                2735

Asn Leu Ser Tyr Asp Ala Lys Leu Glu His Leu Ile Tyr Leu Lys Asn
            2740                2745                2750

Arg Leu Ser Ser Ala Glu Glu Leu Ser Glu Ile Lys Glu Gln Leu Phe
        2755                2760                2765
```

-continued

```
Glu Lys Leu Glu Ser Leu Leu Ile Ile His Asp Ala Asn Ser Arg Leu
    2770                2775                2780

Lys Gln Ala Lys His Phe Tyr Asp Arg Thr Val Arg Val Phe Glu Val
2785                2790                2795                2800

Met Leu Pro Glu Lys Leu Phe Ile Pro Asn Asp Phe Phe Lys Lys Leu
                2805                2810                2815

Glu Gln Leu Ile Lys Pro Lys Asn His Val Thr Phe Met Thr Ser Trp
            2820                2825                2830

Val Glu Phe Leu Arg Asn Ile Gly Leu Lys Tyr Ile Leu Ser Gln Gln
        2835                2840                2845

Gln Leu Leu Gln Phe Ala Lys Glu Ile Ser Val Arg Ala Asn Thr Glu
    2850                2855                2860

Asn Trp Ser Lys Glu Thr Leu Gln Asn Thr Val Asp Ile Leu Leu His
2865                2870                2875                2880

His Ile Phe Gln Glu Arg Met Asp Leu Leu Ser Gly Asn Phe Leu Lys
                2885                2890                2895

Glu Leu Ser Leu Ile Pro Phe Leu Cys Pro Glu Arg Ala Pro Ala Glu
            2900                2905                2910

Phe Ile Arg Phe His Pro Gln Tyr Gln Glu Val Asn Gly Thr Leu Pro
        2915                2920                2925

Leu Ile Lys Phe Asn Gly Ala Gln Val Asn Pro Lys Phe Lys Gln Cys
    2930                2935                2940

Asp Val Leu Gln Leu Leu Trp Thr Ser Cys Pro Ile Leu Pro Glu Lys
2945                2950                2955                2960

Ala Thr Pro Leu Ser Ile Lys Glu Gln Glu Gly Ser Asp Leu Gly Pro
                2965                2970                2975

Gln Glu Gln Leu Glu Gln Val Leu Asn Met Leu Asn Val Asn Leu Asp
            2980                2985                2990

Pro Pro Leu Asp Lys Val Ile Asn Asn Cys Arg Asn Ile Cys Asn Ile
        2995                3000                3005

Thr Thr Leu Asp Glu Glu Met Val Lys Thr Arg Ala Lys Val Leu Arg
    3010                3015                3020

Ser Ile Tyr Glu Phe Leu Ser Ala Glu Lys Arg Glu Phe Arg Phe Gln
3025                3030                3035                3040

Leu Arg Gly Val Ala Phe Val Met Val Glu Asp Gly Trp Lys Leu Leu
                3045                3050                3055

Lys Pro Glu Glu Val Val Ile Asn Leu Glu Tyr Glu Ser Asp Phe Lys
            3060                3065                3070

Pro Tyr Leu Tyr Lys Leu Pro Leu Glu Leu Gly Thr Phe His Gln Leu
        3075                3080                3085

Phe Lys His Leu Gly Thr Glu Asp Ile Ile Ser Thr Lys Gln Tyr Val
    3090                3095                3100

Glu Val Leu Ser Arg Ile Phe Lys Asn Ser Glu Gly Lys Gln Leu Asp
3105                3110                3115                3120

Pro Asn Glu Met Arg Thr Val Lys Arg Val Val Ser Gly Leu Phe Arg
                3125                3130                3135

Ser Leu Gln Asn Asp Ser Val Lys Val Arg Ser Asp Leu Glu Asn Val
            3140                3145                3150

Arg Asp Leu Ala Leu Tyr Leu Pro Ser Gln Asp Gly Arg Leu Val Lys
        3155                3160                3165

Ser Ser Ile Leu Val Phe Asp Asp Ala Pro His Tyr Lys Ser Arg Ile
    3170                3175                3180
```

-continued

```
Gln Gly Asn Ile Gly Val Gln Met Leu Val Asp Leu Ser Gln Cys Tyr
3185                3190                3195                3200

Leu Gly Lys Asp His Gly Phe His Thr Lys Leu Ile Met Leu Phe Pro
                3205                3210                3215

Gln Lys Leu Arg Pro Arg Leu Leu Ser Ser Ile Leu Glu Glu Gln Leu
            3220                3225                3230

Asp Glu Glu Thr Pro Lys Val Cys Gln Phe Gly Ala Leu Cys Ser Leu
        3235                3240                3245

Gln Gly Arg Leu Gln Leu Leu Leu Ser Ser Glu Gln Phe Ile Thr Gly
    3250                3255                3260

Leu Ile Arg Ile Met Lys His Glu Asn Asp Asn Ala Phe Leu Ala Asn
3265                3270                3275                3280

Glu Glu Lys Ala Ile Arg Leu Cys Lys Ala Leu Arg Glu Gly Leu Lys
                3285                3290                3295

Val Ser Cys Phe Glu Lys Leu Gln Thr Thr Leu Arg Val Lys Gly Phe
            3300                3305                3310

Asn Pro Ile Pro His Ser Arg Ser Glu Thr Phe Ala Phe Leu Lys Arg
        3315                3320                3325

Phe Gly Asn Ala Val Ile Leu Leu Tyr Ile Gln His Ser Asp Ser Lys
    3330                3335                3340

Asp Ile Asn Phe Leu Leu Ala Leu Ala Met Thr Leu Lys Ser Ala Thr
3345                3350                3355                3360

Asp Asn Leu Ile Ser Asp Thr Ser Tyr Leu Ile Ala Met Leu Gly Cys
                3365                3370                3375

Asn Asp Ile Tyr Arg Ile Gly Glu Lys Leu Asp Ser Leu Gly Val Lys
            3380                3385                3390

Tyr Asp Ser Ser Glu Pro Ser Lys Leu Glu Leu Pro Met Pro Gly Thr
        3395                3400                3405

Pro Ile Pro Ala Glu Ile His Tyr Thr Leu Leu Met Asp Pro Met Asn
    3410                3415                3420

Val Phe Tyr Pro Gly Glu Tyr Val Gly Tyr Leu Val Asp Ala Glu Gly
3425                3430                3435                3440

Gly Asp Ile Tyr Gly Ser Tyr Gln Pro Thr Tyr Thr Tyr Ala Ile Ile
                3445                3450                3455

Val Gln Glu Val Glu Arg Glu Asp Ala Asp Asn Ser Ser Phe Leu Gly
            3460                3465                3470

Lys Ile Tyr Gln Ile Asp Ile Gly Tyr Ser Glu Tyr Lys Ile Val Ser
        3475                3480                3485

Ser Leu Asp Leu Tyr Lys Phe Ser Arg Pro Glu Glu Ser Ser Gln Ser
    3490                3495                3500

Arg Asp Ser Ala Pro Ser Thr Pro Thr Ser Pro Thr Glu Phe Leu Thr
3505                3510                3515                3520

Pro Gly Leu Arg Ser Ile Pro Pro Leu Phe Ser Gly Arg Glu Ser His
                3525                3530                3535

Lys Thr Ser Ser Lys His Gln Ser Pro Lys Lys Leu Lys Val Asn Ser
            3540                3545                3550

Leu Pro Glu Ile Leu Lys Glu Val Thr Ser Val Val Glu Gln Ala Trp
        3555                3560                3565

Lys Leu Pro Glu Ser Glu Arg Lys Lys Ile Ile Arg Arg Leu Tyr Leu
    3570                3575                3580

Lys Trp His Pro Asp Lys Asn Pro Glu Asn His Asp Ile Ala Asn Glu
3585                3590                3595                3600

Val Phe Lys His Leu Gln Asn Glu Ile Asn Arg Leu Glu Lys Gln Ala
```

-continued

```
                3605                3610                3615

Phe Leu Asp Gln Asn Ala Asp Arg Ala Ser Arg Arg Thr Phe Ser Thr
            3620                3625                3630

Ser Ala Ser Arg Phe Gln Ser Asp Lys Tyr Ser Phe Gln Arg Phe Tyr
        3635                3640                3645

Thr Ser Trp Asn Gln Glu Ala Thr Ser His Lys Ser Glu Arg Gln Gln
    3650                3655                3660

Gln Asn Lys Glu Lys Cys Pro Pro Ser Ala Gly Gln Thr Tyr Ser Gln
3665                3670                3675                3680

Arg Phe Phe Val Pro Pro Thr Phe Lys Ser Val Gly Asn Pro Val Glu
                3685                3690                3695

Ala Arg Arg Trp Leu Arg Gln Ala Arg Ala Asn Phe Ser Ala Ala Arg
            3700                3705                3710

Asn Asp Leu His Lys Asn Ala Asn Glu Trp Val Cys Phe Lys Cys Tyr
        3715                3720                3725

Leu Ser Thr Lys Leu Ala Leu Ile Ala Ala Asp Tyr Ala Val Arg Gly
    3730                3735                3740

Lys Ser Asp Lys Asp Val Lys Pro Thr Ala Leu Ala Gln Lys Ile Glu
3745                3750                3755                3760

Glu Tyr Ser Gln Gln Leu Glu Gly Leu Thr Asn Asp Val His Thr Leu
                3765                3770                3775

Glu Ala Tyr Gly Val Asp Ser Leu Lys Thr Arg Tyr Pro Asp Leu Leu
            3780                3785                3790

Pro Phe Pro Gln Ile Pro Asn Asp Arg Phe Thr Ser Glu Val Ala Met
        3795                3800                3805

Arg Val Met Glu Cys Thr Ala Cys Ile Ile Ile Lys Leu Glu Asn Phe
    3810                3815                3820

Met Gln Gln Lys Val
3825
```

<210> SEQ ID NO 3
<211> LENGTH: 11492
<212> TYPE: DNA
<213> ORGANISM: Mus musculus

<400> SEQUENCE: 3

```
atgaatacat tctggcctgg tcgagagttg gtggttcagt ggtatccatt tagtgaagac     60

aaacgtcacc catccctttc atggcttaag atggtttgga agaatctcta tatacatttc    120

tcggaagatt tgactttatt tgatgagatg ccacttatcc ctagaactct actgaatgag    180

gaccagacgt gtgtggaact catcagactc aggatcccat cagtagtcat tttagatgat    240

gaaactgaag ctcagcttcc agaattctta gcagatattg tacaaaaact tggagggatt    300

gtcctgaaaa gactagatac ctctattcag catccacttg ttaaaaaata cattcattcc    360

ccactcccga gtgctatttt gcagataatg gagaagatac ctctacagaa gttgtgtaat    420

aaatagcatc attacttcca acccacaaag atgctctaag gaagtttttg gccagcttaa    480

ctgataccag tgaaaaagag aaaagaataa ttcaagaatt gacaatattc aaaagaatta    540

atcactcatc agatcaaggg atttcctctt acacaaaatt aaaaggatgt aaagttttgg    600

atcataccgc caagcttcca acagatctac ggctatcagt ttcagtaata gatagtagtg    660

atgaagccac cattcgtttg gcaaacatgt tgaaaattga aaaattgaag actacaagct    720

gtttaaagtt tgttttaaaa gatattggaa atgcatttta tacacaggaa gaggtaacac    780

aacttatgct ttggatcctt gagaatctat cctctcttaa aaatgagaat tcaaatgtgc    840
```

-continued

```
ttgattggtt aatgccacta aaattcattc atatgtccca gggacatgtg gtagcagctg    900
gtgatctctt tgatcctgat atagaagtac taagggatct cttttataat gaagaagaag    960
cttgtttccc acctacaatt tttacctcac cagatatcct tcactctttg agacagattg   1020
gcttaaaaaa tgaatccagt ctaaaagaaa aagatgttgt acaagtggca agaaaaattg   1080
aagctttaca ggtcagttcc tgtcagaatc aggatgttct catgaagaaa gccaaaacac   1140
tcttactggt cttgaataaa aaccagacac tcttgcagtc ttctgaaggg aagatggcat   1200
tgaagaaaat caaatgggtt ccagcctgca aggaaagacc tccaaattat cccggttcct   1260
tagtctggaa aggggatctc tgtaatcttt gtgcacctcc agatatgtgt gatgcggcac   1320
atgcagttct agtaggctcc tcacttcctc ttgttgaaag tgtccatgtg aacctggagc   1380
aggcgctcag catcttcaca aagcctacta tcaatgctgt cttaaaacac tttaaaactg   1440
ttgttgactg gtatacttca aaaacccttta gtgatgaaga ttactatcag ttccaacata   1500
ttttgcttga aatttatggg ttcatgcatg atcatctgag tgaagggaag gattctttta   1560
aagccttgaa gtttccatgg gtttggactg gcaaaaactt ttgtcctctt gcccaggctg   1620
tgataaagcc aacccatgat ctggatcttc agccttattt atataatgtg cctaaaacca   1680
tggcaaaatt ccaccagctg ttcaaggctt gtggctcaat agaagagttg acatcagatc   1740
atatttccat ggtcattcag aaagtttatc tcaaaagtga ccaggagttg agtgaagaag   1800
aaagtaaaca aaatcttcat ctcatgttga atattatgag atggctctat agcaatcaga   1860
ttccagcaag ccctaataca ccagttccta tttatcacag cagaaatcct tccaaacttg   1920
tcatgaagcc aattcatgaa tgctgttatt gtgacatcaa agttgatgac ctcaatgact   1980
tgcttgaaga ttcagtggaa ccaattatct tggtacatga agatataccc atgaaaactg   2040
cagaatggct aaaagttccg tgccttagta caagactgat caatcctgaa aacatggggt   2100
ttgagcagtc agggcaaaga gagcctctta ctgtaaggat taaaaatatt ttggaagaat   2160
acccttccgt gtcagatatt tttaaagagc tacttcaaaa tgctgatgat gcaaatgcca   2220
cagaatgcag cttcatgatt gatatgagaa ggaatatgga catacgggaa aatctcctgg   2280
acccagggat ggcagcttgt catggacctg ctctgtggtc attcaacaat tctgaattct   2340
cagattcaga tttcttaaac ataacgaggt taggagagtc tttaaaaagg ggagaagttg   2400
acaaggttgg gaaatttggt cttggtttta attctgtgta ccacatcact gacattccca   2460
tcattatgag cagagaattt atgataatgt ttgatccaaa cataaatcat atcagcaaac   2520
acattaaaga tagatcgaat cctggaatca aaattaattg gagtaagcag cagaaaagac   2580
ttaggaagtt ccccaaccag ttcaaaccat ttatagatgt atttggctgt cagttacctt   2640
tggctgttga agctccttac agctacaatg gaactctttt ccgactgtcc tttagaacac   2700
agcaggaagc aaaagtgagt gaagttagca gtacttgcta caatactgcg gatatttact   2760
ccctagtgga tgaatttagt ctttgtgggc acagacttat catttttact cagagtgtaa   2820
actcgatgta tttgaaatac ttgaaaattg aagaaaccaa tcctagctta gcacaagata   2880
caatcataat taagaaaaaa gtttgcccct ccaaagcatt gaatgcacca gttttaagtg   2940
ttttaaaaga agctgctaaa ctcatgaaga cttgtagcag cagcaacaag aagcttccca   3000
cggatgtgcc aaagtcatct tgcattcttc agatcacagt cgaagaattc caccatgtgt   3060
ttaggaggat tgctgactta cagtcaccac tatttcgagg tccagatgat gacccagcta   3120
ctctctttga aatggctaaa tctggccaat caaaaaagcc atcagatgag ttgccacaaa   3180
```

-continued agacagtaga ttgtaccaca tggcttatat gcacatgcat ggatacagga gaagctctca 3240
agttttcctt gaatgaaagt ggaagaagat tagggctggt tccttgtggg gcagtagggg 3300
ttctcttgca tgaaacccag gaacagaagt ggaccgtgaa accacacata ggagaagtgt 3360
tttgctattt acctctacga atcaaaacag ggttgccaat tcacatcaat gggtgctttg 3420
ctgttacttc aaataggaaa gaaatctgga agacagatac aaaaggtcga tggaatacca 3480
cattcatgag gcatgtcatt gtgaaagctt acttacaagc cctcagtgtc ttacgggacc 3540
tagccattgg tggtgagctg actgattata cttactatgc agtgtggcct gatcctgatc 3600
tagttcatga tgacttctct gtgatctgta aaggatttta tgaagacatt gctcatggga 3660
aggggaagga gttgaccaga gtcttctctg atgggtctat gtgggtttcc atgaagaatg 3720
tgaggtttct ggatgactct atacttcaaa ggaaagatgt tggttcagca gccttcaaga 3780
tatttctgaa gtacctcaag aaaacaggat ccaaaaacct ctgtgctgtt gagcttcctt 3840
cttcagtaaa agcaggattt gaagaggctg gctgtaaaca gatactgctg gaaaatacat 3900
tttcagagaa acagttcttt tcagaagtct tctttcctaa tatccaggaa attgaagcag 3960
aacttagaga tcctctgatg aattttgtcc taaatgaaaa acttgatgag ttctcaggaa 4020
ttcttcgtgt taccccttgt gttccttgct ccttggaggg ccatcctttg gttttgcctt 4080
caagattgat ccatcctgaa ggacgagttg caaagttatt tgatactaaa gatggaagat 4140
tcccttatgg ttccacacag gattacctca atcctattat cttgattaag ctcgttcagt 4200
taggcatggc aaaagatgat attttgtggg atgacatgct agagcgtgca gagtctgtag 4260
ctgagattaa taaaagtgac catgctgctg cctgcttaag gagtagtatt ctgctaagcc 4320
ttattgatga gaagctaaaa ataaaggatc ctagagcaaa ggattttgct gcaaaatatc 4380
aaacaattcc cttcctccca tttctaacaa agccagcagg tttttcttta gaatggaaag 4440
ggaacagctt taagcctgaa accatgtttg cagcaactga catttacaca gctgaatatc 4500
aagatatagt ctgtcttttg caaccaattc ttaatgaaaa ttcccattcc tttagaggct 4560
gtggttcagt gtctttggct gttaaggagt ttttgggttt actaaagaag ccaacagttg 4620
atctggtaat aaaccagttg aagcaagttg caaaatcagt tgatgatggc attacattgt 4680
accaggaaaa tatcaccaac gcttgctaca aatacctcca tgaagcagta ttgcagaatg 4740
aaatggccaa ggcaacaatt attgagaagc taaagccatt ttgtttcatt ctagttgaga 4800
atgtatatgt tgagtcagaa aaggtttctt ttcacttgaa ctttgaagca gcaccatacc 4860
tttatcagtt acctaacaag tataaaaata atttccgtga gctttttgaa agtgtgggtg 4920
tgcgacagtc atttactgtt gaagactttg ccctagtttt ggagtctatt gatcaagaga 4980
gaggaaaaaa acaaataaca gaagagaatt ttcagctttg ccgacgaata atcagtgaag 5040
gcatctggag tctcattaga gaaaagagac aagaattttg tgagaaaaat tatggcaaaa 5100
tattactgcc agacactaac ctgctgctgc tccctgctaa gtcattatgc tacaatgact 5160
gtccctggat aaaagtaaag gactccactg tcaagtattg ccatgccgac ataccccggg 5220
aagtagctgt aaaacttggt gcaataccaa agagacataa agcattagaa agatatgcat 5280
ccaacatctg tttcacagct ctaggtacag aatttgggca gaaagaaaaa ctgaccagca 5340
gaattaagag cattctcaat gcctatcctt cagaaaagga aatgctgaaa gagcttcttc 5400
aaaatgctga tgatgcaaag gccacagaga tctgctttgt gtttgatcct agacagcatc 5460
ctgttgaccg aatatttgat gataagtggg ccccactgca agggccagca ctgtgtgttt 5520
acaacaacca gccatttaca gaagatgatg ttagaggaat tcagaatctt gggaaaggca 5580

-continued

```
ccaaagaagg gaatccttgc aaaacaggac attatggaat cggattcaat tccgtttatc   5640
atattacaga ctgcccttct tttatttctg gcaatgacat cctgggtatt tttgatcccc   5700
atgccagata tgcaccagga gccacatcag ttagccctgg acgcatgttt agagatttgg   5760
atgcagactt tagaacccag ttctcagatg ttctagatct gtacttggga aaccacttta   5820
aactggacaa ttgtacaatg tttagatttc ctctgcgtaa tgcagagatg gcacaagttt   5880
cagaaatttc ttccgttcca tcatcagaca gaatggtcca gaatcttttg gacaagttac   5940
ggtctgatgg ggcagaactt ctaatgtttc tcaaccacat ggagaaaata tctatttgtg   6000
aaatagataa ggccacagga ggtctgaatg tgctctattc agtaaaaggc aagatcactg   6060
atggagaccg attgaaaagg aagcaattcc acgcctctgt aattgacagt gttactaaaa   6120
agagacagct caaggacata ccagttcaac aaataaccta cactatggat actgaggatt   6180
ctgaaggaaa tctgaccaca tggctcatct gtaatagatc aggattttca agtatggaaa   6240
aagtatccaa gagtgtaata tcagctcaca agaaccaaga tatcaccctt ttcccacgtg   6300
gtggagtagc agcctgcatt actcacaatt ataaaaagcc ccacagagcc ttctgctttc   6360
tgcctctctc tttggagaca gggctgccat ttcatgtgaa tggccacttt gctctagatt   6420
cagccagaag aaacttgtgg cgtgatgata atggggttgg tgttcgaagt gactggaata   6480
atagtttaat gacagcatta atagcacctg catatgttga gttactaatc cagttaaaaa   6540
aacggtattt ccctggttct gacccaacat tatcagtttt acagaacaca cccattcatg   6600
tcgtaaagga cacattaaag aagtttctgt ccttctttcc agttaacagg ctggatctgc   6660
agccggactt atattgctta gtaaaagcac tttacagttg cattcatgaa gacatgaagc   6720
gtcttttgcc tgttgttcgg gctccaaata ttgatggctc agatttgcac tctgcagtca   6780
taattacttg gatcaatatg tctacttcaa ataaaactag accatttttt gataacttac   6840
tacaggatga attacagcac cttaaaaatg cagattataa catcacaact cgaaaaacag   6900
tcgcagagaa tgtctacaga ctgaagcacc tgctcttaga aattggtttc aacttggttt   6960
ataactgtga tgaaactgct aacctttacc attgccttgt agatgcagat atccctgtca   7020
gctatgtgac tcctgctgat gttaggtcct tcttaatgac tttctcttct cctgacacta   7080
attgccatat tgggaagctg ccttgtcgtc ttcagcagac taacctaaaa ctttttcaca   7140
gtttaaaact tttagttgat tactgtttta aagatgctga agaaagtgag tttgaagttg   7200
agggactgcc cctactcatt acactggaca gtgtcttgca gatttttgat ggtaaacgac   7260
ccaagtttct aacaacatac catgaattaa ttccatcgcg taaagacttg tttatgaaca   7320
ccttatactt gaaatacagt agtgttttgt tgaactgcaa agttgcaaaa gtgtttgaca   7380
tttccagctt tgctgactta ctctcttctg tgttgcctcg tgagtacaag accaaaaact   7440
gtgcaaagtg gaaagacaat tttgccagtg aatcttggct taagaacgca tggcatttta   7500
tcagtgaatc agtaagtgta acggatgatc aggaagaacc aaagccagca tttgatgtca   7560
ttgttgacat ccttaaagac tgggcattgc ttccaggaac aaagttcact gtgtcaacca   7620
gtcagcttgt ggttcctgag ggagacgtgt tgattcccct gagcctcatg cacattgctg   7680
tgttcccaaa tgctcagagt gataaggttt ttcacgctct gatgaaagct ggctgtattc   7740
agctggcttt gaacaaaatc tgctctaaag acagcgcatt agttcctctg ttgtcatgcc   7800
acacagcaaa catagatagc cctgcaagca tcttgaaggc tgtgcattat atggttcaga   7860
cgtcaacatt tagaactgaa aaactaatgg aaaatgactt tgaagcactt ttgatgtatt   7920
```

-continued

```
tcaactgtaa tttgagtcac ttgatgtccc aagatgacat aaaaatttta aagtccctcc   7980
catgctacaa atccatcagt ggccgctata tgagcattgc aaaatttgga acgtgctatg   8040
tgcttaccaa aagtattcct tcagctgaag tggaaaaatg gacacagtca tcctcttccg   8100
cgtttcttga agaaaaggtg catttaaaag aactctatga ggtgcttggc tgtgtgccag   8160
tagatgatct ggaggtgtat ttgaaacatc ttctgccaaa aattgaaaat ctctcttatg   8220
atgcaaagtt ggagcacctg atttatctga agaatagact ggcaagcatc gaggaaccgt   8280
cagagattaa ggagcaactt tttgaaaaac tggaaagctt attgattatc cacgatgcca   8340
acaatcgact aaagcaagca aaacatttct atgacagaac tgtgagagtt tttgaagtta   8400
tgcttcctga aaaattgttt attcctaagg agttctttaa aaaattggaa caagtaatca   8460
aacctaaaaa tcaagctgca tttatgacgt cctgggtgga attcttgaga aatattggac   8520
tgaagtacgc gctctcccag cagcagttgt tacagtttgc caaggaaatc agtgtgaggg   8580
caaatacaga aaactggtct aaagaaaccc tgcaaagtac agttgacatc cttctccatc   8640
acatattcca agaacgaatg gatttgttat ctggaaattt tctgaaagaa ctgtccttaa   8700
taccattctt gtgtcctgaa cgggcccccg ctgagtacat tcggtttcac cctcagtacc   8760
aggaggtaaa cggaacactt cctcttataa agttcaatgg agcacaagtg aatccaaagt   8820
tcaagcaatg tgatgtactc cagctgctgt ggacatcttg ccctattctt ccagagaaag   8880
ccacaccgtt gagcattaaa gaacaagaag gcagtgacct cgctccacag gaacagcttg   8940
aacaagtttt aaatatgctt aatgttaacc tggacccccc tcttgataag gtcattaata   9000
attgcagaaa catatgcaac ataacaactt tggatgagga aatggtaaaa actagagcaa   9060
aggtcctaag gagcatatat gaatttctga gtgcagaaaa acgagagttc cgttttcagc   9120
ttcggggtgt ggcctttgta atggtagaag acggatggaa acttctgaag cctgaggaag   9180
tagtgataaa cctggagtat gaggctgatt ttaaacctta tctgtacaag ctgcctttag   9240
agcttggcac ttttcatcag ctgttcaaac atttaggtac tgaagatatc atttccacta   9300
agcaatatgt tgaagtgtta agccgaatat tcaaaagctc tgaaggaaag cagctagacc   9360
ctaatgaaat gcgtacagtt aagagagtgg tttctggcct attcaagagt ctacaaaatg   9420
attcagtcaa ggtgaggagt gacctggaga atgcccggga cctcgcactc taccttccaa   9480
gccaggatgg gaagttggtg aagtcaagca tcttggtgtt cgatgatgcg ccacattata   9540
aaagtaggat ccaggggaat attggcgtgc agatgctagt tgatcttagc cagtgctact   9600
tagggaaaga ccatggattt cacactaagc tgataatgct ctttcctcaa aagcttcgac   9660
ctcgtctgct gagcagtata cttgaagagc agcttgatga ggagacccct aaagtgtgcc   9720
agtttggcgc attgtgctct cttcagggaa gactgcagct tctcttgtct tcagagcagt   9780
tcatcacagg actcattcga atcatgaagc atgaaaatga taatgctttc ctggccaatg   9840
aagaaaaagc cataagactt tgcaaagctc taagagaagg gctgaaagtt tcctgttttg   9900
agaagcttca gacaacatta agggttaaag gttttaatcc tattccccat agcaggagtg   9960
aaactttcgc ttttctaaag cgatttggca atgcagtcat cttgctctac atccaacatt  10020
cagacagcaa agacattaac tttctgctag ccttagcgat gacacttaaa tcagcaactg  10080
acaatttgat ttctgacacg tcatacttaa ttgctatgct gggatgcaat gacatttaca  10140
ggatcagtga gaagcttgac agtttagggg tgaaatacga ctcctctgag ccatcaaaac  10200
tggaactccc catgcctggc acaccaatac ccgctgagat ccattacaca ctacttatgg  10260
atccaatgaa tgttttttat cctggggaat atgttggtta ccttgtggat gctgaaggtg  10320
```

-continued

```
gtgatatcta tgggtcatac cagccaacat acacatacgc aattattgtg caagaagttg  10380

aaagagaaga tgctgacaat actagtttct taggaaagat ctatcagatc gatattggct  10440

acagtgaata taagatagtc agctctcttg atctgtacaa gttctcaagg cctgatgaaa  10500

gctcccaaaa cagagacagt gctcccacca caccaacaag ccccaccgaa ttcctgactc  10560

ctggtctgag aagcatccct cctcttttct ctggcaagga gagccacaag tctccctcca  10620

ccaaacacca ttcccccaga aagctcaagg tgaatgcttt accagaaatc ttaaaagaag  10680

tgacatcagt ggtggagcaa gcttggaagc ttccagaatc agagcggaaa aagatcatta  10740

gacgcttgta tttgaagtgg caccctgaca aaaatccaga aaatcatgat attgctaatg  10800

aagtgttcaa gcacctgcag aatgaaatca acagattaga aaaacaggct tttctggatc  10860

aaaatgcaga cagagcttca agaagaacat tttcaacctc tgcatctcga tttcagtcag  10920

acaagtactc atttcaaaga ttttacactt cgtggaatca agaagccaca agtcataaat  10980

ctgaaaggca acagcaaagc aaagagaaat gccctccttc tgctggacag acatactctc  11040

aaaggttctt tgttcctccc accttcaagt cagtgggcaa tccagtggaa gcccggagat  11100

ggttaagaca agccagagca aacttctcag ctgccaggaa tgaccttcac aaaaatgcca  11160

atgaatgggt gtgcttcaag tgttaccttt ccaccaagct ggctttgatt gcagccgact  11220

atgctgtcag gggaaatct gataaagatg taaagccaac tgcacttgca caaaagatag  11280

aggagtacag tcagcagctg gaaggactga caaacgatgt gcacacattg gaagcttatg  11340

gtgtagacag cttgaaaaca aggtaccctg atttgcttcc ttttccgcag attcccaatg  11400

acaggttcac atctgaggtt gccatgaggg tgatggaatg cactgcctgt atcatcataa  11460

aacttgaaaa ttttatacaa cagaaggtgt ga                                11492
```

<210> SEQ ID NO 4
<211> LENGTH: 3830
<212> TYPE: PRT
<213> ORGANISM: Mus musculus

<400> SEQUENCE: 4

```
Met Asn Thr Phe Trp Pro Gly Arg Glu Leu Val Val Gln Trp Tyr Pro
 1               5                  10                  15

Phe Ser Glu Asp Lys Arg His Pro Ser Leu Ser Trp Leu Lys Met Val
            20                  25                  30

Trp Lys Asn Leu Tyr Ile His Phe Ser Glu Asp Leu Thr Leu Phe Asp
        35                  40                  45

Glu Met Pro Leu Ile Pro Arg Thr Leu Leu Asn Glu Asp Gln Thr Cys
    50                  55                  60

Val Glu Leu Ile Arg Leu Arg Ile Pro Ser Val Val Ile Leu Asp Asp
65                  70                  75                  80

Glu Thr Glu Ala Gln Leu Pro Glu Phe Leu Ala Asp Ile Val Gln Lys
                85                  90                  95

Leu Gly Gly Ile Val Leu Lys Arg Leu Asp Thr Ser Ile Gln His Pro
            100                 105                 110

Leu Val Lys Lys Tyr Ile His Ser Pro Leu Pro Ser Ala Ile Leu Gln
        115                 120                 125

Ile Met Glu Lys Ile Pro Leu Gln Lys Leu Cys Asn Gln Ile Ala Ser
    130                 135                 140

Leu Leu Pro Thr His Lys Asp Ala Leu Arg Lys Phe Leu Ala Ser Leu
145                 150                 155                 160
```

-continued

```
Thr Asp Thr Ser Glu Lys Glu Lys Arg Ile Ile Gln Glu Leu Thr Ile
                165                 170                 175

Phe Lys Arg Ile Asn His Ser Ser Asp Gln Gly Ile Ser Ser Tyr Thr
            180                 185                 190

Lys Leu Lys Gly Cys Lys Val Leu Asp His Thr Ala Lys Leu Pro Thr
        195                 200                 205

Asp Leu Arg Leu Ser Val Ser Val Ile Asp Ser Ser Asp Glu Ala Thr
    210                 215                 220

Ile Arg Leu Ala Asn Met Leu Lys Ile Glu Lys Leu Lys Thr Thr Ser
225                 230                 235                 240

Cys Leu Lys Phe Val Leu Lys Asp Ile Gly Asn Ala Phe Tyr Thr Gln
                245                 250                 255

Glu Glu Val Thr Gln Leu Met Leu Trp Ile Leu Glu Asn Leu Ser Ser
            260                 265                 270

Leu Lys Asn Glu Asn Ser Asn Val Leu Asp Trp Leu Met Pro Leu Lys
        275                 280                 285

Phe Ile His Met Ser Gln Gly His Val Val Ala Ala Gly Asp Leu Phe
    290                 295                 300

Asp Pro Asp Ile Glu Val Leu Arg Asp Leu Phe Tyr Asn Glu Glu Glu
305                 310                 315                 320

Ala Cys Phe Pro Pro Thr Ile Phe Thr Ser Pro Asp Ile Leu His Ser
                325                 330                 335

Leu Arg Gln Ile Gly Leu Lys Asn Glu Ser Ser Leu Lys Glu Lys Asp
            340                 345                 350

Val Val Gln Val Ala Arg Lys Ile Glu Ala Leu Gln Val Ser Ser Cys
        355                 360                 365

Gln Asn Gln Asp Val Leu Met Lys Lys Ala Lys Thr Leu Leu Leu Val
    370                 375                 380

Leu Asn Lys Asn Gln Thr Leu Leu Gln Ser Ser Glu Gly Lys Met Ala
385                 390                 395                 400

Leu Lys Lys Ile Lys Trp Val Pro Ala Cys Lys Glu Arg Pro Pro Asn
                405                 410                 415

Tyr Pro Gly Ser Leu Val Trp Lys Gly Asp Leu Cys Asn Leu Cys Ala
            420                 425                 430

Pro Pro Asp Met Cys Asp Ala Ala His Ala Val Leu Val Gly Ser Ser
        435                 440                 445

Leu Pro Leu Val Glu Ser Val His Val Asn Leu Glu Gln Ala Leu Ser
    450                 455                 460

Ile Phe Thr Lys Pro Thr Ile Asn Ala Val Leu Lys His Phe Lys Thr
465                 470                 475                 480

Val Val Asp Trp Tyr Thr Ser Lys Thr Phe Ser Asp Glu Asp Tyr Tyr
                485                 490                 495

Gln Phe Gln His Ile Leu Leu Glu Ile Tyr Gly Phe Met His Asp His
            500                 505                 510

Leu Ser Glu Gly Lys Asp Ser Phe Lys Ala Leu Lys Phe Pro Trp Val
        515                 520                 525

Trp Thr Gly Lys Asn Phe Cys Pro Leu Ala Gln Ala Val Ile Lys Pro
    530                 535                 540

Thr His Asp Leu Asp Leu Gln Pro Tyr Leu Tyr Asn Val Pro Lys Thr
545                 550                 555                 560

Met Ala Lys Phe His Gln Leu Phe Lys Ala Cys Gly Ser Ile Glu Glu
                565                 570                 575

Leu Thr Ser Asp His Ile Ser Met Val Ile Gln Lys Val Tyr Leu Lys
```

-continued

```
            580                 585                 590

Ser Asp Gln Glu Leu Ser Glu Glu Glu Ser Lys Gln Asn Leu His Leu
        595                 600                 605

Met Leu Asn Ile Met Arg Trp Leu Tyr Ser Asn Gln Ile Pro Ala Ser
    610                 615                 620

Pro Asn Thr Pro Val Pro Ile Tyr His Ser Arg Asn Pro Ser Lys Leu
625                 630                 635                 640

Val Met Lys Pro Ile His Glu Cys Cys Tyr Cys Asp Ile Lys Val Asp
                645                 650                 655

Asp Leu Asn Asp Leu Leu Glu Asp Ser Val Glu Pro Ile Ile Leu Val
            660                 665                 670

His Glu Asp Ile Pro Met Lys Thr Ala Glu Trp Leu Lys Val Pro Cys
        675                 680                 685

Leu Ser Thr Arg Leu Ile Asn Pro Glu Asn Met Gly Phe Glu Gln Ser
    690                 695                 700

Gly Gln Arg Glu Pro Leu Thr Val Arg Ile Lys Asn Ile Leu Glu Glu
705                 710                 715                 720

Tyr Pro Ser Val Ser Asp Ile Phe Lys Glu Leu Leu Gln Asn Ala Asp
                725                 730                 735

Asp Ala Asn Ala Thr Glu Cys Ser Phe Met Ile Asp Met Arg Arg Asn
            740                 745                 750

Met Asp Ile Arg Glu Asn Leu Leu Asp Pro Gly Met Ala Ala Cys His
        755                 760                 765

Gly Pro Ala Leu Trp Ser Phe Asn Asn Ser Glu Phe Ser Asp Ser Asp
    770                 775                 780

Phe Leu Asn Ile Thr Arg Leu Gly Glu Ser Leu Lys Arg Gly Glu Val
785                 790                 795                 800

Asp Lys Val Gly Lys Phe Gly Leu Gly Phe Asn Ser Val Tyr His Ile
                805                 810                 815

Thr Asp Ile Pro Ile Ile Met Ser Arg Glu Phe Met Ile Met Phe Asp
            820                 825                 830

Pro Asn Ile Asn His Ile Ser Lys His Ile Lys Asp Arg Ser Asn Pro
        835                 840                 845

Gly Ile Lys Ile Asn Trp Ser Lys Gln Gln Lys Arg Leu Arg Lys Phe
    850                 855                 860

Pro Asn Gln Phe Lys Pro Phe Ile Asp Val Phe Gly Cys Gln Leu Pro
865                 870                 875                 880

Leu Ala Val Glu Ala Pro Tyr Ser Tyr Asn Gly Thr Leu Phe Arg Leu
                885                 890                 895

Ser Phe Arg Thr Gln Gln Glu Ala Lys Val Ser Glu Val Ser Ser Thr
            900                 905                 910

Cys Tyr Asn Thr Ala Asp Ile Tyr Ser Leu Val Asp Glu Phe Ser Leu
        915                 920                 925

Cys Gly His Arg Leu Ile Ile Phe Thr Gln Ser Val Asn Ser Met Tyr
    930                 935                 940

Leu Lys Tyr Leu Lys Ile Glu Glu Thr Asn Pro Ser Leu Ala Gln Asp
945                 950                 955                 960

Thr Ile Ile Ile Lys Lys Lys Val Cys Pro Ser Lys Ala Leu Asn Ala
                965                 970                 975

Pro Val Leu Ser Val Leu Lys Glu Ala Ala Lys Leu Met Lys Thr Cys
            980                 985                 990

Ser Ser Ser Asn Lys Lys Leu Pro Thr Asp Val Pro Lys Ser Ser Cys
        995                 1000                1005
```

-continued

```
Ile Leu Gln Ile Thr Val Glu Glu Phe His His Val Phe Arg Arg Ile
    1010                1015                1020

Ala Asp Leu Gln Ser Pro Leu Phe Arg Gly Pro Asp Asp Asp Pro Ala
1025                1030                1035                1040

Thr Leu Phe Glu Met Ala Lys Ser Gly Gln Ser Lys Lys Pro Ser Asp
                1045                1050                1055

Glu Leu Pro Gln Lys Thr Val Asp Cys Thr Thr Trp Leu Ile Cys Thr
            1060                1065                1070

Cys Met Asp Thr Gly Glu Ala Leu Lys Phe Ser Leu Asn Glu Ser Gly
        1075                1080                1085

Arg Arg Leu Gly Leu Val Pro Cys Gly Ala Val Gly Val Leu Leu His
    1090                1095                1100

Glu Thr Gln Glu Gln Lys Trp Thr Val Lys Pro His Ile Gly Glu Val
1105                1110                1115                1120

Phe Cys Tyr Leu Pro Leu Arg Ile Lys Thr Gly Leu Pro Ile His Ile
                1125                1130                1135

Asn Gly Cys Phe Ala Val Thr Ser Asn Arg Lys Glu Ile Trp Lys Thr
            1140                1145                1150

Asp Thr Lys Gly Arg Trp Asn Thr Thr Phe Met Arg His Val Ile Val
        1155                1160                1165

Lys Ala Tyr Leu Gln Ala Leu Ser Val Leu Arg Asp Leu Ala Ile Gly
    1170                1175                1180

Gly Glu Leu Thr Asp Tyr Thr Tyr Tyr Ala Val Trp Pro Asp Pro Asp
1185                1190                1195                1200

Leu Val His Asp Asp Phe Ser Val Ile Cys Lys Gly Phe Tyr Glu Asp
                1205                1210                1215

Ile Ala His Gly Lys Gly Lys Glu Leu Thr Arg Val Phe Ser Asp Gly
            1220                1225                1230

Ser Met Trp Val Ser Met Lys Asn Val Arg Phe Leu Asp Asp Ser Ile
        1235                1240                1245

Leu Gln Arg Lys Asp Val Gly Ser Ala Ala Phe Lys Ile Phe Leu Lys
    1250                1255                1260

Tyr Leu Lys Lys Thr Gly Ser Lys Asn Leu Cys Ala Val Glu Leu Pro
1265                1270                1275                1280

Ser Ser Val Lys Ala Gly Phe Glu Glu Ala Gly Cys Lys Gln Ile Leu
                1285                1290                1295

Leu Glu Asn Thr Phe Ser Glu Lys Gln Phe Phe Ser Glu Val Phe Phe
            1300                1305                1310

Pro Asn Ile Gln Glu Ile Glu Ala Glu Leu Arg Asp Pro Leu Met Asn
        1315                1320                1325

Phe Val Leu Asn Glu Lys Leu Asp Glu Phe Ser Gly Ile Leu Arg Val
    1330                1335                1340

Thr Pro Cys Val Pro Cys Ser Leu Glu Gly His Pro Leu Val Leu Pro
1345                1350                1355                1360

Ser Arg Leu Ile His Pro Glu Gly Arg Val Ala Lys Leu Phe Asp Thr
                1365                1370                1375

Lys Asp Gly Arg Phe Pro Tyr Gly Ser Thr Gln Asp Tyr Leu Asn Pro
            1380                1385                1390

Ile Ile Leu Ile Lys Leu Val Gln Leu Gly Met Ala Lys Asp Asp Ile
        1395                1400                1405

Leu Trp Asp Asp Met Leu Glu Arg Ala Glu Ser Val Ala Glu Ile Asn
    1410                1415                1420
```

-continued

```
Lys Ser Asp His Ala Ala Ala Cys Leu Arg Ser Ser Ile Leu Leu Ser
1425                1430                1435                1440

Leu Ile Asp Glu Lys Leu Lys Ile Lys Asp Pro Arg Ala Lys Asp Phe
                1445                1450                1455

Ala Ala Lys Tyr Gln Thr Ile Pro Phe Leu Pro Phe Leu Thr Lys Pro
            1460                1465                1470

Ala Gly Phe Ser Leu Glu Trp Lys Gly Asn Ser Phe Lys Pro Glu Thr
        1475                1480                1485

Met Phe Ala Ala Thr Asp Ile Tyr Thr Ala Glu Tyr Gln Asp Ile Val
    1490                1495                1500

Cys Leu Leu Gln Pro Ile Leu Asn Glu Asn Ser His Ser Phe Arg Gly
1505                1510                1515                1520

Cys Gly Ser Val Ser Leu Ala Val Lys Glu Phe Leu Gly Leu Leu Lys
                1525                1530                1535

Lys Pro Thr Val Asp Leu Val Ile Asn Gln Leu Lys Gln Val Ala Lys
            1540                1545                1550

Ser Val Asp Asp Gly Ile Thr Leu Tyr Gln Glu Asn Ile Thr Asn Ala
        1555                1560                1565

Cys Tyr Lys Tyr Leu His Glu Ala Val Leu Gln Asn Glu Met Ala Lys
    1570                1575                1580

Ala Thr Ile Ile Glu Lys Leu Lys Pro Phe Cys Phe Ile Leu Val Glu
1585                1590                1595                1600

Asn Val Tyr Val Glu Ser Glu Lys Val Ser Phe His Leu Asn Phe Glu
                1605                1610                1615

Ala Ala Pro Tyr Leu Tyr Gln Leu Pro Asn Lys Tyr Lys Asn Asn Phe
            1620                1625                1630

Arg Glu Leu Phe Glu Ser Val Gly Val Arg Gln Ser Phe Thr Val Glu
        1635                1640                1645

Asp Phe Ala Leu Val Leu Glu Ser Ile Asp Gln Glu Arg Gly Lys Lys
    1650                1655                1660

Gln Ile Thr Glu Glu Asn Phe Gln Leu Cys Arg Arg Ile Ile Ser Glu
1665                1670                1675                1680

Gly Ile Trp Ser Leu Ile Arg Glu Lys Arg Gln Glu Phe Cys Glu Lys
                1685                1690                1695

Asn Tyr Gly Lys Ile Leu Leu Pro Asp Thr Asn Leu Leu Leu Leu Pro
            1700                1705                1710

Ala Lys Ser Leu Cys Tyr Asn Asp Cys Pro Trp Ile Lys Val Lys Asp
        1715                1720                1725

Ser Thr Val Lys Tyr Cys His Ala Asp Ile Pro Arg Glu Val Ala Val
    1730                1735                1740

Lys Leu Gly Ala Ile Pro Lys Arg His Lys Ala Leu Glu Arg Tyr Ala
1745                1750                1755                1760

Ser Asn Ile Cys Phe Thr Ala Leu Gly Thr Glu Phe Gly Gln Lys Glu
                1765                1770                1775

Lys Leu Thr Ser Arg Ile Lys Ser Ile Leu Asn Ala Tyr Pro Ser Glu
            1780                1785                1790

Lys Glu Met Leu Lys Glu Leu Leu Gln Asn Ala Asp Asp Ala Lys Ala
        1795                1800                1805

Thr Glu Ile Cys Phe Val Phe Asp Pro Arg Gln His Pro Val Asp Arg
    1810                1815                1820

Ile Phe Asp Asp Lys Trp Ala Pro Leu Gln Gly Pro Ala Leu Cys Val
1825                1830                1835                1840

Tyr Asn Asn Gln Pro Phe Thr Glu Asp Asp Val Arg Gly Ile Gln Asn
```

-continued 1845 1850 1855

Leu Gly Lys Gly Thr Lys Glu Gly Asn Pro Cys Lys Thr Gly His Tyr
1860 1865 1870

Gly Ile Gly Phe Asn Ser Val Tyr His Ile Thr Asp Cys Pro Ser Phe
1875 1880 1885

Ile Ser Gly Asn Asp Ile Leu Gly Ile Phe Asp Pro His Ala Arg Tyr
1890 1895 1900

Ala Pro Gly Ala Thr Ser Val Ser Pro Gly Arg Met Phe Arg Asp Leu
1905 1910 1915 1920

Asp Ala Asp Phe Arg Thr Gln Phe Ser Asp Val Leu Asp Leu Tyr Leu
1925 1930 1935

Gly Asn His Phe Lys Leu Asp Asn Cys Thr Met Phe Arg Phe Pro Leu
1940 1945 1950

Arg Asn Ala Glu Met Ala Gln Val Ser Glu Ile Ser Ser Val Pro Ser
1955 1960 1965

Ser Asp Arg Met Val Gln Asn Leu Leu Asp Lys Leu Arg Ser Asp Gly
1970 1975 1980

Ala Glu Leu Leu Met Phe Leu Asn His Met Glu Lys Ile Ser Ile Cys
1985 1990 1995 2000

Glu Ile Asp Lys Ala Thr Gly Gly Leu Asn Val Leu Tyr Ser Val Lys
2005 2010 2015

Gly Lys Ile Thr Asp Gly Asp Arg Leu Lys Arg Lys Gln Phe His Ala
2020 2025 2030

Ser Val Ile Asp Ser Val Thr Lys Lys Arg Gln Leu Lys Asp Ile Pro
2035 2040 2045

Val Gln Gln Ile Thr Tyr Thr Met Asp Thr Glu Asp Ser Glu Gly Asn
2050 2055 2060

Leu Thr Thr Trp Leu Ile Cys Asn Arg Ser Gly Phe Ser Ser Met Glu
2065 2070 2075 2080

Lys Val Ser Lys Ser Val Ile Ser Ala His Lys Asn Gln Asp Ile Thr
2085 2090 2095

Leu Phe Pro Arg Gly Gly Val Ala Ala Cys Ile Thr His Asn Tyr Lys
2100 2105 2110

Lys Pro His Arg Ala Phe Cys Phe Leu Pro Leu Ser Leu Glu Thr Gly
2115 2120 2125

Leu Pro Phe His Val Asn Gly His Phe Ala Leu Asp Ser Ala Arg Arg
2130 2135 2140

Asn Leu Trp Arg Asp Asp Asn Gly Val Gly Val Arg Ser Asp Trp Asn
2145 2150 2155 2160

Asn Ser Leu Met Thr Ala Leu Ile Ala Pro Ala Tyr Val Glu Leu Leu
2165 2170 2175

Ile Gln Leu Lys Lys Arg Tyr Phe Pro Gly Ser Asp Pro Thr Leu Ser
2180 2185 2190

Val Leu Gln Asn Thr Pro Ile His Val Val Lys Asp Thr Leu Lys Lys
2195 2200 2205

Phe Leu Ser Phe Phe Pro Val Asn Arg Leu Asp Leu Gln Pro Asp Leu
2210 2215 2220

Tyr Cys Leu Val Lys Ala Leu Tyr Ser Cys Ile His Glu Asp Met Lys
2225 2230 2235 2240

Arg Leu Leu Pro Val Val Arg Ala Pro Asn Ile Asp Gly Ser Asp Leu
2245 2250 2255

His Ser Ala Val Ile Ile Thr Trp Ile Asn Met Ser Thr Ser Asn Lys
2260 2265 2270

-continued

Thr Arg Pro Phe Phe Asp Asn Leu Leu Gln Asp Glu Leu Gln His Leu
2275 2280 2285

Lys Asn Ala Asp Tyr Asn Ile Thr Thr Arg Lys Thr Val Ala Glu Asn
2290 2295 2300

Val Tyr Arg Leu Lys His Leu Leu Leu Glu Ile Gly Phe Asn Leu Val
2305 2310 2315 2320

Tyr Asn Cys Asp Glu Thr Ala Asn Leu Tyr His Cys Leu Val Asp Ala
2325 2330 2335

Asp Ile Pro Val Ser Tyr Val Thr Pro Ala Asp Val Arg Ser Phe Leu
2340 2345 2350

Met Thr Phe Ser Ser Pro Asp Thr Asn Cys His Ile Gly Lys Leu Pro
2355 2360 2365

Cys Arg Leu Gln Gln Thr Asn Leu Lys Leu Phe His Ser Leu Lys Leu
2370 2375 2380

Leu Val Asp Tyr Cys Phe Lys Asp Ala Glu Glu Ser Glu Phe Glu Val
2385 2390 2395 2400

Glu Gly Leu Pro Leu Leu Ile Thr Leu Asp Ser Val Leu Gln Ile Phe
2405 2410 2415

Asp Gly Lys Arg Pro Lys Phe Leu Thr Thr Tyr His Glu Leu Ile Pro
2420 2425 2430

Ser Arg Lys Asp Leu Phe Met Asn Thr Leu Tyr Leu Lys Tyr Ser Ser
2435 2440 2445

Val Leu Leu Asn Cys Lys Val Ala Lys Val Phe Asp Ile Ser Ser Phe
2450 2455 2460

Ala Asp Leu Leu Ser Ser Val Leu Pro Arg Glu Tyr Lys Thr Lys Asn
2465 2470 2475 2480

Cys Ala Lys Trp Lys Asp Asn Phe Ala Ser Glu Ser Trp Leu Lys Asn
2485 2490 2495

Ala Trp His Phe Ile Ser Glu Ser Val Ser Val Thr Asp Asp Gln Glu
2500 2505 2510

Glu Pro Lys Pro Ala Phe Asp Val Ile Val Asp Ile Leu Lys Asp Trp
2515 2520 2525

Ala Leu Leu Pro Gly Thr Lys Phe Thr Val Ser Thr Ser Gln Leu Val
2530 2535 2540

Val Pro Glu Gly Asp Val Leu Ile Pro Leu Ser Leu Met His Ile Ala
2545 2550 2555 2560

Val Phe Pro Asn Ala Gln Ser Asp Lys Val Phe His Ala Leu Met Lys
2565 2570 2575

Ala Gly Cys Ile Gln Leu Ala Leu Asn Lys Ile Cys Ser Lys Asp Ser
2580 2585 2590

Ala Leu Val Pro Leu Leu Ser Cys His Thr Ala Asn Ile Asp Ser Pro
2595 2600 2605

Ala Ser Ile Leu Lys Ala Val His Tyr Met Val Gln Thr Ser Thr Phe
2610 2615 2620

Arg Thr Glu Lys Leu Met Glu Asn Asp Phe Glu Ala Leu Leu Met Tyr
2625 2630 2635 2640

Phe Asn Cys Asn Leu Ser His Leu Met Ser Gln Asp Asp Ile Lys Ile
2645 2650 2655

Leu Lys Ser Leu Pro Cys Tyr Lys Ser Ile Ser Gly Arg Tyr Met Ser
2660 2665 2670

Ile Ala Lys Phe Gly Thr Cys Tyr Val Leu Thr Lys Ser Ile Pro Ser
2675 2680 2685

-continued

```
Ala Glu Val Glu Lys Trp Thr Gln Ser Ser Ser Ser Ala Phe Leu Glu
    2690                2695                2700

Glu Lys Val His Leu Lys Glu Leu Tyr Glu Val Leu Gly Cys Val Pro
2705                2710                2715                2720

Val Asp Asp Leu Glu Val Tyr Leu Lys His Leu Leu Pro Lys Ile Glu
                2725                2730                2735

Asn Leu Ser Tyr Asp Ala Lys Leu Glu His Leu Ile Tyr Leu Lys Asn
            2740                2745                2750

Arg Leu Ala Ser Ile Glu Glu Pro Ser Glu Ile Lys Glu Gln Leu Phe
        2755                2760                2765

Glu Lys Leu Glu Ser Leu Leu Ile Ile His Asp Ala Asn Asn Arg Leu
    2770                2775                2780

Lys Gln Ala Lys His Phe Tyr Asp Arg Thr Val Arg Val Phe Glu Val
2785                2790                2795                2800

Met Leu Pro Glu Lys Leu Phe Ile Pro Lys Glu Phe Phe Lys Lys Leu
                2805                2810                2815

Glu Gln Val Ile Lys Pro Lys Asn Gln Ala Ala Phe Met Thr Ser Trp
            2820                2825                2830

Val Glu Phe Leu Arg Asn Ile Gly Leu Lys Tyr Ala Leu Ser Gln Gln
        2835                2840                2845

Gln Leu Leu Gln Phe Ala Lys Glu Ile Ser Val Arg Ala Asn Thr Glu
    2850                2855                2860

Asn Trp Ser Lys Glu Thr Leu Gln Ser Thr Val Asp Ile Leu Leu His
2865                2870                2875                2880

His Ile Phe Gln Glu Arg Met Asp Leu Leu Ser Gly Asn Phe Leu Lys
                2885                2890                2895

Glu Leu Ser Leu Ile Pro Phe Leu Cys Pro Glu Arg Ala Pro Ala Glu
            2900                2905                2910

Tyr Ile Arg Phe His Pro Gln Tyr Gln Glu Val Asn Gly Thr Leu Pro
        2915                2920                2925

Leu Ile Lys Phe Asn Gly Ala Gln Val Asn Pro Lys Phe Lys Gln Cys
    2930                2935                2940

Asp Val Leu Gln Leu Leu Trp Thr Ser Cys Pro Ile Leu Pro Glu Lys
2945                2950                2955                2960

Ala Thr Pro Leu Ser Ile Lys Glu Gln Glu Gly Ser Asp Leu Ala Pro
                2965                2970                2975

Gln Glu Gln Leu Glu Gln Val Leu Asn Met Leu Asn Val Asn Leu Asp
            2980                2985                2990

Pro Pro Leu Asp Lys Val Ile Asn Asn Cys Arg Asn Ile Cys Asn Ile
        2995                3000                3005

Thr Thr Leu Asp Glu Glu Met Val Lys Thr Arg Ala Lys Val Leu Arg
    3010                3015                3020

Ser Ile Tyr Glu Phe Leu Ser Ala Glu Lys Arg Glu Phe Arg Phe Gln
3025                3030                3035                3040

Leu Arg Gly Val Ala Phe Val Met Val Glu Asp Gly Trp Lys Leu Leu
                3045                3050                3055

Lys Pro Glu Glu Val Val Ile Asn Leu Glu Tyr Glu Ala Asp Phe Lys
            3060                3065                3070

Pro Tyr Leu Tyr Lys Leu Pro Leu Glu Leu Gly Thr Phe His Gln Leu
        3075                3080                3085

Phe Lys His Leu Gly Thr Glu Asp Ile Ile Ser Thr Lys Gln Tyr Val
    3090                3095                3100

Glu Val Leu Ser Arg Ile Phe Lys Ser Ser Glu Gly Lys Gln Leu Asp
```

-continued

```
3105                3110                3115                3120

Pro Asn Glu Met Arg Thr Val Lys Arg Val Val Ser Gly Leu Phe Lys
                3125                3130                3135

Ser Leu Gln Asn Asp Ser Val Lys Val Arg Ser Asp Leu Glu Asn Ala
            3140                3145                3150

Arg Asp Leu Ala Leu Tyr Leu Pro Ser Gln Asp Gly Lys Leu Val Lys
        3155                3160                3165

Ser Ser Ile Leu Val Phe Asp Asp Ala Pro His Tyr Lys Ser Arg Ile
    3170                3175                3180

Gln Gly Asn Ile Gly Val Gln Met Leu Val Asp Leu Ser Gln Cys Tyr
3185                3190                3195                3200

Leu Gly Lys Asp His Gly Phe His Thr Lys Leu Ile Met Leu Phe Pro
                3205                3210                3215

Gln Lys Leu Arg Pro Arg Leu Leu Ser Ser Ile Leu Glu Glu Gln Leu
            3220                3225                3230

Asp Glu Glu Thr Pro Lys Val Cys Gln Phe Gly Ala Leu Cys Ser Leu
        3235                3240                3245

Gln Gly Arg Leu Gln Leu Leu Leu Ser Ser Glu Gln Phe Ile Thr Gly
    3250                3255                3260

Leu Ile Arg Ile Met Lys His Glu Asn Asp Asn Ala Phe Leu Ala Asn
3265                3270                3275                3280

Glu Glu Lys Ala Ile Arg Leu Cys Lys Ala Leu Arg Glu Gly Leu Lys
                3285                3290                3295

Val Ser Cys Phe Glu Lys Leu Gln Thr Thr Leu Arg Val Lys Gly Phe
            3300                3305                3310

Asn Pro Ile Pro His Ser Arg Ser Glu Thr Phe Ala Phe Leu Lys Arg
        3315                3320                3325

Phe Gly Asn Ala Val Ile Leu Leu Tyr Ile Gln His Ser Asp Ser Lys
    3330                3335                3340

Asp Ile Asn Phe Leu Leu Ala Leu Ala Met Thr Leu Lys Ser Ala Thr
3345                3350                3355                3360

Asp Asn Leu Ile Ser Asp Thr Ser Tyr Leu Ile Ala Met Leu Gly Cys
                3365                3370                3375

Asn Asp Ile Tyr Arg Ile Ser Glu Lys Leu Asp Ser Leu Gly Val Lys
            3380                3385                3390

Tyr Asp Ser Ser Glu Pro Ser Lys Leu Glu Leu Pro Met Pro Gly Thr
        3395                3400                3405

Pro Ile Pro Ala Glu Ile His Tyr Thr Leu Leu Met Asp Pro Met Asn
    3410                3415                3420

Val Phe Tyr Pro Gly Glu Tyr Val Gly Tyr Leu Val Asp Ala Glu Gly
3425                3430                3435                3440

Gly Asp Ile Tyr Gly Ser Tyr Gln Pro Thr Tyr Thr Tyr Ala Ile Ile
                3445                3450                3455

Val Gln Glu Val Glu Arg Glu Asp Ala Asp Asn Thr Ser Phe Leu Gly
            3460                3465                3470

Lys Ile Tyr Gln Ile Asp Ile Gly Tyr Ser Glu Tyr Lys Ile Val Ser
        3475                3480                3485

Ser Leu Asp Leu Tyr Lys Phe Ser Arg Pro Asp Glu Ser Ser Gln Asn
    3490                3495                3500

Arg Asp Ser Ala Pro Thr Thr Pro Thr Ser Pro Thr Glu Phe Leu Thr
3505                3510                3515                3520

Pro Gly Leu Arg Ser Ile Pro Pro Leu Phe Ser Gly Lys Glu Ser His
                3525                3530                3535
```

-continued

```
Lys Ser Pro Ser Thr Lys His His Ser Pro Arg Lys Leu Lys Val Asn
            3540                3545                3550

Ala Leu Pro Glu Ile Leu Lys Glu Val Thr Ser Val Val Glu Gln Ala
        3555                3560                3565

Trp Lys Leu Pro Glu Ser Glu Arg Lys Lys Ile Ile Arg Arg Leu Tyr
    3570                3575                3580

Leu Lys Trp His Pro Asp Lys Asn Pro Glu Asn His Asp Ile Ala Asn
3585                3590                3595                3600

Glu Val Phe Lys His Leu Gln Asn Glu Ile Asn Arg Leu Glu Lys Gln
                3605                3610                3615

Ala Phe Leu Asp Gln Asn Ala Asp Arg Ala Ser Arg Arg Thr Phe Ser
            3620                3625                3630

Thr Ser Ala Ser Arg Phe Gln Ser Asp Lys Tyr Ser Phe Gln Arg Phe
        3635                3640                3645

Tyr Thr Ser Trp Asn Gln Glu Ala Thr Ser His Lys Ser Glu Arg Gln
    3650                3655                3660

Gln Gln Ser Lys Glu Lys Cys Pro Pro Ser Ala Gly Gln Thr Tyr Ser
3665                3670                3675                3680

Gln Arg Phe Phe Val Pro Pro Thr Phe Lys Ser Val Gly Asn Pro Val
                3685                3690                3695

Glu Ala Arg Arg Trp Leu Arg Gln Ala Arg Ala Asn Phe Ser Ala Ala
            3700                3705                3710

Arg Asn Asp Leu His Lys Asn Ala Asn Glu Trp Val Cys Phe Lys Cys
        3715                3720                3725

Tyr Leu Ser Thr Lys Leu Ala Leu Ile Ala Ala Asp Tyr Ala Val Arg
    3730                3735                3740

Gly Lys Ser Asp Lys Asp Val Lys Pro Thr Ala Leu Ala Gln Lys Ile
3745                3750                3755                3760

Glu Glu Tyr Ser Gln Gln Leu Glu Gly Leu Thr Asn Asp Val His Thr
                3765                3770                3775

Leu Glu Ala Tyr Gly Val Asp Ser Leu Lys Thr Arg Tyr Pro Asp Leu
            3780                3785                3790

Leu Pro Phe Pro Gln Ile Pro Asn Asp Arg Phe Thr Ser Glu Val Ala
        3795                3800                3805

Met Arg Val Met Glu Cys Thr Ala Cys Ile Ile Ile Lys Leu Glu Asn
    3810                3815                3820

Phe Ile Gln Gln Lys Val
3825                3830
```

<210> SEQ ID NO 5

<400> SEQUENCE: 5

000

<210> SEQ ID NO 6

<400> SEQUENCE: 6

000

<210> SEQ ID NO 7
<211> LENGTH: 12792
<212> TYPE: DNA
<213> ORGANISM: Homo sapiens

<400> SEQUENCE: 7

-continued

```
atgatttaca ggaagaccat gtactcagct gcagcttcta aatccagaac gatttgcacg     60
tcttatcaag gaagtaatga atacattctg gcctggcaga gaattgattg ttcaatggta    120
tccatttgat gaaaacagaa atcacccatc tgtttcatgg cttaagatgg tttggaaaaa    180
tctttatata catttttcag aggatttgac tttatttgat gagatgccac ttatccccag    240
aactatacta gaggaaggtc agacatgtgt ggaactcatt agactcagga ttccatcgtt    300
agtcatttta gacgatgaat ctgaagcaca gcttccagaa tttttagcag acattgtaca    360
aaaacttgga gggtttgtcc ttaaaaaatt agatgcatct atacaacatc cgcttattaa    420
aaaatatatt cattcaccat taccaagtgc tgttttgcag ataatggaga agatgccatt    480
gcagaaattg tgtaatcaaa taacttcgct acttccaaca cacaaagatg ccctgaggaa    540
gttcttggct agtttaaccg atagcagtga gaaagagaaa agaattattc aagaattggc    600
aatattcaag cgcattaacc attcttctga tcagggaatt tcctcttata caaaattgaa    660
aggttgtaaa gtcttacacc atactgccaa actcccagca gatctgcgac tttctatttc    720
agtaatagac agtagtgatg aagctactat tcgtctggca aacatgttga aaatagaaca    780
gttaaagacc actagctgct taaagcttgt tttaaaagat attgaaaatg cattttattc    840
acatgaagag gtaacacagc ttatgttatg ggtccttgag aatctatctt ctcttaaaaa    900
tgagaatcca aatgtgcttg agtggttaac accattaaaa ttcatccaga tatcacagga    960
acagatggta tcagctggtg aactctttga ccctgatata gaagtactaa aggatctctt   1020
ttgtaatgaa gaaggaacct atttcccacc ctcagttttt acctcaccag atattcttca   1080
ctccttaaga cagattggtt taaaaaacga agccagtctc aaagaaaagg atgttgtgca   1140
agtggcaaaa aaaattgaag ccttacaggt cggtgcttgt cctgatcaag atgttcttct   1200
gaagaaagcc aaaaccctct tactggtttt aaataagaat cacacactgt tgcaatcatc   1260
tgaaggaaag atgacattga agaaaataaa atgggttcca gcctgcaagg aaaggcctcc   1320
aaattatcca ggctctttgg tctggaaagg agatctctgt aatctctgtg caccaccaga   1380
tatgtgtgat gtaggccatg caattctcat tggctcctca cttcctcttg ttgaaagtat   1440
ccatgtaaac ctggaaaaag cattagggat cttcacaaaa cctagcctta gtgctgtctt   1500
aaaacacttt aaaattgttg ttgattggta ttcttcaaaa acctttagtg atgaagacta   1560
ctatcaattc cagcatattt tgcttgagat ttacggattc atgcatgatc atctaaatga   1620
agggaaagat tcttttagag ccttaaaatt tccatgggtt tggactggca aaaagttttg   1680
tccacttgcc caggctgtga ttaaaccaat ccatgatctt gaccttcagc cttatttgca   1740
taatgtacct aaaaccatgg caaaattcca ccaactattt aaggtctgtg gttcaataga   1800
ggagttgaca tcagatcata tttccatggt tattcagaag atatatctca aaagtgacca   1860
agatctcagt gaacaagaaa gcaaacaaaa tcttcatctt atgttgaata ttatcagatg   1920
gctgtatagc aatcagattc cagcaagccc caacacacca gttcctatac atcatagcaa   1980
aaatccttct aaacttatca tgaagccaat tcacgaatgc tgttattgtg acattaaagt   2040
tgatgacctt aatgacttac ttgaagattc tgtggaacca atcattttgg tgcatgagga   2100
catacccatg aaaactgcag aatggctaaa agttccatgc cttagtacaa gactgataaa   2160
tcctgaaaac atgggatttg agcagtcagg acaaagagag ccacttactg taagaattaa   2220
aaatattctg gaagaatacc cttcagtgtc agatattttt aaagaactac ttcaaaacgc   2280
tgatgatgca aatgcaacag aatgcagttt cttgattgat atgagaagaa atatggacat   2340
```

-continued

```
aagagagaat ctcctagacc cagggatggc agcttgtcat ggacctgctt tgtggtcatt   2400
caacaattct caattctcag attcagattt tgtgaacata actaggttag gagaatcttt   2460
aaaaagggga gaagttgaca aagttggaaa atttggtctt ggatttaatt ctgtgtacca   2520
tatcactgac attcccatca ttatgagtcg ggaattcatg ataatgttcg atccaaacat   2580
aaatcatatc agtaaacaca ttaaagacaa atccaatcct gggatcaaaa ttaattggag   2640
taaacaacag aaaagactta gaaaatttcc taatcagttc aaaccattta tagatgtatt   2700
tggctgtcag ttacctttga ctgtagaagc accttacagc tataatggaa cccttttccg   2760
actgtccttt agaactcaac aggaagcaaa agtgagtgaa gttagtagta cgtgctacaa   2820
tacagcagat atttattctc ttgtggatga atttagtctc tgtggacaca ggcttatcat   2880
tttcactcag agtgtaaagt caatgtattt gaagtacttg aaaattgagg aaaccaaccc   2940
cagtttagca caagatacag taataattaa aaaaaaatcc tgctcttcca aagcattgaa   3000
cacacctgtc ttaagtgttt taaaagaggc tgctaagctc atgaagactt gcagcagcag   3060
taataaaaag cttcccagtg atgaaccaaa gtcatcttgc attcttcaga tcacagtgga   3120
agaatttcac catgtgttca gaaggattgc tgatttacag tcgccacttt ttagaggtcc   3180
agatgatgac ccagctgctc tctttgaaat ggctaagtct ggccaatcaa aaaagccatc   3240
agatgagttg tcacagaaaa cagtagagtg taccacgtgg cttctgtgta cttgcatgga   3300
cacaggagag gctctgaagt tttccctgag tgagagtgga agaagactag gactggttcc   3360
atgtggggca gtaggagttc agctgtcaga aatccaggac cagaagtgga cagtgaaacc   3420
acacattgga gaggtgtttt gctatttacc tttacgaata aaaacaggct tgccagttca   3480
tatcaatggg tgctttgctg ttacatcaaa taggaaagaa atctggaaaa cagatacaaa   3540
aggacgatgg aataccacgt tcatgagaca tgttattgtg aaagcttact tacaggtact   3600
gagtgtctta cgggacctgg ccactagtgg ggagctaatg gattatactt actatgcagt   3660
atggcccgat cctgatttag ttcatgatga tttttctgta atttgccaag gattttatga   3720
agatatagct catggaaaag ggaaagaact gaccaaagtc ttctctgatg gatctacttg   3780
ggtttccatg aagaacgtaa gatttctaga tgactctata cttaaaagaa gagatgttgg   3840
ttcagcagcc ttcaagatat ttttgaaata cctcaagaag actgggtcca aaaacctttg   3900
tgctgttgaa cttccttctt cggtaaaatt aggatttgaa gaagctggct gcaaacagat   3960
actacttgaa aacacatttt cagagaaaca gttttttttct gaagtgtttt ttccaaatat   4020
tcaagaaatt gaagcagaac ttagagatcc tttaatgatc tttgttctaa atgaaaaagt   4080
tgatgagttc tcgggagttc ttcgtgttac tccatgtatt ccttgttcct tggaggggca   4140
tcctttggtt ttgccatcaa gattgatcca ccccgaagga cgagttgcaa agttatttga   4200
tattaaagat gggagattcc cttatggttc tactcaggat tatctcaatc ctattatttt   4260
gattaaacta gttcagttag gtatggcaaa agatgatatt ttatgggatg atatgctaga   4320
acgtgcagtg tcagtagctg aaattaataa aagtgatcat gttgctgcat gcctaagaag   4380
tagtatctta ttgagtctta tcgatgagaa actaaaaata agggatccta gagcaaagga   4440
ttttgctgca aaatatcaaa caatccgctt ccttccattt ctgacaaaac cagcaggttt   4500
ttctttggac tggaaaggca acagttttaa gcctgaaacc atgtttgcag caactgacct   4560
ttatacagct gaacatcaag atatagtttg tcttttgcaa ccaattctaa atgaaaattc   4620
ccattctttt agaggttgtg gttcagtgtc attggctgtt aaagagtttt tgggattact   4680
caagaagcca acagttgatc tggttataaa ccaattgaaa gaagtagcaa aatcagttga   4740
```

-continued tgatggaatt acactgtacc aggagaatat caccaatgct tgctacaaat accttcatga 4800
agccttgatg caaaatgaaa tcactaagat gtcaattatt gataagttaa aaccctttag 4860
cttcattcta gttgagaatg catatgttga ctcagaaaag gtttcttttc atttaaattt 4920
tgaggcggca ccatacettt atcagttgcc taataagtat aaaaataatt tccgcgaact 4980
ttttgaaacc gtgggtgtga ggcagtcatg cactgttgaa gattttgctc ttgttttgga 5040
atctattgat caagaaagag gaacaaagca aataacagaa gagaattttc agctttgccg 5100
acgaataatc agtgaaggaa tatggagtct cattagagaa aagaaacaag aattttgtga 5160
gaaaaattat ggcaagatat tattgccaga tactaatctt atgcttctcc ctgctaaatc 5220
gttatgctac aatgattgcc cttggataaa agtaaaggat accactgtaa aatattgtca 5280
tgctgacata cccagggaag tagcagtaaa actaggagca gtcccaaagc gacacaaagc 5340
cttagaaaga tatgcatcca atgtctgttt tacaacactt ggcacagaat ttgggcagaa 5400
agaaaaattg accagcagaa ttaagagcat ccttaatgca tatccttctg aaaaggaaat 5460
gttgaaagag cttcttcaaa atgctgatga tgcaaaggcg acagaaatct gttttgtgtt 5520
tgatcctaga cagcatccag ttgatagaat atttgatgat aagtgggccc cattgcaagg 5580
gccagcactt tgtgtgtaca acaaccagcc atttacagaa gatgatgtta gaggaattca 5640
gaatcttgga aaaggcacga aagagggaaa tccttataaa actggacagt atggaatagg 5700
attcaattct gtgtatcata tcacagactg cccatctttt atttctggca atgacatcct 5760
gtgtattttt gatcctcatg ccagatatgc accaggggcc acatccatta gtcccggacg 5820
catgtttaga gatttggatg cagattttag gacacagttc tcagatgttc tggatcttta 5880
tctgggaacc cattttaaac tggataattg cacaatgttc agatttcctc ttcgtaatgc 5940
agaaatggca aaagtttcgg aaatttcgtc tgttccagca tcagacagaa tggtccagaa 6000
tcttttggac aaactgcgct cagatggggc agaacttcta atgtttctta atcacatgga 6060
aaaaatttct atttgtgaaa tagataagag tactggagct ctaaatgtgc tgtattcagt 6120
aaagggcaaa atcacagatg gagacagatt gaaaaggaaa caatttcatg catctgtaat 6180
tgatagtgtt actaaaaaga ggcagctcaa agacatacca gttcaacaaa taacctatac 6240
tatggatact gaggactctg aaggaaatct tactacgtgg ctaatttgta atagatcagg 6300
cttttcaagt atggagaaag tatctaaaag tgtcatatca gctcacaaga accaagatat 6360
tactcttttc ccacgtggtg gagtagctgc ctgcattact cacaactata aaaaacccca 6420
tagggccttc tgtttttttgc ctctttcttt ggagactggg ctgccatttc atgtgaatgg 6480
ccactttgca ctggattcag ccagaaggaa cctgtggcgt gatgataatg gagttggtgt 6540
tcgaagtgac tggaataaca gtttaatgac agcattaata gctcctgcat atgtgaattg 6600
ctaatacagt taaaaaaacg gtatttccct ggttctgatc caacattatc agtgttacag 6660
aacaccccta ttcatgttgt aaaggacact ttaaagaagt ttttatcgtt tttcccagtt 6720
aaccgtcttg atctacagcc agatttatat tgtctagtga aagcacttta caattgcatt 6780
cacgaagaca tgaaacgtct tttacctgtt gtgcgggctc caaatattga tggctctgac 6840
ttgcactctg cagttataat tacttggatc aatatgtcta cttctaataa aactagacca 6900
ttttttgaca atttactaca ggatgaatta caacacctta aaaatgcaga ttataatatc 6960
accacacgca aaacagtagc agagaatgtc tataggctga aacatctcct tttagaaatt 7020
ggtttcaact tggtttataa ctgtgatgaa actgctaatc tttaccactg tcttatagat 7080

-continued

```
gcagatattc ctgttagtta tgtgacccct gctgatatca gatctttttt aatgacattt   7140
tcctctcctg acactaattg ccatattggg aagctgcctt gtcgtctgca gcagactaat   7200
ctaaaacttt ttcatagttt aaaactttta gttgattatt gttttaaaga tgcagaagaa   7260
aatgagattg aagttgaggg attgcccctt ctcatcacac tggacagtgt tttgcaaact   7320
tttgatgcaa aacgacccaa gtttctaaca acatatcatg aattgattcc atcccgcaaa   7380
gacttgttta tgaatacatt atatttgaaa tatagtaata ttttattgaa ctgtaaagtt   7440
gcaaaagtgt ttgacatttc cagctttgct gatttgttat cctctgtgtt gcctcgagaa   7500
tataagacca aaagttgcac aaagtggaaa gacaattttg caagtgagtc ttggcttaag   7560
aatgcatggc attttattag tgaatctgta agtgtgaaag aagatcagga agaaacaaaa   7620
ccaacatttg acattgttgt tgatactcta aaagactggg cattgcttcc aggaacaaag   7680
tttactgttt cagccaacca gcttgtggtt cctgaaggag atgttctgct tcctctcagc   7740
cttatgcaca ttgcagtttt tccaaatgcc cagagtgata aagtttttca tgctctaatg   7800
aaagccggct gtattcagct tgctttgaac aaaatctgtt ccaaagacag tgcatttgtt   7860
cctttgttgt catgtcacac agcaaatata gagagcccca caagcatctt gaaggctcta   7920
cattatatgg tccaaacttc aacatttaga gcagaaaaat tagtagaaaa tgattttgag   7980
gcacttttga tgtatttcaa ctgcaatttg aatcatttga tgtcccaaga tgatataaaa   8040
attctaaagt cacttccgtg ctataaatcc atcagtggcc gctatgtaag cattggaaaa   8100
tttggaacat gctacgtact tacaaaaagt atcccttcag ctgaagtgga gaaatggaca   8160
caatcatcat catctgcatt tcttgaagaa aaaatacact taaaagaact atatgaggtg   8220
attggttgtg tacctgtaga tgatcttgag gtatatttga aacacctctt accaaaaatt   8280
gaaaatctct cttatgatgc aaaattagag cacttgatct accttaagaa tagattatca   8340
agtgctgagg aattatcaga gattaaggaa caactttttg aaaaactgga aagtttattg   8400
ataatccatg atgctaacag tagactaaag caagcaaagc atttctatga tagaactgtg   8460
agagtttttg aagttatgct tcctgaaaaa ttgtttattc ctaatgattt ctttaagaaa   8520
ttggaacaac ttataaaacc caaaaatcat gttacattta tgacatcctg ggtggaattc   8580
ttaagaaata ttggactaaa atacatactt tctcagcagc agttgttaca gtttgctaag   8640
gaaatcagtg tgagggctaa tacagaaaac tggtccaaag aaacattgca aaatacagtt   8700
gatatccttc tgcatcatat attccaagaa cgaatggatt tgttatctgg aaattttctg   8760
aaagaactat ctttaatacc attcttatgt cctgagcggg cccccgcgga attcattaga   8820
tttcatcctc aatatcaaga ggtaaatgga acacttcctc ttataaagtt caatggagca   8880
caggtaaatc caaaattcaa gcaatgtgat gtactccagc tgttatggac atcctgccct   8940
attcttccag agaaagctac acccttaagc attaaagaac aagaaggtag tgaccttggt   9000
ccacaagaac agcttgaaca agttttaaat atgcttaatg ttaacctgga tcctcctctt   9060
gataaggtaa tcaataactg cagaaacata tgcaacataa cgacgttgga tgaagaaatg   9120
gtaaaaacta gagcaaaagt cttaaggagc atatatgaat tcctcagtgc agaaaaaagg   9180
gaatttcgtt ttcagttgcg aggggttgct tttgtgatgg tagaagatgg ttggaaactt   9240
ctgaagcctg aggaggtagt cataaaccta gaatatgaat ctgattttaa accttatttg   9300
tacaagctac ctttagaact tggcacattt caccagttgt tcaaacactt aggtactgaa   9360
gatattattt caactaagca atatgttgaa gtgttgagcc gcatatttaa aaattctgag   9420
ggcaaacaat tagatcctaa tgaaatgcgt acagttaaga gagtagtttc tggtctgttc   9480
```

-continued

```
aggagtctac agaatgattc agtcaaggtg aggagtgatc tcgagaatgt acgagacctt   9540
gcgctttacc tcccaagcca ggatggtaga ttggtaaagt caagcatctt agtgtttgac   9600
gatgcgccac attataaaag tagaatccag gggaatattg gtgtgcaaat gttagttgat   9660
ctcagccagt gctacttagg gaaagaccat ggatttcaca ctaagttgat aatgctcttt   9720
cctcaaaaac ttagacctcg attattgagc agtatacttg aagaacaatt agatgaagag   9780
actcccaaag tttgtcagtt tggagcgttg tgttctcttc aaggaagatt gcagttactc   9840
ttgtcttctg aacagttcat tacaggactg attagaatta tgaagcatga aaatgataat   9900
gcttttctgg ccaatgaaga aaaagccata agactttgca aagccctaag agaaggattg   9960
aaagtatcct gctttgaaaa gcttcaaaca acattaagag ttaaaggttt taatcctatt  10020
ccccacagca gaagtgaaac ttttgctttt ttgaagcgat ttggtaatgc agtcatcttg  10080
ctctacattc aacattcaga cagtaaagac attaatttcc tgttagcact ggcaatgact  10140
cttaaatcag caactgacaa tttgatttct gacacttcat atttaattgc tatgctagga  10200
tgcaatgata tttacaggat tggtgagaaa cttgacagtt taggagtgaa atatgactct  10260
tcggagccat caaaactgga acttccaatg cctggcacac caattcctgc tgaaattcat  10320
tacactctgc ttatggaccc aatgaatgtt ttttacccgg gagaatatgt tgggtacctt  10380
gttgatgctg aaggtggtga tatctatgga tcataccagc caacatacac atatgcaatt  10440
attgtacaag aagttgaaag agaagatgct gacaattcta gttttctagg aaagatatat  10500
cagatagata ttggttatag tgaatataaa atagttagct ctcttgatct gtataagttt  10560
tcaagacctg aggaaagctc tcaaagcagg gacagtgctc cttctacacc aaccagcccc  10620
actgagttcc tcacccctgg cctgagaagc attcctcctc ttttctctgg tagagagagc  10680
cacaagactt cttccaaaca tcagtccccc aaaaagctta aggttaattc tttaccagaa  10740
atcttaaaag aagtgacatc tgtggtggag caagcatgga agcttccaga atcggaacga  10800
aaaaagatta ttaggcggtt gtatttgaaa tggcatcctg acaaaaatcc agagaaccat  10860
gacattgcca atgaagtttt taaacatttg cagaatgaaa tcaacagatt agaaaaacag  10920
gcttttctag atcaaaatgc agacagggcc tccagacgaa cattttcaac ctcagcatcc  10980
cgatttcagt cagacaaata ctcatttcag agattctata cttcatggaa tcaagaagca  11040
acgagccata aatctgaaag acagcaacag aacaaagaaa aatgcccccc ttcagccgga  11100
cagacttact ctcaaaggtt ctttgttcct cccactttca agtcggttgg caatccagtg  11160
gaagcacgca gatggctaag acaagccaga gcaaacttct cagctgccag gaatgacctt  11220
cataaaaatg ccaatgagtg ggtgtgcttt aaatgttacc tttctaccaa gttagctttg  11280
attgcagctg actatgctgt gaggggaaag tctgataaag atgtaaaacc aactgcactt  11340
gctcagaaaa tagaggaata tagtcagcaa cttgaaggac tgacaaatga tgttcacaca  11400
ttggaagctt atggtgtaga cagtttaaaa acaagatacc ctgatttgct tccctttcct  11460
cagatcccaa atgacaggtt cacttctgag gttgctatga gggtgatgga atgtactgcc  11520
tgtatcataa taaaacttga aaattttatg caacaaaaag tgtgaagata tttaacgaaa  11580
aaaaaggtag atcttgaatg tgttgtagca cgaataaatt gctgtacttc attaagcttc  11640
attgccaatt agctaggaat tgttaagcac attgcagatt gttcttggag aattctggag  11700
ttgttatgaa catgaatacc aacggaaaac cttaactgaa tctaaaagaa aactattttg  11760
aagatggtgg tgagctgcaa aatagctgga tggatttgaa tgattgggat gatacatcat  11820
```

-continued

```
tgaactgcac tttatataac caaagcttag cagtttgtta gataagagtc tatgtatgtc  11880

tctggttagg atgaagttaa ttttatgttt ttaacatggt atttttgaag gagctaatga  11940

aacactggac atataattgg tttaaacata aggggaatta agtctttgta gtctgtcatt  12000

tttttaagtg gatcctcttg gatgcgttat tttctcatca gctggctctg atcatgaatt  12060

tgttgtaatt ttatgttgta ctcagtgcat ttaagaaatg gtagagtatt ttaatcctat  12120

tacttgacta agagtgtgaa ggtagtactt tttagagtgc actgagtgca ctttacatct  12180

ttatttaaat tttttttaa catcttatgt ttacaggctt cctgtttgat gaagatagca  12240

acggaaaact caaaatggtg gcagttctta ttaccagttg ttagtattgt ttctggaaac  12300

tgcttgccaa gacaacattt attaactgtt agaacacttg ctttatgttt gtgtgtacat  12360

attttccaca aatgttataa tttatatagt gtggttgaac aggatgcaat cttttgttgt  12420

ctaaaggtgc tgcagttaaa aaaaaaacaa ccttttcttt caatatggca tgtagtggag  12480

tttttttaac tttaaaaaca tcaaaaattg ttaaaatcat tgtgttatct agtagtttat  12540

aattatcggc ttatatttcc ccatgaatga tcagaactga catttaattc atgtttgtct  12600

cgccatgctt ctttacttta acatatttct tttgcagaat gtaaaaggta atgataatta  12660

gtttatataa gtgtactggc tgtaaatgat gctaaatata ctttatgcaa ttaagggctt  12720

acagaacatg ttgaaacttt ttttactttt attgggaata aggaatgttt gcacctccac  12780

attttattgc tt                                                     12792
```

<210> SEQ ID NO 8
<211> LENGTH: 2175
<212> TYPE: PRT
<213> ORGANISM: Homo sapiens

<400> SEQUENCE: 8

```
Met Asn Thr Phe Trp Pro Gly Arg Glu Leu Ile Val Gln Trp Tyr Pro
 1               5                  10                  15

Phe Asp Glu Asn Arg Asn His Pro Ser Val Ser Trp Leu Lys Met Val
            20                  25                  30

Trp Lys Asn Leu Tyr Ile His Phe Ser Glu Asp Leu Thr Leu Phe Asp
        35                  40                  45

Glu Met Pro Leu Ile Pro Arg Thr Ile Leu Glu Glu Gly Gln Thr Cys
    50                  55                  60

Val Glu Leu Ile Arg Leu Arg Ile Pro Ser Leu Val Ile Leu Asp Asp
65                  70                  75                  80

Glu Ser Glu Ala Gln Leu Pro Glu Phe Leu Ala Asp Ile Val Gln Lys
                85                  90                  95

Leu Gly Gly Phe Val Leu Lys Lys Leu Asp Ala Ser Ile Gln His Pro
            100                 105                 110

Leu Ile Lys Lys Tyr Ile His Ser Pro Leu Pro Ser Ala Val Leu Gln
        115                 120                 125

Ile Met Glu Lys Met Pro Leu Gln Lys Leu Cys Asn Gln Ile Thr Ser
    130                 135                 140

Leu Leu Pro Thr His Lys Asp Ala Leu Arg Lys Phe Leu Ala Ser Leu
145                 150                 155                 160

Thr Asp Ser Ser Glu Lys Glu Lys Arg Ile Ile Gln Glu Leu Ala Ile
                165                 170                 175

Phe Lys Arg Ile Asn His Ser Ser Asp Gln Gly Ile Ser Ser Tyr Thr
            180                 185                 190

Lys Leu Lys Gly Cys Lys Val Leu His His Thr Ala Lys Leu Pro Ala
```

-continued

```
        195                 200                 205

Asp Leu Arg Leu Ser Ile Ser Val Ile Asp Ser Ser Asp Glu Ala Thr
    210                 215                 220

Ile Arg Leu Ala Asn Met Leu Lys Ile Glu Gln Leu Lys Thr Thr Ser
225                 230                 235                 240

Cys Leu Lys Leu Val Leu Lys Asp Ile Glu Asn Ala Phe Tyr Ser His
                245                 250                 255

Glu Glu Val Thr Gln Leu Met Leu Trp Val Leu Glu Asn Leu Ser Ser
            260                 265                 270

Leu Lys Asn Glu Asn Pro Asn Val Leu Glu Trp Leu Thr Pro Leu Lys
        275                 280                 285

Phe Ile Gln Ile Ser Gln Glu Gln Met Val Ser Ala Gly Glu Leu Phe
    290                 295                 300

Asp Pro Asp Ile Glu Val Leu Lys Asp Leu Phe Cys Asn Glu Glu Gly
305                 310                 315                 320

Thr Tyr Phe Pro Pro Ser Val Phe Thr Ser Pro Asp Ile Leu His Ser
                325                 330                 335

Leu Arg Gln Ile Gly Leu Lys Asn Glu Ala Ser Leu Lys Glu Lys Asp
            340                 345                 350

Val Val Gln Val Ala Lys Lys Ile Glu Ala Leu Gln Val Gly Ala Cys
        355                 360                 365

Pro Asp Gln Asp Val Leu Leu Lys Lys Ala Lys Thr Leu Leu Leu Val
    370                 375                 380

Leu Asn Lys Asn His Thr Leu Leu Gln Ser Ser Glu Gly Lys Met Thr
385                 390                 395                 400

Leu Lys Lys Ile Lys Trp Val Pro Ala Cys Lys Glu Arg Pro Pro Asn
                405                 410                 415

Tyr Pro Gly Ser Leu Val Trp Lys Gly Asp Leu Cys Asn Leu Cys Ala
            420                 425                 430

Pro Pro Asp Met Cys Asp Val Gly His Ala Ile Leu Ile Gly Ser Ser
        435                 440                 445

Leu Pro Leu Val Glu Ser Ile His Val Asn Leu Glu Lys Ala Leu Gly
    450                 455                 460

Ile Phe Thr Lys Pro Ser Leu Ser Ala Val Leu Lys His Phe Lys Ile
465                 470                 475                 480

Val Val Asp Trp Tyr Ser Ser Lys Thr Phe Ser Asp Glu Asp Tyr Tyr
                485                 490                 495

Gln Phe Gln His Ile Leu Leu Glu Ile Tyr Gly Phe Met His Asp His
            500                 505                 510

Leu Asn Glu Gly Lys Asp Ser Phe Arg Ala Leu Lys Phe Pro Trp Val
        515                 520                 525

Trp Thr Gly Lys Lys Phe Cys Pro Leu Ala Gln Ala Val Ile Lys Pro
    530                 535                 540

Ile His Asp Leu Asp Leu Gln Pro Tyr Leu His Asn Val Pro Lys Thr
545                 550                 555                 560

Met Ala Lys Phe His Gln Leu Phe Lys Val Cys Gly Ser Ile Glu Glu
                565                 570                 575

Leu Thr Ser Asp His Ile Ser Met Val Ile Gln Lys Ile Tyr Leu Lys
            580                 585                 590

Ser Asp Gln Asp Leu Ser Glu Gln Glu Ser Lys Gln Asn Leu His Leu
        595                 600                 605

Met Leu Asn Ile Ile Arg Trp Leu Tyr Ser Asn Gln Ile Pro Ala Ser
    610                 615                 620
```

-continued

```
Pro Asn Thr Pro Val Pro Ile His His Ser Lys Asn Pro Ser Lys Leu
625                 630                 635                 640

Ile Met Lys Pro Ile His Glu Cys Cys Tyr Cys Asp Ile Lys Val Asp
                645                 650                 655

Asp Leu Asn Asp Leu Leu Glu Asp Ser Val Glu Pro Ile Ile Leu Val
            660                 665                 670

His Glu Asp Ile Pro Met Lys Thr Ala Glu Trp Leu Lys Val Pro Cys
        675                 680                 685

Leu Ser Thr Arg Leu Ile Asn Pro Glu Asn Met Gly Phe Glu Gln Ser
    690                 695                 700

Gly Gln Arg Glu Pro Leu Thr Val Arg Ile Lys Asn Ile Leu Glu Glu
705                 710                 715                 720

Tyr Pro Ser Val Ser Asp Ile Phe Lys Glu Leu Leu Gln Asn Ala Asp
                725                 730                 735

Asp Ala Asn Ala Thr Glu Cys Ser Phe Leu Ile Asp Met Arg Arg Asn
            740                 745                 750

Met Asp Ile Arg Glu Asn Leu Leu Asp Pro Gly Met Ala Ala Cys His
        755                 760                 765

Gly Pro Ala Leu Trp Ser Phe Asn Asn Ser Gln Phe Ser Asp Ser Asp
    770                 775                 780

Phe Val Asn Ile Thr Arg Leu Gly Glu Ser Leu Lys Arg Gly Glu Val
785                 790                 795                 800

Asp Lys Val Gly Lys Phe Gly Leu Gly Phe Asn Ser Val Tyr His Ile
                805                 810                 815

Thr Asp Ile Pro Ile Ile Met Ser Arg Glu Phe Met Ile Met Phe Asp
            820                 825                 830

Pro Asn Ile Asn His Ile Ser Lys His Ile Lys Asp Lys Ser Asn Pro
        835                 840                 845

Gly Ile Lys Ile Asn Trp Ser Lys Gln Gln Lys Arg Leu Arg Lys Phe
    850                 855                 860

Pro Asn Gln Phe Lys Pro Phe Ile Asp Val Phe Gly Cys Gln Leu Pro
865                 870                 875                 880

Leu Thr Val Glu Ala Pro Tyr Ser Tyr Asn Gly Thr Leu Phe Arg Leu
                885                 890                 895

Ser Phe Arg Thr Gln Gln Glu Ala Lys Val Ser Glu Val Ser Ser Thr
            900                 905                 910

Cys Tyr Asn Thr Ala Asp Ile Tyr Ser Leu Val Asp Glu Phe Ser Leu
        915                 920                 925

Cys Gly His Arg Leu Ile Ile Phe Thr Gln Ser Val Lys Ser Met Tyr
    930                 935                 940

Leu Lys Tyr Leu Lys Ile Glu Glu Thr Asn Pro Ser Leu Ala Gln Asp
945                 950                 955                 960

Thr Val Ile Ile Lys Lys Lys Ser Cys Ser Ser Lys Ala Leu Asn Thr
                965                 970                 975

Pro Val Leu Ser Val Leu Lys Glu Ala Ala Lys Leu Met Lys Thr Cys
            980                 985                 990

Ser Ser Ser Asn Lys Lys Leu Pro Ser Asp Glu Pro Lys Ser Ser Cys
        995                 1000                1005

Ile Leu Gln Ile Thr Val Glu Glu Phe His His Val Phe Arg Arg Ile
    1010                1015                1020

Ala Asp Leu Gln Ser Pro Leu Phe Arg Gly Pro Asp Asp Asp Pro Ala
1025                1030                1035                1040
```

-continued

```
Ala Leu Phe Glu Met Ala Lys Ser Gly Gln Ser Lys Lys Pro Ser Asp
                1045                1050                1055

Glu Leu Ser Gln Lys Thr Val Glu Cys Thr Thr Trp Leu Leu Cys Thr
            1060                1065                1070

Cys Met Asp Thr Gly Glu Ala Leu Lys Phe Ser Leu Ser Glu Ser Gly
        1075                1080                1085

Arg Arg Leu Gly Leu Val Pro Cys Gly Ala Val Gly Val Gln Leu Ser
    1090                1095                1100

Glu Ile Gln Asp Gln Lys Trp Thr Val Lys Pro His Ile Gly Glu Val
1105                1110                1115                1120

Phe Cys Tyr Leu Pro Leu Arg Ile Lys Thr Gly Leu Pro Val His Ile
                1125                1130                1135

Asn Gly Cys Phe Ala Val Thr Ser Asn Arg Lys Glu Ile Trp Lys Thr
            1140                1145                1150

Asp Thr Lys Gly Arg Trp Asn Thr Thr Phe Met Arg His Val Ile Val
        1155                1160                1165

Lys Ala Tyr Leu Gln Val Leu Ser Val Leu Arg Asp Leu Ala Thr Ser
    1170                1175                1180

Gly Glu Leu Met Asp Tyr Thr Tyr Tyr Ala Val Trp Pro Asp Pro Asp
1185                1190                1195                1200

Leu Val His Asp Asp Phe Ser Val Ile Cys Gln Gly Phe Tyr Glu Asp
                1205                1210                1215

Ile Ala His Gly Lys Gly Lys Glu Leu Thr Lys Val Phe Ser Asp Gly
            1220                1225                1230

Ser Thr Trp Val Ser Met Lys Asn Val Arg Phe Leu Asp Asp Ser Ile
        1235                1240                1245

Leu Lys Arg Arg Asp Val Gly Ser Ala Ala Phe Lys Ile Phe Leu Lys
    1250                1255                1260

Tyr Leu Lys Lys Thr Gly Ser Lys Asn Leu Cys Ala Val Glu Leu Pro
1265                1270                1275                1280

Ser Ser Val Lys Leu Gly Phe Glu Glu Ala Gly Cys Lys Gln Ile Leu
                1285                1290                1295

Leu Glu Asn Thr Phe Ser Glu Lys Gln Phe Phe Ser Glu Val Phe Phe
            1300                1305                1310

Pro Asn Ile Gln Glu Ile Glu Ala Glu Leu Arg Asp Pro Leu Met Ile
        1315                1320                1325

Phe Val Leu Asn Glu Lys Val Asp Glu Phe Ser Gly Val Leu Arg Val
    1330                1335                1340

Thr Pro Cys Ile Pro Cys Ser Leu Glu Gly His Pro Leu Val Leu Pro
1345                1350                1355                1360

Ser Arg Leu Ile His Pro Glu Gly Arg Val Ala Lys Leu Phe Asp Ile
                1365                1370                1375

Lys Asp Gly Arg Phe Pro Tyr Gly Ser Thr Gln Asp Tyr Leu Asn Pro
            1380                1385                1390

Ile Ile Leu Ile Lys Leu Val Gln Leu Gly Met Ala Lys Asp Asp Ile
        1395                1400                1405

Leu Trp Asp Asp Met Leu Glu Arg Ala Val Ser Val Ala Glu Ile Asn
    1410                1415                1420

Lys Ser Asp His Val Ala Ala Cys Leu Arg Ser Ser Ile Leu Leu Ser
1425                1430                1435                1440

Leu Ile Asp Glu Lys Leu Lys Ile Arg Asp Pro Arg Ala Lys Asp Phe
                1445                1450                1455

Ala Ala Lys Tyr Gln Thr Ile Arg Phe Leu Pro Phe Leu Thr Lys Pro
```

-continued

```
            1460                1465                1470

Ala Gly Phe Ser Leu Asp Trp Lys Gly Asn Ser Phe Lys Pro Glu Thr
        1475                1480                1485

Met Phe Ala Ala Thr Asp Leu Tyr Thr Ala Glu His Gln Asp Ile Val
    1490                1495                1500

Cys Leu Leu Gln Pro Ile Leu Asn Glu Asn Ser His Ser Phe Arg Gly
1505                1510                1515                1520

Cys Gly Ser Val Ser Leu Ala Val Lys Glu Phe Leu Gly Leu Leu Lys
                1525                1530                1535

Lys Pro Thr Val Asp Leu Val Ile Asn Gln Leu Lys Glu Val Ala Lys
            1540                1545                1550

Ser Val Asp Asp Gly Ile Thr Leu Tyr Gln Glu Asn Ile Thr Asn Ala
        1555                1560                1565

Cys Tyr Lys Tyr Leu His Glu Ala Leu Met Gln Asn Glu Ile Thr Lys
    1570                1575                1580

Met Ser Ile Ile Asp Lys Leu Lys Pro Phe Ser Phe Ile Leu Val Glu
1585                1590                1595                1600

Asn Ala Tyr Val Asp Ser Glu Lys Val Ser Phe His Leu Asn Phe Glu
                1605                1610                1615

Ala Ala Pro Tyr Leu Tyr Gln Leu Pro Asn Lys Tyr Lys Asn Asn Phe
            1620                1625                1630

Arg Glu Leu Phe Glu Thr Val Gly Val Arg Gln Ser Cys Thr Val Glu
        1635                1640                1645

Asp Phe Ala Leu Val Leu Glu Ser Ile Asp Gln Glu Arg Gly Thr Lys
    1650                1655                1660

Gln Ile Thr Glu Glu Asn Phe Gln Leu Cys Arg Arg Ile Ile Ser Glu
1665                1670                1675                1680

Gly Ile Trp Ser Leu Ile Arg Glu Lys Lys Gln Glu Phe Cys Glu Lys
                1685                1690                1695

Asn Tyr Gly Lys Ile Leu Leu Pro Asp Thr Asn Leu Met Leu Leu Pro
            1700                1705                1710

Ala Lys Ser Leu Cys Tyr Asn Asp Cys Pro Trp Ile Lys Val Lys Asp
        1715                1720                1725

Thr Thr Val Lys Tyr Cys His Ala Asp Ile Pro Arg Glu Val Ala Val
    1730                1735                1740

Lys Leu Gly Ala Val Pro Lys Arg His Lys Ala Leu Glu Arg Tyr Ala
1745                1750                1755                1760

Ser Asn Val Cys Phe Thr Thr Leu Gly Thr Glu Phe Gly Gln Lys Glu
                1765                1770                1775

Lys Leu Thr Ser Arg Ile Lys Ser Ile Leu Asn Ala Tyr Pro Ser Glu
            1780                1785                1790

Lys Glu Met Leu Lys Glu Leu Leu Gln Asn Ala Asp Asp Ala Lys Ala
        1795                1800                1805

Thr Glu Ile Cys Phe Val Phe Asp Pro Arg Gln His Pro Val Asp Arg
    1810                1815                1820

Ile Phe Asp Asp Lys Trp Ala Pro Leu Gln Gly Pro Ala Leu Cys Val
1825                1830                1835                1840

Tyr Asn Asn Gln Pro Phe Thr Glu Asp Asp Val Arg Gly Ile Gln Asn
                1845                1850                1855

Leu Gly Lys Gly Thr Lys Glu Gly Asn Pro Tyr Lys Thr Gly Gln Tyr
            1860                1865                1870

Gly Ile Gly Phe Asn Ser Val Tyr His Ile Thr Asp Cys Pro Ser Phe
        1875                1880                1885
```

-continued

Ile Ser Gly Asn Asp Ile Leu Cys Ile Phe Asp Pro His Ala Arg Tyr
    1890                1895                1900

Ala Pro Gly Ala Thr Ser Ile Ser Pro Gly Arg Met Phe Arg Asp Leu
1905                1910                1915                1920

Asp Ala Asp Phe Arg Thr Gln Phe Ser Asp Val Leu Asp Leu Tyr Leu
                1925                1930                1935

Gly Thr His Phe Lys Leu Asp Asn Cys Thr Met Phe Arg Phe Pro Leu
            1940                1945                1950

Arg Asn Ala Glu Met Ala Lys Val Ser Glu Ile Ser Ser Val Pro Ala
        1955                1960                1965

Ser Asp Arg Met Val Gln Asn Leu Leu Asp Lys Leu Arg Ser Asp Gly
    1970                1975                1980

Ala Glu Leu Leu Met Phe Leu Asn His Met Glu Lys Ile Ser Ile Cys
1985                1990                1995                2000

Glu Ile Asp Lys Ser Thr Gly Ala Leu Asn Val Leu Tyr Ser Val Lys
                2005                2010                2015

Gly Lys Ile Thr Asp Gly Asp Arg Leu Lys Arg Lys Gln Phe His Ala
            2020                2025                2030

Ser Val Ile Asp Ser Val Thr Lys Lys Arg Gln Leu Lys Asp Ile Pro
        2035                2040                2045

Val Gln Gln Ile Thr Tyr Thr Met Asp Thr Glu Asp Ser Glu Gly Asn
    2050                2055                2060

Leu Thr Thr Trp Leu Ile Cys Asn Arg Ser Gly Phe Ser Ser Met Glu
2065                2070                2075                2080

Lys Val Ser Lys Ser Val Ile Ser Ala His Lys Asn Gln Asp Ile Thr
                2085                2090                2095

Leu Phe Pro Arg Gly Gly Val Ala Ala Cys Ile Thr His Asn Tyr Lys
            2100                2105                2110

Lys Pro His Arg Ala Phe Cys Phe Leu Pro Leu Ser Leu Glu Thr Gly
        2115                2120                2125

Leu Pro Phe His Val Asn Gly His Phe Ala Leu Asp Ser Ala Arg Arg
    2130                2135                2140

Asn Leu Trp Arg Asp Asp Asn Gly Val Gly Val Arg Ser Asp Trp Asn
2145                2150                2155                2160

Asn Ser Leu Met Thr Ala Leu Ile Ala Pro Ala Tyr Val Asn Cys
                2165                2170                2175

<210> SEQ ID NO 9
<211> LENGTH: 12717
<212> TYPE: DNA
<213> ORGANISM: Homo sapiens

<400> SEQUENCE: 9
atgaatacat tctggcctgg cagagaattg attgttcaat ggtatccatt tgatgaaaac 60
agaaatcacc catctgtttc atggcttaag atggtttgga aaaatcttta tatacatttt 120
tcagaggatt tgactttatt tgatgagatg ccacttatcc ccagaactat actagaggaa 180
ggtcagacat gtgtggaact cattagactc aggattccat cgttagtcat tttagacgat 240
gaatctgaag cacagcttcc agaattttta gcagacattg tacaaaaact tggagggttt 300
gtccttaaaa aattagatgc atctatacaa catccgctta ttaaaaaata tattcattca 360
ccattaccaa gtgctgtttt gcagataatg gagaagatgc cattgcagaa attgtgtaat 420
caaataactt cgctacttcc aacacacaaa gatgccctga ggaagttctt ggctagttta 480

-continued

```
accgatagca gtgagaaaga gaaaagaatt attcaagaat tggcaatatt caagcgcatt    540
aaccattctt ctgatcaggg aatttcctct tatacaaaat tgaaaggttg taaagtctta    600
caccatactg ccaaactccc agcagatctg cgactttcta tttcagtaat agacagtagt    660
gatgaagcta ctattcgtct ggcaaacatg ttgaaaatag aacagttaaa gaccactagc    720
tgcttaaagc ttgttttaaa agatattgaa aatgcatttt attcacatga agaggtaaca    780
cagcttatgt tatgggtcct tgagaatcta tcttctctta aaaatgagaa tccaaatgtg    840
cttgagtggt taacaccatt aaaattcatc cagatatcac aggaacagat ggtatcagct    900
ggtgaactct ttgaccctga tatagaagta ctaaaggatc tcttttgtaa tgaagaagga    960
acctatttcc caccctcagt tttacctca ccagatattc ttcactcctt aagacagatt   1020
ggtttaaaaa acgaagccag tctcaaagaa aaggatgttg tgcaagtggc aaaaaaaatt   1080
gaagccttac aggtcggtgc ttgtcctgat caagatgttc ttctgaagaa agccaaaacc   1140
ctcttactgg ttttaaataa gaatcacaca ctgttgcaat catctgaagg aaagatgaca   1200
ttgaagaaaa taaaatgggt tccagcctgc aaggaaaggc ctccaaatta tccaggctct   1260
ttggtctgga aaggagatct ctgtaatctc tgtgcaccac cagatatgtg tgatgtaggc   1320
catgcaattc tcattggctc ctcacttcct cttgttgaaa gtatccatgt aaacctggaa   1380
aaagcattag ggatcttcac aaaacctagc cttagtgctg tcttaaaaca ctttaaaatt   1440
gttgttgatt ggtattcttc aaaaaccttt agtgatgaag actactatca attccagcat   1500
attttgcttg agatttacgg attcatgcat gatcatctaa atgaagggaa agattctttt   1560
agagccttaa aatttccatg ggtttggact ggcaaaaagt tttgtccact tgcccaggct   1620
gtgattaaac caatccatga tcttgacctt cagccttatt tgcataatgt acctaaaacc   1680
atggcaaaat tccaccaact atttaaggtc tgtggttcaa tagaggagtt gacatcagat   1740
catatttcca tggttattca gaagatatat ctcaaaagtg accaagatct cagtgaacaa   1800
gaaagcaaac aaaatcttca tcttatgttg aatattatca gatggctgta tagcaatcag   1860
attccagcaa gccccaacac accagttcct atacatcata gcaaaaatcc ttctaaactt   1920
atcatgaagc caattcacga atgctgttat tgtgacatta aagttgatga ccttaatgac   1980
ttacttgaag attctgtgga accaatcatt ttggtgcatg aggacatacc catgaaaact   2040
gcagaatggc taaaagttcc atgccttagt acaagactga taaatcctga aaacatggga   2100
tttgagcagt caggacaaag agagccactt actgtaagaa ttaaaaatat tctggaagaa   2160
tacccttcag tgtcagatat ttttaaagaa ctacttcaaa acgctgatga tgcaaatgca   2220
acagaatgca gtttcttgat tgatatgaga agaaatatgg acataagaga gaatctccta   2280
gacccaggga tggcagcttg tcatggacct gctttgtggt cattcaacaa ttctcaattc   2340
tcagattcag attttgtgaa cataactagg ttaggagaat ctttaaaaag gggagaagtt   2400
gacaaagttg gaaaatttgg tcttggattt aattctgtgt accatatcac tgacattccc   2460
atcattatga gtcgggaatt catgataatg ttcgatccaa acataaatca tatcagtaaa   2520
cacattaaag acaaatccaa tcctgggatc aaaattaatt ggagtaaaca acagaaaaga   2580
cttagaaaat ttcctaatca gttcaaacca tttatagatg tatttggctg tcagttacct   2640
ttgactgtag aagcacctta cagctataat ggaacccttt tccgactgtc ctttagaact   2700
caacaggaag caaaagtgag tgaagttagt agtacgtgct acaatacagc agatatttat   2760
tctcttgtgg atgaatttag tctctgtgga cacaggctta tcattttcac tcagagtgta   2820
aagtcaatgt atttgaagta cttgaaaatt gaggaaacca accccagttt agcacaagat   2880
```

-continued

```
acagtaataa ttaaaaaaaa atcctgctct tccaaagcat tgaacacacc tgtcttaagt   2940
gttttaaaag aggctgctaa gctcatgaag acttgcagca gcagtaataa aaagcttccc   3000
agtgatgaac caaagtcatc ttgcattctt cagatcacag tggaagaatt tcaccatgtg   3060
ttcagaagga ttgctgattt acagtcgcca ctttttagag gtccagatga tgacccagct   3120
gctctctttg aaatggctaa gtctggccaa tcaaaaaagc catcagatga gttgtcacag   3180
aaaacagtag agtgtaccac gtggcttctg tgtacttgca tggacacagg agaggctctg   3240
aagttttccc tgagtgagag tggaagaaga ctaggactgg ttccatgtgg ggcagtagga   3300
gttcagctgt cagaaatcca ggaccagaag tggacagtga aaccacacat tggagaggtg   3360
ttttgctatt tacctttacg aataaaaaca ggcttgccag ttcatatcaa tgggtgcttt   3420
gctgttacat caaataggaa agaaatctgg aaaacagata caaaaggacg atggaatacc   3480
acgttcatga gacatgttat tgtgaaagct tacttacagg tactgagtgt cttacgggac   3540
ctggccacta gtggggagct aatggattat acttactatg cagtatggcc cgatcctgat   3600
ttagttcatg atgatttttc tgtaatttgc caaggatttt atgaagatat agctcatgga   3660
aaagggaaag aactgaccaa agtcttctct gatggatcta cttgggtttc catgaagaac   3720
gtaagatttc tagatgactc tatacttaaa agaagagatg ttggttcagc agccttcaag   3780
atatttttga aatacctcaa gaagactggg tccaaaaacc tttgtgctgt tgaacttcct   3840
tcttcggtaa aattaggatt tgaagaagct ggctgcaaac agatactact tgaaaacaca   3900
ttttcagaga aacagttttt ttctgaagtg ttttttccaa atattcaaga aattgaagca   3960
gaacttagag atcctttaat gatctttgtt ctaaatgaaa aagttgatga gttctcggga   4020
gttcttcgtg ttactccatg tattccttgt tccttggagg ggcatccttt ggttttgcca   4080
tcaagattga tccaccccga aggacgagtt gcaaagttat ttgatattaa agatgggaga   4140
ttcccttatg gttctactca ggattatctc aatcctatta ttttgattaa actagttcag   4200
ttaggtatgg caaaagatga tattttatgg gatgatatgc tagaacgtgc agtgtcagta   4260
gctgaaatta ataaaagtga tcatgttgct gcatgcctaa gaagtagtat cttattgagt   4320
cttatcgatg agaaactaaa aataagggat cctagagcaa aggattttgc tgcaaaatat   4380
caaacaatcc gcttccttcc atttctgaca aaaccagcag gtttttcttt ggactggaaa   4440
ggcaacagtt ttaagcctga aaccatgttt gcagcaactg acctttatac agctgaacat   4500
caagatatag tttgtctttt gcaaccaatt ctaaatgaaa attcccattc ttttagaggt   4560
tgtggttcag tgtcattggc tgttaaagag tttttgggat tactcaagaa gccaacagtt   4620
gatctggtta taaaccaatt gaaagaagta gcaaaatcag ttgatgatgg aattacactg   4680
taccaggaga atatcaccaa tgcttgctac aaataccttc atgaagcctt gatgcaaaat   4740
gaaatcacta agatgtcaat tattgataag ttaaaaccct ttagcttcat tctagttgag   4800
aatgcatatg ttgactcaga aaaggtttct tttcatttaa attttgaggc ggcaccatac   4860
ctttatcagt tgcctaataa gtataaaaat aatttccgcg aactttttga aaccgtgggt   4920
gtgaggcagt catgcactgt tgaagatttt gctcttgttt tggaatctat tgatcaagaa   4980
agaggaacaa agcaaataac agaagagaat tttcagcttt gccgacgaat aatcagtgaa   5040
ggaatatgga gtctcattag agaaaagaaa caagaatttt gtgagaaaaa ttatggcaag   5100
atattattgc cagatactaa tcttatgctt ctccctgcta aatcgttatg ctacaatgat   5160
tgcccttgga taaaagtaaa ggataccact gtaaaatatt gtcatgctga catacccagg   5220
```

-continued

```
gaagtagcag taaaactagg agcagtccca aagtgacaca aagccttaga aagatatgca   5280
tccaatgtct gttttacaac acttggcaca gaatttgggc agaaagaaaa attgaccagc   5340
agaattaaga gcatccttaa tgcatatcct tctgaaaagg aaatgttgaa agagcttctt   5400
caaaatgctg atgatgcaaa ggcgacagaa atctgttttg tgtttgatcc tagacagcat   5460
ccagttgata gaatatttga tgataagtgg gccccattgc aagggccagc actttgtgtg   5520
tacaacaacc agccatttac agaagatgat gttagaggaa ttcagaatct tggaaaaggc   5580
acgaaagagg gaaatcctta taaaactgga cagtatggaa taggattcaa ttctgtgtat   5640
catatcacag actgcccatc ttttatttct ggcaatgaca tcctgtgtat tttttgatcct   5700
catgccagat atgcaccagg ggccacatcc attagtcccg gacgcatgtt tagagatttg   5760
gatgcagatt ttaggacaca gttctcagat gttctggatc tttatctggg aacccatttt   5820
aaactggata attgcacaat gttcagattt cctcttcgta atgcagaaat ggcaaaagtt   5880
tcggaaattt cgtctgttcc agcatcagac agaatggtcc agaatctttt ggacaaactg   5940
cgctcagatg gggcagaact tctaatgttt cttaatcaca tggaaaaaat ttctatttgt   6000
gaaatagata agagtactgg agctctaaat gtgctgtatt cagtaaaggg caaaatcaca   6060
gatggagaca gattgaaaag gaaacaattt catgcatctg taattgatag tgttactaaa   6120
aagaggcagc tcaaagacat accagttcaa caaataacct atactatgga tactgaggac   6180
tctgaaggaa atcttactac gtggctaatt tgtaatagat caggcttttc aagtatggag   6240
aaagtatcta aaagtgtcat atcagctcac aagaaccaag atattactct tttcccacgt   6300
ggtggagtag ctgcctgcat tactcacaac tataaaaaac cccatagggc cttctgtttt   6360
ttgcctcttt ctttggagac tgggctgcca tttcatgtga atggccactt tgcactggat   6420
tcagccagaa ggaacctgtg gcgtgatgat aatggagttg gtgttcgaag tgactggaat   6480
aacagtttaa tgacagcatt aatagctcct gcatatgttg aattgctaat acagttaaaa   6540
aaacggtatt tccctggttc tgatccaaca ttatcagtgt tacagaacac ccctattcat   6600
gttgtaaagg acactttaaa gaagtttttta tcgtttttcc cagttaaccg tcttgatcta   6660
cagccagatt tatattgtct agtgaaagca ctttacaatt gcattcacga agacatgaaa   6720
cgtcttttac ctgttgtgcg ggctccaaat attgatggct ctgacttgca ctctgcagtt   6780
ataattactt ggatcaatat gtctacttct aataaaacta gaccattttt tgacaattta   6840
ctacaggatg aattacaaca ccttaaaaat gcagattata atatcaccac acgcaaaaca   6900
gtagcagaga atgtctatag gctgaaacat ctccttttag aaattggttt caacttggtt   6960
tataactgtg atgaaactgc taatctttac cactgtctta tagatgcaga tattcctgtt   7020
agttatgtga cccctgctga tatcagatct tttttaatga cattttcctc tcctgacact   7080
aattgccata ttgggaagct gccttgtcgt ctgcagcaga ctaatctaaa actttttcat   7140
agtttaaaac ttttagttga ttattgtttt aaagatgcag aagaaaatga gattgaagtt   7200
gagggattgc cccttctcat cacactggac agtgttttgc aaacttttga tgcaaaacga   7260
cccaagtttc taacaacata tcatgaattg attccatccc gcaaagactt gtttatgaat   7320
acattatatt tgaaatatag taatatttta ttgaactgta aagttgcaaa agtgtttgac   7380
atttccagct ttgctgattt gttatcctct gtgttgcctc gagaatataa gaccaaaagt   7440
tgcacaaagt ggaaagacaa ttttgcaagt gagtcttggc ttaagaatgc atggcatttt   7500
attagtgaat ctgtaagtgt gaaagaagat caggaagaaa caaaaccaac atttgacatt   7560
gttgttgata ctctaaaaga ctgggcattg cttccaggaa caaagtttac tgtttcagcc   7620
```

-continued

```
aaccagcttg tggttcctga aggagatgtt ctgcttcctc tcagccttat gcacattgca   7680
gtttttccaa atgcccagag tgataaagtt tttcatgctc taatgaaagc cggctgtatt   7740
cagcttgctt tgaacaaaat ctgttccaaa gacagtgcat ttgttccttt gttgtcatgt   7800
cacacagcaa atatagagag ccccacaagc atcttgaagg ctctacatta tatggtccaa   7860
acttcaacat ttagagcaga aaaattagta gaaaatgatt ttgaggcact tttgatgtat   7920
ttcaactgca atttgaatca tttgatgtcc caagatgata taaaaattct aaagtcactt   7980
ccgtgctata aatccatcag tggccgctat gtaagcattg gaaaatttgg aacatgctac   8040
gtacttacaa aaagtatccc ttcagctgaa gtggagaaat ggacacaatc atcatcatct   8100
gcatttcttg aagaaaaaat acacttaaaa gaactatatg aggtgattgg ttgtgtacct   8160
gtagatgatc ttgaggtata tttgaaacac ctcttaccaa aaattgaaaa tctctcttat   8220
gatgcaaaat tagagcactt gatctacctt aagaatagat tatcaagtgc tgaggaatta   8280
tcagagatta aggaacaact ttttgaaaaa ctggaaagtt tattgataat ccatgatgct   8340
aacagtagac taaagcaagc aaagcatttc tatgatagaa ctgtgagagt ttttgaagtt   8400
atgcttcctg aaaaattgtt tattcctaat gatttcttta agaaattgga acaacttata   8460
aaacccaaaa atcatgttac atttatgaca tcctgggtgg aattcttaag aaatattgga   8520
ctaaaataca tactttctca gcagcagttg ttacagtttg ctaaggaaat cagtgtgagg   8580
gctaatacag aaaactggtc caaagaaaca ttgcaaaata cagttgatat ccttctgcat   8640
catatattcc aagaacgaat ggatttgtta tctggaaatt ttctgaaaga actatcttta   8700
ataccattct tatgtcctga gcgggccccc gcggaattca ttagatttca tcctcaatat   8760
caagaggtaa atggaacact tcctcttata aagttcaatg gagcacaggt aaatccaaaa   8820
ttcaagcaat gtgatgtact ccagctgtta tggacatcct gccctattct tccagagaaa   8880
gctacaccct taagcattaa agaacaagaa ggtagtgacc ttggtccaca agaacagctt   8940
gaacaagttt taaatatgct taatgttaac ctggatcctc ctcttgataa ggtaatcaat   9000
aactgcagaa acatatgcaa cataacgacg ttggatgaag aaatggtaaa aactagagca   9060
aaagtcttaa ggagcatata tgaattcctc agtgcagaaa aagggaattt tcgttttcag   9120
ttgcgagggg ttgcttttgt gatggtagaa gatggttgga aacttctgaa gcctgaggag   9180
gtagtcataa acctagaata tgaatctgat tttaaacctt atttgtacaa gctaccttta   9240
gaacttggca catttcacca gttgttcaaa cacttaggta ctgaagatat tatttcaact   9300
aagcaatatg ttgaagtgtt gagccgcata tttaaaaatt ctgagggcaa acaattagat   9360
cctaatgaaa tgcgtacagt taagagagta gtttctggtc tgttcaggag tctacagaat   9420
gattcagtca aggtgaggag tgatctcgag aatgtacgag accttgcgct ttacctccca   9480
agccaggatg gtagattggt aaagtcaagc atcttagtgt ttgacgatgc gccacattat   9540
aaaagtagaa tccaggggaa tattggtgtg caaatgttag ttgatctcag ccagtgctac   9600
ttagggaaag accatggatt tcacactaag ttgataatgc tctttcctca aaaacttaga   9660
cctcgattat tgagcagtat acttgaagaa caattagatg aagagactcc caaagtttgt   9720
cagtttggag cgttgtgttc tcttcaagga agattgcagt tactcttgtc ttctgaacag   9780
ttcattacag gactgattag aattatgaag catgaaaatg ataatgcttt tctggccaat   9840
gaagaaaaag ccataagact ttgcaaagcc ctaagagaag gattgaaagt atcctgcttt   9900
gaaaagcttc aaacaacatt aagagttaaa ggttttaatc ctattcccca cagcagaagt   9960
```

-continued

```
gaaacttttg cttttttgaa gcgatttggt aatgcagtca tcttgctcta cattcaacat  10020
tcagacagta aagacattaa tttcctgtta gcactggcaa tgactcttaa atcagcaact  10080
gacaatttga tttctgacac ttcatattta attgctatgc taggatgcaa tgatatttac  10140
aggattggtg agaaacttga cagtttagga gtgaaatatg actcttcgga gccatcaaaa  10200
ctggaacttc caatgcctgg cacaccaatt cctgctgaaa ttcattacac tctgcttatg  10260
gacccaatga atgtttttta cccgggagaa tatgttgggt accttgttga tgctgaaggt  10320
ggtgatatct atggatcata ccagccaaca tacacatatg caattattgt acaagaagtt  10380
gaaagagaag atgctgacaa ttctagtttt ctaggaaaga tatatcagat agatattggt  10440
tatagtgaat ataaaatagt tagctctctt gatctgtata agttttcaag acctgaggaa  10500
agctctcaaa gcagggacag tgctccttct acaccaacca gccccactga gttcctcacc  10560
cctggcctga gaagcattcc tcctcttttc tctggtagag agagccacaa gacttcttcc  10620
aaacatcagt cccccaaaaa gcttaaggtt aattctttac cagaaatctt aaaagaagtg  10680
acatctgtgg tggagcaagc atggaagctt ccagaatcgg aacgaaaaaa gattattagg  10740
cggttgtatt tgaaatggca tcctgacaaa aatccagaga accatgacat tgccaatgaa  10800
gtttttaaac atttgcagaa tgaaatcaac agattagaaa aacaggcttt tctagatcaa  10860
aatgcagaca gggcctccag acgaacattt tcaacctcag catcccgatt tcagtcagac  10920
aaatactcat ttcagagatt ctatacttca tggaatcaag aagcaacgag ccataaatct  10980
gaaagacagc aacagaacaa agaaaaatgc ccccttcag ccggacagac ttactctcaa  11040
aggttctttg ttcctcccac tttcaagtcg gttggcaatc cagtggaagc acgcagatgg  11100
ctaagacaag ccagagcaaa cttctcagct gccaggaatg accttcataa aaatgccaat  11160
gagtgggtgt gctttaaatg ttacctttct accaagttag ctttgattgc agctgactat  11220
gctgtgaggg gaaagtctga taaagatgta aaaccaactg cacttgctca gaaaatagag  11280
gaatatagtc agcaacttga aggactgaca aatgatgttc acacattgga agcttatggt  11340
gtagacagtt taaaaacaag ataccctgat ttgcttccct ttcctcagat cccaaatgac  11400
aggttcactt ctgaggttgc tatgagggtg atggaatgta ctgcctgtat cataataaaa  11460
cttgaaaatt ttatgcaaca aaaagtgtga agatatttaa cgaaaaaaaa ggtagatctt  11520
gaatgtgttg tagcacgaat aaattgctgt acttcattaa gcttcattgc caattagcta  11580
ggaattgtta agcacattgc agattgttct tggagaattc tggagttgtt atgaacatga  11640
ataccaacgg aaaaccttaa ctgaatctaa aagaaaacta ttttgaagat ggtggtgagc  11700
tgcaaaatag ctggatggat ttgaatgatt gggatgatac atcattgaac tgcactttat  11760
ataaccaaag cttagcagtt tgttagataa gagtctatgt atgtctctgg ttaggatgaa  11820
gttaatttta tgtttttaac atggtatttt tgaaggagct aatgaaacac tggacatata  11880
attggtttaa acataagggg aattaagtct ttgtagtctg tcattttttt aagtggatcc  11940
tcttggatgc gttattttct catcagctgg ctctgatcat gaatttgttg taattttatg  12000
ttgtactcag tgcatttaag aaatggtaga gtattttaat cctattactt gactaagagt  12060
gtgaaggtag tactttttag agtgcactga gtgcacttta catctttatt taaatttttt  12120
tttaacatct tatgtttaca ggcttcctgt ttgatgaaga tagcaacgga aaactcaaaa  12180
tggtggcagt tcttattacc agttgttagt attgtttctg gaaactgctt gccaagacaa  12240
catttattaa ctgttagaac acttgcttta tgtttgtgtg tacatatttt ccacaaatgt  12300
tataatttat atagtgtggt tgaacaggat gcaatctttt gttgtctaaa ggtgctgcag  12360
```

-continued

```
ttaaaaaaaa aacaaccttt tctttcaata tggcatgtag tggagttttt ttaactttaa  12420

aaacatcaaa aattgttaaa atcattgtgt tatctagtag tttataatta tcggcttata  12480

tttccccatg aatgatcaga actgacattt aattcatgtt tgtctcgcca tgcttcttta  12540

ctttaacata tttcttttgc agaatgtaaa aggtaatgat aattagttta tataagtgta  12600

ctggctgtaa atgatgctaa atatacttta tgcaattaag ggcttacaga acatgttgaa  12660

acttttttta cttttattgg gaataaggaa tgtttgcacc tccacatttt attgctt     12717


<210> SEQ ID NO 10
<211> LENGTH: 3559
<212> TYPE: PRT
<213> ORGANISM: Homo sapiens

<400> SEQUENCE: 10

Phe His Gly Leu Arg Trp Phe Gly Lys Ile Phe Ile Tyr Ile Phe Gln
 1               5                  10                  15

Arg Ile Leu Tyr Leu Met Arg Cys His Leu Ser Pro Glu Leu Tyr Arg
            20                  25                  30

Lys Val Arg His Val Trp Asn Ser Leu Asp Ser Gly Phe His Arg Ser
        35                  40                  45

Phe Thr Met Asn Leu Lys His Ser Phe Gln Asn Phe Gln Thr Leu Tyr
    50                  55                  60

Lys Asn Leu Glu Gly Leu Ser Leu Lys Asn Met His Leu Tyr Asn Ile
65                  70                  75                  80

Arg Leu Leu Lys Asn Ile Phe Ile His His Tyr Gln Val Leu Phe Cys
                85                  90                  95

Arg Trp Arg Arg Cys His Cys Arg Asn Cys Val Ile Lys Leu Arg Tyr
            100                 105                 110

Phe Gln His Thr Lys Met Pro Gly Ser Ser Trp Leu Val Pro Ile Ala
        115                 120                 125

Val Arg Lys Arg Lys Glu Leu Phe Lys Asn Trp Gln Tyr Ser Ser Ala
    130                 135                 140

Leu Thr Ile Leu Leu Ile Arg Glu Phe Pro Leu Ile Gln Asn Lys Val
145                 150                 155                 160

Val Lys Ser Tyr Thr Ile Leu Pro Asn Ser Gln Gln Ile Cys Asp Phe
                165                 170                 175

Leu Phe Gln Thr Val Val Met Lys Leu Leu Phe Val Trp Gln Thr Cys
            180                 185                 190

Lys Asn Ser Arg Pro Leu Ala Ala Ser Leu Phe Lys Ile Leu Lys Met
        195                 200                 205

His Phe Ile His Met Lys Arg His Ser Leu Cys Tyr Gly Ser Leu Arg
    210                 215                 220

Ile Tyr Leu Leu Leu Lys Met Arg Ile Gln Met Cys Leu Ser Gly His
225                 230                 235                 240

His Asn Ser Ser Arg Tyr His Arg Asn Arg Trp Tyr Gln Leu Val Asn
                245                 250                 255

Ser Leu Thr Leu Ile Lys Tyr Arg Ile Ser Phe Val Met Lys Lys Glu
            260                 265                 270

Pro Ile Ser His Pro Gln Phe Leu Pro His Gln Ile Phe Phe Thr Pro
        275                 280                 285

Asp Arg Leu Val Lys Thr Lys Pro Val Ser Lys Lys Arg Met Leu Cys
    290                 295                 300

Lys Trp Gln Lys Lys Leu Lys Pro Tyr Arg Ser Val Leu Val Leu Ile
```

-continued

```
305                 310                 315                 320

Lys Met Phe Phe Arg Lys Pro Lys Pro Ser Tyr Trp Phe Ile Arg Ile
                325                 330                 335

Thr His Cys Cys Asn His Leu Lys Glu Arg His Arg Lys Asn Gly Phe
            340                 345                 350

Gln Pro Ala Arg Lys Gly Leu Gln Ile Ile Gln Ala Leu Trp Ser Gly
        355                 360                 365

Lys Glu Ile Ser Val Ile Ser Val His His Gln Ile Cys Val Met Ala
    370                 375                 380

Met Gln Phe Ser Leu Ala Pro His Phe Leu Leu Leu Lys Val Ser Met
385                 390                 395                 400

Thr Trp Lys Lys His Gly Ser Ser Gln Asn Leu Ala Leu Val Leu Ser
                405                 410                 415

Asn Thr Leu Lys Leu Leu Leu Ile Gly Ile Leu Gln Lys Pro Leu Val
            420                 425                 430

Met Lys Thr Thr Ile Asn Ser Ser Ile Phe Cys Leu Arg Phe Thr Asp
        435                 440                 445

Ser Cys Met Ile Ile Met Lys Gly Lys Ile Leu Leu Glu Pro Asn Phe
    450                 455                 460

His Gly Phe Gly Leu Ala Lys Ser Phe Val His Leu Pro Arg Leu Leu
465                 470                 475                 480

Asn Gln Ser Met Ile Leu Thr Phe Ser Leu Ile Cys Ile Met Tyr Leu
                485                 490                 495

Lys Pro Trp Gln Asn Ser Thr Asn Tyr Leu Arg Ser Val Val Gln Arg
            500                 505                 510

Ser His Gln Ile Ile Phe Pro Trp Leu Phe Arg Arg Tyr Ile Ser Lys
        515                 520                 525

Val Thr Lys Ile Ser Val Asn Lys Lys Ala Asn Lys Ile Phe Ile Leu
    530                 535                 540

Cys Ile Leu Ser Asp Gly Cys Ile Ala Ile Arg Phe Gln Gln Ala Pro
545                 550                 555                 560

Thr His Gln Phe Leu Tyr Ile Ile Ala Lys Ile Leu Leu Asn Leu Ser
                565                 570                 575

Ser Gln Phe Thr Asn Ala Val Ile Val Thr Leu Lys Leu Met Thr Leu
            580                 585                 590

Met Thr Tyr Leu Lys Ile Leu Trp Asn Gln Ser Phe Trp Cys Met Arg
        595                 600                 605

Thr Tyr Pro Lys Leu Gln Asn Gly Lys Phe His Ala Leu Val Gln Asp
    610                 615                 620

Ile Leu Lys Thr Trp Asp Leu Ser Ser Gln Asp Lys Glu Ser His Leu
625                 630                 635                 640

Leu Glu Leu Lys Ile Phe Trp Lys Asn Thr Leu Gln Cys Gln Ile Phe
                645                 650                 655

Leu Lys Asn Tyr Phe Lys Thr Leu Met Met Gln Met Gln Gln Asn Ala
            660                 665                 670

Val Ser Leu Ile Glu Glu Ile Trp Thr Glu Arg Ile Ser Thr Gln Gly
        675                 680                 685

Trp Gln Leu Val Met Asp Leu Leu Cys Gly His Ser Thr Ile Leu Asn
    690                 695                 700

Ser Gln Ile Gln Ile Leu Thr Leu Gly Glu Asn Leu Lys Gly Glu Lys
705                 710                 715                 720

Leu Thr Lys Leu Glu Asn Leu Val Leu Asp Leu Ile Leu Cys Thr Ile
                725                 730                 735
```

-continued

```
Ser Leu Thr Phe Pro Ser Leu Val Gly Asn Ser Cys Ser Ile Gln Thr
            740                 745                 750

Ile Ile Ser Val Asn Thr Leu Lys Thr Asn Pro Ile Leu Gly Ser Lys
        755                 760                 765

Leu Ile Gly Val Asn Asn Arg Lys Asp Leu Glu Asn Phe Leu Ile Ser
    770                 775                 780

Ser Asn His Leu Met Tyr Leu Ala Val Ser Tyr Leu Leu Lys His Leu
785                 790                 795                 800

Thr Ala Ile Met Glu Pro Phe Ser Asp Cys Pro Leu Glu Leu Asn Arg
                805                 810                 815

Lys Gln Lys Val Lys Leu Val Val Arg Ala Thr Ile Gln Gln Ile Phe
            820                 825                 830

Ile Leu Leu Trp Met Asn Leu Val Ser Val Asp Thr Gly Leu Ser Phe
        835                 840                 845

Ser Leu Arg Val Ser Gln Cys Ile Ser Thr Lys Leu Arg Lys Pro Thr
    850                 855                 860

Pro Val His Lys Ile Gln Leu Lys Lys Asn Pro Ala Leu Pro Lys His
865                 870                 875                 880

Thr His Leu Ser Val Phe Lys Arg Leu Leu Ser Ser Arg Leu Ala Ala
                885                 890                 895

Ala Val Ile Lys Ser Phe Pro Val Met Asn Gln Ser His Leu Ala Phe
            900                 905                 910

Phe Arg Ser Gln Trp Lys Asn Phe Thr Met Cys Ser Glu Gly Leu Leu
        915                 920                 925

Ile Tyr Ser Arg His Phe Leu Glu Val Gln Met Met Thr Gln Leu Leu
    930                 935                 940

Ser Leu Lys Trp Leu Ser Leu Ala Asn Gln Lys Ser His Gln Met Ser
945                 950                 955                 960

Cys His Arg Lys Gln Ser Val Pro Arg Gly Phe Cys Val Leu Ala Trp
                965                 970                 975

Thr Gln Glu Arg Leu Ser Phe Pro Val Arg Val Glu Glu Asp Asp Trp
            980                 985                 990

Phe His Val Gly Gln Glu Phe Ser Cys Gln Lys Ser Arg Thr Arg Ser
        995                 1000                1005

Gly Gln Asn His Thr Leu Glu Arg Cys Phe Ala Ile Tyr Leu Tyr Glu
    1010                1015                1020

Lys Gln Ala Cys Gln Phe Ile Ser Met Gly Ala Leu Leu Leu His Gln
1025                1030                1035                1040

Ile Gly Lys Lys Ser Gly Lys Gln Ile Gln Lys Asp Asp Gly Ile Pro
                1045                1050                1055

Arg Ser Asp Met Leu Leu Lys Leu Thr Tyr Arg Tyr Val Ser Tyr Gly
            1060                1065                1070

Thr Trp Pro Leu Val Gly Ser Trp Ile Ile Leu Thr Met Gln Tyr Gly
        1075                1080                1085

Pro Ile Leu Ile Phe Met Met Ile Phe Leu Phe Ala Lys Asp Phe Met
    1090                1095                1100

Lys Ile Leu Met Glu Lys Gly Lys Asn Pro Lys Ser Ser Leu Met Asp
1105                1110                1115                1120

Leu Leu Gly Phe Pro Arg Thr Asp Phe Met Thr Leu Tyr Leu Lys Glu
                1125                1130                1135

Glu Met Leu Val Gln Gln Pro Ser Arg Tyr Phe Asn Thr Ser Arg Arg
            1140                1145                1150
```

-continued

```
Leu Gly Pro Lys Thr Phe Val Leu Leu Asn Phe Leu Leu Arg Asn Asp
        1155                1160                1165

Leu Lys Lys Leu Ala Ala Asn Arg Tyr Tyr Leu Lys Thr His Phe Gln
    1170                1175                1180

Arg Asn Ser Phe Phe Leu Lys Cys Phe Phe Gln Ile Phe Lys Lys Leu
1185                1190                1195                1200

Lys Gln Asn Leu Glu Ile Leu Ser Leu Phe Met Lys Lys Leu Met Ser
                1205                1210                1215

Ser Arg Glu Phe Phe Val Leu Leu His Val Phe Leu Val Pro Trp Arg
            1220                1225                1230

Gly Ile Leu Trp Phe Cys His Gln Asp Ser Thr Pro Lys Asp Glu Leu
        1235                1240                1245

Gln Ser Tyr Leu Ile Leu Lys Met Gly Asp Ser Leu Met Val Leu Leu
    1250                1255                1260

Arg Ile Ile Ser Ile Leu Leu Phe Leu Asn Phe Ser Val Trp Gln Lys
1265                1270                1275                1280

Met Ile Phe Tyr Gly Met Ile Cys Asn Val Gln Cys Gln Leu Lys Leu
                1285                1290                1295

Ile Lys Val Ile Met Leu Leu His Ala Glu Val Val Ser Tyr Val Leu
            1300                1305                1310

Ser Met Arg Asn Lys Gly Ile Leu Glu Gln Arg Ile Leu Leu Gln Asn
        1315                1320                1325

Ile Lys Gln Ser Ala Ser Phe His Phe Gln Asn Gln Gln Val Phe Leu
    1330                1335                1340

Trp Thr Gly Lys Ala Thr Val Leu Ser Leu Lys Pro Cys Leu Gln Gln
1345                1350                1355                1360

Leu Thr Phe Ile Gln Leu Asn Ile Lys Ile Phe Val Phe Cys Asn Gln
                1365                1370                1375

Phe Met Lys Ile Pro Ile Leu Leu Glu Val Val Val Gln Cys His Trp
            1380                1385                1390

Leu Leu Lys Ser Phe Trp Asp Tyr Ser Arg Ser Gln Gln Leu Ile Trp
        1395                1400                1405

Leu Thr Asn Lys Lys Gln Asn Gln Leu Met Met Glu Leu His Cys Thr
    1410                1415                1420

Arg Arg Ile Ser Pro Met Leu Ala Thr Asn Thr Phe Met Lys Pro Cys
1425                1430                1435                1440

Lys Met Lys Ser Leu Arg Cys Gln Leu Leu Ile Ser Asn Pro Leu Ala
                1445                1450                1455

Ser Phe Leu Arg Met His Met Leu Thr Gln Lys Arg Phe Leu Phe Ile
            1460                1465                1470

Ile Leu Arg Arg His His Thr Phe Ile Ser Cys Leu Ile Ser Ile Lys
        1475                1480                1485

Ile Ile Ser Ala Asn Phe Leu Lys Pro Trp Val Gly Ser His Ala Leu
    1490                1495                1500

Leu Lys Ile Leu Leu Leu Phe Trp Asn Leu Leu Ile Lys Lys Glu Glu
1505                1510                1515                1520

Gln Ser Lys Gln Lys Arg Ile Phe Ser Phe Ala Asp Glu Ser Val Lys
                1525                1530                1535

Glu Tyr Gly Val Ser Leu Glu Lys Arg Asn Lys Asn Phe Val Arg Lys
            1540                1545                1550

Ile Met Ala Arg Tyr Tyr Cys Gln Ile Leu Ile Leu Cys Phe Ser Leu
        1555                1560                1565

Leu Asn Arg Tyr Ala Thr Met Ile Ala Leu Gly Lys Arg Ile Pro Leu
```

-continued

```
    1570                1575                1580

Asn Ile Val Met Leu Thr Tyr Pro Gly Lys Gln Asn Glu Gln Ser Gln
1585                1590                1595                1600

Ser Asp Thr Lys Pro Lys Asp Met His Pro Met Ser Val Leu Gln His
                1605                1610                1615

Leu Ala Gln Asn Leu Gly Arg Lys Lys Asn Pro Ala Glu Leu Arg Ala
            1620                1625                1630

Ser Leu Met His Ile Leu Leu Lys Arg Lys Cys Lys Ser Phe Phe Lys
        1635                1640                1645

Met Leu Met Met Gln Arg Arg Gln Lys Ser Val Leu Cys Leu Ile Leu
    1650                1655                1660

Asp Ser Ile Gln Leu Ile Glu Tyr Leu Met Ile Ser Gly Pro His Cys
1665                1670                1675                1680

Lys Gly Gln His Phe Val Cys Thr Thr Thr Ser His Leu Gln Lys Met
                1685                1690                1695

Met Leu Glu Glu Phe Arg Ile Leu Glu Lys Ala Arg Lys Arg Glu Ile
            1700                1705                1710

Leu Ile Lys Leu Asp Ser Met Glu Asp Ser Ile Leu Cys Ile Ile Ser
        1715                1720                1725

Gln Thr Ala His Leu Leu Phe Leu Ala Met Thr Ser Cys Val Phe Leu
    1730                1735                1740

Ile Leu Met Pro Asp Met His Gln Gly Pro His Pro Leu Val Pro Asp
1745                1750                1755                1760

Ala Cys Leu Glu Ile Trp Met Gln Ile Leu Gly His Ser Ser Gln Met
                1765                1770                1775

Phe Trp Ile Phe Ile Trp Glu Pro Ile Leu Asn Trp Ile Ile Ala Gln
            1780                1785                1790

Cys Ser Asp Phe Leu Phe Val Met Gln Lys Trp Gln Lys Phe Arg Lys
        1795                1800                1805

Phe Arg Leu Phe Gln His Gln Thr Glu Trp Ser Arg Ile Phe Trp Thr
    1810                1815                1820

Asn Cys Ala Gln Met Gly Gln Asn Phe Cys Phe Leu Ile Thr Trp Lys
1825                1830                1835                1840

Lys Phe Leu Phe Val Lys Ile Arg Val Leu Glu Leu Met Cys Cys Ile
                1845                1850                1855

Gln Arg Ala Lys Ser Gln Met Glu Thr Asp Lys Gly Asn Asn Phe Met
            1860                1865                1870

His Leu Leu Ile Val Leu Leu Lys Arg Gly Ser Ser Lys Thr Tyr Gln
        1875                1880                1885

Phe Asn Lys Pro Ile Leu Trp Ile Leu Arg Thr Leu Lys Glu Ile Leu
    1890                1895                1900

Leu Arg Gly Phe Val Ile Asp Gln Ala Phe Gln Val Trp Arg Lys Tyr
1905                1910                1915                1920

Leu Lys Val Ser Tyr Gln Leu Thr Arg Thr Lys Ile Leu Leu Phe Ser
                1925                1930                1935

His Val Val Glu Leu Pro Ala Leu Leu Thr Thr Ile Lys Asn Pro Ile
            1940                1945                1950

Gly Pro Ser Val Phe Cys Leu Phe Leu Trp Arg Leu Gly Cys His Phe
        1955                1960                1965

Met Met Ala Thr Leu His Trp Ile Gln Pro Glu Gly Thr Cys Gly Val
    1970                1975                1980

Met Ile Met Glu Leu Val Phe Glu Val Thr Gly Ile Thr Val Gln His
1985                1990                1995                2000
```

-continued

```
Leu Leu His Met Leu Asn Cys Tyr Ser Lys Asn Gly Ile Ser Leu Val
                2005                2010                2015

Leu Ile Gln His Tyr Gln Cys Tyr Arg Thr Pro Leu Phe Met Leu Arg
            2020                2025                2030

Thr Leu Arg Ser Phe Tyr Arg Phe Ser Gln Leu Thr Val Leu Ile Tyr
        2035                2040                2045

Ser Gln Ile Tyr Ile Val Lys His Phe Thr Ile Ala Phe Thr Lys Thr
    2050                2055                2060

Asn Val Phe Tyr Leu Leu Cys Gly Leu Gln Ile Leu Met Ala Leu Thr
2065                2070                2075                2080

Cys Thr Leu Gln Leu Leu Leu Gly Ser Ile Cys Leu Leu Leu Ile Lys
                2085                2090                2095

Leu Asp His Phe Leu Thr Ile Tyr Tyr Arg Met Asn Tyr Asn Thr Leu
            2100                2105                2110

Lys Met Gln Ile Ile Ile Ser Pro His Ala Lys Gln Gln Arg Met Ser
        2115                2120                2125

Ile Gly Asn Ile Ser Phe Lys Leu Val Ser Thr Trp Phe Ile Thr Val
    2130                2135                2140

Met Lys Leu Leu Ile Phe Thr Thr Val Leu Met Gln Ile Phe Leu Leu
2145                2150                2155                2160

Val Met Pro Leu Leu Ile Ser Asp Leu Phe His Phe Pro Leu Leu Thr
                2165                2170                2175

Leu Ile Ala Ile Leu Gly Ser Cys Leu Val Val Cys Ser Arg Leu Ile
            2180                2185                2190

Asn Phe Phe Ile Val Asn Phe Leu Ile Ile Val Leu Lys Met Gln Lys
        2195                2200                2205

Lys Met Arg Leu Lys Leu Arg Asp Cys Pro Phe Ser Ser His Trp Thr
    2210                2215                2220

Val Phe Cys Lys Leu Leu Met Gln Asn Asp Pro Ser Phe Gln His Ile
2225                2230                2235                2240

Met Asn Phe His Pro Ala Lys Thr Cys Leu Ile His Tyr Ile Asn Ile
                2245                2250                2255

Val Ile Phe Tyr Thr Val Lys Leu Gln Lys Cys Leu Thr Phe Pro Ala
            2260                2265                2270

Leu Leu Ile Cys Tyr Pro Leu Cys Cys Leu Glu Asn Ile Arg Pro Lys
        2275                2280                2285

Val Ala Gln Ser Gly Lys Thr Ile Leu Gln Val Ser Leu Gly Leu Arg
    2290                2295                2300

Met His Gly Ile Leu Leu Val Asn Leu Val Lys Lys Ile Arg Lys Lys
2305                2310                2315                2320

Gln Asn Gln His Leu Thr Leu Leu Leu Ile Leu Lys Thr Gly His Cys
                2325                2330                2335

Phe Gln Glu Gln Ser Leu Leu Phe Gln Pro Thr Ser Leu Trp Phe Leu
            2340                2345                2350

Lys Glu Met Phe Cys Phe Leu Ser Ala Leu Cys Thr Leu Gln Phe Phe
        2355                2360                2365

Gln Met Pro Arg Val Ile Lys Phe Phe Met Leu Lys Pro Ala Val Phe
    2370                2375                2380

Ser Leu Leu Thr Lys Ser Val Pro Lys Thr Val His Leu Phe Leu Cys
2385                2390                2395                2400

Cys His Val Thr Gln Gln Ile Arg Ala Pro Gln Ala Ser Arg Leu Tyr
                2405                2410                2415
```

-continued

```
Ile Ile Trp Ser Lys Leu Gln His Leu Glu Gln Lys Asn Lys Met Ile
            2420                2425                2430

Leu Arg His Phe Cys Ile Ser Thr Ala Ile Ile Ile Cys Pro Lys Met
        2435                2440                2445

Ile Lys Phe Ser His Phe Arg Ala Ile Asn Pro Ser Val Ala Ala Met
    2450                2455                2460

Ala Leu Glu Asn Leu Glu His Ala Thr Tyr Leu Gln Lys Val Ser Leu
2465                2470                2475                2480

Gln Leu Lys Trp Arg Asn Gly His Asn His His His Leu His Phe Leu
                2485                2490                2495

Lys Lys Lys Tyr Thr Lys Asn Tyr Met Arg Leu Val Val Tyr Leu Met
            2500                2505                2510

Ile Leu Arg Tyr Ile Asn Thr Ser Tyr Gln Lys Leu Lys Ile Ser Leu
        2515                2520                2525

Met Met Gln Asn Ser Thr Ser Thr Leu Arg Ile Asp Tyr Gln Val Leu
    2530                2535                2540

Arg Asn Tyr Gln Arg Leu Arg Asn Asn Phe Leu Lys Asn Trp Lys Val
2545                2550                2555                2560

Tyr Ser Met Met Leu Thr Val Asp Ser Lys Gln Ser Ile Ser Met Ile
                2565                2570                2575

Glu Leu Glu Phe Leu Lys Leu Cys Phe Leu Lys Asn Cys Leu Phe Leu
            2580                2585                2590

Met Ile Ser Leu Arg Asn Trp Asn Asn Leu Asn Pro Lys Ile Met Leu
        2595                2600                2605

His Leu His Pro Gly Trp Asn Ser Glu Ile Leu Asp Asn Thr Tyr Phe
    2610                2615                2620

Leu Ser Ser Ser Cys Tyr Ser Leu Leu Arg Lys Ser Val Gly Leu Ile
2625                2630                2635                2640

Gln Lys Thr Gly Pro Lys Lys His Cys Lys Ile Gln Leu Ile Ser Phe
                2645                2650                2655

Cys Ile Ile Tyr Ser Lys Asn Glu Trp Ile Cys Tyr Leu Glu Ile Phe
            2660                2665                2670

Lys Asn Tyr Leu Tyr His Ser Tyr Val Leu Ser Gly Pro Pro Arg Asn
        2675                2680                2685

Ser Leu Asp Phe Ile Leu Asn Ile Lys Arg Met Glu His Phe Leu Leu
    2690                2695                2700

Ser Ser Met Glu His Arg Ile Gln Asn Ser Ser Asn Val Met Tyr Ser
2705                2710                2715                2720

Ser Cys Tyr Gly His Pro Ala Leu Phe Phe Gln Arg Lys Leu His Pro
                2725                2730                2735

Ala Leu Lys Asn Lys Lys Val Val Thr Leu Val His Lys Asn Ser Leu
            2740                2745                2750

Asn Lys Phe Ile Cys Leu Met Leu Thr Trp Ile Leu Leu Leu Ile Arg
        2755                2760                2765

Ser Ile Thr Ala Glu Thr Tyr Ala Thr Arg Arg Trp Met Lys Lys Trp
    2770                2775                2780

Lys Leu Glu Gln Lys Ser Gly Ala Tyr Met Asn Ser Ser Val Gln Lys
2785                2790                2795                2800

Lys Gly Asn Phe Val Phe Ser Cys Glu Gly Leu Leu Leu Trp Lys Met
                2805                2810                2815

Val Gly Asn Phe Ser Leu Arg Arg Ser Thr Asn Met Asn Leu Ile Leu
            2820                2825                2830

Asn Leu Ile Cys Thr Ser Tyr Leu Asn Leu Ala His Phe Thr Ser Cys
```

-continued

```
        2835                2840                2845

Ser Asn Thr Val Leu Lys Ile Leu Phe Gln Leu Ser Asn Met Leu Lys
    2850                2855                2860

Cys Ala Ala Tyr Leu Lys Ile Leu Arg Ala Asn Asn Ile Leu Met Lys
2865                2870                2875                2880

Cys Val Gln Leu Arg Glu Phe Leu Val Cys Ser Gly Val Tyr Arg Met
                2885                2890                2895

Ile Gln Ser Arg Gly Val Ile Ser Arg Met Tyr Glu Thr Leu Arg Phe
            2900                2905                2910

Thr Ser Gln Ala Arg Met Val Asp Trp Ser Gln Ala Ser Cys Leu Thr
        2915                2920                2925

Met Arg His Ile Ile Lys Val Glu Ser Arg Gly Ile Leu Val Cys Lys
    2930                2935                2940

Cys Leu Ile Ser Ala Ser Ala Thr Gly Lys Thr Met Asp Phe Thr Leu
2945                2950                2955                2960

Ser Cys Ser Phe Leu Lys Asn Leu Asp Leu Asp Tyr Ala Val Tyr Leu
                2965                2970                2975

Lys Asn Asn Met Lys Arg Leu Pro Lys Phe Val Ser Leu Glu Arg Cys
            2980                2985                2990

Val Leu Phe Lys Glu Asp Cys Ser Tyr Ser Cys Leu Leu Asn Ser Ser
        2995                3000                3005

Leu Gln Asp Leu Glu Leu Ser Met Lys Met Ile Met Leu Phe Trp Pro
    3010                3015                3020

Met Lys Lys Lys Pro Asp Phe Ala Lys Pro Glu Lys Asp Lys Tyr Pro
3025                3030                3035                3040

Ala Leu Lys Ser Phe Lys Gln His Glu Leu Lys Val Leu Ile Leu Phe
                3045                3050                3055

Pro Thr Ala Glu Val Lys Leu Leu Leu Phe Ser Asp Leu Val Met Gln
            3060                3065                3070

Ser Ser Cys Ser Thr Phe Asn Ile Gln Thr Val Lys Thr Leu Ile Ser
        3075                3080                3085

Cys His Trp Gln Leu Leu Asn Gln Gln Leu Thr Ile Phe Leu Thr Leu
    3090                3095                3100

His Ile Leu Leu Cys Asp Ala Met Ile Phe Thr Gly Leu Val Arg Asn
3105                3110                3115                3120

Leu Thr Val Glu Asn Met Thr Leu Arg Ser His Gln Asn Trp Asn Phe
                3125                3130                3135

Gln Cys Leu Ala His Gln Phe Leu Leu Lys Phe Ile Thr Leu Cys Leu
            3140                3145                3150

Trp Thr Gln Met Phe Phe Thr Arg Glu Asn Met Leu Gly Thr Leu Leu
        3155                3160                3165

Met Leu Lys Val Val Ile Ser Met Asp His Thr Ser Gln His Thr His
    3170                3175                3180

Met Gln Leu Leu Tyr Lys Lys Leu Lys Glu Lys Met Leu Thr Ile Leu
3185                3190                3195                3200

Val Phe Glu Arg Tyr Ile Arg Ile Leu Val Ile Val Asn Ile Lys Leu
                3205                3210                3215

Ala Leu Leu Ile Cys Ile Ser Phe Gln Asp Leu Arg Lys Ala Leu Lys
            3220                3225                3230

Ala Gly Thr Val Leu Leu Leu His Gln Pro Ala Pro Leu Ser Ser Ser
        3235                3240                3245

Pro Leu Ala Glu Ala Phe Leu Leu Phe Ser Leu Val Glu Arg Ala Thr
    3250                3255                3260
```

-continued

```
Arg Leu Leu Pro Asn Ile Ser Pro Pro Lys Ser Leu Arg Leu Ile Leu
3265                3270                3275                3280

Tyr Gln Lys Ser Lys Lys His Leu Trp Trp Ser Lys His Gly Ser Phe
                3285                3290                3295

Gln Asn Arg Asn Glu Lys Arg Leu Leu Gly Gly Cys Ile Asn Gly Ile
            3300                3305                3310

Leu Thr Lys Ile Gln Arg Thr Met Thr Leu Pro Met Lys Phe Leu Asn
        3315                3320                3325

Ile Cys Arg Met Lys Ser Thr Asp Lys Asn Arg Leu Phe Ile Lys Met
    3330                3335                3340

Gln Thr Gly Pro Pro Asp Glu His Phe Gln Pro Gln His Pro Asp Phe
3345                3350                3355                3360

Ser Gln Thr Asn Thr His Phe Arg Asp Ser Ile Leu His Gly Ile Lys
                3365                3370                3375

Lys Gln Arg Ala Ile Asn Leu Lys Asp Ser Asn Arg Thr Lys Lys Asn
            3380                3385                3390

Ala Pro Leu Gln Pro Asp Arg Leu Thr Leu Lys Gly Ser Leu Phe Leu
        3395                3400                3405

Pro Leu Ser Ser Arg Leu Ala Ile Gln Trp Lys His Ala Asp Gly Asp
    3410                3415                3420

Lys Pro Glu Gln Thr Ser Gln Leu Pro Gly Met Thr Phe Ile Lys Met
3425                3430                3435                3440

Pro Met Ser Gly Cys Ala Leu Asn Val Thr Phe Leu Pro Ser Leu Leu
                3445                3450                3455

Gln Leu Thr Met Leu Gly Glu Ser Leu Ile Lys Met Asn Gln Leu His
            3460                3465                3470

Leu Leu Arg Lys Arg Asn Ile Val Ser Asn Leu Lys Asp Gln Met Met
        3475                3480                3485

Phe Thr His Trp Lys Leu Met Val Thr Val Lys Gln Asp Thr Leu Ile
    3490                3495                3500

Cys Phe Pro Phe Leu Arg Ser Gln Met Thr Gly Ser Leu Leu Arg Leu
3505                3510                3515                3520

Leu Gly Trp Asn Val Leu Pro Val Ser Asn Leu Lys Ile Leu Cys Asn
                3525                3530                3535

Lys Lys Cys Glu Asp Ile Arg Lys Lys Arg Ile Leu Asn Val Leu His
            3540                3545                3550

Glu Ile Ala Val Leu His Ala
        3555
```

<210> SEQ ID NO 11
<211> LENGTH: 12793
<212> TYPE: DNA
<213> ORGANISM: Homo sapiens

<400> SEQUENCE: 11

```
atgatttaca ggaagaccat gtactcagct gcagcttcta aatccagaac gatttgcacg      60

tcttatcaag gaagtaatga atacattctg gcctggcaga gaattgattg ttcaatggta     120

tccatttgat gaaaacagaa atcacccatc tgtttcatgg cttaagatgg tttggaaaaa     180

tctttatata catttttcag aggatttgac tttatttgat gagatgccac ttatccccag     240

aactatacta gaggaaggtc agacatgtgt ggaactcatt agactcagga ttccatcgtt     300

agtcatttta gacgatgaat ctgaagcaca gcttccagaa tttttagcag acattgtaca     360

aaaacttgga gggtttgtcc ttaaaaaatt agatgcatct atacaacatc cgcttattaa     420
```

-continued

```
aaaatatatt cattcaccat taccaagtgc tgttttgcag ataatggaga agatgccatt    480
gcagaaattg tgtaatcaaa taacttcgct acttccaaca cacaaagatg ccctgaggaa    540
gttcttggct agtttaaccg atagcagtga gaaagagaaa agaattattc aagaattggc    600
aatattcaag cgcattaacc attcttctga tcagggaatt tcctcttata caaaattgaa    660
aggttgtaaa gtcttacacc atactgccaa actcccagca gatctgcgac tttctatttc    720
agtaatagac agtagtgatg aagctactat tcgtctggca aacatgttga aaatagaaca    780
gttaaagacc actagctgct taaagcttgt tttaaaagat attgaaaatg cattttattc    840
acatgaagag gtaacacagc ttatgttatg ggtccttgag aatctatctt ctcttaaaaa    900
tgagaatcca aatgtgcttg agtggttaac accattaaaa ttcatccaga tatcacagga    960
acagatggta tcagctggtg aactctttga ccctgatata gaagtactaa aggatctctt   1020
ttgtaatgaa gaaggaacct atttcccacc ctcagttttt acctcaccag atattcttca   1080
ctccttaaga cagattggtt taaaaaacga agccagtctc aaagaaaagg atgttgtgca   1140
agtggcaaaa aaaattgaag ccttacaggt cggtgcttgt cctgatcaag atgttcttct   1200
gaagaaagcc aaaaccctct tactggtttt aaataagaat cacacactgt tgcaatcatc   1260
tgaaggaaag atgacattga agaaaataaa atgggttcca gcctgcaagg aaaggcctcc   1320
aaattatcca ggctctttgg tctggaaagg agatctctgt aatctctgtg caccaccaga   1380
tatgtgtgat gtaggccatg caattctcat tggctcctca cttcctcttg ttgaaagtat   1440
ccatgtaaac ctggaaaaag cattagggat cttcacaaaa cctagcctta gtgctgtctt   1500
aaaacacttt aaaattgttg ttgattggta ttcttcaaaa acctttagtg atgaagacta   1560
ctatcaattc cagcatattt tgcttgagat ttacggattc atgcatgatc atctaaatga   1620
agggaaagat tcttttagag ccttaaaatt tccatgggtt tggactggca aaaagttttg   1680
tccacttgcc caggctgtga ttaaaccaat ccatgatctt gaccttcagc cttatttgca   1740
taatgtacct aaaaccatgg caaaattcca ccaactattt aaggtctgtg gttcaataga   1800
ggagttgaca tcagatcata tttccatggt tattcagaag atatatctca aaagtgacca   1860
agatctcagt gaacaagaaa gcaaacaaaa tcttcatctt atgttgaata ttatcagatg   1920
gctgtatagc aatcagattc cagcaagccc caacacacca gttcctatac atcatagcaa   1980
aaatccttct aaacttatca tgaagccaat tcacgaatgc tgttattgtg acattaaagt   2040
tgatgacctt aatgacttac ttgaagattc tgtggaacca atcattttgg tgcatgagga   2100
catacccatg aaaactgcag aatggctaaa agttccatgc cttagtacaa gactgataaa   2160
tcctgaaaac atgggatttg agcagtcagg acaaagagag ccacttactg taagaattaa   2220
aaatattctg gaagaatacc cttcagtgtc agatattttt aaagaactac ttcaaaacgc   2280
tgatgatgca aatgcaacag aatgcagttt cttgattgat atgagaagaa atatggacat   2340
aagagagaat ctcctagacc cagggatggc agcttgtcat ggacctgctt tgtggtcatt   2400
caacaattct caattctcag attcagattt tgtgaacata actaggttag gagaatcttt   2460
aaaaagggga gaagttgaca aagttggaaa atttggtctt ggatttaatt ctgtgtacca   2520
tatcactgac attcccatca ttatgagtcg ggaattcatg ataatgttcg atccaaacat   2580
aaatcatatc agtaaacaca ttaaagacaa atccaatcct gggatcaaaa ttaattggag   2640
taaacaacag aaaagactta gaaaatttcc taatcagttc aaaccattta tagatgtatt   2700
tggctgtcag ttacctttga ctgtagaagc accttacagc tataatggaa cccttttccg   2760
```

-continued

```
actgtccttt agaactcaac aggaagcaaa agtgagtgaa gttagtagta cgtgctacaa   2820
tacagcagat atttattctc ttgtggatga atttagtctc tgtggacaca ggcttatcat   2880
tttcactcag agtgtaaagt caatgtattt gaagtacttg aaaattgagg aaaccaaccc   2940
cagtttagca caagatacag taataattaa aaaaaaatcc tgctcttcca aagcattgaa   3000
cacacctgtc ttaagtgttt taaaagaggc tgctaagctc atgaagactt gcagcagcag   3060
taataaaaag cttcccagtg atgaaccaaa gtcatcttgc attcttcaga tcacagtgga   3120
agaatttcac catgtgttca gaaggattgc tgatttacag tcgccacttt ttagaggtcc   3180
agatgatgac ccagctgctc tctttgaaat ggctaagtct ggccaatcaa aaaagccatc   3240
agatgagttg tcacagaaaa cagtagagtg taccacgtgg cttctgtgta cttgcatgga   3300
cacaggagag gctctgaagt ttccctgag tgagagtgga agaagactag gactggttcc   3360
atgtggggca gtaggagttc agctgtcaga aatccaggac cagaagtgga cagtgaaacc   3420
acacattgga gaggtgtttt gctatttacc tttacgaata aaaacaggct tgccagttca   3480
tatcaatggg tgctttgctg ttacatcaaa taggaaagaa atctggaaaa cagatacaaa   3540
aggacgatgg aataccacgt tcatgagaca tgttattgtg aaagcttact tacaggtact   3600
gagtgtctta cgggacctgg ccactagtgg ggagctaatg gattatactt actatgcagt   3660
atggcccgat cctgatttag ttcatgatga tttttctgta atttgccaag gattttatga   3720
agatatagct catggaaaag ggaaagaact gaccaaagtc ttctctgatg gatctacttg   3780
ggtttccatg aagaacgtaa gatttctaga tgactctata cttaaaagaa gagatgttgg   3840
ttcagcagcc ttcaagatat ttttgaaata cctcaagaag actgggtcca aaaacctttg   3900
tgctgttgaa cttccttctt cggtaaaatt aggatttgaa gaagttggct gcaaacagat   3960
actacttgaa aacacatttt cagagaaaca gtttttttct gaagtgtttt ttccaaatat   4020
tcaagaaatt gaagcagaac ttagagatcc tttaatgatc tttgttctaa atgaaaaagt   4080
tgatgagttc tcgggagttc ttcgtgttac tccatgtatt ccttgttcct tggaggggca   4140
tcctttggtt ttgccatcaa gattgatcca ccccgaagga cgagttgcaa agttatttga   4200
tattaaagat gggagattcc cttatggttc tactcaggat tatctcaatc ctattatttt   4260
gattaaacta gttcagttag gtatggcaaa agatgatatt ttatgggatg atatgctaga   4320
acgtgcagtg tcagtagctg aaattaataa aagtgatcat gttgctgcat gcctaagaag   4380
tagtatctta ttgagtctta tcgatgagaa actaaaaata agggatccta gagcaaagga   4440
ttttgctgca aaatatcaaa caatccgctt ccttccattt ctgacaaaac cagcaggttt   4500
ttctttggac tggaaaggca acagttttaa gcctgaaacc atgtttgcag caactgacct   4560
ttatacagct gaacatcaag atatagtttg tcttttgcaa ccaattctaa atgaaaattc   4620
ccattctttt agaggttgtg gttcagtgtc attggctgtt aaagagtttt tgggattact   4680
caagaagcca acagttgatc tggttataaa ccaattgaaa gaagtagcaa aatcagttga   4740
tgatggaatt acactgtacc aggagaatat caccaatgct tgctacaaat accttcatga   4800
agccttgatg caaaatgaaa tcactaagat gtcaattatt gataagttaa aaccctttag   4860
cttcattcta gttgagaatg catatgttga ctcagaaaag gtttcttttc atttaaattt   4920
tgaggcggca ccatacottt atcagttgcc taataagtat aaaaataatt tccgcgaact   4980
ttttgaaacc gtgggtgtga ggcagtcatg cactgttgaa gattttgctc ttgttttgga   5040
atctattgat caagaaagag gaacaaagca aataacagaa gagaattttc agctttgccg   5100
acgaataatc agtgaaggaa tatggagtct cattagagaa aagaaacaag aattttgtga   5160
```

-continued

```
gaaaaattat ggcaagatat tattgccaga tactaatctt atgcttctcc ctgctaaatc   5220
gttatgctac aatgattgcc cttggataaa agtaaaggat accactgtaa aatattgtca   5280
tgctgacata cccagggaag tagcagtaaa actaggagca gtcccaaagc gacacaaagc   5340
cttagaaaga tatgcatcca atgtctgttt tacaacactt ggcacagaat ttgggcagaa   5400
agaaaaattg accagcagaa ttaagagcat ccttaatgca tatccttctg aaaaggaaat   5460
gttgaaagag cttcttcaaa atgctgatga tgcaaaggcg acagaaatct gttttgtgtt   5520
tgatcctaga cagcatccag ttgatagaat atttgatgat aagtgggccc cattgcaagg   5580
gccagcactt tgtgtgtaca acaaccagcc atttacagaa gatgatgtta gaggaattca   5640
gaatcttgga aaaggcacga aagagggaaa tccttataaa actggacagt atggaatagg   5700
attcaattct gtgtatcata tcacagactg cccatctttt atttctggca atgacatcct   5760
gtgtattttt gatcctcatg ccagatatgc accaggggcc acatccatta gtcccggacg   5820
catgtttaga gatttggatg cagattttag gacacagttc tcagatgttc tggatcttta   5880
tctgggaacc cattttaaac tggataattg cacaatgttc agatttcctc ttcgtaatgc   5940
agaaatggca aaagtttcgg aaatttcgtc tgttccagca tcagacagaa tggtccagaa   6000
tcttttggac aaactgcgct cagatggggc agaacttcta atgtttctta atcacatgga   6060
aaaaatttct atttgtgaaa tagataagag tactggagct ctaaatgtgc tgtattcagt   6120
aaagggcaaa atcacagatg gagacagatt gaaaaggaaa caatttcatg catctgtaat   6180
tgatagtgtt actaaaaaga ggcagctcaa agacatacca gttcaacaaa taacctatac   6240
tatggatact gaggactctg aaggaaatct tactacgtgg ctaatttgta atagatcagg   6300
cttttcaagt atggagaaag tatctaaaag tgtcatatca gctcacaaga accaagatat   6360
tactcttttc ccacgtggtg gagtagctgc ctgcattact cacaactata aaaaacccca   6420
tagggccttc tgtttttgc ctctttcttt ggagactggg ctgccatttc atgtgaatgg   6480
ccactttgca ctggattcag ccagaaggaa cctgtggcgt gatgataatg gagttggtgt   6540
tcgaagtgac tggaataaca gtttaatgac agcattaata gctcctgcat atgttgaatt   6600
gctaatacag ttaaaaaaac ggtatttccc tggttctgat ccaacattat cagtgttaca   6660
gaacacccct attcatgttg taaaggacac tttaaagaag tttttatcgt ttttcccagt   6720
taaccgtctt gatctacagc cagatttata ttgtctagtg aaagcacttt acaattgcat   6780
tcacgaagac atgaaacgtc ttttacctgt tgtgcgggct ccaaatattg atggctctga   6840
cttgcactct gcagttataa ttacttggat caatatgtct acttctaata aaactagacc   6900
attttttgac aatttactac aggatgaatt acaacacctt aaaaatgcag attataaatat   6960
caccacacgc aaaacagtag cagagaatgt ctataggctg aaacatctcc ttttagaaat   7020
tggtttcaac ttggtttata actgtgatga aactgctaat ctttaccact gtcttataga   7080
tgcagatatt cctgttagtt atgtgacccc tgctgatatc agatcttttt taatgacatt   7140
ttcctctcct gacactaatt gccatattgg gaagctgcct tgtcgtctgc agcagactaa   7200
tctaaaactt tttcatagtt taaaactttt agttgattat tgttttaaag atgcagaaga   7260
aaatgagatt gaagttgagg gattgcccct tctcatcaca ctggacagtg ttttgcaaac   7320
ttttgatgca aaacgaccca agtttctaac aacatatcat gaattgattc catcccgcaa   7380
agacttgttt atgaatacat tatatttgaa atatagtaat attttattga actgtaaagt   7440
tgcaaaagtg tttgacattt ccagctttgc tgatttgtta tcctctgtgt tgcctcgaga   7500
```

-continued

```
atataagacc aaaagttgca caaagtggaa agacaatttt gcaagtgagt cttggcttaa   7560
gaatgcatgg cattttatta gtgaatctgt aagtgtgaaa gaagatcagg aagaaacaaa   7620
accaacattt gacattgttg ttgatactct aaaagactgg gcattgcttc caggaacaaa   7680
gtttactgtt tcagccaacc agcttgtggt tcctgaagga gatgttctgc ttcctctcag   7740
ccttatgcac attgcagttt ttccaaatgc ccagagtgat aaagtttttc atgctctaat   7800
gaaagccggc tgtattcagc ttgctttgaa caaaatctgt tccaaagaca gtgcatttgt   7860
tcctttgttg tcatgtcaca cagcaaatat agagagcccc acaagcatct tgaaggctct   7920
acattatatg gtccaaactt caacatttag agcagaaaaa ttagtagaaa atgattttga   7980
ggcacttttg atgtatttca actgcaattt gaatcatttg atgtcccaag atgatataaa   8040
aattctaaag tcacttccgt gctataaatc catcagtggc cgctatgtaa gcattggaaa   8100
atttggaaca tgctacgtac ttacaaaaag tatcccttca gctgaagtgg agaaatggac   8160
acaatcatca tcatctgcat ttcttgaaga aaaaatacac ttaaaagaac tatatgaggt   8220
gattggttgt gtacctgtag atgatcttga ggtatatttg aaacacctct taccaaaaat   8280
tgaaaatctc tcttatgatg caaaattaga gcacttgatc taccttaaga atagattatc   8340
aagtgctgag gaattatcag agattaagga acaacttttt gaaaaactgg aaagtttatt   8400
gataatccat gatgctaaca gtagactaaa gcaagcaaag catttctatg atagaactgt   8460
gagagttttt gaagttatgc ttcctgaaaa attgtttatt cctaatgatt tctttaagaa   8520
attggaacaa cttataaaac ccaaaaatca tgttacattt atgacatcct gggtggaatt   8580
cttaagaaat attggactaa aatacatact ttctcagcag cagttgttac agtttgctaa   8640
ggaaatcagt gtgagggcta atacagaaaa ctggtccaaa gaaacattgc aaaatacagt   8700
tgatatcctt ctgcatcata tattccaaga acgaatggat ttgttatctg gaaatttttct   8760
gaaagaacta tctttaatac cattcttatg tcctgagcgg gcccccgcgg aattcattag   8820
atttcatcct caatatcaag aggtaaatgg aacacttcct cttataaagt tcaatggagc   8880
acaggtaaat ccaaaattca agcaatgtga tgtactccag ctgttatgga catcctgccc   8940
tattcttcca gagaaagcta cacccttaag cattaaagaa caagaaggta gtgaccttgg   9000
tccacaagaa cagcttgaac aagttttaaa tatgcttaat gttaacctgg atcctcctct   9060
tgataaggta atcaataact gcagaaacat atgcaacata acgacgttgg atgaagaaat   9120
ggtaaaaact agagcaaaag tcttaaggag catatatgaa ttcctcagtg cagaaaaaag   9180
ggaatttcgt tttcagttgc gaggggttgc ttttgtgatg gtagaagatg gttggaaact   9240
tctgaagcct gaggaggtag tcataaacct agaatatgaa tctgatttta aaccttattt   9300
gtacaagcta cctttagaac ttggcacatt tcaccagttg ttcaaacact taggtactga   9360
agatattatt tcaactaagc aatatgttga agtgttgagc cgcatattta aaaattctga   9420
gggcaaacaa ttagatccta atgaaatgcg tacagttaag agagtagttt ctggtctgtt   9480
caggagtcta cagaatgatt cagtcaaggt gaggagtgat ctcgagaatg tacgagacct   9540
tgcgctttac ctcccaagcc aggatggtag attggtaaag tcaagcatct tagtgtttga   9600
cgatgcgcca cattataaaa gtagaatcca ggggaatatt ggtgtgcaaa tgttagttga   9660
tctcagccag tgctacttag ggaaagacca tggatttcac actaagttga taatgctctt   9720
tcctcaaaaa cttagacctc gattattgag cagtatactt gaagaacaat tagatgaaga   9780
gactcccaaa gtttgtcagt ttggagcgtt gtgttctctt caaggaagat tgcagttact   9840
cttgtcttct gaacagttca ttacaggact gattagaatt atgaagcatg aaaatgataa   9900
```

-continued

```
tgcttttctg gccaatgaag aaaaagccat aagactttgc aaagccctaa gagaaggatt   9960
gaaagtatcc tgctttgaaa agcttcaaac aacattaaga gttaaaggtt ttaatcctat  10020
tccccacagc agaagtgaaa cttttgcttt tttgaagcga tttggtaatg cagtcatctt  10080
gctctacatt caacattcag acagtaaaga cattaatttc ctgttagcac tggcaatgac  10140
tcttaaatca gcaactgaca atttgatttc tgacacttca tatttaattg ctatgctagg  10200
atgcaatgat atttacagga ttggtgagaa acttgacagt ttaggagtga aatatgactc  10260
ttcggagcca tcaaaactgg aacttccaat gcctggcaca ccaattcctg ctgaaattca  10320
ttacactctg cttatggacc caatgaatgt tttttacccg ggagaatatg ttgggtacct  10380
tgttgatgct gaaggtggtg atatctatgg atcataccag ccaacataca catatgcaat  10440
tattgtacaa gaagttgaaa gagaagatgc tgacaattct agttttctag gaaagatata  10500
tcagatagat attggttata gtgaatataa aatagttagc tctcttgatc tgtataagtt  10560
ttcaagacct gaggaaagct ctcaaagcag ggacagtgct ccttctacac caaccagccc  10620
cactgagttc ctcacccctg gcctgagaag cattcctcct cttttctctg gtagagagag  10680
ccacaagact tcttccaaac atcagtcccc caaaaagctt aaggttaatt ctttaccaga  10740
aatcttaaaa gaagtgacat ctgtggtgga gcaagcatgg aagcttccag aatcggaacg  10800
aaaaaagatt attaggcggt tgtatttgaa atggcatcct gacaaaaatc cagagaacca  10860
tgacattgcc aatgaagttt ttaaacattt gcagaatgaa atcaacagat tagaaaaaca  10920
ggcttttcta gatcaaaatg cagacagggc ctccagacga acattttcaa cctcagcatc  10980
ccgatttcag tcagacaaat actcatttca gagattctat acttcatgga atcaagaagc  11040
aacgagccat aaatctgaaa gacagcaaca gaacaaagaa aaatgccccc cttcagccgg  11100
acagacttac tctcaaaggt tctttgttcc tcccactttc aagtcggttg gcaatccagt  11160
ggaagcacgc agatggctaa gacaagccag agcaaacttc tcagctgcca ggaatgacct  11220
tcataaaaat gccaatgagt gggtgtgctt taaatgttac ctttctacca agttagcttt  11280
gattgcagct gactatgctg tgaggggaaa gtctgataaa gatgtaaaac caactgcact  11340
tgctcagaaa atagaggaat atagtcagca acttgaagga ctgacaaatg atgttcacac  11400
attggaagct tatggtgtag acagtttaaa aacaagatac cctgatttgc ttccctttcc  11460
tcagatccca aatgacaggt tcacttctga ggttgctatg agggtgatgg aatgtactgc  11520
ctgtatcata ataaaacttg aaaattttat gcaacaaaaa gtgtgaagat atttaacgaa  11580
aaaaaaggta gatcttgaat gtgttgtagc acgaataaat tgctgtactt cattaagctt  11640
cattgccaat tagctaggaa ttgttaagca cattgcagat tgttcttgga gaattctgga  11700
gttgttatga acatgaatac caacggaaaa ccttaactga atctaaaaga aaactatttt  11760
gaagatggtg gtgagctgca aaatagctgg atggatttga atgattggga tgatacatca  11820
ttgaactgca ctttatataa ccaaagctta gcagtttgtt agataagagt ctatgtatgt  11880
ctctggttag gatgaagtta attttatgtt tttaacatgg tatttttgaa ggagctaatg  11940
aaacactgga catataattg gtttaaacat aaggggaatt aagtctttgt agtctgtcat  12000
ttttttaagt ggatcctctt ggatgcgtta ttttctcatc agctggctct gatcatgaat  12060
ttgttgtaat tttatgttgt actcagtgca tttaagaaat ggtagagtat tttaatccta  12120
ttacttgact aagagtgtga aggtagtact ttttagagtg cactgagtgc actttacatc  12180
tttatttaaa ttttttttta acatcttatg tttacaggct tcctgtttga tgaagatagc  12240
```

-continued aacggaaaac tcaaaatggt ggcagttctt attaccagtt gttagtattg tttctggaaa 12300
ctgcttgcca agacaacatt tattaactgt tagaacactt gctttatgtt tgtgtgtaca 12360
tattttccac aaatgttata atttatatag tgtggttgaa caggatgcaa tcttttgttg 12420
tctaaaggtg ctgcagttaa aaaaaaaaca accttttctt tcaatatggc atgtagtgga 12480
gtttttttaa ctttaaaaac atcaaaaatt gttaaaatca ttgtgttatc tagtagttta 12540
taattatcgg cttatatttc cccatgaatg atcagaactg acatttaatt catgtttgtc 12600
tcgccatgct tctttacttt aacatatttc ttttgcagaa tgtaaaaggt aatgataatt 12660
agtttatata agtgtactgg ctgtaaatga tgctaaatat actttatgca attaagggct 12720
tacagaacat gttgaaactt tttttacttt tattgggaat aaggaatgtt tgcacctcca 12780
cattttattg ctt 12793

<210> SEQ ID NO 12
<211> LENGTH: 12793
<212> TYPE: DNA
<213> ORGANISM: Homo sapiens

<400> SEQUENCE: 12
atgatttaca ggaagaccat gtactcagct gcagcttcta aatccagaac gatttgcacg 60
tcttatcaag gaagtaatga atacattctg gcctggcaga gaattgattg ttcaatggta 120
tccatttgat gaaaacagaa atcacccatc tgtttcatgg cttaagatgg tttggaaaaa 180
tctttatata catttttcag aggatttgac tttatttgat gagatgccac ttatccccag 240
aactatacta gaggaaggtc agacatgtgt ggaactcatt agactcagga ttccatcgtt 300
agtcatttta gacgatgaat ctgaagcaca gcttccagaa tttttagcag acattgtaca 360
aaaacttgga gggtttgtcc ttaaaaaatt agatgcatct atacaacatc cgcttattaa 420
aaaatatatt cattcaccat taccaagtgc tgttttgcag ataatggaga agatgccatt 480
gcagaaattg tgtaatcaaa taacttcgct acttccaaca cacaaagatg ccctgaggaa 540
gttcttggct agtttaaccg atagcagtga gaaagagaaa agaattattc aagaattggc 600
aatattcaag cgcattaacc attcttctga tcagggaatt tcctcttata caaaattgaa 660
aggttgtaaa gtcttacacc atactgccaa actcccagca gatctgcgac tttctatttc 720
agtaatagac agtagtgatg aagctactat tcgtctggca aacatgttga aaatagaaca 780
gttaaagacc actagctgct taaagcttgt tttaaaagat attgaaaatg cattttattc 840
acatgaagag gtaacacagc ttatgttatg ggtccttgag aatctatctt ctcttaaaaa 900
tgagaatcca aatgtgcttg agtggttaac accattaaaa ttcatccaga tatcacagga 960
acagatggta tcagctggtg aactctttga ccctgatata gaagtactaa aggatctctt 1020
ttgtaatgaa gaaggaacct atttcccacc ctcagttttt acctcaccag atattcttca 1080
ctccttaaga cagattggtt taaaaaacga agccagtctc aaagaaaagg atgttgtgca 1140
agtggcaaaa aaaattgaag ccttacaggt cggtgcttgt cctgatcaag atgttcttct 1200
gaagaaagcc aaaaccctct tactggtttt aaataagaat cacacactgt tgcaatcatc 1260
tgaaggaaag atgacattga agaaaataaa atgggttcca gcctgcaagg aaaggcctcc 1320
aaattatcca ggctctttgg tctggaaagg agatctctgt aatctctgtg caccaccaga 1380
tatgtgtgat gtaggccatg caattctcat tggctcctca cttcctcttg ttgaaagtat 1440
ccatgtaaac ctggaaaaag cattagggat cttcacaaaa cctagcctta gtgctgtctt 1500
aaaacacttt aaaattgttg ttgattggta ttcttcaaaa acctttagtg atgaagacta 1560

-continued

```
ctatcaattc cagcatattt tgcttgagat ttacggattc atgcatgatc atctaaatga   1620
agggaaagat tcttttagag ccttaaaatt tccatgggtt tggactggca aaaagttttg   1680
tccacttgcc caggctgtga ttaaaccaat ccatgatctt gaccttcagc cttatttgca   1740
taatgtacct aaaaccatgg caaaattcca ccaactattt aaggtctgtg gttcaataga   1800
ggagttgaca tcagatcata tttccatggt tattcagaag atatatctca aaagtgacca   1860
agatctcagt gaacaagaaa gcaaacaaaa tcttcatctt atgttgaata ttatcagatg   1920
gctgtatagc aatcagattc cagcaagccc caacacacca gttcctatac atcatagcaa   1980
aaatccttct aaacttatca tgaagccaat tcacgaatgc tgttattgtg acattaaagt   2040
tgatgacctt aatgacttac ttgaagattc tgtggaacca atcattttgg tgcatgagga   2100
catacccatg aaaactgcag aatggctaaa agttccatgc cttagtacaa gactgataaa   2160
tcctgaaaac atgggatttg agcagtcagg acaaagagag ccacttactg taagaattaa   2220
aaatattctg gaagaatacc cttcagtgtc agatattttt aaagaactac ttcaaaacgc   2280
tgatgatgca aatgcaacag aatgcagttt cttgattgat atgagaagaa atatggacat   2340
aagagagaat ctcctagacc cagggatggc agcttgtcat ggacctgctt tgtggtcatt   2400
caacaattct caattctcag attcagattt tgtgaacata actaggttag gagaatcttt   2460
aaaaagggga gaagttgaca aagttggaaa atttggtctt ggatttaatt ctgtgtacca   2520
tatcactgac attcccatca ttatgagtcg ggaattcatg ataatgttcg atccaaacat   2580
aaatcatatc agtaaacaca ttaaagacaa atccaatcct gggatcaaaa ttaattggag   2640
taaacaacag aaaagactta gaaaatttcc taatcagttc aaaccattta tagatgtatt   2700
tggctgtcag ttacctttga ctgtagaagc accttacagc tataatggaa cccttttccg   2760
actgtccttt agaactcaac aggaagcaaa agtgagtgaa gttagtagta cgtgctacaa   2820
tacagcagat atttattctc ttgtggatga atttagtctc tgtggacaca ggcttatcat   2880
tttcactcag agtgtaaagt caatgtattt gaagtacttg aaaattgagg aaaccaaccc   2940
cagtttagca caagatacag taataattaa aaaaaaatcc tgctcttcca aagcattgaa   3000
cacacctgtc ttaagtgttt taaaagaggc tgctaagctc atgaagactt gcagcagcag   3060
taataaaaag cttcccagtg atgaaccaaa gtcatcttgc attcttcaga tcacagtgga   3120
agaatttcac catgtgttca gaaggattgc tgatttacag tcgccacttt ttagaggtcc   3180
agatgatgac ccagctgctc tctttgaaat ggctaagtct ggccaatcaa aaaagccatc   3240
agatgagttg tcacagaaaa cagtagagtg taccacgtgg cttctgtgta cttgcatgga   3300
cacaggagag gctctgaagt tttccctgag tgagagtgga agaagactag gactggttcc   3360
atgtggggca gtaggagttc agctgtcaga aatccaggac cagaagtgga cagtgaaacc   3420
acacattgga gaggtgtttt gctatttacc tttacgaata aaaacaggct tgccagttca   3480
tatcaatggg tgctttgctg ttacatcaaa taggaaagaa atctggaaaa cagatacaaa   3540
aggacgatgg aataccacgt tcatgagaca tgttattgtg aaagcttact tacaggtact   3600
gagtgtctta cgggacctgg ccactagtgg ggagctaatg gattatactt actatgcagt   3660
atggcccgat cctgatttag ttcatgatga tttttctgta atttgccaag gattttatga   3720
agatatagct catggaaaag ggaaagaact gaccaaagtc ttctctgatg gatctacttg   3780
ggtttccatg aagaacgtaa gatttctaga tgactctata cttaaaagaa gagatgttgg   3840
ttcagcagcc ttcaagatat ttttgaaata cctcaagaag actgggtcca aaaacctttg   3900
```

-continued

```
tgctgttgaa cttccttctt cggtaaaatt aggatttgaa gaagctggct gcaaacagat   3960
actacttgaa aacacatttt cagagaaaca gtttttttct gaagtgtttt ttccaaatat   4020
tcaagaaatt gaagcagaac ttagagatcc tttaatgatc tttgttctaa atgaaaaagt   4080
tgatgagttc tcgggagttc ttcgtgttac tccatgtatt ccttgttcct tggaggggca   4140
tcctttggtt ttgccatcaa gattgatcca ccccgaagga cgagttgcaa agttatttga   4200
tattaaagat gggagattcc cttatggttc tactcaggat tatctcaatc ctattatttt   4260
gattaaacta gttcagttag gtatggcaaa agatgatatt ttatgggatg atatgctaga   4320
acgtgcagtg tcagtagctg aaattaataa aagtgatcat gttgctgcat gcctaagaag   4380
tagtatctta ttgagtctta tcgatgagaa actaaaaata agggatccta gagcaaagga   4440
ttttgctgca aaatatcaaa caatccgctt ccttccattt ctgacaaaac cagcaggttt   4500
ttctttggac tggaaaggca acagttttaa gcctgaaacc atgtttgcag caactgacct   4560
ttatacagct gaacatcaag atatagtttg tcttttgcaa ccaattctaa atgaaaattc   4620
ccattctttt agaggttgtg gttcagtgtc attggctgtt aaagagtttt tgggattact   4680
caagaagcca acagttgatc tggttataaa ccaattgaaa gaagtagcaa aatcagttga   4740
tgatggaatt acactgtacc aggagaatat caccaatgct tgctacaaat accttcatga   4800
agccttgatg caaaatgaaa tcactaagat gtcaattatt gataagttaa aacccttag    4860
cttcattcta gttgagaatg catatgttga ctcagaaaag gtttcttttc atttaaattt   4920
tgaggcggca ccatacctt  atcagttgcc taataagtat aaaaataatt tccgcgaact   4980
ttttgaaacc gtgggtgtga ggcagtcatg cactgttgaa gattttgctc ttgttttgga   5040
atctattgat caagaaagag gaacaaagca aataacagaa gagaattttc agctttgccg   5100
acgaataatc agtgaaggaa tatggagtct cattagagaa aagaaacaag aattttgtga   5160
gaaaaattat ggcaagatat tattgccaga tactaatctt atgcttctcc ctgctaaatc   5220
gttatgctac aatgattgcc cttggataaa agtaaaggat accactgtaa aatattgtca   5280
tgctgacata cccagggaag tagcagtaaa actaggagca gtcccaaagc gacacaaagc   5340
cttagaaaga tatgcatcca atgtctgttt tacaacactt ggcacagaat ttgggcagaa   5400
agaaaaattg accagcagaa ttaagagcat ccttaatgca tatccttctg aaaaggaaat   5460
gttgaaagag cttcttcaaa atgctgatga tgcaaaggcg acagaaatct gttttgtgtt   5520
tgatcctaga cagcatccag ttgatagaat atttgatgat aagtgggccc cattgcaagg   5580
gccagcactt tgtgtgtaca acaaccagcc atttacagaa gatgatgtta gaggaattca   5640
gaatcttgga aaaggcacga aagagggaaa tccttataaa actggacagt atggaatagg   5700
attcaattct gtgtatcata tcacagactg cccatctttt atttctggca atgacatcct   5760
gtgtattttt gatcctcatg ccagatatgc accaggggcc acatccatta gtcccggacg   5820
catgtttaga gatttggatg cagattttag gacacagttc tcagatgttc tggatcttta   5880
tctgggaacc cattttaaac tggataattg cacaatgttc agatttcctc ttcgtaatgc   5940
agaaatggca aaagtttcgg aaatttcgtc tgttccagca tcagacagaa tggtccagaa   6000
tcttttggac aaactgcgct cagatggggc agaacttcta atgtttctta atcacatgga   6060
aaaaatttct atttgtgaaa tagataagag tactggagct ctaaatgtgc tgtattcagt   6120
aaagggcaaa atcacagatg gagacagatt gaaaaggaaa caatttcatg catctgtaat   6180
tgatagtgtt actaaaaaga ggcagctcaa agacatacca gttcaacaaa taacctatac   6240
tatggatact gaggactctg aaggaaatct tactacgtgg ctaatttgta atagatcagg   6300
```

-continued

```
cttttcaagt atggagaaag tatctaaaag tgtcatatca gctcacaaga accaagatat   6360
tactcttttc ccacgtggtg gagtagctgc ctgcattact cacaactata aaaaacccca   6420
tagggccttc tgtttttgc ctctttcttt ggagactggg ctgccatttc atgtgaatgg   6480
ccactttgca ctggattcag ccagaaggaa cctgtggcgt gatgataatg gagttggtgt   6540
tcgaagtgac tggaataaca gtttaatgac agcattaata gctcctgcat atgttgaatt   6600
gccaatacag ttaaaaaaac ggtatttccc tggttctgat ccaacattat cagtgttaca   6660
gaacacccct attcatgttg taaaggacac tttaaagaag tttttatcgt ttttcccagt   6720
taaccgtctt gatctacagc cagatttata ttgtctagtg aaagcacttt acaattgcat   6780
tcacgaagac atgaaacgtc ttttacctgt tgtgcgggct ccaaatattg atggctctga   6840
cttgcactct gcagttataa ttacttggat caatatgtct acttctaata aaactagacc   6900
attttttgac aatttactac aggatgaatt acaacacctt aaaaatgcag attataatat   6960
caccacacgc aaaacagtag cagagaatgt ctataggctg aaacatctcc ttttagaaat   7020
tggtttcaac ttggtttata actgtgatga aactgctaat ctttaccact gtcttataga   7080
tgcagatatt cctgttagtt atgtgacccc tgctgatatc agatcttttt taatgacatt   7140
ttcctctcct gacactaatt gccatattgg gaagctgcct tgtcgtctgc agcagactaa   7200
tctaaaactt tttcatagtt taaaactttt agttgattat tgttttaaag atgcagaaga   7260
aaatgagatt gaagttgagg gattgcccct tctcatcaca ctggacagtg ttttgcaaac   7320
ttttgatgca aaacgaccca agtttctaac aacatatcat gaattgattc catcccgcaa   7380
agacttgttt atgaatacat tatatttgaa atatagtaat attttattga actgtaaagt   7440
tgcaaaagtg tttgacattt ccagctttgc tgatttgtta tcctctgtgt tgcctcgaga   7500
atataagacc aaaagttgca caaagtggaa agacaatttt gcaagtgagt cttggcttaa   7560
gaatgcatgg cattttatta gtgaatctgt aagtgtgaaa gaagatcagg aagaaacaaa   7620
accaacattt gacattgttg ttgatactct aaaagactgg gcattgcttc caggaacaaa   7680
gtttactgtt tcagccaacc agcttgtggt tcctgaagga gatgttctgc ttcctctcag   7740
ccttatgcac attgcagttt ttccaaatgc ccagagtgat aaagtttttc atgctctaat   7800
gaaagccggc tgtattcagc ttgctttgaa caaaatctgt tccaaagaca gtgcatttgt   7860
tcctttgttg tcatgtcaca cagcaaatat agagagcccc acaagcatct tgaaggctct   7920
acattatatg gtccaaactt caacatttag agcagaaaaa ttagtagaaa atgattttga   7980
ggcacttttg atgtatttca actgcaattt gaatcatttg atgtcccaag atgatataaa   8040
aattctaaag tcacttccgt gctataaatc catcagtggc cgctatgtaa gcattggaaa   8100
atttggaaca tgctacgtac ttacaaaaag tatcccttca gctgaagtgg agaaatggac   8160
acaatcatca tcatctgcat ttcttgaaga aaaaatacac ttaaaagaac tatatgaggt   8220
gattggttgt gtacctgtag atgatcttga ggtatatttg aaacacctct taccaaaaat   8280
tgaaaatctc tcttatgatg caaaattaga gcacttgatc taccttaaga atagattatc   8340
aagtgctgag gaattatcag agattaagga acaacttttt gaaaaactgg aaagtttatt   8400
gataatccat gatgctaaca gtagactaaa gcaagcaaag catttctatg atagaactgt   8460
gagagttttt gaagttatgc ttcctgaaaa attgtttatt cctaatgatt tctttaagaa   8520
attggaacaa cttataaaac ccaaaaatca tgttacattt atgacatcct gggtggaatt   8580
cttaagaaat attggactaa aatacatact ttctcagcag cagttgttac agtttgctaa   8640
```

-continued

```
ggaaatcagt gtgagggcta atacagaaaa ctggtccaaa gaaacattgc aaaatacagt   8700
tgatatcctt ctgcatcata tattccaaga acgaatggat ttgttatctg gaaatttttct   8760
gaaagaacta tctttaatac cattcttatg tcctgagcgg gcccccgcgg aattcattag   8820
atttcatcct caatatcaag aggtaaatgg aacacttcct cttataaagt tcaatggagc   8880
acaggtaaat ccaaaattca agcaatgtga tgtactccag ctgttatgga catcctgccc   8940
tattcttcca gagaaagcta cacccttaag cattaaagaa caagaaggta gtgaccttgg   9000
tccacaagaa cagcttgaac aagttttaaa tatgcttaat gttaacctgg atcctcctct   9060
tgataaggta atcaataact gcagaaacat atgcaacata acgacgttgg atgaagaaat   9120
ggtaaaaact agagcaaaag tcttaaggag catatatgaa ttcctcagtg cagaaaaaag   9180
ggaatttcgt tttcagttgc gaggggttgc ttttgtgatg gtagaagatg gttggaaact   9240
tctgaagcct gaggaggtag tcataaacct agaatatgaa tctgatttta aaccttattt   9300
gtacaagcta cctttagaac ttggcacatt tcaccagttg ttcaaacact taggtactga   9360
agatattatt tcaactaagc aatatgttga agtgttgagc cgcatattta aaaattctga   9420
gggcaaacaa ttagatccta atgaaatgcg tacagttaag agagtagttt ctggtctgtt   9480
caggagtcta cagaatgatt cagtcaaggt gaggagtgat ctcgagaatg tacgagacct   9540
tgcgctttac ctcccaagcc aggatggtag attggtaaag tcaagcatct tagtgtttga   9600
cgatgcgcca cattataaaa gtagaatcca ggggaatatt ggtgtgcaaa tgttagttga   9660
tctcagccag tgctacttag ggaaagacca tggatttcac actaagttga taatgctctt   9720
tcctcaaaaa cttagacctc gattattgag cagtatactt gaagaacaat tagatgaaga   9780
gactcccaaa gtttgtcagt ttggagcgtt gtgttctctt caaggaagat tgcagttact   9840
cttgtcttct gaacagttca ttacaggact gattagaatt atgaagcatg aaaatgataa   9900
tgcttttctg gccaatgaag aaaaagccat aagactttgc aaagccctaa gagaaggatt   9960
gaaagtatcc tgctttgaaa agcttcaaac aacattaaga gttaaaggtt ttaatcctat  10020
tccccacagc agaagtgaaa cttttgcttt tttgaagcga tttggtaatg cagtcatctt  10080
gctctacatt caacattcag acagtaaaga cattaatttc ctgttagcac tggcaatgac  10140
tcttaaatca gcaactgaca atttgatttc tgacacttca tatttaattg ctatgctagg  10200
atgcaatgat atttacagga ttggtgagaa acttgacagt ttaggagtga aatatgactc  10260
ttcggagcca tcaaaactgg aacttccaat gcctggcaca ccaattcctg ctgaaattca  10320
ttacactctg cttatggacc caatgaatgt tttttacccg ggagaatatg ttgggtacct  10380
tgttgatgct gaaggtggtg atatctatgg atcataccag ccaacataca catatgcaat  10440
tattgtacaa gaagttgaaa gagaagatgc tgacaattct agttttctag gaaagatata  10500
tcagatagat attggttata gtgaatataa aatagttagc tctcttgatc tgtataagtt  10560
ttcaagacct gaggaaagct ctcaaagcag ggacagtgct ccttctacac caaccagccc  10620
cactgagttc ctcacccctg gcctgagaag cattcctcct cttttctctg gtagagagag  10680
ccacaagact tcttccaaac atcagtcccc caaaaagctt aaggttaatt ctttaccaga  10740
aatcttaaaa gaagtgacat ctgtggtgga gcaagcatgg aagcttccag aatcggaacg  10800
aaaaaagatt attaggcggt tgtatttgaa atggcatcct gacaaaaatc cagagaacca  10860
tgacattgcc aatgaagttt ttaaacattt gcagaatgaa atcaacagat tagaaaaaca  10920
ggcttttcta gatcaaaatg cagacagggc ctccagacga acattttcaa cctcagcatc  10980
ccgatttcag tcagacaaat actcatttca gagattctat acttcatgga atcaagaagc  11040
```

-continued

```
aacgagccat aaatctgaaa gacagcaaca gaacaaagaa aaatgccccc cttcagccgg  11100
acagacttac tctcaaaggt tctttgttcc tcccactttc aagtcggttg gcaatccagt  11160
ggaagcacgc agatggctaa gacaagccag agcaaacttc tcagctgcca ggaatgacct  11220
tcataaaaat gccaatgagt gggtgtgctt taaatgttac ctttctacca agttagcttt  11280
gattgcagct gactatgctg tgaggggaaa gtctgataaa gatgtaaaac caactgcact  11340
tgctcagaaa atagaggaat atagtcagca acttgaagga ctgacaaatg atgttcacac  11400
attggaagct tatggtgtag acagtttaaa aacaagatac cctgatttgc ttccctttcc  11460
tcagatccca aatgacaggt tcacttctga ggttgctatg agggtgatgg aatgtactgc  11520
ctgtatcata ataaaacttg aaaattttat gcaacaaaaa gtgtgaagat atttaacgaa  11580
aaaaaaggta gatcttgaat gtgttgtagc acgaataaat tgctgtactt cattaagctt  11640
cattgccaat tagctaggaa ttgttaagca cattgcagat tgttcttgga gaattctgga  11700
gttgttatga acatgaatac caacggaaaa ccttaactga atctaaaaga aaactatttt  11760
gaagatggtg gtgagctgca aaatagctgg atggatttga atgattggga tgatacatca  11820
ttgaactgca ctttatataa ccaaagctta gcagtttgtt agataagagt ctatgtatgt  11880
ctctggttag gatgaagtta attttatgtt tttaacatgg tatttttgaa ggagctaatg  11940
aaacactgga catataattg gtttaaacat aaggggaatt aagtctttgt agtctgtcat  12000
ttttttaagt ggatcctctt ggatgcgtta ttttctcatc agctggctct gatcatgaat  12060
ttgttgtaat tttatgttgt actcagtgca tttaagaaat ggtagagtat tttaatccta  12120
ttacttgact aagagtgtga aggtagtact ttttagagtg cactgagtgc actttacatc  12180
tttatttaaa ttttttttta acatcttatg tttacaggct tcctgtttga tgaagatagc  12240
aacggaaaac tcaaaatggt ggcagttctt attaccagtt gttagtattg tttctggaaa  12300
ctgcttgcca agacaacatt tattaactgt tagaacactt gctttatgtt tgtgtgtaca  12360
tattttccac aaatgttata atttatatag tgtggttgaa caggatgcaa tcttttgttg  12420
tctaaaggtg ctgcagttaa aaaaaaaaca accttttctt tcaatatggc atgtagtgga  12480
gtttttttaa ctttaaaaac atcaaaaatt gttaaaatca ttgtgttatc tagtagttta  12540
taattatcgg cttatatttc cccatgaatg atcagaactg acatttaatt catgtttgtc  12600
tcgccatgct tctttacttt aacatatttc ttttgcagaa tgtaaaaggt aatgataatt  12660
agtttatata agtgtactgg ctgtaaatga tgctaaatat actttatgca attaagggct  12720
tacagaacat gttgaaactt tttttacttt tattgggaat aaggaatgtt tgcacctcca  12780
cattttattg ctt                                                     12793
```

<210> SEQ ID NO 13
<211> LENGTH: 12717
<212> TYPE: DNA
<213> ORGANISM: Homo sapiens

<400> SEQUENCE: 13

```
atgaatacat tctggcctgg cagagaattg attgttcaat ggtatccatt tgatgaaaac     60
agaaatcacc catctgtttc atggcttaag atggtttgga aaaatcttta tatacatttt    120
tcagaggatt tgactttatt tgatgagatg ccacttatcc ccagaactat actagaggaa    180
ggtcagacat gtgtggaact cattagactc aggattccat cgttagtcat tttagacgat    240
gaatctgaag cacagcttcc agaattttta gcagacattg tacaaaaact tggagggttt    300
```

-continued

```
gtccttaaaa aattagatgc atctatacaa catccgctta ttaaaaaata tattcattca    360
ccattaccaa gtgctgtttt gcagataatg gagaagatgc cattgcagaa attgtgtaat    420
caaataactt cgctacttcc aacacacaaa gatgccctga ggaagttctt ggctagttta    480
accgatagca gtgagaaaga gaaaagaatt attcaagaat tggcaatatt caagcgcatt    540
aaccattctt ctgatcaggg aatttcctct tatacaaaat tgaaaggttg taaagtctta    600
caccatactg ccaaactccc agcagatctg cgactttcta tttcagtaat agacagtagt    660
gatgaagcta ctattcgtct ggcaaacatg ttgaaaatag aacagttaaa gaccactagc    720
tgcttaaagc ttgttttaaa agatattgaa aatgcatttt attcacatga agaggtaaca    780
cagcttatgt tatgggtcct tgagaatcta tcttctctta aaaatgagaa tccaaatgtg    840
cttgagtggt taacaccatt aaaattcatc cagatatcac aggaacagat ggtatcagct    900
ggtgaactct ttgaccctga tatagaagta ctaaaggatc tcttttgtaa tgaagaagga    960
acctatttcc caccctcagt tttacctca ccagatattc ttcactcctt aagacagatt   1020
ggtttaaaaa acgaagccag tctcaaagaa aaggatgttg tgcaagtggc aaaaaaaatt   1080
gaagccttac aggtcggtgc ttgtcctgat caagatgttc ttctgaagaa agccaaaacc   1140
ctcttactgg ttttaaataa gaatcacaca ctgttgcaat catctgaagg aaagatgaca   1200
ttgaagaaaa taaaatgggt tccagcctgc aaggaaaggc ctccaaatta tccaggctct   1260
ttggtctgga aaggagatct ctgtaatctc tgtgcaccac cagatatgtg tgatgtaggc   1320
catgcaattc tcattggctc ctcacttcct cttgttgaaa gtatccatgt aaacctggaa   1380
aaagcattag ggatcttcac aaaacctagc cttagtgctg tcttaaaaca ctttaaaatt   1440
gttgttgatt ggtattcttc aaaaaccttt agtgatgaag actactatca attccagcat   1500
attttgcttg agatttacgg attcatgcat gatcatctaa atgaagggaa agattctttt   1560
agagccttaa aatttccatg ggtttggact ggcaaaaagt tttgtccact tgcccaggct   1620
gtgattaaac caatccatga tcttgacctt cagccttatt tgcataatgt acctaaaacc   1680
atggcaaaat tccaccaact atttaaggtc tgtggttcaa tagaggagtt gacatcagat   1740
catatttcca tggttattca gaagatatat ctcaaaagtg accaagatct cagtgaacaa   1800
gaaagcaaac aaaatcttca tcttatgttg aatattatca gatggctgta tagcaatcag   1860
attccagcaa gccccaacac accagttcct atacatcata gcaaaaatcc ttctaaactt   1920
atcatgaagc caattcacga atgctgttat tgtgacatta aagttgatga ccttaatgac   1980
ttacttgaag attctgtgga accaatcatt ttggtgcatg aggacatacc catgaaaact   2040
gcagaatggc taaaagttcc atgccttagt acaagactga taaatcctga aaacatggga   2100
tttgagcagt caggacaaag agagccactt actgtaagaa ttaaaaatat tctggaagaa   2160
tacccttcag tgtcagatat ttttaaagaa ctacttcaaa acgctgatga tgcaaatgca   2220
acagaatgca gtttcttgat tgatatgaga agaaatatgg acataagaga gaatctccta   2280
gacccaggga tggcagcttg tcatggacct gctttgtggt cattcaacaa ttctcaattc   2340
tcagattcag attttgtgaa cataactagg ttaggagaat ctttaaaaag gggagaagtt   2400
gacaaagttg gaaaatttgg tcttggattt aattctgtgt accatatcac tgacattccc   2460
atcattatga gtcgggaatt catgataatg ttcgatccaa acataaatca tatcagtaaa   2520
cacattaaag acaaatccaa tcctgggatc aaaattaatt ggagtaaaca acagaaaaga   2580
cttagaaaat ttcctaatca gttcaaacca tttatagatg tatttggctg tcagttacct   2640
ttgactgtag aagcacctta cagctataat ggaacccttt tccgactgtc ctttagaact   2700
```

-continued

```
caacaggaag caaaagtgag tgaagttagt agtacgtgct acaatacagc agatatttat   2760
tctcttgtgg atgaatttag tctctgtgga cacaggctta tcattttcac tcagagtgta   2820
aagtcaatgt atttgaagta cttgaaaatt gaggaaacca accccagttt agcacaagat   2880
acagtaataa ttaaaaaaaa atcctgctct tccaaagcat tgaacacacc tgtcttaagt   2940
gttttaaaag aggctgctaa gctcatgaag acttgcagca gcagtaataa aaagcttccc   3000
agtgatgaac caaagtcatc ttgcattctt cagatcacag tggaagaatt tcaccatgtg   3060
ttcagaagga ttgctgattt acagtcgcca ctttttagag gtccagatga tgacccagct   3120
gctctctttg aaatggctaa gtctggccaa tcaaaaaagc catcagatga gttgtcacag   3180
aaaacagtag agtgtaccac gtggcttctg tgtacttgca tggacacagg agaggctctg   3240
aagttttccc tgagtgagag tggaagaaga ctaggactgg ttccatgtgg ggcagtagga   3300
gttcagctgt cagaaatcca ggaccagaag tggacagtga aaccacacat tggagaggtg   3360
ttttgctatt tacctttacg aataaaaaca ggcttgccag ttcatatcaa tgggtgcttt   3420
gctgttacat caaataggaa agaaatctgg aaaacagata caaaaggacg atggaatacc   3480
acgttcatga gacatgttat tgtgaaagct tacttacagg tactgagtgt cttacgggac   3540
ctggccacta gtggggagct aatggattat acttactatg cagtatggcc cgatcctgat   3600
ttagttcatg atgatttttc tgtaatttgc caaggatttt atgaagatat agctcatgga   3660
aaagggaaag aactgaccaa agtcttctct gatggatcta cttgggtttc catgaagaac   3720
gtaagatttc tagatgactc tatacttaaa agaagagatg ttggttcagc agccttcaag   3780
atatttttga aatacctcaa gaagactggg tccaaaaacc tttgtgctgt tgaacttcct   3840
tcttcggtaa aattaggatt tgaagaagct ggctgcaaac agatactact tgaaaacaca   3900
ttttcagaga aacagttttt ttctgaagtg ttttttccaa atattcaaga aattgaagca   3960
gaacttagag atcctttaat gatctttgtt ctaaatgaaa aagttgatga gttctcggga   4020
gttcttcgtg ttactccatg tattccttgt tccttggagg ggcatccttt ggttttgcca   4080
tcaagattga tccaccccga aggacgagtt gcaaagttat ttgatattaa agatgggaga   4140
ttcccttatg gttctactca ggattatctc aatcctatta ttttgattaa actagttcag   4200
ttaggtatgg caaaagatga tattttatgg gatgatatgc tagaacgtgc agtgtcagta   4260
gctgaaatta ataaaagtga tcatgttgct gcatgcctaa gaagtagtat cttattgagt   4320
cttatcgatg agaaactaaa aataagggat cctagagcaa aggattttgc tgcaaaatat   4380
caaacaatcc gcttccttcc atttctgaca aaaccagcag gtttttcttt ggactggaaa   4440
ggcaacagtt ttaagcctga aaccatgttt gcagcaactg acctttatac agctgaacat   4500
caagatatag tttgtctttt gcaaccaatt ctaaatgaaa attcccattc ttttagaggt   4560
tgtggttcag tgtcattggc tgttaaagag tttttgggat tactcaagaa gccaacagtt   4620
gatctggtta taaaccaatt gaaagaagta gcaaaatcag ttgatgatgg aattacactg   4680
taccaggaga atatcaccaa tgcttgctac aaataccttc atgaagcctt gatgcaaaat   4740
gaaatcacta agatgtcaat tattgataag ttaaaaccct ttagcttcat tctagttgag   4800
aatgcatatg ttgactcaga aaaggtttct tttcatttaa attttgaggc ggcaccatac   4860
ctttatcagt tgcctaataa gtataaaaat aatttccgcg aactttttga aaccgtgggt   4920
gtgaggcagt catgcactgt tgaagatttt gctcttgttt tggaatctat tgatcaagaa   4980
agaggaacaa agcaaataac agaagagaat tttcagcttt gccgacgaat aatcagtgaa   5040
```

-continued

```
ggaatatgga gtctcattag agaaaagaaa caagaatttt gtgagaaaaa ttatggcaag   5100
atattattgc cagatactaa tcttatgctt ctccctgcta aatcgttatg ctacaatgat   5160
tgcccttgga taaaagtaaa ggataccact gtaaaatatt gtcatgctga catacccagg   5220
gaagtagcag taaaactagg agcagtccca aagcgacaca aagccttaga aagatatgca   5280
tccaatgtct gttttacaac acttggcaca gaatttgggc agaaagaaaa attgaccagc   5340
agaattaaga gcatccttaa tgcatatcct tctgaaaagg aaatgttgaa agagcttctt   5400
caaaatgctg atgatgcaaa ggcgacagaa atctgttttg tgtttgatcc tagacagcat   5460
ccagttgata gaatatttga tgataagtgg gccccattgc aagggccagc actttgtgtg   5520
tacaacaacc agccatttac agaagatgat gttagaggaa ttcagaatct tggaaaaggc   5580
acgaaagagg gaaatcctta taaaactgga cagtatggaa taggattcaa ttctgtgtat   5640
catatcacag actgcccatc ttttatttct ggcaatgaca tcctgtgtat ttttgatcct   5700
catgccagat atgcaccagg ggccacatcc attagtcccg gacgcatgtt tagagatttg   5760
gatgcagatt ttaggacaca gttctcagat gttctggatc tttatctggg aacccatttt   5820
aaactggata attgcacaat gttcagattt cctcttcgta atgcagaaat ggcaaaagtt   5880
tcggaaattt cgtctgttcc agcatcagac agaatggtcc agaatctttt ggacaaactg   5940
cgctcagatg gggcagaact tctaatgttt cttaatcaca tggaaaaaat ttctatttgt   6000
gaaatagata agagtactgg agctctaaat gtgctgtatt cagtaaaggg caaaatcaca   6060
gatggagaca gattgaaaag gaaacaattt catgcatctg taattgatag tgttactaaa   6120
aagaggcagc tcaaagacat accagttcaa caaataacct atactatgga tactgaggac   6180
tctgaaggaa atcttactac gtggctaatt tgtaatagat caggcttttc aagtatggag   6240
aaagtatcta aaagtgtcat atcagctcac aagaaccaag atattactct tttcccacgt   6300
ggtggagtag ctgcctgcat tactcacaac tataaaaaac cccatagggc cttctgtttt   6360
ttgcctcttt ctttggagac tgggctgcca tttcatgtga atggccactt tgcactggat   6420
tcagccagaa ggaacctgtg gcgtgatgat aatggagttg gtgttcgaag tgactggaat   6480
aacagtttaa tgacagcatt aatagctcct gcatatgttg aattgctaat acagttaaaa   6540
aaacggtatt tccctggttc tgatccaaca ttatcagtgt tacagaacac ccctattcat   6600
gttgtaaagg acactttaaa gaagttttta tcgtttttcc cagttaaccg tcttgatcta   6660
cagccagatt tatattgtct agtgaaagca ctttacaatt gcattcacga agacatgaaa   6720
cgtcttttac ctgttgtgcg ggctccaaat attgatggct ctgacttgca ctctgcagtt   6780
ataattactt ggatcaatat gtctacttct aataaaacta gaccattttt tgacaattta   6840
ctacaggatg aattacaaca ccttaaaaat gcagattata atatcaccac acgcaaaaca   6900
gtagcagaga atgtctatag gctgaaacat ctccttttag aaattggttt caacttggtt   6960
tataactgtg atgaaactgc taatctttac cactgtctta tagatgcaga tattcctgtt   7020
agttatgtga cccctgctga tatcagatct tttttaatga cattttcctc tcctgacact   7080
aattgccata ttgggaagct gccttgtcgt ctgcagcaga ctaatctaaa actttttcat   7140
agtttaaaac ttttagttga ttattgtttt aaagatgcag aagaaaatga gattgaagtt   7200
gagggattgc cccttctcat cacactggac agtgttttgc aaacttttga tgcaaaacga   7260
cccaagtttc taacaacata tcatgaattg attccatccc gcaaagactt gtttatgaat   7320
acattatatt tgaaatatag taatatttta ttgaactgta aagttgcaaa agtgtttgac   7380
atttccagct ttgctgattt gttatcctct gtgttgcctc gagaatataa gaccaaaagt   7440
```

-continued

```
tgcacaaagt ggaaagacaa ttttgcaagt gagtcttggc ttaagaatgc atggcatttt   7500
attagtgaat ctgtaagtgt gaaagaagat caggaagaaa caaaaccaac atttgacatt   7560
gttgttgata ctctaaaaga ctgggcattg cttccaggaa caaagtttac tgtttcagcc   7620
aaccagcttg tggttcctga aggagatgtt ctgcttcctc tcagccttat gcacattgca   7680
gtttttccaa atgcccagag tgataaagtt tttcatgctc taatgaaagc tggctgtatt   7740
cagcttgctt tgaacaaaat ctgttccaaa gacagtgcat ttgttccttt gttgtcatgt   7800
cacacagcaa atatagagag ccccacaagc atcttgaagg ctctacatta tatggtccaa   7860
acttcaacat ttagagcaga aaaattagta gaaaatgatt ttgaggcact tttgatgtat   7920
ttcaactgca atttgaatca tttgatgtcc caagatgata taaaaattct aaagtcactt   7980
ccgtgctata aatccatcag tggccgctat gtaagcattg gaaaatttgg aacatgctac   8040
gtacttacaa aaagtatccc ttcagctgaa gtggagaaat ggacacaatc atcatcatct   8100
gcatttcttg aagaaaaaat acacttaaaa gaactatatg aggtgattgg ttgtgtacct   8160
gtagatgatc ttgaggtata tttgaaacac ctcttaccaa aaattgaaaa tctctcttat   8220
gatgcaaaat tagagcactt gatctacctt aagaatagat tatcaagtgc tgaggaatta   8280
tcagagatta aggaacaact ttttgaaaaa ctggaaagtt tattgataat ccatgatgct   8340
aacagtagac taaagcaagc aaagcatttc tatgatagaa ctgtgagagt ttttgaagtt   8400
atgcttcctg aaaaattgtt tattcctaat gatttcttta agaaattgga acaacttata   8460
aaacccaaaa atcatgttac atttatgaca tcctgggtgg aattcttaag aaatattgga   8520
ctaaaataca tactttctca gcagcagttg ttacagtttg ctaaggaaat cagtgtgagg   8580
gctaatacag aaaactggtc caaagaaaca ttgcaaaata cagttgatat ccttctgcat   8640
catatattcc aagaacgaat ggatttgtta tctggaaatt ttctgaaaga actatcttta   8700
ataccattct tatgtcctga gcgggccccc gcggaattca ttagatttca tcctcaatat   8760
caagaggtaa atggaacact tcctcttata aagttcaatg gagcacaggt aaatccaaaa   8820
ttcaagcaat gtgatgtact ccagctgtta tggacatcct gccctattct tccagagaaa   8880
gctacaccct taagcattaa agaacaagaa ggtagtgacc ttggtccaca agaacagctt   8940
gaacaagttt taaatatgct taatgttaac ctggatcctc ctcttgataa ggtaatcaat   9000
aactgcagaa acatatgcaa cataacgacg ttggatgaag aaatggtaaa aactagagca   9060
aaagtcttaa ggagcatata tgaattcctc agtgcagaaa aaagggaatt tcgttttcag   9120
ttgcgagggg ttgcttttgt gatggtagaa gatggttgga aacttctgaa gcctgaggag   9180
gtagtcataa acctagaata tgaatctgat tttaaacctt atttgtacaa gctacccttta   9240
gaacttggca catttcacca gttgttcaaa cacttaggta ctgaagatat tatttcaact   9300
aagcaatatg ttgaagtgtt gagccgcata tttaaaaatt ctgagggcaa acaattagat   9360
cctaatgaaa tgcgtacagt taagagagta gtttctggtc tgttcaggag tctacagaat   9420
gattcagtca aggtgaggag tgatctcgag aatgtacgag accttgcgct ttacctccca   9480
agccaggatg gtagattggt aaagtcaagc atcttagtgt ttgacgatgc gccacattat   9540
aaaagtagaa tccaggggaa tattggtgtg caaatgttag ttgatctcag ccagtgctac   9600
ttagggaaag accatggatt tcacactaag ttgataatgc tctttcctca aaaacttaga   9660
cctcgattat tgagcagtat acttgaagaa caattagatg aagagactcc caaagtttgt   9720
cagtttggag cgttgtgttc tcttcaagga agattgcagt tactcttgtc ttctgaacag   9780
```

-continued

```
ttcattacag gactgattag aattatgaag catgaaaatg ataatgcttt tctggccaat   9840
gaagaaaaag ccataagact ttgcaaagcc ctaagagaag gattgaaagt atcctgcttt   9900
gaaaagcttc aaacaacatt aagagttaaa ggttttaatc ctattcccca cagcagaagt   9960
gaaacttttg ctttttgaa gcgatttggt aatgcagtca tcttgctcta cattcaacat  10020
tcagacagta aagacattaa tttcctgtta gcactggcaa tgactcttaa atcagcaact  10080
gacaatttga tttctgacac ttcatattta attgctatgc taggatgcaa tgatatttac  10140
aggattggtg agaaacttga cagtttagga gtgaaatatg actcttcgga gccatcaaaa  10200
ctggaacttc caatgcctgg cacaccaatt cctgctgaaa ttcattacac tctgcttatg  10260
gacccaatga atgtttttta cccgggagaa tatgttgggt accttgttga tgctgaaggt  10320
ggtgatatct atggatcata ccagccaaca tacacatatg caattattgt acaagaagtt  10380
gaaagagaag atgctgacaa ttctagtttt ctaggaaaga tatatcagat agatattggt  10440
tatagtgaat ataaaatagt tagctctctt gatctgtata agttttcaag acctgaggaa  10500
agctctcaaa gcagggacag tgctccttct acaccaacca gccccactga gttcctcacc  10560
cctggcctga gaagcattcc tcctcttttc tctggtagag agagccacaa gacttcttcc  10620
aaacatcagt cccccaaaaa gcttaaggtt aattctttac cagaaatctt aaaagaagtg  10680
acatctgtgg tggagcaagc atggaagctt ccagaatcgg aacgaaaaaa gattattagg  10740
cggttgtatt tgaaatggca tcctgacaaa aatccagaga accatgacat tgccaatgaa  10800
gtttttaaac atttgcagaa tgaaatcaac agattagaaa aacaggcttt tctagatcaa  10860
aatgcagaca gggcctccag acgaacattt tcaacctcag catcccgatt tcagtcagac  10920
aaatactcat ttcagagatt ctatacttca tggaatcaag aagcaacgag ccataaatct  10980
gaaagacagc aacagaacaa agaaaaatgc ccccccttcag ccggacagac ttactctcaa  11040
aggttctttg ttcctcccac tttcaagtcg gttggcaatc cagtggaagc acgcagatgg  11100
ctaagacaag ccagagcaaa cttctcagct gccaggaatg accttcataa aaatgccaat  11160
gagtgggtgt gctttaaatg ttacctttct accaagttag ctttgattgc agctgactat  11220
gctgtgaggg gaaagtctga taaagatgta aaaccaactg cacttgctca gaaaatagag  11280
gaatatagtc agcaacttga aggactgaca aatgatgttc acacattgga agcttatggt  11340
gtagacagtt taaaaacaag ataccctgat ttgcttccct ttcctcagat cccaaatgac  11400
aggttcactt ctgaggttgc tatgagggtg atggaatgta ctgcctgtat cataataaaa  11460
cttgaaaatt ttatgcaaca aaaagtgtga agatatttaa cgaaaaaaaa ggtagatctt  11520
gaatgtgttg tagcacgaat aaattgctgt acttcattaa gcttcattgc caattagcta  11580
ggaattgtta agcacattgc agattgttct tggagaattc tggagttgtt atgaacatga  11640
ataccaacgg aaaaccttaa ctgaatctaa aagaaaacta ttttgaagat ggtggtgagc  11700
tgcaaaatag ctggatggat ttgaatgatt gggatgatac atcattgaac tgcactttat  11760
ataaccaaag cttagcagtt tgttagataa gagtctatgt atgtctctgg ttaggatgaa  11820
gttaatttta tgtttttaac atggtatttt tgaaggagct aatgaaacac tggacatata  11880
attggtttaa acataagggg aattaagtct ttgtagtctg tcattttttt aagtggatcc  11940
tcttggatgc gttattttct catcagctgg ctctgatcat gaatttgttg taattttatg  12000
ttgtactcag tgcatttaag aaatggtaga gtattttaat cctattactt gactaagagt  12060
gtgaaggtag tactttttag agtgcactga gtgcacttta catctttatt taaatttttt  12120
tttaacatct tatgtttaca ggcttcctgt ttgatgaaga tagcaacgga aaactcaaaa  12180
```

-continued

```
tggtggcagt tcttattacc agttgttagt attgtttctg gaaactgctt gccaagacaa  12240
catttattaa ctgttagaac acttgcttta tgtttgtgtg tacatatttt ccacaaatgt  12300
tataatttat atagtgtggt tgaacaggat gcaatctttt gttgtctaaa ggtgctgcag  12360
ttaaaaaaaa aacaaccttt tctttcaata tggcatgtag tggagttttt ttaactttaa  12420
aaacatcaaa aattgttaaa atcattgtgt tatctagtag tttataatta tcggcttata  12480
tttccccatg aatgatcaga actgacattt aattcatgtt tgtctcgcca tgcttcttta  12540
ctttaacata tttcttttgc agaatgtaaa aggtaatgat aattagttta tataagtgta  12600
ctggctgtaa atgatgctaa atatacttta tgcaattaag ggcttacaga acatgttgaa  12660
actttttta cttttattgg gaataaggaa tgtttgcacc tccacatttt attgctt     12717
```

<210> SEQ ID NO 14
<211> LENGTH: 12717
<212> TYPE: DNA
<213> ORGANISM: Homo sapiens

<400> SEQUENCE: 14

```
atgaatacat tctggcctgg cagagaattg attgttcaat ggtatccatt tgatgaaaac     60
agaaatcacc catctgtttc atggcttaag atggtttgga aaaatcttta tatacatttt    120
tcagaggatt tgactttatt tgatgagatg ccacttatcc ccagaactat actagaggaa    180
ggtcagacat gtgtggaact cattagactc aggattccat cgttagtcat tttagacgat    240
gaatctgaag cacagcttcc agaattttta gcagacattg tacaaaaact tggagggttt    300
gtccttaaaa aattagatgc atctatacaa catccgctta ttaaaaaata tattcattca    360
ccattaccaa gtgctgtttt gcagataatg gagaagatgc cattgcagaa attgtgtaat    420
caaataactt cgctacttcc aacacacaaa gatgccctga ggaagttctt ggctagttta    480
accgatagca gtgagaaaga gaaaagaatt attcaagaat tggcaatatt caagcgcatt    540
aaccattctt ctgatcaggg aatttcctct tatacaaaat tgaaaggttg taaagtctta    600
caccatactg ccaaactccc agcagatctg cgactttcta tttcagtaat agacagtagt    660
gatgaagcta ctattcgtct ggcaaacatg ttgaaaatag aacagttaaa gaccactagc    720
tgcttaaagc ttgttttaaa agatattgaa aatgcatttt attcacatga agaggtaaca    780
cagcttatgt tatgggtcct tgagaatcta tcttctctta aaaatgagaa tccaaatgtg    840
cttgagtggt taacaccatt aaaattcatc cagatatcac aggaacagat ggtatcagct    900
ggtgaactct ttgaccctga tatagaagta ctaaaggatc tcttttgtaa tgaagaagga    960
acctatttcc caccctcagt tttacctca ccagatattc ttcactcctt aagacagatt   1020
ggtttaaaaa acgaagccag tctcaaagaa aaggatgttg tgcaagtggc aaaaaaaatt   1080
gaagccttac aggtcggtgc ttgtcctgat caagatgttc ttctgaagaa agccaaaacc   1140
ctcttactgg ttttaaataa gaatcacaca ctgttgcaat catctgaagg aaagatgaca   1200
ttgaagaaaa taaaatgggt tccagcctgc aaggaaaggc ctccaaatta tccaggctct   1260
ttggtctgga aaggagatct ctgtaatctc tgtgcaccac cagatatgtg tgatgtaggc   1320
catgcaattc tcattggctc ctcacttcct cttgttgaaa gtatccatgt aaacctggaa   1380
aaagcattag ggatcttcac aaaacctagc cttagtgctg tcttaaaaca ctttaaaatt   1440
gttgttgatt ggtattcttc aaaaaccttt agtgatgaag actactatca attccagcat   1500
attttgcttg agatttacgg attcatgcat gatcatctaa atgaagggaa agattctttt   1560
```

-continued

```
agagccttaa aatttccatg ggtttggact ggcaaaaagt tttgtccact tgcccaggct   1620
gtgattaaac caatccatga tcttgacctt cagccttatt tgcataatgt acctaaaacc   1680
atggcaaaat tccaccaact atttaaggtc tgtggttcaa tagaggagtt gacatcagat   1740
catatttcca tggttattca gaagatatat ctcaaaagtg accaagatct cagtgaacaa   1800
gaaagcaaac aaaatcttca tcttatgttg aatattatca gatggctgta tagcaatcag   1860
attccagcaa gccccaacac accagttcct atacatcata gcaaaaatcc ttctaaactt   1920
atcatgaagc caattcacga atgctgttat tgtgacatta aagttgatga ccttaatgac   1980
ttacttgaag attctgtgga accaatcatt ttggtgcatg aggacatacc catgaaaact   2040
gcagaatggc taaaagttcc atgccttagt acaagactga taaatcctga aaacatggga   2100
tttgagcagt caggacaaag agagccactt actgtaagaa ttaaaaatat tctggaagaa   2160
tacccttcag tgtcagatat ttttaaagaa ctacttcaaa acgctgatga tgcaaatgca   2220
acagaatgca gtttcttgat tgatatgaga agaaatatgg acataagaga gaatctccta   2280
gacccaggga tggcagcttg tcatggacct gctttgtggt cattcaacaa ttctcaattc   2340
tcagattcag attttgtgaa cataactagg ttaggagaat ctttaaaaag gggagaagtt   2400
gacaaagttg gaaaatttgg tcttggattt aattctgtgt accatatcac tgacattccc   2460
atcattatga gtcgggaatt catgataatg ttcgatccaa acataaatca tatcagtaaa   2520
cacattaaag acaaatccaa tcctgggatc aaaattaatt ggagtaaaca acagaaaaga   2580
cttagaaaat ttcctaatca gttcaaacca tttatagatg tatttggctg tcagttacct   2640
ttgactgtag aagcacctta cagctataat ggaacccttt tccgactgtc ctttagaact   2700
caacaggaag caaaagtgag tgaagttagt agtacgtgct acaatacagc agatatttat   2760
tctcttgtgg atgaatttag tctctgtgga cacaggctta tcattttcac tcagagtgta   2820
aagtcaatgt atttgaagta cttgaaaatt gaggaaacca accccagttt agcacaagat   2880
acagtaataa ttaaaaaaaa atcctgctct tccaaagcat tgaacacacc tgtcttaagt   2940
gttttaaaag aggctgctaa gctcatgaag acttgcagca gcagtaataa aaagcttccc   3000
agtgatgaac caaagtcatc ttgcattctt cagatcacag tggaagaatt tcaccatgtg   3060
ttcagaagga ttgctgattt acagtcgcca ctttttagag gtccagatga tgacccagct   3120
gctctctttg aaatggctaa gtctggccaa tcaaaaaagc catcagatga gttgtcacag   3180
aaaacagtag agtgtaccac gtggcttctg tgtacttgca tggacacagg agaggctctg   3240
aagttttccc tgagtgagag tggaagaaga ctaggactgg ttccatgtgg ggcagtagga   3300
gttcagctgt cagaaatcca ggaccagaag tggacagtga aaccacacat tggagaggtg   3360
ttttgctatt tacctttacg aataaaaaca ggcttgccag ttcatatcaa tgggtgcttt   3420
gctgttacat caaataggaa agaaatctgg aaaacagata caaaaggacg atggaatacc   3480
acgttcatga gacatgttat tgtgaaagct tacttacagg tactgagtgt cttacgggac   3540
ctggccacta gtggggagct aatggattat acttactatg cagtatggcc cgatcctgat   3600
ttagttcatg atgatttttc tgtaatttgc caaggatttt atgaagatat agctcatgga   3660
aaagggaaag aactgaccaa agtcttctct gatggatcta cttgggtttc catgaagaac   3720
gtaagatttc tagatgactc tatacttaaa agaagagatg ttggttcagc agccttcaag   3780
atatttttga aatacctcaa gaagactggg tccaaaaacc tttgtgctgt tgaacttcct   3840
tcttcggtaa aattaggatt tgaagaagct ggctgcaaac agatactact tgaaaacaca   3900
ttttcagaga aacagttttt ttctgaagtg ttttttccaa atattcaaga aattgaagca   3960
```

-continued

```
gaacttagag atcctttaat gatctttgtt ctaaatgaaa aagttgatga gttctcggga   4020
gttcttcgtg ttactccatg tattccttgt tccttggagg ggcatccttt ggttttgcca   4080
tcaagattga tccaccccga aggacgagtt gcaaagttat ttgatattaa agatgggaga   4140
ttcccttatg gttctactca ggattatctc aatcctatta ttttgattaa actagttcag   4200
ttaggtatgg caaaagatga tattttatgg gatgatatgc tagaacgtgc agtgtcagta   4260
gctgaaatta ataaaagtga tcatgttgct gcatgcctaa gaagtagtat cttattgagt   4320
cttatcgatg agaaactaaa aataagggat cctagagcaa aggattttgc tgcaaaatat   4380
caaacaatcc gcttccttcc atttctgaca aaaccagcag gtttttcttt ggactggaaa   4440
ggcaacagtt ttaagcctga aaccatgttt gcagcaactg acctttatac agctgaacat   4500
caagatatag tttgtctttt gcaaccaatt ctaaatgaaa attcccattc ttttagaggt   4560
tgtggttcag tgtcattggc tgttaaagag tttttgggat tactcaagaa gccaacagtt   4620
gatctggtta taaaccaatt gaaagaagta gcaaaatcag ttgatgatgg aattacactg   4680
taccaggaga atatcaccaa tgcttgctac aaataccttc atgaagcctt gatgcaaaat   4740
gaaatcacta agatgtcaat tattgataag ttaaaaccct ttagcttcat tctagttgag   4800
aatgcatatg ttgactcaga aaaggtttct tttcatttaa attttgaggc ggcaccatac   4860
ctttatcagt tgcctaataa gtataaaaat aatttccgcg aactttttga aaccgtgggt   4920
gtgaggcagt catgcactgt tgaagatttt gctcttgttt tggaatctat tgatcaagaa   4980
agaggaacaa agcaaataac agaagagaat tttcagcttt gccgacgaat aatcagtgaa   5040
ggaatatgga gtctcattag agaaaagaaa caagaatttt gtgagaaaaa ttatggcaag   5100
atattattgc cagatactaa tcttatgctt ctccctgcta aatcgttatg ctacaatgat   5160
tgcccttgga taaaagtaaa ggataccact gtaaaatatt gtcatgctga catacccagg   5220
gaagtagcag taaaactagg agcagtccca aagcgacaca aagccttaga aagatatgca   5280
tccaatgtct gttttacaac acttggcaca gaatttgggc agaaagaaaa attgaccagc   5340
agaattaaga gcatccttaa tgcatatcct tctgaaaagg aaatgttgaa agagcttctt   5400
caaaatgctg atgatgcaaa ggcgacagaa atctgttttg tgtttgatcc tagacagcat   5460
ccagttgata gaatatttga tgataagtgg gccccattgc aagggccagc actttgtgtg   5520
tacaacaacc agccatttac agaagatgat gttagaggaa ttcagaatct tggaaaaggc   5580
acgaaagagg gaaatcctta taaaactgga cagtatggaa taggattcaa ttctgtgtat   5640
catatcacag actgcccatc ttttatttct ggcaatgaca tcctgtgtat ttttgatcct   5700
catgccagat atgcaccagg ggccacatcc attagtcccg gacgcatgtt tagagatttg   5760
gatgcagatt ttaggacaca gttctcagat gttctggatc tttatctggg aacccatttt   5820
aaactggata attgcacaat gttcagattt cctcttcgta atgcagaaat ggcaaaagtt   5880
tcggaaattt cgtctgttcc agcatcagac agaatggtcc agaatctttt ggacaaactg   5940
cgctcagatg gggcagaact tctaatgttt cttaatcaca tggaaaaaat ttctatttgt   6000
gaaatagata agagtactgg agctctaaat gtgctgtatt cagtaaaggg caaaatcaca   6060
gatggagaca gattgaaaag gaaacaattt catgcatctg taattgatag tgttactaaa   6120
aagaggcagc tcaaagacat accagttcaa caaataacct atactatgga tactgaggac   6180
tctgaaggaa atcttactac gtggctaatt tgtaatagat caggcttttc aagtatggag   6240
aaagtatcta aaagtgtcat atcagctcac aagaaccaag atattactct tttcccacgt   6300
```

-continued

```
ggtggagtag ctgcctgcat tactcacaac tataaaaaac cccatagggc cttctgtttt   6360
ttgcctcttt ctttggagac tgggctgcca tttcatgtga atggccactt tgcactggat   6420
tcagccagaa ggaacctgtg gcgtgatgat aatggagttg gtgttcgaag tgactggaat   6480
aacagtttaa tgacagcatt aatagctcct gcatatgttg aattgctaat acagttaaaa   6540
aaacggtatt tccctggttc tgatccaaca ttatcagtgt tacagaacac ccctattcat   6600
gttgtaaagg acactttaaa gaagtttttta tcgtttttcc cagttaaccg tcttgatcta   6660
cagccagatt tatattgtct agtgaaagca ctttacaatt gcattcacga agacatgaaa   6720
cgtcttttac ctgttgtgcg ggctccaaat attgatggct ctgacttgca ctctgcagtt   6780
ataattactt ggatcaatat gtctacttct aataaaacta gaccattttt tgacaattta   6840
ctacaggatg aattacaaca ccttaaaaat gcagattata atatcaccac acgcaaaaca   6900
gtagcagaga atgtctatag gctgaaacat ctccttttag aaattggttt caacttggtt   6960
tataactgtg atgaaactgc taatctttac cactgtctta tagatgcaga tattcctgtt   7020
agttatgtga cccctgctga tatcagatct tttttaatga cattttcctc tcctgacact   7080
aattgccata ttgggaagct gccttgtcgt ctgcagcaga ctaatctaaa actttttcat   7140
agtttaaaac ttttagttga ttattgtttt aaagatgcag aagaaaatga gattgaagtt   7200
gagggattgc cccttctcat cacactggac agtgttttgc aaacttttga tgcaaaacga   7260
cccaagtttc taacaacata tcatgaattg attccatccc gcaaagactt gtttatgaat   7320
acattatatt tgaaatatag taatatttta ttgaactgta aagttgcaaa agtgtttgac   7380
atttccagct ttgctgattt gttatcctct gtgttgcctc gagaatataa gaccaaaagt   7440
tgcacaaagt ggaaagacaa ttttgcaagt gagtcttggc ttaagaatgc atggcatttt   7500
attagtgaat ctgtaagtgt gaaagaagat caggaagaaa caaaaccaac atttgacatt   7560
gttgttgata ctctaaaaga ctgggcattg cttccaggaa caaagtttac tgtttcagcc   7620
aaccagcttg tggttcctga aggagatgtt ctgcttcctc tcagccttat gcacattgca   7680
gtttttccaa atgcccagag tgataaagtt tttcatgctc taatgaaagc cggctgtatt   7740
cagcttgctt tgaacaaaat ctgttccaaa gacagtgcat ttgttccttt gttgtcatgt   7800
cacacagcaa atatagagag ccccacaagc atcttgaagg ctctacatta tatggtccaa   7860
acttcaacat ttagagcaga aaaattagta gaaaatgatt ttgaggcact tttgatgtat   7920
ttcaactgca atttgaatca tttgatgtcc caagatgata taaaaattct aaagtcactt   7980
ccgtgctata aatccatcag tggccgctat gtaagcattg gaaaatttgg aacatgctac   8040
gtacttacaa aaagtatccc ttcagctgaa gtggagaaat ggacacaatc atcatcatct   8100
gcatttcttg aagaaaaaat acacttaaaa gaactatatg aggtgattgg ttgtgtacct   8160
gtagatgatc ttgaggtata tttgaaacac ctcttaccaa aaattgaaaa tctctcttat   8220
gatgcaaaat tagagcactt gatctacctt aagaatagat tatcaagtgc tgaggaatta   8280
tcagagatta aggaacaact tttgaaaaa ctggaaagtt tattgataat ccatgatgct   8340
aacagtagac taaagcaagc aaagcatttc tatgatagaa ctgtgagagt tttgaagtt   8400
atgcttcctg aaaaattgtt tattcctaat gatttcttta agaaattgga acaacttata   8460
aaacccaaaa atcatgttac atttatgaca tcctgggtgg aattcttaag aaatattgga   8520
ctaaaataca tactttctca gcagcagttg ttacagtttg ctaaggaaat cagtgtgagg   8580
gctaatacag aaaactggtc caaagaaaca ttgcaaaata cagttgatat ccttctgcat   8640
catatattcc aagaacgaat ggatttgtta tctggaaatt ttctgaaaga actatcttta   8700
```

-continued

```
ataccattct tatgtcctga gcgggccccc gcggaattca ttagatttca tcctcaatat   8760
caagaggtaa atggaacact tcctcttata aagttcaatg gagcacaggt aaatccaaaa   8820
ttcaagcaat gtgatgtact ccagctgtta tggacatcct gccctattct tccagagaaa   8880
gctacaccct taagcattaa agaacaagaa ggtagtgacc ttggtccaca agaacagctt   8940
gaacaagttt taaatatgct taatgttaac ctggatcctc ctcttgataa ggtaatcaat   9000
aactgcagaa acatatgcaa cataacgacg ttggatgaag aaatggtaaa aactagagca   9060
aaagtcttaa ggagcatata tgaattcctc agtgcagaaa aaagggaatt tcgttttcag   9120
ttgcgagggg ttgcttttgt gatggtagaa gatggttgga aacttctgaa gcctgaggag   9180
gtagtcataa acctagaata tgaatctgat tttaaacctt atttgtacaa gctacccttta  9240
gaacttggca catttcacca gttgttcaaa cacttaggta ctgaagatat tatttcaact   9300
aagcaatatg ttgaagtgtt gagccgcata tttaaaaatt ctgagggcaa acaattagat   9360
cctaatgaaa tgcgtacagt taagagagta gtttctggtc tgttcaggag tctacagaat   9420
gattcagtca aggtgaggag tgatctcgag aatgtacgag accttgcgct ttacctccca   9480
agccaggatg gtagattggt aaagtcaagc atcttagtgt ttgacgatgc gccacattat   9540
aaaagtagaa tccaggggaa tattggtgtg caaatgttag ttgatctcag ccagtgctac   9600
ttagggaaag accatggatt tcacactaag ttgataatgc tctttcctca aaaacttaga   9660
cctcgattat tgagcagtat acttgaagaa caattagatg aagagactcc caaagtttgt   9720
cagtttggag cgttgtgttc tcttcaagga agattgcagt tactcttgtc ttctgaacag   9780
ttcattacag gactgattag aattatgaag catgaaaatg ataatgcttt tctggccaat   9840
gaagaaaaag ccataagact ttgcaaagcc ctaagagaag gattgaaagt atcctgcttt   9900
gaaaagcttc aaacaacatt aagagttaaa ggttttaatc ctattcccca cagcagaagt   9960
gaaacttttg ctttttttgaa gcgatttggt aatgcagtca tcttgctcta cattcaacat  10020
tcagacagta aagacattaa tttcctgtta gcattggcaa tgactcttaa atcagcaact  10080
gacaatttga tttctgacac ttcatattta attgctatgc taggatgcaa tgatatttac  10140
aggattggtg agaaacttga cagtttagga gtgaaatatg actcttcgga gccatcaaaa  10200
ctggaacttc caatgcctgg cacaccaatt cctgctgaaa ttcattacac tctgcttatg  10260
gacccaatga atgtttttta cccgggagaa tatgttgggt accttgttga tgctgaaggt  10320
ggtgatatct atggatcata ccagccaaca tacacatatg caattattgt acaagaagtt  10380
gaaagagaag atgctgacaa ttctagtttt ctaggaaaga tatatcagat agatattggt  10440
tatagtgaat ataaaatagt tagctctctt gatctgtata agttttcaag acctgaggaa  10500
agctctcaaa gcagggacag tgctccttct acaccaacca gccccactga gttcctcacc  10560
cctggcctga gaagcattcc tcctcttttc tctggtagag agagccacaa gacttcttcc  10620
aaacatcagt cccccaaaaa gcttaaggtt aattctttac cagaaatctt aaaagaagtg  10680
acatctgtgg tggagcaagc atggaagctt ccagaatcgg aacgaaaaaa gattattagg  10740
cggttgtatt tgaaatggca tcctgacaaa aatccagaga accatgacat tgccaatgaa  10800
gtttttaaac atttgcagaa tgaaatcaac agattagaaa aacaggcttt tctagatcaa  10860
aatgcagaca gggcctccag acgaacattt tcaacctcag catcccgatt tcagtcagac  10920
aaatactcat ttcagagatt ctatacttca tggaatcaag aagcaacgag ccataaatct  10980
gaaagacagc aacagaacaa agaaaaatgc ccccttcag ccggacagac ttactctcaa   11040
```

-continued

```
aggttctttg ttcctcccac tttcaagtcg gttggcaatc cagtggaagc acgcagatgg  11100
ctaagacaag ccagagcaaa cttctcagct gccaggaatg accttcataa aaatgccaat  11160
gagtgggtgt gctttaaatg ttacctttct accaagttag ctttgattgc agctgactat  11220
gctgtgaggg gaaagtctga taaagatgta aaaccaactg cacttgctca gaaaatagag  11280
gaatatagtc agcaacttga aggactgaca aatgatgttc acacattgga agcttatggt  11340
gtagacagtt taaaaacaag ataccctgat ttgcttccct ttcctcagat cccaaatgac  11400
aggttcactt ctgaggttgc tatgagggtg atggaatgta ctgcctgtat cataataaaa  11460
cttgaaaatt ttatgcaaca aaaagtgtga agatatttaa cgaaaaaaaa ggtagatctt  11520
gaatgtgttg tagcacgaat aaattgctgt acttcattaa gcttcattgc caattagcta  11580
ggaattgtta agcacattgc agattgttct tggagaattc tggagttgtt atgaacatga  11640
ataccaacgg aaaaccttaa ctgaatctaa aagaaaacta ttttgaagat ggtggtgagc  11700
tgcaaaatag ctggatggat ttgaatgatt gggatgatac atcattgaac tgcactttat  11760
ataaccaaag cttagcagtt tgttagataa gagtctatgt atgtctctgg ttaggatgaa  11820
gttaatttta tgtttttaac atggtatttt tgaaggagct aatgaaacac tggacatata  11880
attggtttaa acataagggg aattaagtct ttgtagtctg tcattttttt aagtggatcc  11940
tcttggatgc gttattttct catcagctgg ctctgatcat gaatttgttg taattttatg  12000
ttgtactcag tgcatttaag aaatggtaga gtattttaat cctattactt gactaagagt  12060
gtgaaggtag tactttttag agtgcactga gtgcacttta catctttatt taaatttttt  12120
tttaacatct tatgtttaca ggcttcctgt ttgatgaaga tagcaacgga aaactcaaaa  12180
tggtggcagt tcttattacc agttgttagt attgtttctg gaaactgctt gccaagacaa  12240
catttattaa ctgttagaac acttgcttta tgtttgtgtg tacatatttt ccacaaatgt  12300
tataatttat atagtgtggt tgaacaggat gcaatctttt gttgtctaaa ggtgctgcag  12360
ttaaaaaaaa aacaaccttt tctttcaata tggcatgtag tggagttttt ttaactttaa  12420
aaacatcaaa aattgttaaa atcattgtgt tatctagtag tttataatta tcggcttata  12480
tttccccatg aatgatcaga actgacattt aattcatgtt tgtctcgcca tgcttcttta  12540
ctttaacata tttcttttgc agaatgtaaa aggtaatgat aattagttta tataagtgta  12600
ctggctgtaa atgatgctaa atatacttta tgcaattaag ggcttacaga acatgttgaa  12660
acttttttta cttttattgg gaataaggaa tgtttgcacc tccacatttt attgctt     12717
```

<210> SEQ ID NO 15
<211> LENGTH: 12793
<212> TYPE: DNA
<213> ORGANISM: Homo sapiens

<400> SEQUENCE: 15

```
atgatttaca ggaagaccat gtactcagct gcagcttcta aatccagaac gatttgcacg     60
tcttatcaag gaagtaatga atacattctg gcctggcaga gaattgattg ttcaatggta    120
tccatttgat gaaaacagaa atcacccatc tgtttcatgg cttaagatgg tttggaaaaa    180
tctttatata catttttcag aggatttgac tttatttgat gagatgccac ttatccccag    240
aactatacta gaggaaggtc agacatgtgt ggaactcatt agactcagga ttccatcgtt    300
agtcatttta gacgatgaat ctgaagcaca gcttccagaa tttttagcag acattgtaca    360
aaaacttgga gggtttgtcc ttaaaaaatt agatgcatct atacaacatc cgcttattaa    420
aaaatatatt cattcaccat taccaagtgc tgttttgcag ataatggaga agatgccatt    480
```

-continued

```
gcagaaattg tgtaatcaaa taacttcgct acttccaaca cacaaagatg ccctgaggaa    540
gttcttggct agtttaaccg atagcagtga gaaagagaaa agaattattc aagaattggc    600
aatattcaag cgcattaacc attcttctga tcagggaatt tcctcttata caaaattgaa    660
aggttgtaaa gtcttacacc atactgccaa actcccagca gatctgcgac tttctatttc    720
agtaatagac agtagtgatg aagctactat tcgtctggca aacatgttga aaatagaaca    780
gttaaagacc actagctgct taaagcttgt tttaaaagat attgaaaatg cattttattc    840
acatgaagag gtaacacagc ttatgttatg ggtccttgag aatctatctt ctcttaaaaa    900
tgagaatcca aatgtgcttg agtggttaac accattaaaa ttcatccaga tatcacagga    960
acagatggta tcagctggtg aactctttga ccctgatata gaagtactaa aggatctctt   1020
ttgtaatgaa gaaggaacct atttcccacc ctcagttttt acctcaccag atattcttca   1080
ctccttaaga cagattggtt taaaaaacga agccagtctc aaagaaaagg atgttgtgca   1140
agtggcaaaa aaaattgaag ccttacaggt cggtgcttgt cctgatcaag atgttcttct   1200
gaagaaagcc aaaaccctct tactggtttt aaataagaat cacacactgt tgcaatcatc   1260
tgaaggaaag atgacattga agaaaataaa atgggttcca gcctgcaagg aaaggcctcc   1320
aaattatcca ggctctttgg tctggaaagg agatctctgt aatctctgtg caccaccaga   1380
tatgtgtgat gtaggccatg caattctcat tggctcctca cttcctcttg ttgaaagtat   1440
ccatgtaaac ctggaaaaag cattagggat cttcacaaaa cctagcctta gtgctgtctt   1500
aaaacacttt aaaattgttg ttgattggta ttcttcaaaa acctttagtg atgaagacta   1560
ctatcaattc cagcatattt tgcttgagat ttacggattc atgcatgatc atctaaatga   1620
agggaaagat tcttttagag ccttaaaatt tccatgggtt tggactggca aaaagttttg   1680
tccacttgcc caggctgtga ttaaaccaat ccatgatctt gaccttcagc cttatttgca   1740
taatgtacct aaaaccatgg caaaattcca ccaactattt aaggtctgtg gttcaataga   1800
ggagttgaca tcagatcata tttccatggt tattcagaag atatatctca aaagtgacca   1860
agatctcagt gaacaagaaa gcaaacaaaa tcttcatctt atgttgaata ttatcagatg   1920
gctgtatagc aatcagattc cagcaagccc caacacacca gttcctatac atcatagcaa   1980
aaatccttct aaacttatca tgaagccaat tcacgaatgc tgttattgtg acattaaagt   2040
tgatgacctt aatgacttac ttgaagattc tgtggaacca atcattttgg tgcatgagga   2100
catacccatg aaaactgcag aatggctaaa agttccatgc cttagtacaa gactgataaa   2160
tcctgaaaac atgggatttg agcagtcagg acaaagagag ccacttactg taagaattaa   2220
aaatattctg gaagaatacc cttcagtgtc agatattttt aaagaactac ttcaaaacgc   2280
tgatgatgca aatgcaacag aatgcagttt cttgattgat atgagaagaa atatggacat   2340
aagagagaat ctcctagacc cagggatggc agcttgtcat ggacctgctt tgtggtcatt   2400
caacaattct caattctcag attcagattt tgtgaacata actaggttag gagaatcttt   2460
aaaaagggga gaagttgaca aagttggaaa atttggtctt ggatttaatt ctgtgtacca   2520
tatcactgac attcccatca ttatgagtcg gggaattcatg ataatgttcg atccaaacat   2580
aaatcatatc agtaaacaca ttaaagacaa atccaatcct gggatcaaaa ttaattggag   2640
taaacaacag aaaagactta gaaaatttcc taatcagttc aaaccattta tagatgtatt   2700
tggctgtcag ttacctttga ctgtagaagc accttacagc tataatggaa ccccttttccg   2760
actgtccttt agaactcaac aggaagcaaa agtgagtgaa gttagtagta cgtgctacaa   2820
```

-continued

```
tacagcagat atttattctc ttgtggatga atttagtctc tgtggacaca ggcttatcat   2880
tttcactcag agtgtaaagt caatgtattt gaagtacttg aaaattgagg aaaccaaccc   2940
cagtttagca caagatacag taataattaa aaaaaaatcc tgctcttcca aagcattgaa   3000
cacacctgtc ttaagtgttt taaaagaggc tgctaagctc atgaagactt gcagcagcag   3060
taataaaaag cttcccagtg atgaaccaaa gtcatcttgc attcttcaga tcacagtgga   3120
agaatttcac catgtgttca gaaggattgc tgatttacag tcgccacttt ttagaggtcc   3180
agatgatgac ccagctgctc tctttgaaat ggctaagtct ggccaatcaa aaaagccatc   3240
agatgagttg tcacagaaaa cagtagagtg taccacgtgg cttctgtgta cttgcatgga   3300
cacaggagag gctctgaagt tttccctgag tgagagtgga agaagactag gactggttcc   3360
atgtggggca gtaggagttc agctgtcaga aatccaggac cagaagtgga cagtgaaacc   3420
acacattgga gaggtgtttt gctatttacc tttacgaata aaaacaggct tgccagttca   3480
tatcaatggg tgctttgctg ttacatcaaa taggaaagaa atctggaaaa cagatacaaa   3540
aggacgatgg aataccacgt tcatgagaca tgttattgtg aaagcttact tacaggtact   3600
gagtgtctta cgggacctgg ccactagtgg ggagctaatg gattatactt actatgcagt   3660
atggcccgat cctgatttag ttcatgatga tttttctgta atttgccaag gattttatga   3720
agatatagct catggaaaag ggaaagaact gaccaaagtc ttctctgatg gatctacttg   3780
ggtttccatg aagaacgtaa gatttctaga tgactctata cttaaaagaa gagatgttgg   3840
ttcagcagcc ttcaagatat ttttgaaata cctcaagaag actgggtcca aaaacctttg   3900
tgctgttgaa cttccttctt cggtaaaatt aggatttgaa gaagctggct gcaaacagat   3960
actacttgaa aacacatttt cagagaaaca gtttttttct gaagtgtttt ttccaaatat   4020
tcaagaaatt gaagcagaac ttagagatcc tttaatgatc tttgttctaa atgaaaaagt   4080
tgatgagttc tcgggagttc ttcgtgttac tccatgtatt ccttgttcct tggaggggca   4140
tcctttggtt ttgccatcaa gattgatcca ccccgaagga cgagttgcaa agttatttga   4200
tattaaagat gggagattcc cttatggttc tactcaggat tatctcaatc ctattatttt   4260
gattaaacta gttcagttag gtatggcaaa agatgatatt ttatgggatg atatgctaga   4320
acgtgcagtg tcagtagctg aaattaataa aagtgatcat gttgctgcat gcctaagaag   4380
tagtatctta ttgagtctta tcgatgagaa actaaaaata agggatccta gagcaaagga   4440
ttttgctgca aaatatcaaa caatccgctt ccttccattt ctgacaaaac cagcaggttt   4500
ttctttggac tggaaaggca acagttttaa gcctgaaacc atgtttgcag caactgacct   4560
ttatacagct gaacatcaag atatagtttg tcttttgcaa ccaattctaa atgaaaattc   4620
ccattctttt agaggttgtg gttcagtgtc attggctgtt aaagagtttt tgggattact   4680
caagaagcca acagttgatc tggttataaa ccaattgaaa gaagtagcaa aatcagttga   4740
tgatggaatt acactgtacc aggagaatat caccaatgct tgctacaaat accttcatga   4800
agccttgatg caaaatgaaa tcactaagat gtcaattatt gataagttaa aaccctttag   4860
cttcattcta gttgagaatg catatgttga ctcagaaaag gtttcttttc atttaaattt   4920
tgaggcggca ccatacettt atcagttgcc taataagtat aaaaataatt tccgcgaact   4980
ttttgaaacc gtgggtgtga ggcagtcatg cactgttgaa gattttgctc ttgttttgga   5040
atctattgat caagaaagag gaacaaagca aataacagaa gagaattttc agctttgccg   5100
acgaataatc agtgaaggaa tatggagtct cattagagaa aagaaacaag aattttgtga   5160
gaaaaattat ggcaagatat tattgccaga tactaatctt atgcttctcc ctgctaaatc   5220
```

-continued

```
gttatgctac aatgattgcc cttggataaa agtaaaggat accactgtaa aatattgtca   5280
tgctgacata cccagggaag tagcagtaaa actaggagca gtcccaaagc gacacaaagc   5340
cttagaaaga tatgcatcca atgtctgttt tacaacactt ggcacagaat ttgggcagaa   5400
agaaaaattg accagcagaa ttaagagcat ccttaatgca tatccttctg aaaaggaaat   5460
gttgaaagag cttcttcaaa atgctgatga tgcaaaggcg acagaaatct gttttgtgtt   5520
tgatcctaga cagcatccag ttgatagaat atttgatgat aagtgggccc cattgcaagg   5580
gccagcactt tgtgtgtaca acaaccagcc atttacagaa gatgatgtta gaggaattca   5640
gaatcttgga aaaggcacga aagagggaaa tccttataaa actggacagt atggaatagg   5700
attcaattct gtgtatcata tcacagactg cccatctttt atttctggca atgacatcct   5760
gtgtattttt gatcctcatg ccagatatgc accaggggcc acatccatta gtcccggacg   5820
catgtttaga gatttggatg cagattttag gacacagttc tcagatgttc tggatcttta   5880
tctgggaacc cattttaaac tggataattg cacaatgttc agatttcctc ttcgtaatgc   5940
agaaatggca aaagtttcgg aaatttcgtc tgttccagca tcagacagaa tggtccagaa   6000
tcttttggac aaactgcgct cagatggggc agaacttcta atgtttctta atcacatgga   6060
aaaaatttct atttgtgaaa tagataagag tactggagct ctaaatgtgc tgtattcagt   6120
aaagggcaaa atcacagatg gagacagatt gaaaaggaaa caatttcatg catctgtaat   6180
tgatagtgtt actaaaaaga ggcagctcaa agacatacca gttcaacaaa taacctatac   6240
tatggatact gaggactctg aaggaaatct tactacgtgg ctaatttgta atagatcagg   6300
cttttcaagt atggagaaag tatctaaaag tgtcatatca gctcacaaga accaagatat   6360
tactcttttc ccacgtggtg gagtagctgc ctgcattact cacaactata aaaaacccca   6420
tagggccttc tgtttttttgc ctctttcttt ggagactggg ctgccatttc atgtgaatgg   6480
ccactttgca ctggattcag ccagaaggaa cctgtggcgt gatgataatg gagttggtgt   6540
tcgaagtgac tggaataaca gtttaatgac agcattaata gctcctgcat atgttgaatt   6600
gctaatacag ttaaaaaaac ggtatttccc tggttctgat ccaacattat cagtgttaca   6660
gaacacccct attcatgttg taaaggacac tttaaagaag tttttatcgt tttcccagt   6720
taaccgtctt gatctacagc cagatttata ttgtctagtg aaagcacttt acaattgcat   6780
tcacgaagac atgaaacgtc ttttacctgt tgtgcgggct ccaaatattg atggctctga   6840
cttgcactct gcagttataa ttacttggat caatatgtct acttctaata aaactagacc   6900
attttttgac aatttactac aggatgaatt acaacacctt aaaaatgcag attataatat   6960
caccacacgc aaaacagtag cagagaatgt ctataggctg aaacatctcc ttttagaaat   7020
tggtttcaac ttggtttata actgtgatga aactgctaat ctttaccact gtcttataga   7080
tgcagatatt cctgttagtt atgtgacccc tgctgatatc agatcttttt taatgacatt   7140
ttcctctcct gacactaatt gccatattgg gaagctgcct tgtcgtctgc agcagactaa   7200
tctaaaactt tttcatagtt taaaactttt agttgattat tgttttaaag atgcagaaga   7260
aaatgagatt gaagttgagg gattgcccct tctcatcaca ctggacagtg ttttgcaaac   7320
ttttgatgca aaacgaccca agtttctaac aacatatcat gaattgattc catcccgcaa   7380
agacttgttt atgaatacat tatatttgaa atatagtaat attttattga actgtaaagt   7440
tgcaaaagtg tttgacattt ccagctttgc tgatttgtta tcctctgtgt tgcctcgaga   7500
atataagacc aaaagttgca caaagtggaa agacaatttt gcaagtgagt cttggcttaa   7560
```

-continued

```
gaatgcatgg cattttatta gtgaatctgt aagtgtgaaa gaagatcagg aagaaacaaa   7620
accaacattt gacattgttg ttgatactct aaaagactgg gcattgcttc caggaacaaa   7680
gtttactgtt tcagccaacc agcttgtggt tcctgaagga gatgttctgc ttcctctcag   7740
ccttatgcac attgcagttt ttccaaatgc ccagagtgat aaagtttttc atgctctaat   7800
gaaagccggc tgtattcagc ttgctttgaa caaaatctgt tccaaagaca gtgcacttgt   7860
tcctttgttg tcatgtcaca cagcaaatat agagagcccc acaagcatct tgaaggctct   7920
acattatatg gtccaaactt caacatttag agcagaaaaa ttagtagaaa atgattttga   7980
ggcacttttg atgtatttca actgcaattt gaatcatttg atgtcccaag atgatataaa   8040
aattctaaag tcacttccgt gctataaatc catcagtggc cgctatgtaa gcattggaaa   8100
atttggaaca tgctacgtac ttacaaaaag tatcccttca gctgaagtgg agaaatggac   8160
acaatcatca tcatctgcat ttcttgaaga aaaaatacac ttaaaagaac tatatgaggt   8220
gattggttgt gtacctgtag atgatcttga ggtatatttg aaacacctct taccaaaaat   8280
tgaaaatctc tcttatgatg caaaattaga gcacttgatc taccttaaga atagattatc   8340
aagtgctgag gaattatcag agattaagga acaacttttt gaaaaactgg aaagtttatt   8400
gataatccat gatgctaaca gtagactaaa gcaagcaaag catttctatg atagaactgt   8460
gagagttttt gaagttatgc ttcctgaaaa attgtttatt cctaatgatt tctttaagaa   8520
attggaacaa cttataaaac ccaaaaatca tgttacattt atgacatcct gggtggaatt   8580
cttaagaaat attggactaa aatacatact ttctcagcag cagttgttac agtttgctaa   8640
ggaaatcagt gtgagggcta atacagaaaa ctggtccaaa gaaacattgc aaaatacagt   8700
tgatatcctt ctgcatcata tattccaaga acgaatggat ttgttatctg gaaatttttct   8760
gaaagaacta tctttaatac cattcttatg tcctgagcgg gcccccgcgg aattcattag   8820
atttcatcct caatatcaag aggtaaatgg aacacttcct cttataaagt tcaatggagc   8880
acaggtaaat ccaaaattca agcaatgtga tgtactccag ctgttatgga catcctgccc   8940
tattcttcca gagaaagcta caccccttaag cattaaagaa caagaaggta gtgaccttgg   9000
tccacaagaa cagcttgaac aagttttaaa tatgcttaat gttaacctgg atcctcctct   9060
tgataaggta atcaataact gcagaaacat atgcaacata acgacgttgg atgaagaaat   9120
ggtaaaaact agagcaaaag tcttaaggag catatatgaa ttcctcagtg cagaaaaaag   9180
ggaatttcgt tttcagttgc gaggggttgc ttttgtgatg gtagaagatg gttggaaact   9240
tctgaagcct gaggaggtag tcataaacct agaatatgaa tctgatttta aaccttattt   9300
gtacaagcta cctttagaac ttggcacatt tcaccagttg ttcaaacact taggtactga   9360
agatattatt tcaactaagc aatatgttga agtgttgagc cgcatattta aaaattctga   9420
gggcaaacaa ttagatccta atgaaatgcg tacagttaag agagtagttt ctggtctgtt   9480
caggagtcta cagaatgatt cagtcaaggt gaggagtgat ctcgagaatg tacgagacct   9540
tgcgctttac ctcccaagcc aggatggtag attggtaaag tcaagcatct tagtgtttga   9600
cgatgcgcca cattataaaa gtagaatcca ggggaatatt ggtgtgcaaa tgttagttga   9660
tctcagccag tgctacttag ggaaagacca tggatttcac actaagttga taatgctctt   9720
tcctcaaaaa cttagacctc gattattgag cagtatactt gaagaacaat tagatgaaga   9780
gactcccaaa gtttgtcagt ttggagcgtt gtgttctctt caaggaagat tgcagttact   9840
cttgtcttct gaacagttca ttacaggact gattagaatt atgaagcatg aaaatgataa   9900
tgcttttctg gccaatgaag aaaaagccat aagactttgc aaagccctaa gagaaggatt   9960
```

-continued

```
gaaagtatcc tgctttgaaa agcttcaaac aacattaaga gttaaaggtt ttaatcctat  10020
tccccacagc agaagtgaaa cttttgcttt tttgaagcga tttggtaatg cagtcatctt  10080
gctctacatt caacattcag acagtaaaga cattaatttc ctgttagcac tggcaatgac  10140
tcttaaatca gcaactgaca atttgatttc tgacacttca tatttaattg ctatgctagg  10200
atgcaatgat atttacagga ttggtgagaa acttgacagt ttaggagtga aatatgactc  10260
ttcggagcca tcaaaactgg aacttccaat gcctggcaca ccaattcctg ctgaaattca  10320
ttacactctg cttatggacc caatgaatgt tttttacccg ggagaatatg ttgggtacct  10380
tgttgatgct gaaggtggtg atatctatgg atcataccag ccaacataca catatgcaat  10440
tattgtacaa gaagttgaaa gagaagatgc tgacaattct agttttctag gaaagatata  10500
tcagatagat attggttata gtgaatataa aatagttagc tctcttgatc tgtataagtt  10560
ttcaagacct gaggaaagct ctcaaagcag ggacagtgct ccttctacac caaccagccc  10620
cactgagttc ctcacccctg gcctgagaag cattcctcct cttttctctg gtagagagag  10680
ccacaagact tcttccaaac atcagtcccc caaaaagctt aaggttaatt ctttaccaga  10740
aatcttaaaa gaagtgacat ctgtggtgga gcaagcatgg aagcttccag aatcggaacg  10800
aaaaaagatt attaggcggt tgtatttgaa atggcatcct gacaaaaatc cagagaacca  10860
tgacattgcc aatgaagttt ttaaacattt gcagaatgaa atcaacagat tagaaaaaca  10920
ggcttttcta gatcaaaatg cagacagggc ctccagacga acattttcaa cctcagcatc  10980
ccgatttcag tcagacaaat actcatttca gagattctat acttcatgga atcaagaagc  11040
aacgagccat aaatctgaaa gacagcaaca gaacaaagaa aaatgccccc cttcagccgg  11100
acagacttac tctcaaaggt tctttgttcc tcccactttc aagtcggttg gcaatccagt  11160
ggaagcacgc agatggctaa gacaagccag agcaaacttc tcagctgcca ggaatgacct  11220
tcataaaaat gccaatgagt gggtgtgctt taaatgttac ctttctacca agttagcttt  11280
gattgcagct gactatgctg tgaggggaaa gtctgataaa gatgtaaaac caactgcact  11340
tgctcagaaa atagaggaat atagtcagca acttgaagga ctgacaaatg atgttcacac  11400
attggaagct tatggtgtag acagtttaaa aacaagatac cctgatttgc ttccctttcc  11460
tcagatccca aatgacaggt tcacttctga ggttgctatg agggtgatgg aatgtactgc  11520
ctgtatcata ataaaacttg aaaattttat gcaacaaaaa gtgtgaagat atttaacgaa  11580
aaaaaaggta gatcttgaat gtgttgtagc acgaataaat tgctgtactt cattaagctt  11640
cattgccaat tagctaggaa ttgttaagca cattgcagat tgttcttgga gaattctgga  11700
gttgttatga acatgaatac caacggaaaa ccttaactga atctaaaaga aaactatttt  11760
gaagatggtg gtgagctgca aaatagctgg atggatttga atgattggga tgatacatca  11820
ttgaactgca ctttatataa ccaaagctta gcagtttgtt agataagagt ctatgtatgt  11880
ctctggttag gatgaagtta attttatgtt tttaacatgg tatttttgaa ggagctaatg  11940
aaacactgga catataattg gtttaaacat aaggggaatt aagtctttgt agtctgtcat  12000
ttttttaagt ggatcctctt ggatgcgtta ttttctcatc agctggctct gatcatgaat  12060
ttgttgtaat tttatgttgt actcagtgca tttaagaaat ggtagagtat tttaatccta  12120
ttacttgact aagagtgtga aggtagtact ttttagagtg cactgagtgc actttacatc  12180
tttatttaaa ttttttttta acatcttatg tttacaggct tcctgtttga tgaagatagc  12240
aacggaaaac tcaaaatggt ggcagttctt attaccagtt gttagtattg tttctggaaa  12300
```

-continued

```
ctgcttgcca agacaacatt tattaactgt tagaacactt gctttatgtt tgtgtgtaca  12360

tattttccac aaatgttata atttatatag tgtggttgaa caggatgcaa tcttttgttg  12420

tctaaaggtg ctgcagttaa aaaaaaaaca accttttctt tcaatatggc atgtagtgga  12480

gtttttttaa ctttaaaaac atcaaaaatt gttaaaatca ttgtgttatc tagtagttta  12540

taattatcgg cttatatttc cccatgaatg atcagaactg acatttaatt catgtttgtc  12600

tcgccatgct tctttacttt aacatatttc ttttgcagaa tgtaaaaggt aatgataatt  12660

agtttatata agtgtactgg ctgtaaatga tgctaaatat actttatgca attaagggct  12720

tacagaacat gttgaaactt tttttacttt tattgggaat aaggaatgtt tgcacctcca  12780

cattttattg ctt                                                     12793
```

<210> SEQ ID NO 16
<211> LENGTH: 3829
<212> TYPE: PRT
<213> ORGANISM: Homo sapiens

<400> SEQUENCE: 16

```
Met Asn Thr Phe Trp Pro Gly Arg Glu Leu Ile Val Gln Trp Tyr Pro
 1               5                  10                  15

Phe Asp Glu Asn Arg Asn His Pro Ser Val Ser Trp Leu Lys Met Val
            20                  25                  30

Trp Lys Asn Leu Tyr Ile His Phe Ser Glu Asp Leu Thr Leu Phe Asp
        35                  40                  45

Glu Met Pro Leu Ile Pro Arg Thr Ile Leu Glu Glu Gly Gln Thr Cys
    50                  55                  60

Val Glu Leu Ile Arg Leu Arg Ile Pro Ser Leu Val Ile Leu Asp Asp
65                  70                  75                  80

Glu Ser Glu Ala Gln Leu Pro Glu Phe Leu Ala Asp Ile Val Gln Lys
                85                  90                  95

Leu Gly Gly Phe Val Leu Lys Lys Leu Asp Ala Ser Ile Gln His Pro
            100                 105                 110

Leu Ile Lys Lys Tyr Ile His Ser Pro Leu Pro Ser Ala Val Leu Gln
        115                 120                 125

Ile Met Glu Lys Met Pro Leu Gln Lys Leu Cys Asn Gln Ile Thr Ser
    130                 135                 140

Leu Leu Pro Thr His Lys Asp Ala Leu Arg Lys Phe Leu Ala Ser Leu
145                 150                 155                 160

Thr Asp Ser Ser Glu Lys Glu Lys Arg Ile Ile Gln Glu Leu Ala Ile
                165                 170                 175

Phe Lys Arg Ile Asn His Ser Ser Asp Gln Gly Ile Ser Ser Tyr Thr
            180                 185                 190

Lys Leu Lys Gly Cys Lys Val Leu His His Thr Ala Lys Leu Pro Ala
        195                 200                 205

Asp Leu Arg Leu Ser Ile Ser Val Ile Asp Ser Ser Asp Glu Ala Thr
    210                 215                 220

Ile Arg Leu Ala Asn Met Leu Lys Ile Glu Gln Leu Lys Thr Thr Ser
225                 230                 235                 240

Cys Leu Lys Leu Val Leu Lys Asp Ile Glu Asn Ala Phe Tyr Ser His
                245                 250                 255

Glu Glu Val Thr Gln Leu Met Leu Trp Val Leu Glu Asn Leu Ser Ser
            260                 265                 270

Leu Lys Asn Glu Asn Pro Asn Val Leu Glu Trp Leu Thr Pro Leu Lys
        275                 280                 285
```

-continued

```
Phe Ile Gln Ile Ser Gln Glu Gln Met Val Ser Ala Gly Glu Leu Phe
    290                 295                 300

Asp Pro Asp Ile Glu Val Leu Lys Asp Leu Phe Cys Asn Glu Glu Gly
305                 310                 315                 320

Thr Tyr Phe Pro Pro Ser Val Phe Thr Ser Pro Asp Ile Leu His Ser
                325                 330                 335

Leu Arg Gln Ile Gly Leu Lys Asn Glu Ala Ser Leu Lys Glu Lys Asp
            340                 345                 350

Val Val Gln Val Ala Lys Lys Ile Glu Ala Leu Gln Val Gly Ala Cys
        355                 360                 365

Pro Asp Gln Asp Val Leu Leu Lys Lys Ala Lys Thr Leu Leu Leu Val
    370                 375                 380

Leu Asn Lys Asn His Thr Leu Leu Gln Ser Ser Glu Gly Lys Met Thr
385                 390                 395                 400

Leu Lys Lys Ile Lys Trp Val Pro Ala Cys Lys Glu Arg Pro Pro Asn
                405                 410                 415

Tyr Pro Gly Ser Leu Val Trp Lys Gly Asp Leu Cys Asn Leu Cys Ala
            420                 425                 430

Pro Pro Asp Met Cys Asp Val Gly His Ala Ile Leu Ile Gly Ser Ser
        435                 440                 445

Leu Pro Leu Val Glu Ser Ile His Val Asn Leu Glu Lys Ala Leu Gly
    450                 455                 460

Ile Phe Thr Lys Pro Ser Leu Ser Ala Val Leu Lys His Phe Lys Ile
465                 470                 475                 480

Val Val Asp Trp Tyr Ser Ser Lys Thr Phe Ser Asp Glu Asp Tyr Tyr
                485                 490                 495

Gln Phe Gln His Ile Leu Leu Glu Ile Tyr Gly Phe Met His Asp His
            500                 505                 510

Leu Asn Glu Gly Lys Asp Ser Phe Arg Ala Leu Lys Phe Pro Trp Val
        515                 520                 525

Trp Thr Gly Lys Lys Phe Cys Pro Leu Ala Gln Ala Val Ile Lys Pro
    530                 535                 540

Ile His Asp Leu Asp Leu Gln Pro Tyr Leu His Asn Val Pro Lys Thr
545                 550                 555                 560

Met Ala Lys Phe His Gln Leu Phe Lys Val Cys Gly Ser Ile Glu Glu
                565                 570                 575

Leu Thr Ser Asp His Ile Ser Met Val Ile Gln Lys Ile Tyr Leu Lys
            580                 585                 590

Ser Asp Gln Asp Leu Ser Glu Gln Glu Ser Lys Gln Asn Leu His Leu
        595                 600                 605

Met Leu Asn Ile Ile Arg Trp Leu Tyr Ser Asn Gln Ile Pro Ala Ser
    610                 615                 620

Pro Asn Thr Pro Val Pro Ile His His Ser Lys Asn Pro Ser Lys Leu
625                 630                 635                 640

Ile Met Lys Pro Ile His Glu Cys Cys Tyr Cys Asp Ile Lys Val Asp
                645                 650                 655

Asp Leu Asn Asp Leu Leu Glu Asp Ser Val Glu Pro Ile Ile Leu Val
            660                 665                 670

His Glu Asp Ile Pro Met Lys Thr Ala Glu Trp Leu Lys Val Pro Cys
        675                 680                 685

Leu Ser Thr Arg Leu Ile Asn Pro Glu Asn Met Gly Phe Glu Gln Ser
    690                 695                 700
```

-continued

```
Gly Gln Arg Glu Pro Leu Thr Val Arg Ile Lys Asn Ile Leu Glu Glu
705                 710                 715                 720

Tyr Pro Ser Val Ser Asp Ile Phe Lys Glu Leu Leu Gln Asn Ala Asp
                725                 730                 735

Asp Ala Asn Ala Thr Glu Cys Ser Phe Leu Ile Asp Met Arg Arg Asn
            740                 745                 750

Met Asp Ile Arg Glu Asn Leu Leu Asp Pro Gly Met Ala Ala Cys His
        755                 760                 765

Gly Pro Ala Leu Trp Ser Phe Asn Asn Ser Gln Phe Ser Asp Ser Asp
    770                 775                 780

Phe Val Asn Ile Thr Arg Leu Gly Glu Ser Leu Lys Arg Gly Glu Val
785                 790                 795                 800

Asp Lys Val Gly Lys Phe Gly Leu Gly Phe Asn Ser Val Tyr His Ile
                805                 810                 815

Thr Asp Ile Pro Ile Ile Met Ser Arg Glu Phe Met Ile Met Phe Asp
            820                 825                 830

Pro Asn Ile Asn His Ile Ser Lys His Ile Lys Asp Lys Ser Asn Pro
        835                 840                 845

Gly Ile Lys Ile Asn Trp Ser Lys Gln Gln Lys Arg Leu Arg Lys Phe
    850                 855                 860

Pro Asn Gln Phe Lys Pro Phe Ile Asp Val Phe Gly Cys Gln Leu Pro
865                 870                 875                 880

Leu Thr Val Glu Ala Pro Tyr Ser Tyr Asn Gly Thr Leu Phe Arg Leu
                885                 890                 895

Ser Phe Arg Thr Gln Gln Glu Ala Lys Val Ser Glu Val Ser Ser Thr
            900                 905                 910

Cys Tyr Asn Thr Ala Asp Ile Tyr Ser Leu Val Asp Glu Phe Ser Leu
        915                 920                 925

Cys Gly His Arg Leu Ile Ile Phe Thr Gln Ser Val Lys Ser Met Tyr
    930                 935                 940

Leu Lys Tyr Leu Lys Ile Glu Glu Thr Asn Pro Ser Leu Ala Gln Asp
945                 950                 955                 960

Thr Val Ile Ile Lys Lys Lys Ser Cys Ser Ser Lys Ala Leu Asn Thr
                965                 970                 975

Pro Val Leu Ser Val Leu Lys Glu Ala Ala Lys Leu Met Lys Thr Cys
            980                 985                 990

Ser Ser Ser Asn Lys Lys Leu Pro Ser Asp Glu Pro Lys Ser Ser Cys
        995                 1000                1005

Ile Leu Gln Ile Thr Val Glu Glu Phe His His Val Phe Arg Arg Ile
    1010                1015                1020

Ala Asp Leu Gln Ser Pro Leu Phe Arg Gly Pro Asp Asp Asp Pro Ala
1025                1030                1035                1040

Ala Leu Phe Glu Met Ala Lys Ser Gly Gln Ser Lys Lys Pro Ser Asp
                1045                1050                1055

Glu Leu Ser Gln Lys Thr Val Glu Cys Thr Thr Trp Leu Leu Cys Thr
            1060                1065                1070

Cys Met Asp Thr Gly Glu Ala Leu Lys Phe Ser Leu Ser Glu Ser Gly
        1075                1080                1085

Arg Arg Leu Gly Leu Val Pro Cys Gly Ala Val Gly Val Gln Leu Ser
    1090                1095                1100

Glu Ile Gln Asp Gln Lys Trp Thr Val Lys Pro His Ile Gly Glu Val
1105                1110                1115                1120

Phe Cys Tyr Leu Pro Leu Arg Ile Lys Thr Gly Leu Pro Val His Ile
```

-continued

```
            1125                1130                1135

Asn Gly Cys Phe Ala Val Thr Ser Asn Arg Lys Glu Ile Trp Lys Thr
        1140                1145                1150

Asp Thr Lys Gly Arg Trp Asn Thr Thr Phe Met Arg His Val Ile Val
    1155                1160                1165

Lys Ala Tyr Leu Gln Val Leu Ser Val Leu Arg Asp Leu Ala Thr Ser
    1170                1175                1180

Gly Glu Leu Met Asp Tyr Thr Tyr Tyr Ala Val Trp Pro Asp Pro Asp
1185                1190                1195                1200

Leu Val His Asp Asp Phe Ser Val Ile Cys Gln Gly Phe Tyr Glu Asp
            1205                1210                1215

Ile Ala His Gly Lys Gly Lys Glu Leu Thr Lys Val Phe Ser Asp Gly
        1220                1225                1230

Ser Thr Trp Val Ser Met Lys Asn Val Arg Phe Leu Asp Asp Ser Ile
    1235                1240                1245

Leu Lys Arg Arg Asp Val Gly Ser Ala Ala Phe Lys Ile Phe Leu Lys
    1250                1255                1260

Tyr Leu Lys Lys Thr Gly Ser Lys Asn Leu Cys Ala Val Glu Leu Pro
1265                1270                1275                1280

Ser Ser Val Lys Leu Gly Phe Glu Glu Ala Gly Cys Lys Gln Ile Leu
            1285                1290                1295

Leu Glu Asn Thr Phe Ser Glu Lys Gln Phe Phe Ser Glu Val Phe Phe
        1300                1305                1310

Pro Asn Ile Gln Glu Ile Glu Ala Glu Leu Arg Asp Pro Leu Met Ile
    1315                1320                1325

Phe Val Leu Asn Glu Lys Val Asp Glu Phe Ser Gly Val Leu Arg Val
    1330                1335                1340

Thr Pro Cys Ile Pro Cys Ser Leu Glu Gly His Pro Leu Val Leu Pro
1345                1350                1355                1360

Ser Arg Leu Ile His Pro Glu Gly Arg Val Ala Lys Leu Phe Asp Ile
            1365                1370                1375

Lys Asp Gly Arg Phe Pro Tyr Gly Ser Thr Gln Asp Tyr Leu Asn Pro
        1380                1385                1390

Ile Ile Leu Ile Lys Leu Val Gln Leu Gly Met Ala Lys Asp Asp Ile
    1395                1400                1405

Leu Trp Asp Asp Met Leu Glu Arg Ala Val Ser Val Ala Glu Ile Asn
    1410                1415                1420

Lys Ser Asp His Val Ala Ala Cys Leu Arg Ser Ser Ile Leu Leu Ser
1425                1430                1435                1440

Leu Ile Asp Glu Lys Leu Lys Ile Arg Asp Pro Arg Ala Lys Asp Phe
            1445                1450                1455

Ala Ala Lys Tyr Gln Thr Ile Arg Phe Leu Pro Phe Leu Thr Lys Pro
        1460                1465                1470

Ala Gly Phe Ser Leu Asp Trp Lys Gly Asn Ser Phe Lys Pro Glu Thr
    1475                1480                1485

Met Phe Ala Ala Thr Asp Leu Tyr Thr Ala Glu His Gln Asp Ile Val
    1490                1495                1500

Cys Leu Leu Gln Pro Ile Leu Asn Glu Asn Ser His Ser Phe Arg Gly
1505                1510                1515                1520

Cys Gly Ser Val Ser Leu Ala Val Lys Glu Phe Leu Gly Leu Leu Lys
            1525                1530                1535

Lys Pro Thr Val Asp Leu Val Ile Asn Gln Leu Lys Glu Val Ala Lys
        1540                1545                1550
```

-continued

Ser Val Asp Asp Gly Ile Thr Leu Tyr Gln Glu Asn Ile Thr Asn Ala
1555 1560 1565

Cys Tyr Lys Tyr Leu His Glu Ala Leu Met Gln Asn Glu Ile Thr Lys
1570 1575 1580

Met Ser Ile Ile Asp Lys Leu Lys Pro Phe Ser Phe Ile Leu Val Glu
1585 1590 1595 1600

Asn Ala Tyr Val Asp Ser Glu Lys Val Ser Phe His Leu Asn Phe Glu
1605 1610 1615

Ala Ala Pro Tyr Leu Tyr Gln Leu Pro Asn Lys Tyr Lys Asn Asn Phe
1620 1625 1630

Arg Glu Leu Phe Glu Thr Val Gly Val Arg Gln Ser Cys Thr Val Glu
1635 1640 1645

Asp Phe Ala Leu Val Leu Glu Ser Ile Asp Gln Glu Arg Gly Thr Lys
1650 1655 1660

Gln Ile Thr Glu Glu Asn Phe Gln Leu Cys Arg Arg Ile Ile Ser Glu
1665 1670 1675 1680

Gly Ile Trp Ser Leu Ile Arg Glu Lys Lys Gln Glu Phe Cys Glu Lys
1685 1690 1695

Asn Tyr Gly Lys Ile Leu Leu Pro Asp Thr Asn Leu Met Leu Leu Pro
1700 1705 1710

Ala Lys Ser Leu Cys Tyr Asn Asp Cys Pro Trp Ile Lys Val Lys Asp
1715 1720 1725

Thr Thr Val Lys Tyr Cys His Ala Asp Ile Pro Arg Glu Val Ala Val
1730 1735 1740

Lys Leu Gly Ala Val Pro Lys Arg His Lys Ala Leu Glu Arg Tyr Ala
1745 1750 1755 1760

Ser Asn Val Cys Phe Thr Thr Leu Gly Thr Glu Phe Gly Gln Lys Glu
1765 1770 1775

Lys Leu Thr Ser Arg Ile Lys Ser Ile Leu Asn Ala Tyr Pro Ser Glu
1780 1785 1790

Lys Glu Met Leu Lys Glu Leu Leu Gln Asn Ala Asp Asp Ala Lys Ala
1795 1800 1805

Thr Glu Ile Cys Phe Val Phe Asp Pro Arg Gln His Pro Val Asp Arg
1810 1815 1820

Ile Phe Asp Asp Lys Trp Ala Pro Leu Gln Gly Pro Ala Leu Cys Val
1825 1830 1835 1840

Tyr Asn Asn Gln Pro Phe Thr Glu Asp Asp Val Arg Gly Ile Gln Asn
1845 1850 1855

Leu Gly Lys Gly Thr Lys Glu Gly Asn Pro Tyr Lys Thr Gly Gln Tyr
1860 1865 1870

Gly Ile Gly Phe Asn Ser Val Tyr His Ile Thr Asp Cys Pro Ser Phe
1875 1880 1885

Ile Ser Gly Asn Asp Ile Leu Cys Ile Phe Asp Pro His Ala Arg Tyr
1890 1895 1900

Ala Pro Gly Ala Thr Ser Ile Ser Pro Gly Arg Met Phe Arg Asp Leu
1905 1910 1915 1920

Asp Ala Asp Phe Arg Thr Gln Phe Ser Asp Val Leu Asp Leu Tyr Leu
1925 1930 1935

Gly Thr His Phe Lys Leu Asp Asn Cys Thr Met Phe Arg Phe Pro Leu
1940 1945 1950

Arg Asn Ala Glu Met Ala Lys Val Ser Glu Ile Ser Ser Val Pro Ala
1955 1960 1965

-continued

```
Ser Asp Arg Met Val Gln Asn Leu Leu Asp Lys Leu Arg Ser Asp Gly
    1970                1975                1980

Ala Glu Leu Leu Met Phe Leu Asn His Met Glu Lys Ile Ser Ile Cys
1985                1990                1995                2000

Glu Ile Asp Lys Ser Thr Gly Ala Leu Asn Val Leu Tyr Ser Val Lys
                2005                2010                2015

Gly Lys Ile Thr Asp Gly Asp Arg Leu Lys Arg Lys Gln Phe His Ala
            2020                2025                2030

Ser Val Ile Asp Ser Val Thr Lys Lys Arg Gln Leu Lys Asp Ile Pro
        2035                2040                2045

Val Gln Gln Ile Thr Tyr Thr Met Asp Thr Glu Asp Ser Glu Gly Asn
    2050                2055                2060

Leu Thr Thr Trp Leu Ile Cys Asn Arg Ser Gly Phe Ser Ser Met Glu
2065                2070                2075                2080

Lys Val Ser Lys Ser Val Ile Ser Ala His Lys Asn Gln Asp Ile Thr
                2085                2090                2095

Leu Phe Pro Arg Gly Gly Val Ala Ala Cys Ile Thr His Asn Tyr Lys
            2100                2105                2110

Lys Pro His Arg Ala Phe Cys Phe Leu Pro Leu Ser Leu Glu Thr Gly
        2115                2120                2125

Leu Pro Phe His Val Asn Gly His Phe Ala Leu Asp Ser Ala Arg Arg
    2130                2135                2140

Asn Leu Trp Arg Asp Asp Asn Gly Val Gly Val Arg Ser Asp Trp Asn
2145                2150                2155                2160

Asn Ser Leu Met Thr Ala Leu Ile Ala Pro Ala Tyr Val Glu Leu Leu
                2165                2170                2175

Ile Gln Leu Lys Lys Arg Tyr Phe Pro Gly Ser Asp Pro Thr Leu Ser
            2180                2185                2190

Val Leu Gln Asn Thr Pro Ile His Val Val Lys Asp Thr Leu Lys Lys
        2195                2200                2205

Phe Leu Ser Phe Phe Pro Val Asn Arg Leu Asp Leu Gln Pro Asp Leu
    2210                2215                2220

Tyr Cys Leu Val Lys Ala Leu Tyr Asn Cys Ile His Glu Asp Met Lys
2225                2230                2235                2240

Arg Leu Leu Pro Val Val Arg Ala Pro Asn Ile Asp Gly Ser Asp Leu
                2245                2250                2255

His Ser Ala Val Ile Ile Thr Trp Ile Asn Met Ser Thr Ser Asn Lys
            2260                2265                2270

Thr Arg Pro Phe Phe Asp Asn Leu Leu Gln Asp Glu Leu Gln His Leu
        2275                2280                2285

Lys Asn Ala Asp Tyr Asn Ile Thr Thr Arg Lys Thr Val Ala Glu Asn
    2290                2295                2300

Val Tyr Arg Leu Lys His Leu Leu Leu Glu Ile Gly Phe Asn Leu Val
2305                2310                2315                2320

Tyr Asn Cys Asp Glu Thr Ala Asn Leu Tyr His Cys Leu Ile Asp Ala
                2325                2330                2335

Asp Ile Pro Val Ser Tyr Val Thr Pro Ala Asp Ile Arg Ser Phe Leu
            2340                2345                2350

Met Thr Phe Ser Ser Pro Asp Thr Asn Cys His Ile Gly Lys Leu Pro
        2355                2360                2365

Cys Arg Leu Gln Gln Thr Asn Leu Lys Leu Phe His Ser Leu Lys Leu
    2370                2375                2380

Leu Val Asp Tyr Cys Phe Lys Asp Ala Glu Glu Asn Glu Ile Glu Val
```

-continued

```
2385                2390                2395                2400

Glu Gly Leu Pro Leu Leu Ile Thr Leu Asp Ser Val Leu Gln Thr Phe
                2405                2410                2415

Asp Ala Lys Arg Pro Lys Phe Leu Thr Thr Tyr His Glu Leu Ile Pro
            2420                2425                2430

Ser Arg Lys Asp Leu Phe Met Asn Thr Leu Tyr Leu Lys Tyr Ser Asn
        2435                2440                2445

Ile Leu Leu Asn Cys Lys Val Ala Lys Val Phe Asp Ile Ser Ser Phe
    2450                2455                2460

Ala Asp Leu Leu Ser Ser Val Leu Pro Arg Glu Tyr Lys Thr Lys Ser
2465                2470                2475                2480

Cys Thr Lys Trp Lys Asp Asn Phe Ala Ser Glu Ser Trp Leu Lys Asn
                2485                2490                2495

Ala Trp His Phe Ile Ser Glu Ser Val Ser Val Lys Glu Asp Gln Glu
            2500                2505                2510

Glu Thr Lys Pro Thr Phe Asp Ile Val Val Asp Thr Leu Lys Asp Trp
        2515                2520                2525

Ala Leu Leu Pro Gly Thr Lys Phe Thr Val Ser Ala Asn Gln Leu Val
    2530                2535                2540

Val Pro Glu Gly Asp Val Leu Leu Pro Leu Ser Leu Met His Ile Ala
2545                2550                2555                2560

Val Phe Pro Asn Ala Gln Ser Asp Lys Val Phe His Ala Leu Met Lys
                2565                2570                2575

Ala Gly Cys Ile Gln Leu Ala Leu Asn Lys Ile Cys Ser Lys Asp Ser
            2580                2585                2590

Ala Leu Val Pro Leu Leu Ser Cys His Thr Ala Asn Ile Glu Ser Pro
        2595                2600                2605

Thr Ser Ile Leu Lys Ala Leu His Tyr Met Val Gln Thr Ser Thr Phe
    2610                2615                2620

Arg Ala Glu Lys Leu Val Glu Asn Asp Phe Glu Ala Leu Leu Met Tyr
2625                2630                2635                2640

Phe Asn Cys Asn Leu Asn His Leu Met Ser Gln Asp Asp Ile Lys Ile
                2645                2650                2655

Leu Lys Ser Leu Pro Cys Tyr Lys Ser Ile Ser Gly Arg Tyr Val Ser
            2660                2665                2670

Ile Gly Lys Phe Gly Thr Cys Tyr Val Leu Thr Lys Ser Ile Pro Ser
        2675                2680                2685

Ala Glu Val Glu Lys Trp Thr Gln Ser Ser Ser Ser Ala Phe Leu Glu
    2690                2695                2700

Glu Lys Ile His Leu Lys Glu Leu Tyr Glu Val Ile Gly Cys Val Pro
2705                2710                2715                2720

Val Asp Asp Leu Glu Val Tyr Leu Lys His Leu Leu Pro Lys Ile Glu
                2725                2730                2735

Asn Leu Ser Tyr Asp Ala Lys Leu Glu His Leu Ile Tyr Leu Lys Asn
            2740                2745                2750

Arg Leu Ser Ser Ala Glu Glu Leu Ser Glu Ile Lys Glu Gln Leu Phe
        2755                2760                2765

Glu Lys Leu Glu Ser Leu Leu Ile Ile His Asp Ala Asn Ser Arg Leu
    2770                2775                2780

Lys Gln Ala Lys His Phe Tyr Asp Arg Thr Val Arg Val Phe Glu Val
2785                2790                2795                2800

Met Leu Pro Glu Lys Leu Phe Ile Pro Asn Asp Phe Phe Lys Lys Leu
                2805                2810                2815
```

-continued

```
Glu Gln Leu Ile Lys Pro Lys Asn His Val Thr Phe Met Thr Ser Trp
            2820                2825                2830

Val Glu Phe Leu Arg Asn Ile Gly Leu Lys Tyr Ile Leu Ser Gln Gln
        2835                2840                2845

Gln Leu Leu Gln Phe Ala Lys Glu Ile Ser Val Arg Ala Asn Thr Glu
    2850                2855                2860

Asn Trp Ser Lys Glu Thr Leu Gln Asn Thr Val Asp Ile Leu Leu His
2865                2870                2875                2880

His Ile Phe Gln Glu Arg Met Asp Leu Leu Ser Gly Asn Phe Leu Lys
                2885                2890                2895

Glu Leu Ser Leu Ile Pro Phe Leu Cys Pro Glu Arg Ala Pro Ala Glu
            2900                2905                2910

Phe Ile Arg Phe His Pro Gln Tyr Gln Glu Val Asn Gly Thr Leu Pro
        2915                2920                2925

Leu Ile Lys Phe Asn Gly Ala Gln Val Asn Pro Lys Phe Lys Gln Cys
    2930                2935                2940

Asp Val Leu Gln Leu Leu Trp Thr Ser Cys Pro Ile Leu Pro Glu Lys
2945                2950                2955                2960

Ala Thr Pro Leu Ser Ile Lys Glu Gln Glu Gly Ser Asp Leu Gly Pro
                2965                2970                2975

Gln Glu Gln Leu Glu Gln Val Leu Asn Met Leu Asn Val Asn Leu Asp
            2980                2985                2990

Pro Pro Leu Asp Lys Val Ile Asn Asn Cys Arg Asn Ile Cys Asn Ile
        2995                3000                3005

Thr Thr Leu Asp Glu Glu Met Val Lys Thr Arg Ala Lys Val Leu Arg
    3010                3015                3020

Ser Ile Tyr Glu Phe Leu Ser Ala Glu Lys Arg Glu Phe Arg Phe Gln
3025                3030                3035                3040

Leu Arg Gly Val Ala Phe Val Met Val Glu Asp Gly Trp Lys Leu Leu
                3045                3050                3055

Lys Pro Glu Glu Val Val Ile Asn Leu Glu Tyr Glu Ser Asp Phe Lys
            3060                3065                3070

Pro Tyr Leu Tyr Lys Leu Pro Leu Glu Leu Gly Thr Phe His Gln Leu
        3075                3080                3085

Phe Lys His Leu Gly Thr Glu Asp Ile Ile Ser Thr Lys Gln Tyr Val
    3090                3095                3100

Glu Val Leu Ser Arg Ile Phe Lys Asn Ser Glu Gly Lys Gln Leu Asp
3105                3110                3115                3120

Pro Asn Glu Met Arg Thr Val Lys Arg Val Val Ser Gly Leu Phe Arg
                3125                3130                3135

Ser Leu Gln Asn Asp Ser Val Lys Val Arg Ser Asp Leu Glu Asn Val
            3140                3145                3150

Arg Asp Leu Ala Leu Tyr Leu Pro Ser Gln Asp Gly Arg Leu Val Lys
        3155                3160                3165

Ser Ser Ile Leu Val Phe Asp Asp Ala Pro His Tyr Lys Ser Arg Ile
    3170                3175                3180

Gln Gly Asn Ile Gly Val Gln Met Leu Val Asp Leu Ser Gln Cys Tyr
3185                3190                3195                3200

Leu Gly Lys Asp His Gly Phe His Thr Lys Leu Ile Met Leu Phe Pro
                3205                3210                3215

Gln Lys Leu Arg Pro Arg Leu Leu Ser Ser Ile Leu Glu Glu Gln Leu
            3220                3225                3230
```

-continued

Asp Glu Glu Thr Pro Lys Val Cys Gln Phe Gly Ala Leu Cys Ser Leu
3235 3240 3245

Gln Gly Arg Leu Gln Leu Leu Leu Ser Ser Glu Gln Phe Ile Thr Gly
3250 3255 3260

Leu Ile Arg Ile Met Lys His Glu Asn Asp Asn Ala Phe Leu Ala Asn
3265 3270 3275 3280

Glu Glu Lys Ala Ile Arg Leu Cys Lys Ala Leu Arg Glu Gly Leu Lys
3285 3290 3295

Val Ser Cys Phe Glu Lys Leu Gln Thr Thr Leu Arg Val Lys Gly Phe
3300 3305 3310

Asn Pro Ile Pro His Ser Arg Ser Glu Thr Phe Ala Phe Leu Lys Arg
3315 3320 3325

Phe Gly Asn Ala Val Ile Leu Leu Tyr Ile Gln His Ser Asp Ser Lys
3330 3335 3340

Asp Ile Asn Phe Leu Leu Ala Leu Ala Met Thr Leu Lys Ser Ala Thr
3345 3350 3355 3360

Asp Asn Leu Ile Ser Asp Thr Ser Tyr Leu Ile Ala Met Leu Gly Cys
3365 3370 3375

Asn Asp Ile Tyr Arg Ile Gly Glu Lys Leu Asp Ser Leu Gly Val Lys
3380 3385 3390

Tyr Asp Ser Ser Glu Pro Ser Lys Leu Glu Leu Pro Met Pro Gly Thr
3395 3400 3405

Pro Ile Pro Ala Glu Ile His Tyr Thr Leu Leu Met Asp Pro Met Asn
3410 3415 3420

Val Phe Tyr Pro Gly Glu Tyr Val Gly Tyr Leu Val Asp Ala Glu Gly
3425 3430 3435 3440

Gly Asp Ile Tyr Gly Ser Tyr Gln Pro Thr Tyr Thr Tyr Ala Ile Ile
3445 3450 3455

Val Gln Glu Val Glu Arg Glu Asp Ala Asp Asn Ser Ser Phe Leu Gly
3460 3465 3470

Lys Ile Tyr Gln Ile Asp Ile Gly Tyr Ser Glu Tyr Lys Ile Val Ser
3475 3480 3485

Ser Leu Asp Leu Tyr Lys Phe Ser Arg Pro Glu Glu Ser Ser Gln Ser
3490 3495 3500

Arg Asp Ser Ala Pro Ser Thr Pro Thr Ser Pro Thr Glu Phe Leu Thr
3505 3510 3515 3520

Pro Gly Leu Arg Ser Ile Pro Pro Leu Phe Ser Gly Arg Glu Ser His
3525 3530 3535

Lys Thr Ser Ser Lys His Gln Ser Pro Lys Lys Leu Lys Val Asn Ser
3540 3545 3550

Leu Pro Glu Ile Leu Lys Glu Val Thr Ser Val Val Glu Gln Ala Trp
3555 3560 3565

Lys Leu Pro Glu Ser Glu Arg Lys Lys Ile Ile Arg Arg Leu Tyr Leu
3570 3575 3580

Lys Trp His Pro Asp Lys Asn Pro Glu Asn His Asp Ile Ala Asn Glu
3585 3590 3595 3600

Val Phe Lys His Leu Gln Asn Glu Ile Asn Arg Leu Glu Lys Gln Ala
3605 3610 3615

Phe Leu Asp Gln Asn Ala Asp Arg Ala Ser Arg Arg Thr Phe Ser Thr
3620 3625 3630

Ser Ala Ser Arg Phe Gln Ser Asp Lys Tyr Ser Phe Gln Arg Phe Tyr
3635 3640 3645

Thr Ser Trp Asn Gln Glu Ala Thr Ser His Lys Ser Glu Arg Gln Gln

-continued

```
    3650                3655                3660

Gln Asn Lys Glu Lys Cys Pro Pro Ser Ala Gly Gln Thr Tyr Ser Gln
3665                3670                3675                3680

Arg Phe Phe Val Pro Pro Thr Phe Lys Ser Val Gly Asn Pro Val Glu
                3685                3690                3695

Ala Arg Arg Trp Leu Arg Gln Ala Arg Ala Asn Phe Ser Ala Ala Arg
            3700                3705                3710

Asn Asp Leu His Lys Asn Ala Asn Glu Trp Val Cys Phe Lys Cys Tyr
        3715                3720                3725

Leu Ser Thr Lys Leu Ala Leu Ile Ala Ala Asp Tyr Ala Val Arg Gly
    3730                3735                3740

Lys Ser Asp Lys Asp Val Lys Pro Thr Ala Leu Ala Gln Lys Ile Glu
3745                3750                3755                3760

Glu Tyr Ser Gln Gln Leu Glu Gly Leu Thr Asn Asp Val His Thr Leu
                3765                3770                3775

Glu Ala Tyr Gly Val Asp Ser Leu Lys Thr Arg Tyr Pro Asp Leu Leu
            3780                3785                3790

Pro Phe Pro Gln Ile Pro Asn Asp Arg Phe Thr Ser Glu Val Ala Met
        3795                3800                3805

Arg Val Met Glu Cys Thr Ala Cys Ile Ile Ile Lys Leu Glu Asn Phe
    3810                3815                3820

Met Gln Gln Lys Val
3825


<210> SEQ ID NO 17
<211> LENGTH: 11
<212> TYPE: DNA
<213> ORGANISM: Homo sapiens

<400> SEQUENCE: 17

acccctattc a                                                            11


<210> SEQ ID NO 18
<211> LENGTH: 10
<212> TYPE: DNA
<213> ORGANISM: Homo sapiens

<400> SEQUENCE: 18

accccattca                                                              10


<210> SEQ ID NO 19
<211> LENGTH: 10
<212> TYPE: DNA
<213> ORGANISM: Homo sapiens

<400> SEQUENCE: 19

aaagcgacac                                                              10


<210> SEQ ID NO 20
<211> LENGTH: 10
<212> TYPE: DNA
<213> ORGANISM: Homo sapiens
<220> FEATURE:
<221> NAME/KEY: misc_feature
<222> LOCATION: (1)...(10)
<223> OTHER INFORMATION: n = A,T,C or G

<400> SEQUENCE: 20

aaagngacac                                                              10
```

-continued

<210> SEQ ID NO 21
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 21
ccttccagta ctgtgttatt tgtgag 26

<210> SEQ ID NO 22
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 22
caagaacttc ctcagggcat c 21

<210> SEQ ID NO 23
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 23
gatgcatcta tacaacatcc gct 23

<210> SEQ ID NO 24
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 24
gggtgggaaa taggttcctt c 21

<210> SEQ ID NO 25
<211> LENGTH: 23
<212> TYPE: DNA
<213> ORGANISM: Artificial Sequence
<220> FEATURE:
<223> OTHER INFORMATION: oligonucleotide primers

<400> SEQUENCE: 25
aaaaatgaga atccaaatgt gct 23

<210> SEQ ID NO 26
<211> LENGTH: 24
<212> TYPE: DNA
<213> ORGANISM: Artificial Sequence
<220> FEATURE:
<223> OTHER INFORMATION: oligonucleotide primers

<400> SEQUENCE: 26
gcactaaggc taggttttgt gaag 24

<210> SEQ ID NO 27
<211> LENGTH: 21
<212> TYPE: DNA
<213> ORGANISM: Artificial Sequence
<220> FEATURE:
<223> OTHER INFORMATION: oligonucleotide primers -continued

<400> SEQUENCE: 27
gctcctcact tcctcttgtt g 21

<210> SEQ ID NO 28
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 28
cgtgaattgg cttcatgata a 21

<210> SEQ ID NO 29
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 29
agcaatcaga ttccagcaag c 21

<210> SEQ ID NO 30
<211> LENGTH: 22
<212> TYPE: DNA
<213> ORGANISM: Artificial Sequence
<220> FEATURE:
<223> OTHER INFORMATION: oligonucleotide primers

<400> SEQUENCE: 30
gatgggaatg tcagtgatat gg 22

<210> SEQ ID NO 31
<211> LENGTH: 22
<212> TYPE: DNA
<213> ORGANISM: Artificial Sequence
<220> FEATURE:
<223> OTHER INFORMATION: oligonucleotide primers

<400> SEQUENCE: 31
gggagaagtt gacaaagttg ga 22

<210> SEQ ID NO 32
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 32
ctttggttca tcactgggaa g 21

<210> SEQ ID NO 33
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 33
tccaaagcat tgaacacacc t 21

<210> SEQ ID NO 34

-continued

<211> LENGTH: 21
<212> TYPE: DNA
<213> ORGANISM: Artificial Sequence
<220> FEATURE:
<223> OTHER INFORMATION: oligonucleotide primers

<400> SEQUENCE: 34
caggtcccgt aagacactca g 21

<210> SEQ ID NO 35
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 35
caatgggtgc tttgctgtta c 21

<210> SEQ ID NO 36
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 36
cgaagaactc ccgagaactc a 21

<210> SEQ ID NO 37
<211> LENGTH: 22
<212> TYPE: DNA
<213> ORGANISM: Artificial Sequence
<220> FEATURE:
<223> OTHER INFORMATION: oligonucleotide primers

<400> SEQUENCE: 37
gctggctgca aacagatact ac 22

<210> SEQ ID NO 38
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 38
gcaaacatgg tttcaggctt a 21

<210> SEQ ID NO 39
<211> LENGTH: 22
<212> TYPE: DNA
<213> ORGANISM: Artificial Sequence
<220> FEATURE:
<223> OTHER INFORMATION: oligonucleotide primers

<400> SEQUENCE: 39
caaacaatcc gcttccttcc at 22

<210> SEQ ID NO 40
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 40

-continued attattcgtc ggcaaagctg a 21

<210> SEQ ID NO 41
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 41
ttccgcgaac tttttgaaac c 21

<210> SEQ ID NO 42
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 42
acacaaagtg ctggcccttg c 21

<210> SEQ ID NO 43
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 43
gatgcaaagg cgacagaaat c 21

<210> SEQ ID NO 44
<211> LENGTH: 24
<212> TYPE: DNA
<213> ORGANISM: Artificial Sequence
<220> FEATURE:
<223> OTHER INFORMATION: oligonucleotide primers

<400> SEQUENCE: 44
atacagcaca tttagagctc cagt 24

<210> SEQ ID NO 45
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 45
gcatcagaca gaatggtcca g 21

<210> SEQ ID NO 46
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 46
gcaattcaac atatgcagga g 21

<210> SEQ ID NO 47
<211> LENGTH: 20
<212> TYPE: DNA

-continued

<213> ORGANISM: Artificial Sequence
<220> FEATURE:
<223> OTHER INFORMATION: oligonucleotide primers

<400> SEQUENCE: 47
gtgaatggcc actttgcact 20

<210> SEQ ID NO 48
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 48
tgatatcagc aggggtcaca t 21

<210> SEQ ID NO 49
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 49
accacacgca aaacagtagc a 21

<210> SEQ ID NO 50
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 50
gccatgcatt cttaagccaa g 21

<210> SEQ ID NO 51
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 51
tgacatttcc agctttgctg a 21

<210> SEQ ID NO 52
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 52
agcggccact gatggattta t 21

<210> SEQ ID NO 53
<211> LENGTH: 22
<212> TYPE: DNA
<213> ORGANISM: Artificial Sequence
<220> FEATURE:
<223> OTHER INFORMATION: oligonucleotide primers

<400> SEQUENCE: 53
aaatgatttt gaggcacttt tg 22

-continued

<210> SEQ ID NO 54
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 54
ttccacccag gatgtcataa a 21

<210> SEQ ID NO 55
<211> LENGTH: 24
<212> TYPE: DNA
<213> ORGANISM: Artificial Sequence
<220> FEATURE:
<223> OTHER INFORMATION: oligonucleotide primers

<400> SEQUENCE: 55
acagtagact aaagcaagca aagc 24

<210> SEQ ID NO 56
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 56
atcaagagga ggatccaggt t 21

<210> SEQ ID NO 57
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 57
catcctgccc tattcttcca g 21

<210> SEQ ID NO 58
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 58
taaagcgcaa ggtctcgtac a 21

<210> SEQ ID NO 59
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 59
tgagggcaaa caattagatc c 21

<210> SEQ ID NO 60
<211> LENGTH: 21
<212> TYPE: DNA
<213> ORGANISM: Artificial Sequence
<220> FEATURE:

-continued

<223> OTHER INFORMATION: oligonucleotide primers

<400> SEQUENCE: 60
tctgctgtgg ggaataggat t 21

<210> SEQ ID NO 61
<211> LENGTH: 22
<212> TYPE: DNA
<213> ORGANISM: Artificial Sequence
<220> FEATURE:
<223> OTHER INFORMATION: oligonucleotide primers

<400> SEQUENCE: 61
gcaaagccct aagagaagga tt 22

<210> SEQ ID NO 62
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 62
tgctttgaga gctttcctca g 21

<210> SEQ ID NO 63
<211> LENGTH: 24
<212> TYPE: DNA
<213> ORGANISM: Artificial Sequence
<220> FEATURE:
<223> OTHER INFORMATION: oligonucleotide primers

<400> SEQUENCE: 63
tgaaagagaa gatgctgaca attc 24

<210> SEQ ID NO 64
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 64
gtaagtctgt ccggctgaag g 21

<210> SEQ ID NO 65
<211> LENGTH: 21
<212> TYPE: DNA
<213> ORGANISM: Artificial Sequence
<220> FEATURE:
<223> OTHER INFORMATION: oligonucleotide primers

<400> SEQUENCE: 65
catcccgatt tcagtcagac a 21

<210> SEQ ID NO 66
<211> LENGTH: 23
<212> TYPE: DNA
<213> ORGANISM: Artificial Sequence
<220> FEATURE:
<223> OTHER INFORMATION: oligonucleotide primers

<400> SEQUENCE: 66
ttcgtgctac aacacattca aga 23

-continued

<210> SEQ ID NO 67
<211> LENGTH: 129
<212> TYPE: PRT
<213> ORGANISM: Homo sapiens

<400> SEQUENCE: 67

```
Gly Gln Arg Glu Pro Leu Thr Val Arg Ile Lys Asn Ile Leu Glu Glu
 1               5                  10                  15

Tyr Pro Ser Val Ser Asp Ile Phe Lys Glu Ile Leu Gln Asn Ala Asp
            20                  25                  30

Asp Ala Asn Ala Thr Glu Cys Ser Phe Leu Ile Asp Met Arg Arg Asn
        35                  40                  45

Met Asp Ile Arg Glu Asn Leu Leu Asp Pro Gly Met Ala Ala Cys His
    50                  55                  60

Gly Pro Ala Leu Trp Ser Phe Asn Asn Ser Gln Phe Ser Asp Ser Asp
65                  70                  75                  80

Phe Val Asn Ile Thr Arg Leu Gly Glu Ser Leu Lys Arg Gly Glu Val
                85                  90                  95

Asp Lys Val Gly Lys Phe Gly Leu Gly Phe Asn Ser Val Tyr His Ile
            100                 105                 110

Thr Asp Ile Pro Ile Ile Met Ser Arg Glu Phe Met Ile Met Phe Asp
        115                 120                 125

Pro
```

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72
<211> LENGTH: 25
<212> TYPE: DNA
<213> ORGANISM: Artificial Sequence
<220> FEATURE:
<223> OTHER INFORMATION: oligonucleotide primers

<400> SEQUENCE: 72
tcattcatat gtcccaggga catgt 25

<210> SEQ ID NO 73
<211> LENGTH: 11
<212> TYPE: DNA

-continued

```
<213> ORGANISM: Artificial Sequence
<220> FEATURE:
<223> OTHER INFORMATION: oligonucleotide primers

<400> SEQUENCE: 73

acccctattc a                                                   11
```